(12) United States Patent
Izhar et al.

(10) Patent No.: US 11,946,077 B2
(45) Date of Patent: Apr. 2, 2024

(54) OMNI-59, 61, 67, 76, 79, 80, 81, AND 82 CRISPR NUCLEASES

(71) Applicant: EmendoBio Inc., Wilmington, DE (US)

(72) Inventors: Lior Izhar, Tel Aviv (IL); Liat Rockah, Rishon LeZion (IL); Nadav Marbach Bar, Rehovot (IL); Nurit Meron, Ramat Gan (IL)

(73) Assignee: EmendoBio Inc.

( * ) Notice: Subject to any disclaimer, the term of this patent is extended or adjusted under 35 U.S.C. 154(b) by 0 days.

(21) Appl. No.: 17/905,617

(22) PCT Filed: Jun. 4, 2021

(86) PCT No.: PCT/US2021/035928
§ 371 (c)(1),
(2) Date: Sep. 2, 2022

(87) PCT Pub. No.: WO2021/248016
PCT Pub. Date: Dec. 9, 2021

(65) Prior Publication Data
US 2023/0122086 A1  Apr. 20, 2023

Related U.S. Application Data

(60) Provisional application No. 63/122,564, filed on Dec. 8, 2020, provisional application No. 63/034,610, filed on Jun. 4, 2020.

(51) Int. Cl.
*C12N 9/22* (2006.01)

(52) U.S. Cl.
CPC ............ *C12N 9/22* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 8,697,359 B1* | 4/2014 | Zhang | C12N 15/85 435/6.13 |
| 2019/0264232 A1 | 8/2019 | Hou et al. | |
| 2021/0024924 A1* | 1/2021 | Qi | C12N 9/22 |
| 2022/0202913 A1 | 6/2022 | Baram | |

FOREIGN PATENT DOCUMENTS

| | | |
|---|---|---|
| WO | WO 2018/172556 A1 | 9/2018 |
| WO | WO 2019/214604 | 11/2019 |
| WO | WO 2021/248016 | 12/2021 |

OTHER PUBLICATIONS

UniProtKB Accession No. A0A4V4U8M3 "CRISPR-associated endonuclease Cas9".
Notification of Transmittal of The International Search Report and the Written Opinion of the International Searching Authority, or the Declaration, dated Mar. 1, 2022 in connection with PCT International Application No. PCT/US 2021/035928.
International Search Report dated Mar. 1, 2022 in connection with PCT International Application No. PCT/US2021/035928.
Written Opinion of the International Searching Authority dated Mar. 1, 2022 in connection with PCT International Application No. PCT/US2021/035928.
International Preliminary Report on Patentability dated Dec. 15, 2022, in connection with PCT International Application No. PCT/US2021/035928.

* cited by examiner

*Primary Examiner* — Nancy J Leith
(74) *Attorney, Agent, or Firm* — Seyfarth Shaw LLP; Jamaica Szeliga

(57) ABSTRACT

The present invention provides a non-naturally occurring composition comprising a CRISPR nuclease comprising a sequence having at least 95% identity to the amino acid sequence selected from the group consisting of SEQ ID NOs: 1-8 or a nucleic acid molecule comprising a sequence encoding the CRISPR nuclease.

21 Claims, 17 Drawing Sheets

Specification includes a Sequence Listing.

OMNI-61

| V1 | V3 |
|---|---|
| NSHNAC | NSHNAC |
| positions 1-7 | positions 1-7 |

| 1 | 2 | 3 | 4 | 5 | 6 | 7 | 8 | Ratio |
|---|---|---|---|---|---|---|---|---|
|   |   |   | C | A | A | C |   | 0.51 |
|   |   |   | T | A | A | C |   | 0.66 |
|   |   |   | T | C | A | C |   | 0.68 |
|   |   |   | C | C | A | C |   | 0.69 |
|   |   |   |   | A | A | C | C | 0.72 |
|   |   |   |   | C | A | C | G | 0.73 |
|   |   | G | T | A | A |   |   | 0.73 |
|   | C | C | A | A |   |   |   | 0.74 |
|   |   |   |   | T | C | T | G | 0.76 |
|   |   |   |   | A | A | C | T | 0.76 |
|   |   |   | C | T | C | A |   | 0.79 |
|   |   |   | A | G | T | A |   | 0.79 |
|   |   |   |   | A | A | C | A | 0.80 |
|   |   | C | A | A | A |   |   | 0.81 |
|   |   |   |   | A | A | T | C | 0.82 |
|   | A | C | A | G |   |   |   | 0.82 |
|   |   | G | T | C | A |   |   | 0.82 |

| 1 | 2 | 3 | 4 | 5 | 6 | 7 | 8 | Ratio |
|---|---|---|---|---|---|---|---|---|
|   |   |   | C | A | A | C |   | 0.40 |
|   |   |   | T | C | A | C |   | 0.51 |
|   |   |   | T | A | A | C |   | 0.52 |
|   |   |   | C | C | A | C |   | 0.54 |
|   |   |   |   | A | A | C | C | 0.60 |
|   |   | G | T | A | A |   |   | 0.63 |
|   |   |   |   | A | A | C | T | 0.64 |
|   |   | G | T | C | A |   |   | 0.65 |
|   |   |   |   | C | A | C | T | 0.70 |
|   |   |   |   | C | A | C | C | 0.71 |
|   |   |   |   | A | A | C | A | 0.71 |
|   |   |   |   | C | A | C | G | 0.73 |
|   |   | G | C | A | A |   |   | 0.73 |
|   |   |   |   | A | C | C | A | 0.75 |
|   |   | G | C | A | C |   |   | 0.76 |
|   |   | A | T | C | A |   |   | 0.76 |
|   |   |   | T | C | A | T |   | 0.77 |
|   |   |   |   | A | C | C | G | 0.78 |

Fig. 2B

OMNI-67

| 1 | 2 | 3 | 4 | 5 | 6 | 7 | 8 | Ratio |
|---|---|---|---|---|---|---|---|-------|
|   |   | A | G | C | A |   |   | 0.04 |
|   |   | G | G | C | A |   |   | 0.05 |
|   |   |   | G | C | A | T |   | 0.06 |
|   |   | A | A | C | A |   |   | 0.07 |
|   |   |   | A | C | A | T |   | 0.07 |
| C | A | G | C |   |   |   |   | 0.08 |
|   |   |   | G | C | C | T |   | 0.08 |
|   |   | A | G | C | C |   |   | 0.08 |
|   |   | G | G | C | C |   |   | 0.09 |
|   |   | G | A | C | A |   |   | 0.09 |
|   |   |   | G | C | A | G |   | 0.10 |
|   |   |   | G | C | A | A |   | 0.10 |
| T | A | G | C |   |   |   |   | 0.12 |
|   |   |   | G | C | T | T |   | 0.13 |
|   |   | C | G | G | C |   |   | 0.14 |
|   |   | T | G | G | C |   |   | 0.15 |
|   |   | C | G | A | C |   |   | 0.17 |
|   |   | G | A | G | C |   |   | 0.20 |

| 1 | 2 | 3 | 4 | 5 | 6 | 7 | 8 | Ratio |
|---|---|---|---|---|---|---|---|-------|
|   |   | A | G | C | A |   |   | 0.05 |
|   |   |   | G | C | A | T |   | 0.06 |
|   |   | A | G | C | C |   |   | 0.07 |
|   |   | G | G | C | A |   |   | 0.07 |
|   |   |   | G | C | C | T |   | 0.08 |
|   |   |   | A | C | A | T |   | 0.08 |
|   |   | A | A | C | A |   |   | 0.08 |
|   |   | G | A | C | A |   |   | 0.08 |
| C | A | G | C |   |   |   |   | 0.09 |
|   |   | G | G | C | C |   |   | 0.10 |
| T | A | G | C |   |   |   |   | 0.12 |
|   |   |   | G | C | A | G |   | 0.13 |
|   |   |   | G | C | T | T |   | 0.15 |
|   |   | T | G | G | C |   |   | 0.15 |
|   |   |   | A | C | C | T |   | 0.16 |
|   |   | C | G | G | C |   |   | 0.16 |
|   |   | G | A | G | C |   |   | 0.17 |
|   |   | C | G | A | C |   |   | 0.18 |

OMNI-76 positions 1-7

| 1 | 2 | 3 | 4 | 5 | 6 | 7 | 8 | Ratio |
|---|---|---|---|---|---|---|---|---|
|   |   | G | T | A | T |   |   | 0.80 |
|   |   | G | G | C | T |   |   | 0.80 |
| A | G | G | T |   |   |   |   | 0.80 |
|   |   |   |   | A | T | G | A | 0.81 |
|   |   | G | G | G | G |   |   | 0.82 |
| G | G | G | A |   |   |   |   | 0.82 |
|   |   | G | G | A | T |   |   | 0.83 |
|   |   | G | C | C | T |   |   | 0.84 |
| A | G | G | G |   |   |   |   | 0.85 |
|   |   | G | G | A | T |   |   | 0.85 |
|   |   | C | T | T | A |   |   | 0.85 |
|   |   |   | T | T | G | G |   | 0.86 |
| T | G | G | A |   |   |   |   | 0.86 |
|   |   | G | C | T | G |   |   | 0.86 |
|   |   | T | C | T | C |   |   | 0.87 |
|   |   | C | T | T | G |   |   | 0.87 |
| T | G | C | G |   |   |   |   | 0.87 |
| C | C | A | A |   |   |   |   | 0.87 |

OMNI-79 positions 1-4 positions 1-4

| 1 | 2 | 3 | 4 | 5 | 6 | 7 | 8 | Ratio |
|---|---|---|---|---|---|---|---|-------|
|   | G | A | G | G |   |   |   | 0.03 |
|   | G | G | C | T |   |   |   | 0.04 |
| A | G | G | C |   |   |   |   | 0.04 |
|   | G | G | G | T |   |   |   | 0.04 |
| G | G | A | G |   |   |   |   | 0.04 |
| T | G | G | G |   |   |   |   | 0.04 |
|   | G | G | A | C |   |   |   | 0.04 |
| C | G | G | A |   |   |   |   | 0.04 |
|   | G | G | A | T |   |   |   | 0.05 |
| C | G | G | T |   |   |   |   | 0.05 |
|   | G | G | A | A |   |   |   | 0.05 |
|   | G | G | T | A |   |   |   | 0.05 |
|   | G | G | C | A |   |   |   | 0.19 |
|   | G | G | C | G |   |   |   | 0.22 |
|   | G | G | A | G |   |   |   | 0.26 |
|   | G | G | T | A |   |   |   | 0.29 |
|   | G | G | T | G |   |   |   | 0.30 |
|   | G | G | A | A |   |   |   | 0.32 |

| 1 | 2 | 3 | 4 | 5 | 6 | 7 | 8 | Ratio |
|---|---|---|---|---|---|---|---|-------|
| A | G | G | C |   |   |   |   | 0.05 |
|   | G | A | C | G |   |   |   | 0.05 |
| C | G | G | A |   |   |   |   | 0.05 |
|   | G | G | A | C |   |   |   | 0.05 |
| A | G | G | G |   |   |   |   | 0.05 |
|   | G | G | T | C |   |   |   | 0.05 |
| G | G | A | C |   |   |   |   | 0.05 |
|   | G | G | A | A |   |   |   | 0.05 |
| A | G | G | A |   |   |   |   | 0.06 |
|   | G | G | C | T |   |   |   | 0.06 |
| C | G | G | C |   |   |   |   | 0.06 |
|   | G | G | G | A |   |   |   | 0.06 |
|   | G | G | C | A |   |   |   | 0.33 |
|   | G | G | C | G |   |   |   | 0.34 |
|   | G | G | A | G |   |   |   | 0.35 |
|   | G | G | T | G |   |   |   | 0.37 |
|   | G | G | T | A |   |   |   | 0.37 |
|   | G | G | A | A |   |   |   | 0.40 |

OMNI-80

| V1 | V2 |
|---|---|
| NNRGAY | NNRGAY |
| positions 1-8 | positions 1-8 |

| 1 | 2 | 3 | 4 | 5 | 6 | 7 | 8 | Ratio |
|---|---|---|---|---|---|---|---|---|
|   |   |   | G | G | A | C |   | 0.34 |
| A | G | G | A |   |   |   |   | 0.54 |
|   |   | A | G | A | C |   |   | 0.56 |
| G | G | G | A |   |   |   |   | 0.62 |
|   |   | G | G | A | T |   |   | 0.64 |
|   |   |   | G | A | C | T |   | 0.68 |
| C | G | G | A |   |   |   |   | 0.68 |
|   |   |   | G | A | C | A |   | 0.71 |
|   |   |   | G | A | C | C |   | 0.77 |
| G | A | G | G |   |   |   |   | 0.77 |
|   |   |   | T | C | G | C |   | 0.82 |
|   |   |   | A | C | T | G |   | 0.82 |
|   |   |   | G | A | T | T |   | 0.84 |
| A | A | G | G |   |   |   |   | 0.84 |
|   |   |   | G | A | C | G |   | 0.84 |
|   |   |   | G | G | A | A |   | 0.85 |
|   |   |   | T | A | C | T |   | 0.86 |

| 1 | 2 | 3 | 4 | 5 | 6 | 7 | 8 | Ratio |
|---|---|---|---|---|---|---|---|---|
|   |   |   | G | G | A | C |   | 0.44 |
|   |   | A | G | A | C |   |   | 0.59 |
|   | A | G | G | A |   |   |   | 0.60 |
|   |   |   | G | G | A | T |   | 0.68 |
|   |   |   | G | A | C | T |   | 0.73 |
| G | G | G | A |   |   |   |   | 0.74 |
|   |   |   | G | A | C | A |   | 0.76 |
| G | G | G | G |   |   |   |   | 0.76 |
|   | C | G | G | A |   |   |   | 0.76 |
| G | A | G | G |   |   |   |   | 0.78 |
| C | C | A | A |   |   |   |   | 0.79 |
|   |   |   | G | A | C | C |   | 0.79 |
| T | C | T | C |   |   |   |   | 0.80 |
|   |   |   | C | A | A | G |   | 0.80 |
| G | T | G | G |   |   |   |   | 0.81 |
| T | C | C | G |   |   |   |   | 0.81 |
|   |   | G | G | C | C |   |   | 0.81 |
|   |   |   | A | C | A | T |   | 0.82 |

Fig. 2F

OMNI-81

V1 positions 1-7

| 1 | 2 | 3 | 4 | 5 | 6 | 7 | 8 | Ratio |
|---|---|---|---|---|---|---|---|---|
|   |   | A | A | A | A |   |   | 0.07 |
|   |   | G | A | A | A |   |   | 0.08 |
|   |   | A | G | A | A |   |   | 0.08 |
|   |   | G | G | A | A |   |   | 0.14 |
|   | C | A | A | A |   |   |   | 0.29 |
|   |   |   | A | A | A | G |   | 0.34 |
|   | C | A | G | A |   |   |   | 0.36 |
|   | C | G | A | A |   |   |   | 0.37 |
|   |   |   | A | A | A | A |   | 0.38 |
|   |   |   | G | A | A | G |   | 0.42 |
| G | G | A | A |   |   |   |   | 0.43 |
|   |   |   | G | A | A | A |   | 0.43 |
|   |   | C | A | A | A |   |   | 0.45 |
|   |   |   | G | A | A | T |   | 0.47 |
|   |   |   | A | A | A | T |   | 0.48 |
| G | A | A | A |   |   |   |   | 0.48 |
| G | A | G | A |   |   |   |   | 0.48 |
|   |   |   | A | A | A | G |   | 0.51 |

V2 positions 1-7

| 1 | 2 | 3 | 4 | 5 | 6 | 7 | 8 | Ratio |
|---|---|---|---|---|---|---|---|---|
|   |   | G | A | A | A |   |   | 0.05 |
|   |   | A | A | A | A |   |   | 0.07 |
|   |   | A | G | A | A |   |   | 0.07 |
|   |   | G | G | A | A |   |   | 0.12 |
|   | C | A | A | A |   |   |   | 0.25 |
|   | C | A | G | A |   |   |   | 0.30 |
|   | C | G | A | A |   |   |   | 0.32 |
|   |   |   | A | A | A | A |   | 0.33 |
|   | G | G | A | A |   |   |   | 0.34 |
|   |   |   | A | A | A | G |   | 0.38 |
|   | G | A | A | A |   |   |   | 0.38 |
|   | C | A | A | A |   |   |   | 0.40 |
|   |   |   | G | A | A | G |   | 0.43 |
| T | A | A | A |   |   |   |   | 0.43 |
|   |   |   | A | A | A | T |   | 0.43 |
|   | A | A | A | G |   |   |   | 0.43 |
|   |   | G | A | A | A |   |   | 0.47 |
|   |   |   | A | A | A | C |   | 0.50 |

OMNI-82

| Average OMNI79 V1 | | | | | | |
|---|---|---|---|---|---|---|
| | P1 | P2 | P3 | P4 | P5 | P6 |
| A | 26.17% | 14.66% | 16.70% | 27.83% | 38.23% | 40.59% |
| T | 21.00% | 12.77% | 16.58% | 25.92% | 18.24% | 21.24% |
| C | 22.88% | 14.31% | 11.81% | 20.08% | 23.19% | 22.06% |
| G | 29.95% | 58.26% | 54.90% | 26.17% | 20.34% | 16.11% |
| | | | | | | |

| Average OMNI79 V2 | | | | | | |
|---|---|---|---|---|---|---|
| | P1 | P2 | P3 | P4 | P5 | P6 |
| A | 35.21% | 14.08% | 17.70% | 27.11% | 39.56% | 24.42% |
| T | 19.90% | 10.21% | 14.47% | 25.47% | 14.99% | 29.38% |
| C | 18.44% | 8.81% | 10.27% | 23.89% | 15.68% | 26.14% |
| G | 26.44% | 66.90% | 57.56% | 23.54% | 29.76% | 20.06% |
| | | | | | | |

*OMNI-79 gRNA molecule*

*SpSpCAP1 gRNA molecule*

*SpSaNXO2 gRNA molecule*

SEQUENCE LISTING

```
<160> NUMBER OF SEQ ID NOS: 243

<210> SEQ ID NO 1
<211> LENGTH: 1049
<212> TYPE: PRT
<213> ORGANISM: Comamonadaceae bacterium NML00-0135

<400> SEQUENCE: 1

Met Asn Val Trp Lys Gly Thr Gly Phe Val Ser Arg Lys Arg Asn Ile
1               5                   10                  15

Ile Arg Tyr Arg Leu Ala Leu Asp Leu Gly Ser Thr Ser Leu Gly Trp
            20                  25                  30

Ala Ile Leu Arg Leu Asn Ala Asp Asn Gln Pro Thr Ala Ile Leu Lys
        35                  40                  45

Ala Gly Val Arg Ile Phe Ser Asp Gly Arg Asn Pro Lys Asp Gly Ser
    50                  55                  60

Ser Leu Ala Val Thr Arg Arg Ala Ala Arg Ala Met Arg Arg Arg Arg
65                  70                  75                  80

Asp Arg Leu Leu Lys Arg Lys Ala Arg Met Leu Asp Lys Leu Ile Ala
                85                  90                  95

His Gly Phe Phe Pro Gln Asp Glu Ala Ala Arg Lys Ala Leu Glu Val
            100                 105                 110

Leu Asn Pro Tyr Gln Leu Arg Ala Glu Gly Leu Gln Arg Ala Leu Met
        115                 120                 125

Pro Gly Glu Phe Ala Arg Ala Met Phe His Ile Asn Gln Arg Arg Gly
    130                 135                 140

Phe Lys Ser Asn Arg Lys Thr Asp Lys Lys Asp Ser Asp Ser Gly Ala
145                 150                 155                 160

Leu Lys Thr Ala Ile Ser Gln Leu Arg Gln Gln Leu Gln Asn Glu Asn
```

-continued

```
                165                 170                 175
Ala Arg Thr Val Gly Glu Trp Leu Trp Gln Arg Leu Gln Ala Gly Gln
            180                 185                 190

Gly Thr Arg Ala Arg Tyr Arg Glu Thr Arg Ile Ala Thr Asp Thr Gly
            195                 200                 205

Lys Gly Lys Ile Asp Lys Ser Tyr Asp Leu Tyr Ile Asp Arg Gln Met
            210                 215                 220

Val Ala Asp Glu Phe Asp Ala Leu Trp Ala Val Gln Ala Ala Phe Asn
225                 230                 235                 240

Pro Val Leu Phe Asn Glu Gln Ala Arg Ala Glu Leu Arg Asp Thr Leu
                245                 250                 255

Leu His Gln Arg Pro Leu Arg Pro Ala Lys Pro Gly Arg Cys Thr Leu
                260                 265                 270

Leu Pro Glu Glu Glu Arg Ala Pro Leu Ala Leu Pro Ser Thr Gln Arg
                275                 280                 285

Phe Arg Ile Leu Gln Glu Val Asn His Leu Arg Ile Leu His Pro Asp
                290                 295                 300

Leu Arg Glu Glu Ala Leu Thr Leu Asp Arg Arg Asn Ala Ile Val Ala
305                 310                 315                 320

Leu Leu Glu Asn Arg Gly Lys Val Thr Phe Gln Ala Met Arg Arg Thr
                325                 330                 335

Leu Asn Leu Gly Asp Ala Val Gln Phe Asn Leu Glu Asp Ala Lys Arg
                340                 345                 350

Arg Glu Leu Lys Gly Asn Ala Thr Thr Ala Ala Leu Ser Lys Lys Glu
                355                 360                 365

Leu Phe Gly Ala Ala Trp His Asp Phe Asp Glu Ala Leu Gln Asp Asp
                370                 375                 380

Ile Val Leu Arg Leu Val Thr Glu Glu Ser Glu Ala Glu Leu Val Gln
385                 390                 395                 400

Trp Leu Ile Glu Asn Thr Gly Val Asp Glu Ala Arg Ala Thr Ala Ile
                405                 410                 415

Ala Asn Thr Gly Leu Pro Glu Gly Tyr Gly Ser Leu Ser Arg Lys Ala
                420                 425                 430

Leu Ala Arg Ile Val Pro Ala Leu Arg Ala Glu Val Ile Thr Tyr Asp
                435                 440                 445

Lys Ala Val Gln Ala Ala Gly Phe Ala His His Ser Asp Leu Arg Phe
                450                 455                 460

Ser Phe Glu Tyr Asp Ser Ala Asp Val Glu Gln Val Gly Glu Arg Ile
465                 470                 475                 480

Asp Lys Thr Thr Gly Glu Ile Leu Pro Val Ser Ala Phe Lys Gln Leu
                485                 490                 495

Pro Tyr Tyr Gly Lys Ala Leu Gln Arg His Val Ala Phe Gly Ser Gly
                500                 505                 510

Asn Pro Gln Asp Pro Glu Glu Lys Arg Tyr Gly Lys Ile Ala Asn Pro
                515                 520                 525

Thr Val His Ile Gly Leu Asn Gln Val Arg Val Val Asn Asp Leu
                530                 535                 540

Ile Arg Arg Tyr Gly Arg Pro Thr Glu Ile Val Val Glu Leu Ala Arg
545                 550                 555                 560

Glu Leu Lys Gln Ser Arg Glu Gln Lys Leu Glu Ala Gln Arg Lys Gln
                565                 570                 575

Ala Asp Asn Gln Lys Arg Asn Ala Arg Ile Arg Ala Glu Ile Ala Pro
                580                 585                 590
```

```
Ile Leu Gly Ile Ser Glu Glu Arg Val Lys His Ala Asp Ile Gln Lys
        595                 600                 605
Trp Ile Leu Trp Glu Glu Leu Ser Phe Asp Val Ala Asp Arg Arg Cys
        610                 615                 620
Pro Tyr Ser Gly Val Gln Ile Ser Ala Arg Met Leu Leu Ser Asp Glu
625                 630                 635                 640
Val Glu Ile Glu His Ile Leu Pro Phe Ser Gln Thr Leu Asp Asp Ser
                    645                 650                 655
Leu Asn Asn Lys Thr Val Ser Met Arg Gln Ala Asn Arg Ile Lys Gly
                660                 665                 670
Asn Arg Thr Pro Trp Gln Ala Arg Gln Asp Phe Glu Ala Gln Gly Trp
                675                 680                 685
Pro Tyr Glu Gly Met Gln Gln Arg Ala Glu Arg Met Pro Arg Ala Lys
                690                 695                 700
Arg Tyr Arg Phe Ala Pro Asp Gly Tyr Glu Arg Trp Leu Gly Glu Asp
705                 710                 715                 720
Gln Gly Phe Leu Ala Arg Ala Leu Asn Asp Thr Arg Tyr Leu Ser Arg
                725                 730                 735
Ile Ala Arg Asp Tyr Leu Thr Leu Val Cys Pro Gly Gly Val Arg Val
                740                 745                 750
Ile Pro Gly Arg Met Thr Ala Leu Leu Arg Ala Lys Phe Gly Leu Asn
                755                 760                 765
Gly Val Leu Ser Leu Ser Gly Glu Lys Asn Arg Asp Asp His Arg His
                770                 775                 780
His Ala Val Asp Ala Cys Val Ile Gly Val Thr Asp Gln Gly Leu Leu
785                 790                 795                 800
Gln Arg Phe Ala Glu Ala Ser Ala Met Ala Arg Gln Gln Gly Leu Glu
                805                 810                 815
Lys Leu Val Glu Thr Met Pro Leu Pro Trp Glu Thr Tyr Pro Ala His
                820                 825                 830
Val Gln Arg Ala Val Gln Asn Ile Trp Val Ser His Arg Pro Asp His
                835                 840                 845
Gly His Glu Gly Gly Met Met Glu Glu Thr Ser Tyr Gly Ile Ser Lys
                850                 855                 860
Asp Gly Arg Ile Lys Gln Arg Arg Lys Ala Asp Gly Ser Gln Gly Arg
865                 870                 875                 880
Glu Ile Ser Asn Leu Ile Arg Ile Ser Glu Pro Ser Gln Pro Glu Arg
                885                 890                 895
His Gly Val Asp Ala Glu Gly Gln Pro Leu Pro Tyr Lys Gly Tyr Val
                900                 905                 910
Gly Gly Ser Asn Tyr Cys Ile Glu Ile Thr Arg Asn Asp Lys Gly Lys
                915                 920                 925
Trp Glu Gly Glu Val Ile Ser Thr Phe Arg Ala Tyr Gln Ile Val Arg
                930                 935                 940
Lys His Gly Val Ala Arg Leu Arg His Pro Glu Met Ala Gln Asn Gly
945                 950                 955                 960
Lys Ala Leu Val Met Arg Leu Met Ile Asp Asp Cys Val Arg Leu Glu
                965                 970                 975
Leu Asp Gly Arg Glu Glu Thr Met Arg Val Val Ile Pro Arg Asn
                980                 985                 990
Gly Gln Val Phe Met Ala Pro Leu His Glu Ala Asn Val Asp Ala Arg
                995                 1000                1005
```

-continued

```
Asn Arg Asp Lys Asn Asp Pro Phe Ser Tyr Ile Ser Lys Met Ala
    1010                1015                1020

Gly Ser Phe Leu Lys Ala Lys Ala Arg His Ile Thr Ile Ser Pro
    1025                1030                1035

Ile Gly Glu Leu His Asp Pro Gly Phe Lys Gly
    1040                1045

<210> SEQ ID NO 2
<211> LENGTH: 1021
<212> TYPE: PRT
<213> ORGANISM: Demequina sediminicola

<400> SEQUENCE: 2

Met Thr Gly Thr Asp Ala Thr Ala His Ser His Thr Pro Tyr Arg Leu
1               5                   10                  15

Gly Leu Asp Val Gly Thr Gly Ser Leu Gly Trp Ala Val Val Glu Leu
            20                  25                  30

Asp Thr Asp Gly Asn Pro Val Arg Ile Val Arg Thr Gly Ser Arg Ile
        35                  40                  45

Tyr Gly Ser Gly Arg Lys Pro Lys Asp Phe Ser Ser Leu Ala Ala Asp
    50                  55                  60

Arg Arg Ala Ala Arg Gln Met Arg Lys Gln Arg Asp Arg Tyr Leu Gln
65                  70                  75                  80

Arg Arg Thr Arg Leu Met His Glu Leu Val Ala Ala Gly Leu Met Pro
                85                  90                  95

Glu Ala Glu Val Glu Arg Gln Lys Leu Lys Asp Leu Asn Pro Tyr Leu
            100                 105                 110

Leu Arg Ala Arg Gly Val Lys Glu Glu Leu Thr Ala His Glu Leu Gly
        115                 120                 125

Arg Ala Leu Phe His Leu Gln Gln Arg Arg Gly Phe Lys Ser Asn Arg
    130                 135                 140

Lys Thr Asp Arg Lys Asp Asp Arg Ser Ala Met Lys Ser Ala Ile
145                 150                 155                 160

Ala Ser Leu Gln Ser Asp Leu Gly Asp Asp Thr Leu Gly Thr Tyr Met
                165                 170                 175

Trp Lys Arg Ile Gln Asn Gly Glu Ser Val Arg Ser Arg Pro Arg Lys
            180                 185                 190

Val Gly Ser Lys Asn Glu Tyr Asp Phe Tyr Val Asn Arg Ala Met Val
        195                 200                 205

Glu Asp Glu Phe Asn Gln Leu Trp Asp Tyr Gln Ser Gln Ser His Gly
    210                 215                 220

Asp Leu Leu Thr Asp Glu Ala Arg Ile Arg Val His Asp Ala Ile Phe
225                 230                 235                 240

Ser Gln Arg Pro Leu Lys Pro Val Asp Pro Gly Arg Cys Thr Phe Glu
                245                 250                 255

Thr Asp Gln Arg Arg Ala Pro Lys Ala Leu Pro Ser Ser Gln Leu Phe
            260                 265                 270

Arg Ile Tyr Gln Glu Leu Asn Ala Ile Arg Val Ile Asp Pro Phe Ser
        275                 280                 285

Ser Asp Gln Ala Asp Arg Pro Leu Thr Arg Gln Glu Arg Asp Ala Gly
    290                 295                 300

Ala Ser Phe Leu Leu Gly Arg Val Lys Ala Thr Phe Pro Gln Leu Lys
305                 310                 315                 320

Lys Ala Met Phe Gly Pro Thr Lys Leu Gln Leu Ser Leu Glu Tyr Gly
                325                 330                 335
```

```
Glu Arg Lys Asn Ile Leu Gly Asp Val Val Gly Ser Glu Leu Arg Lys
                340                 345                 350

Ala Gln His Ile Gly Pro Asp Trp Glu Thr Tyr Asp Leu Ala Thr Gln
            355                 360                 365

Asp Leu Ile Val Thr Ile Leu Leu Glu Ala Asp Thr Asp Asp Glu Val
        370                 375                 380

Ile Glu Arg Leu Gln Ala Glu Ser Ser Leu Ser Leu Asp Gln Val His
385                 390                 395                 400

Gly Ala Leu Glu Ala Pro Leu Pro Asp Asp Tyr Leu Arg Leu Ser His
                405                 410                 415

Arg Ala Ile Gly Lys Ile Leu Pro His Leu Lys Asp Glu Trp Asn Glu
            420                 425                 430

Glu Gly Asn Ala Pro Val Met Tyr Asp Ala Ala Val Arg Ala Ala Gly
        435                 440                 445

Tyr Gln Ser His Ser Glu Phe His Ser Gly Val Leu Glu Asp Thr Leu
    450                 455                 460

Pro Tyr Tyr Gly Lys Val Leu Lys Arg Tyr Thr Gln Glu Val Ser Gly
465                 470                 475                 480

Ser Ser Gln Ala Ala Thr Asn Pro Asp Glu Trp Glu Phe Gly Lys Ile
                485                 490                 495

Ala Asn Pro Thr Val His Ile Gly Leu Asn Gln Ile Arg Thr Val Val
            500                 505                 510

Asn Ser Leu Ile Asp Arg Tyr Gly Leu Pro Thr Gln Ile His Val Glu
        515                 520                 525

Val Ala Arg Asp Leu Gly Gln Ser Ala Glu Gly Arg Glu Ala Ala
    530                 535                 540

Ser Asn Arg Ala Lys Asn Glu Arg Ala Asn Glu Ala Leu Asn Ala Arg
545                 550                 555                 560

Leu Thr Glu Leu Gly Gln Arg Thr Asn Phe Ala Asn Arg Glu Arg Leu
                565                 570                 575

Arg Leu Tyr Asp Glu Ile Ser Val Leu Asn His Arg Cys Val Leu Thr
            580                 585                 590

Gly Ile Pro Ile Glu Met Ser Arg Leu Phe Thr Asn Asp Tyr Gln Val
        595                 600                 605

Asp His Ile Leu Pro Phe Ser Arg Thr Leu Asp Asp Ser Arg Gly Asn
    610                 615                 620

Lys Ile Leu Val His His Thr Ala Asn Gln Phe Lys Gly Ala Arg Ser
625                 630                 635                 640

Pro Phe Glu Ala Tyr Ser Glu Thr Ala Asp Trp Asp His Ile Leu Gln
                645                 650                 655

Arg Ala Ser Asp Ala Phe Gly Ala Thr Ser Pro Lys Phe Lys Arg Phe
            660                 665                 670

Ser Ala Asp Ala Met Asp Arg Tyr Ser Asn Gly Glu Gln Asp Phe Ile
        675                 680                 685

Ala Arg Gln Leu Asn Asp Thr Ser Tyr Leu Ala Arg Val Thr Arg Glu
    690                 695                 700

Tyr Leu Gly Ser Ile Val Asp Pro Asp Arg Ile Leu Ala Thr Pro Gly
705                 710                 715                 720

Arg Leu Thr Ser Leu Leu Arg His His Trp Gly Leu Asn Gly Leu Leu
                725                 730                 735

Ser Asp Ala Ala Glu Lys Asn Arg Ser Asp His Arg His His Ala Ile
            740                 745                 750
```

```
Asp Ala Leu Val Val Ala Leu Ser Glu Arg Val Thr Leu Lys Ala Val
            755                 760                 765

Thr Asp Ala Asn Arg Arg Ala Gly Asp Gln Gly Ile Glu Arg Leu Leu
        770                 775                 780

Val Asp Leu Pro Gln Pro Trp Glu Gly Phe Ala Asp His Ala Arg Glu
785                 790                 795                 800

Ser Val Asp Arg Ile Val Val Ser His Lys Pro Asp His Asn Glu Lys
                805                 810                 815

Gly Gln Leu His Glu Thr Ala Tyr Gly Val Leu Glu Gly Pro Asp
            820                 825                 830

Lys Lys Gly Arg Phe Leu Thr Arg Lys Arg Ile Thr Asp Pro Ala Lys
        835                 840                 845

Gly Val Val Gly Ser Trp Glu Gln Pro Lys Trp Arg Asp Val Ile Pro
850                 855                 860

Leu Tyr Arg Arg Gly Glu Gly Pro Asp Ser Thr Leu Pro Tyr Lys Ala
865                 870                 875                 880

Tyr Ile Gly Gly Ser Asn Tyr Cys Ile Glu Ile Val Arg Thr Ala Lys
                885                 890                 895

Gly Lys Trp Ala Gly Glu Val Val Ser Thr His Thr Ala Asn Thr Ala
            900                 905                 910

Glu Tyr Arg Ala Phe Met Ala Glu Pro Gly Ala Tyr Arg Ala Gln Ser
        915                 920                 925

Tyr Ala Gly Gly Asp Leu Val Met Arg Leu Ile Ala Asn Asp Thr Ile
930                 935                 940

Ala Ile Glu Val Gly Asp Ala Gly Arg Gln Ile Met Arg Leu Cys Gln
945                 950                 955                 960

Leu Glu Thr Val Gly Ala Met Tyr Phe Ala Asn Val Arg Glu Gly Asn
                965                 970                 975

Val Ala Ala Arg Ser Arg Ala Arg Asp Asn Asp Phe Ser Leu Leu Lys
            980                 985                 990

Lys Ala Ala Ser Thr Leu Gln Pro Leu Lys Ala Arg Arg Val Phe Val
        995                 1000                1005

Asp Pro Ile Gly Arg Val Phe Asp Pro Asp Phe Lys Glu
    1010                1015                1020

<210> SEQ ID NO 3
<211> LENGTH: 1046
<212> TYPE: PRT
<213> ORGANISM: Fuerstia marisgermanicae

<400> SEQUENCE: 3

Met Asn Tyr Ile Leu Gly Leu Asp Leu Gly Ser Ala Ser Leu Gly Trp
1               5                   10                  15

Ala Val Leu Glu Cys Thr Glu Val Asp Gly Ser Leu Gln Pro Thr Arg
            20                  25                  30

Ile Glu Arg Thr Gly Val Arg Ile Phe Glu Ala Gly Val Glu Gly Asp
        35                  40                  45

Ile Glu Gln Gly Arg Asp Ala Ser Arg Ala Lys Arg Arg Glu Ala
    50                  55                  60

Arg Gln Pro Arg Arg Gln Asn Trp Arg Thr Gln Gln Arg Lys Arg Lys
65                  70                  75                  80

Leu Phe Arg Leu Leu Gln Gln His Gly Leu Leu Pro Ala Ser Glu Lys
                85                  90                  95

Asp Asp Ala Ile Ser Arg Lys Ala Val Phe Asp Gln Leu Asp Lys Glu
            100                 105                 110
```

-continued

Leu Thr Glu Lys His Ile Thr Glu Gly Asp His Thr Ala His Gln His
            115                 120                 125

Leu Pro Tyr Leu Leu Arg Met Leu Ala Ser Gly Ala Lys Val Lys Pro
    130                 135                 140

Phe Glu Leu Gly Arg Ala Ile Tyr Ser Leu Ala Gln Arg Arg Gly Phe
145                 150                 155                 160

Leu Ser Asn Arg Lys Ala Asp Thr Asp Glu Lys Glu Asp Gly Val Val
                165                 170                 175

Lys Ala Ser Ile Ser Glu Leu Gly Gly Gln Ile Ala Gly Arg Thr Ile
            180                 185                 190

Ala Gln Thr Phe Val Glu Asp Ile Ser Pro Asp His Glu Asp Pro Gly
            195                 200                 205

Arg Gln Arg Ile Arg Gln Arg Tyr Thr Ala Arg Glu Met Phe His Asp
    210                 215                 220

Glu Phe Asn Arg Ile Arg Lys Gln Gln Pro His Phe Asp Leu Ala
225                 230                 235                 240

Asp Asn Asp Trp Asp Thr Val Tyr Lys Thr Ile Phe Phe Gln Arg Pro
                245                 250                 255

Leu Lys Ser Gln Arg His Arg Ile Gly Arg Cys Glu Ile Asp Gly Gly
            260                 265                 270

Gln Arg Cys Leu Asp Ala Leu Asp Val Phe Gln Gln Phe Arg Ile Trp
    275                 280                 285

His Ala Val Gln Asn Leu Arg Leu Ala Asp Ala Tyr Ser Leu Gly Arg
290                 295                 300

Asp Gly Arg Leu Thr Leu Glu Glu Gln Lys Ile Val Asp Ala Leu
305                 310                 315                 320

Gln Thr Gln Ala Thr Met Thr Trp Gly Lys Val Val Thr Leu Leu Gly
            325                 330                 335

Leu Lys Arg Gly Thr Lys Phe Thr Ile Gln Glu Trp Asn Thr Lys Gly
            340                 345                 350

Leu Thr Gly His Arg Thr Asn Ser Ala Met Met His Val Phe Gly Asp
    355                 360                 365

Glu Trp Leu Asp Arg Pro Leu Glu Glu Arg Asp Ala Ile Thr Lys Glu
    370                 375                 380

Val Val Tyr Phe Arg Lys Pro Ser Ala Met Arg Lys Arg Gly Gln Glu
385                 390                 395                 400

Ala Trp Gly Leu Ser Glu Gln Ala Ala Leu Leu Pro Ser Thr Arg
                405                 410                 415

Leu Glu Glu Ala His Ala Arg His Ser Ala Ala Thr Leu Ala Ile Phe
            420                 425                 430

Val Glu Arg Met Ser Arg Gly Glu Asp Tyr Ser Thr Ile Arg Lys Asp
    435                 440                 445

Ile Thr Gly Lys Asp Asp Ser Glu Pro Leu Asp Gln Leu Pro Pro Leu
450                 455                 460

Ser Lys Ala Gly Leu Asp Ile Thr Asn Pro Ala Val Ile Arg Gly Leu
465                 470                 475                 480

Thr Glu Leu Arg Lys Val Val Asn Glu Leu Val Arg Gln Tyr Gly Lys
            485                 490                 495

Pro Ile Gly Ile Arg Ile Glu Leu Ser Arg Ser Leu Lys Asn Ser Arg
            500                 505                 510

Asp Lys Arg Ile Lys Leu His Lys Asp Asn Glu Asp Arg Arg Lys Arg
            515                 520                 525

```
Arg Glu Lys Ala Ile Glu Gly Ile Leu Lys Gln Ile Pro Gly Arg Tyr
            530                 535                 540

Ser Gly Asn Asp Ile Glu Lys Trp Leu Ala Glu Glu Cys Gly Trp
545                 550                 555                 560

His Cys Pro Tyr Thr Gly Arg Pro Ile Ser Pro Ser Thr Leu Leu Gly
                565                 570                 575

Ser Gln Pro Gln Phe Asp Ile Glu His Ile Phe Pro Arg Arg Tyr Leu
            580                 585                 590

Asp Asn Ser Phe Ser Asn Lys Thr Leu Cys Tyr His Glu Phe Asn Arg
            595                 600                 605

Asn Val Lys Lys Asn Gln Thr Ala Phe Asp Ala Cys Ser Gly Leu Asp
            610                 615                 620

Ser Trp Asp Glu Ile Leu Gln Arg Val Asn Asn Phe Asp Gly Pro Val
625                 630                 635                 640

Ala Ala Leu Lys Arg Lys Arg Phe Leu Thr Ala Ala Lys Glu Ile Pro
                645                 650                 655

Asp Gly Phe Thr Ser Lys His Leu Asn Asp Asn Arg Tyr Asn Ala Val
                660                 665                 670

Val Ala Lys Lys Tyr Val Ala Met Leu Tyr Gly Gly Leu Ser Asp Ala
            675                 680                 685

Asp Gly Ser Gln Arg Val Phe Ala Val Thr Gly Gly His Thr Ala Leu
            690                 695                 700

Leu Arg Arg Glu Trp Gly Leu Asn Ser Ile Leu Ser Gly Thr Glu Glu
705                 710                 715                 720

Lys Thr Arg Asp Asp His Arg His Ala Val Asp Ala Val Val Ile
                725                 730                 735

Ala Leu Thr Asp Pro Ala Arg Ile Gln Ala Leu Val Asn Ala Ala Glu
                740                 745                 750

Leu Ala Glu Lys Lys Ala Ser Arg Arg Phe Tyr Glu Ala Val Gln Asp
            755                 760                 765

Pro Trp Pro Lys Phe Ser Ser Lys Val Ala Asp Ser Ile Asn Glu Ile
770                 775                 780

Val Val Ser His Arg Pro Thr Arg Thr Leu Pro Gly Ala Leu His Ala
785                 790                 795                 800

Glu Ser Ile Tyr Ser Lys Pro His Ile Asp Lys Asp Gly Asn Thr Asn
                805                 810                 815

His Arg Ile Arg Lys His Ile Thr Lys Leu Ser Ala Thr Glu Leu Lys
                820                 825                 830

Lys Asp Lys Ile Val Asp Pro Ala Ile Arg Asp Leu Val Lys Ala Lys
            835                 840                 845

Leu Lys Glu Leu Gly Glu Ser Asn Pro Ala Lys Ala Phe Ala Glu Glu
850                 855                 860

Lys Asn His Pro Phe Leu Thr Ala Lys Asp Gly Arg Lys Ile Pro Ile
865                 870                 875                 880

His Lys Val Arg Val Phe Ala Asp Lys Lys Pro Arg Ala Ile Ala Lys
                885                 890                 895

Asn Glu Arg Gln Arg Tyr Val Ala Ser Gly Lys Asp Ser Asn Phe Ala
            900                 905                 910

Ser Met Ile Tyr Ala Val Asp Lys Asp Gly His Glu Ile Lys Trp
            915                 920                 925

Glu His Lys Val Ile Thr Arg Leu Glu Ala His Glu Arg Lys Thr Arg
930                 935                 940

Asn Arg Thr Val Asn Gly Glu Lys Val Leu Leu Pro Asp Pro Thr Asp
```

```
                945                 950                 955                 960
       Phe Asn Asp Asp Lys Lys Arg Val Phe Lys Phe Ala Leu Cys Lys Asn
                         965                 970                 975

Asp Thr Val Met Leu Glu Gly Pro Asp Gly Asp Val Ile Cys Arg
                     980                 985                 990

Ile Gln Lys Ile Ser Gln Ala Glu  Ile Gln Leu Cys Pro Leu Ala Thr
                     995                 1000                1005

Pro Ser Val Gln Gly Lys Ala Arg Ser Lys Trp Asn  Gln Ile Gln
               1010                1015                1020

Ser Ile Asp Asn Leu Arg Lys Trp Asn Leu Arg Thr Val Leu Ile
               1025                1030                1035

Ser Pro Thr Gly Ile Glu His Arg
               1040                1045

<210> SEQ ID NO 4
<211> LENGTH: 1036
<212> TYPE: PRT
<213> ORGANISM: Nitrosomonas sp. Nm33

<400> SEQUENCE: 4

Met Leu His Lys Met Arg Tyr Arg Leu Ala Leu Asp Leu Gly Ser Thr
1               5                   10                  15

Ser Leu Gly Trp Ala Met Ile Arg Leu Asp Ala Asn Gln Arg Pro Cys
            20                  25                  30

Ala Val Ile Lys Ala Gly Val Arg Ile Phe Ser Asn Gly Arg Asn Pro
        35                  40                  45

Lys Asp Gly Ser Ser Leu Ala Val Thr Arg Arg Glu Ala Arg Ala Met
50                  55                  60

Arg Arg Arg Arg Asp Arg Leu Leu Lys Arg Lys Ala Arg Met Met Arg
65                  70                  75                  80

Thr Leu Ile Glu Tyr Gly Phe Phe Pro Ala Glu Glu Ala Gln Arg Lys
            85                  90                  95

Ala Leu Glu Thr Leu Asn Pro Tyr Lys Leu Arg Ala Asp Gly Leu Asp
            100                 105                 110

Lys Ala Leu Thr Pro Ala Glu Phe Gly Arg Val Leu Phe His Ile Asn
        115                 120                 125

Gln Arg Arg Gly Phe Lys Ser Asn Arg Lys Thr Asp Lys Lys Asp Thr
    130                 135                 140

Asp Ser Gly Ala Leu Lys Thr Ala Ile Ser Lys Leu Arg Glu Ile Leu
145                 150                 155                 160

Lys Thr Glu Asn Cys Arg Thr Val Gly Glu Trp Leu His Lys Arg Asn
                165                 170                 175

Gln Ala Gly Gln Thr Val Arg Ala Arg Tyr Arg Gln Asp Lys Thr Ile
            180                 185                 190

Lys Asp Asp Gly Lys Ala Lys Ile Asp Lys Tyr Tyr Asp Leu Tyr Ile
        195                 200                 205

Asp Arg Ala Met Ile Glu His Glu Phe Asn Glu Leu Trp Arg Lys Gln
    210                 215                 220

Ala Glu Phe Asn Pro Ala Leu Phe Ser Ser Ala Ala Tyr Thr Asp Leu
225                 230                 235                 240

Lys Asp Val Leu Leu Tyr Gln Arg Pro Leu Lys Pro Val Lys Pro Gly
                245                 250                 255

Arg Cys Thr Phe Met Ser Asp Glu Glu Arg Ala Pro Leu Ala Leu Pro
            260                 265                 270
```

```
Ser Thr Gln Arg Phe Arg Met Tyr Gln Glu Val Asn Asn Leu Arg Ile
            275                 280                 285

Leu Arg Glu Gly Leu Lys Glu Pro Leu Thr Leu Gln Gln Arg Asp
    290                 295                 300

Asp Leu Ile Val Val Leu Glu Arg Asn Asn Lys Arg Thr Phe Thr Gln
305                 310                 315                 320

Ile Lys Lys Leu Leu Gly Val Gly Ala Val Gln Phe Asn Phe Glu
                325                 330                 335

Asp Pro Lys Arg Glu Glu Leu Lys Gly Asn Thr Thr Asn Ala Ile Leu
                340                 345                 350

Gly Lys Lys Glu His Phe Gly Glu Ala Trp Ile Ala Phe Asp Glu Ala
    355                 360                 365

Lys Gln Asp Ala Ile Val Met Gln Leu Ile Lys Glu Asn Glu Ala
    370                 375                 380

Lys Leu Ile Gln Trp Leu Gln Asp Glu Thr Gly Ile Glu Glu Glu Arg
385                 390                 395                 400

Ala Glu Ile Ile Ala Asn Val Gly Leu Pro Glu Gly Tyr Gly Ser Leu
                405                 410                 415

Gly Thr Lys Ala Leu Ala Arg Ile Leu Pro Glu Leu Arg Arg Asp Val
    420                 425                 430

Val Thr Tyr Asp Lys Ala Val Gln Ala Ala Gly Phe Glu His His Ser
    435                 440                 445

Lys Leu Asn Gln Asn Arg Gly Ile Pro Gly Ile Thr Phe Lys Ile Glu
    450                 455                 460

Ser Ile Asp Gln Asp Thr Gly Glu Ile Lys Glu Phe His Ile His Lys
465                 470                 475                 480

Glu Leu Pro Tyr Tyr Gly Glu Tyr Leu Gln Arg His Val Gly Phe Gly
                485                 490                 495

Ser Gly Lys Pro Glu Asp Pro Ile Glu Lys Arg Tyr Gly Lys Ile Ala
                500                 505                 510

Asn Pro Thr Val His Ile Gly Leu Asn Gln Val Arg Leu Ala Val Asn
                515                 520                 525

Ala Leu Ile Lys Arg Tyr Gly His Pro Ser Glu Val Ile Val Glu Val
545                 550                 555                 560

Ala Arg Asp Leu Lys Gln Ser Lys Glu Gln Arg Ser Glu Glu Asn Lys
545                 550                 555                 560

Arg Gln Ala Glu Asn Gln Arg Asn Asn Arg Leu Arg Thr Glu Ile
                565                 570                 575

Ala Arg Ile Leu Gln Ile Asn Glu Glu Gly Ile Arg Arg Asp Asp Ile
                580                 585                 590

Glu Lys Met Ile Leu Trp Ile Glu Leu Ser Ala Asp Val Ala Asp Arg
    595                 600                 605

Lys Cys Pro Tyr Ser Gly Val Pro Ile Ser Ala Thr Met Leu Leu Ser
    610                 615                 620

Asp Glu Val Glu Ile Glu His Ile Leu Pro Phe Ser Gln Thr Leu Asp
625                 630                 635                 640

Asp Ser Leu Asn Asn Lys Thr Val Ala Leu Arg Lys Ala Asn Arg Val
                645                 650                 655

Lys Gly Asp Arg Thr Pro Trp Glu Ala Gln Gln Asp Phe Ala Ala Gln
                660                 665                 670

Gly Trp Ser Tyr Ala Asp Ile Leu Ala Arg Ala Glu Asn Met Arg Lys
                675                 680                 685

Glu Lys Arg Tyr Arg Phe Ala Glu Asp Gly Tyr Lys Arg Trp Leu Lys
```

```
                690                 695                 700
Asp Asp Ala Gly Phe Leu Pro Arg Ala Leu Asn Asp Thr Arg Tyr Leu
705                 710                 715                 720

Ser Arg Val Ala Arg Glu Tyr Leu His Leu Ile Cys Pro Asn Thr Arg
                725                 730                 735

Val Ile Pro Gly Arg Ile Thr Ala Met Leu Arg Ser Gln Phe Gly Leu
                740                 745                 750

Asn Lys Val Leu Gly Leu Asn Gly Glu Lys Asn Arg Asn Asp His Arg
                755                 760                 765

His His Ala Val Asp Ala Cys Val Ile Gly Val Thr Asp Gln Gly Leu
                770                 775                 780

Leu Gln Lys Phe Ala Lys Ala Ser Ala Ser Ala Arg Glu Lys Gln Leu
785                 790                 795                 800

Asn Arg Leu Val Asp Asn Met Glu Ser Pro Trp Lys Asn Tyr Gln Glu
                805                 810                 815

His Val Gln Arg Ala Ile Asp Ala Ile Trp Val Ser His Lys Pro Asp
                820                 825                 830

His Ser His Glu Gly Ala Met His Asn Asp Thr Ala Tyr Gly Leu Arg
                835                 840                 845

Gly Asn Gly Lys Val Ser Phe His Lys Met Met Asp Gly Lys Arg Glu
                850                 855                 860

Tyr Ile Glu Asp Asn Leu Lys Val Ile Glu Ile Ala Asp Thr Lys Ala
865                 870                 875                 880

Ala Glu Arg His Gly Leu Leu Pro Asn Gly Lys Pro Lys Pro Tyr Lys
                885                 890                 895

Gly Tyr Lys Gly Asp Ser Asn Tyr Cys Ile Glu Ile Val Arg Asn Glu
                900                 905                 910

Lys Gly Arg Trp Glu Gly Glu Val Ile Ser Thr Phe Glu Ala Tyr Gln
                915                 920                 925

Leu Val Arg Glu Gln Gly Ala Ala Gln Leu Arg His Pro Ala Leu Gly
930                 935                 940

Ile Ser Gly Lys Pro Leu Val Met Arg Leu Met Ile Asp Asp Thr Val
945                 950                 955                 960

Arg Leu Asp Val Asp Gly Gln Ser Cys Thr Met Arg Ile Ala Lys Leu
                965                 970                 975

Ser Ser Asn Gly Gln Ile Phe Met Ala Asp Ile Cys Glu Ala Asn Val
                980                 985                 990

Asp Ala Arg Asn Arg Asn Lys Glu Asp Ser Phe Ala Tyr Ile Ser Lys
                995                 1000                1005

Met Ala Gly Ser Leu Gln Thr Ala Lys Ala Arg Arg Val Thr Ile
    1010                1015                1020

Ser Pro Ile Gly Glu Leu Arg Asp Ser Gly Phe Lys Gly
1025                1030                1035

<210> SEQ ID NO 5
<211> LENGTH: 1062
<212> TYPE: PRT
<213> ORGANISM: Novosphingobium sp. SYSU G00007

<400> SEQUENCE: 5

Met Glu Lys Arg Leu Gly Leu Asp Ile Gly Thr Asn Ser Ile Gly Trp
1               5                   10                  15

Cys Leu Tyr Glu Gly Asp Ser Ile Leu Asp Ile Gly Val Arg Ile Phe
                20                  25                  30
```

```
Ser Asp Gly Arg Asp Pro Lys Ser Gly Ala Ser Leu Ala Val Asp Arg
         35                  40                  45

Arg Asn Ala Arg Ala Met Arg Arg Arg Asp Arg Tyr Leu Gly Arg
 50                  55                  60

Arg Ser Ala Leu Ile Lys Ala Leu Lys Ala His Gly Leu Phe Pro Ala
 65                  70                  75                  80

Glu Gln Asp Ala Ala Lys Ala Leu Glu Arg Glu Asp Pro Tyr Ser Leu
                 85                  90                  95

Arg Val Arg Ala Leu Asp His Arg Leu Asp Pro His Gln Ile Gly Arg
                100                 105                 110

Ala Ile Phe His Leu Asn Gln Arg Arg Gly Phe Arg Ser Asn Arg Lys
            115                 120                 125

Ala Asp Arg Val Leu Gly Asp Gln Glu Ser Gly Leu Ile Ser Thr Ala
130                 135                 140

Thr Arg Val Leu Asp Glu Ala Met Ala Lys Ser Gly Ala Arg Thr Leu
145                 150                 155                 160

Gly Glu Phe Leu Ala Ser Arg Asp Thr Arg Arg Val Arg Met Arg Pro
                165                 170                 175

Asp Val Lys Gly Tyr Asp Phe Tyr Pro Asn Arg Gln His Tyr Leu Glu
            180                 185                 190

Glu Phe Glu Lys Ile Trp Asp Ala Gln Ser Gln Tyr His Pro Asp Leu
        195                 200                 205

Leu Ser Gln Gln Ala Lys Ser Ala Ile His Arg Ile Phe His Gln
    210                 215                 220

Arg Pro Leu Lys Pro Gln Ala Val Gly Thr Cys Thr Phe Ala Gly Leu
225                 230                 235                 240

His Gly Ile Pro Gly Asp Glu Thr Arg Leu Pro Lys Ala His Pro Leu
                245                 250                 255

Phe Gln Gln Arg Arg Leu Tyr Glu Glu Val Asn Gln Leu Glu Ile Val
            260                 265                 270

Cys Ala Ser Ala Pro Ala Arg Lys Leu Thr Arg Asp Glu Arg Asp Ala
        275                 280                 285

Leu Ile Leu Lys Leu Gln Asp Lys Lys Val Thr Phe Ser Thr Leu
290                 295                 300

Ala Arg Thr Ile Arg Leu Lys Glu Gly Glu Arg Phe Asn Lys Glu Ser
305                 310                 315                 320

Glu Asn Arg Lys Asp Leu Ala Gly Asp Glu Val Arg Ala Glu Met Ser
                325                 330                 335

Asp Lys Thr Arg Phe Gly Arg Arg Trp Phe His Leu Ser Leu Asp Glu
            340                 345                 350

Gln Trp Ser Val Ile Asp Arg Leu Leu Asn Glu Glu Ser Thr Glu Asp
        355                 360                 365

Leu Leu Ala Trp Leu Glu Lys Glu Trp Ser Leu Pro Ser Asp Val Ala
    370                 375                 380

Glu Ala Val Ala Asn Ala His Leu Pro Asp Gly His Gly Arg Phe Gly
385                 390                 395                 400

Leu Thr Ala Thr Val Arg Leu Leu Glu His Leu Lys Ala Asp Val Val
                405                 410                 415

Thr Tyr Ala Glu Ala Ala Arg Arg Ala Gly Phe His His Ser Asp Phe
            420                 425                 430

Arg Asp Gly Ala Cys Tyr Asp Glu Leu Pro Tyr Tyr Gly Glu Ile Leu
        435                 440                 445

Ser Arg Glu Ile Ala Pro Gly Lys Asp Glu Tyr Gly Asp Pro Leu Glu
```

```
                450             455             460
Arg Gln Trp Gly Lys Ile Thr Asn Pro Thr Val His Ile Gly Leu Asn
465                 470                 475                 480

Gln Leu Arg Arg Leu Ile Asn Ala Leu Val Arg Arg His Gly Arg Pro
                485                 490                 495

Asp Phe Ile Phe Val Glu Leu Ala Arg Glu Leu Lys Leu Asn Glu Lys
                500                 505                 510

Gln Lys Ala Asp His Lys Arg Ile Lys Gln Thr Thr Asp Ala Ala
            515                 520                 525

Arg Ala Arg Ala Glu Lys Leu Arg Glu Ile Gly Gln Arg Asp Ser Gly
                530                 535                 540

Ser Asn Arg Met Leu Leu Arg Ile Trp Glu Glu Leu Asn Pro Ser Asn
545                 550                 555                 560

Pro Leu Asp Arg Arg Cys Pro Tyr Cys Ala Glu Pro Ile Ser Ile Glu
                565                 570                 575

Met Leu Met Ser Gly Ser Ala Asp Ile Asp His Ile Val Pro Tyr Ser
                580                 585                 590

Arg Cys Leu Asp Asp Ser Ala Ala Asn Lys Val Val Ala His Asn His
                595                 600                 605

Cys Asn Arg Gln Lys Gly Asn Arg Thr Pro Trp Glu Gln Trp Gly Gln
610                 615                 620

Thr Thr Arg Trp Pro Leu Ile Gln Glu Gln Val Ala Arg Met His Arg
625                 630                 635                 640

Ser Lys Gln Trp Arg Phe Gly Pro Asp Ala Met Glu Arg Val Asp Arg
                645                 650                 655

Asp Gly Gly Phe Ile Ala Arg Gln Leu Thr Asp Thr Gln Tyr Leu Ser
                660                 665                 670

Arg Ile Ala Ala Gln Tyr Leu Ser Ala Leu Tyr Thr Pro Asp Glu Gly
                675                 680                 685

Arg Arg Val Tyr Ala Val Thr Gly Arg Leu Thr Ala Met Leu Arg Arg
                690                 695                 700

Leu Trp Gly Leu Asn Asp Ile Leu Pro Asp His Asn Trp Val Leu Asn
705                 710                 715                 720

Pro His Ser Asn Ala Pro Lys Asn Arg Leu Asp His Arg His His Ala
                725                 730                 735

Ile Asp Ala Ala Val Val Gly Ala Thr Thr Pro Ala Met Ile Gln Gln
                740                 745                 750

Val Ala Arg Ala Ala Ala Arg Ala Glu Glu Gln Asp Leu Asp Arg Leu
                755                 760                 765

Phe Ala Asp Leu Pro Pro Pro Trp Pro Gly Phe Arg Glu Glu Leu Gln
                770                 775                 780

Gly Arg Ile Met Ala Ala Val Val Ser His Lys Pro Asp His Gly Arg
785                 790                 795                 800

Lys Gly Arg Pro Leu Pro Gly Arg Asp Ser Thr Ser Gly Arg Leu His
                805                 810                 815

Asn Asp Thr Ala Tyr Gly Phe Thr Gly Arg Arg Asn Ala Lys Gly Met
                820                 825                 830

Pro Ile Val Val Thr Arg Lys Pro Leu Leu Ala Leu Lys Pro Glu Asp
                835                 840                 845

Leu Thr Asp Pro Glu Arg Ile Pro Asp Pro Ala Leu Gln Gly Ala Leu
                850                 855                 860

Phe Glu Ala Thr Arg Gly Ala Thr Gly Lys Asp Phe Glu Lys Ala Leu
865                 870                 875                 880
```

```
Arg Asp Phe Ser Arg Arg Asp Gly Pro Tyr Gln Gly Ile Arg Arg Ile
                885                 890                 895

Arg Leu Thr Glu Ala Leu Asn Val Ile Pro Ile Arg Asp Arg Thr Gly
                900                 905                 910

His Ala Tyr Lys Gly Val Lys Gly Asp Ala Asn Ala Arg Phe Asp Val
                915                 920                 925

Trp Arg Leu Pro Asp Gly Lys Trp Ile Thr Arg Trp Lys Asp Arg Asp
                930                 935                 940

Gly Ile Glu His Ser Gly Ile Val Ser Leu Phe Asp Ala His Gln Pro
945                 950                 955                 960

Ser Gln Val Tyr His Arg Pro His Pro Ala Ala Lys Lys Val Leu Ser
                965                 970                 975

Leu Arg Gln Asn Asp Leu Val Ala Val Glu His Asp Gly Asp Pro Gly
                980                 985                 990

Lys Ile Met Arg Val Val Lys Phe  Ser Ala Asn Gly Ser  Ile Thr Phe
                995                 1000                1005

Ala Pro  His Asn Glu Ala Gly  Pro Leu Lys Thr Arg  Asp Thr Asp
                1010                1015                1020

Pro Ala  Asp Pro Phe Arg Tyr  Val Thr Thr Val Ala  Ser Gly Leu
                1025                1030                1035

Lys Lys  Met Arg Ala Arg Gln  Val Arg Ile Asp Glu  Leu Gly Lys
                1040                1045                1050

Val His  Asp Pro Gly Pro Arg  Glu Asp
                1055                1060

<210> SEQ ID NO 6
<211> LENGTH: 1075
<212> TYPE: PRT
<213> ORGANISM: Paracoccus bengalensis

<400> SEQUENCE: 6

Met Thr Thr Thr Leu Gly Ile Asp Leu Gly Thr Ser Ser Leu Gly Trp
1               5                   10                  15

Cys Leu Ile Glu Asp Glu His Arg Ile Leu Asp Leu Gly Val Ile Ile
                20                  25                  30

Phe Ser Ala Ala Gly Ala Gly Arg Asp Pro Gln Ser Gly Ala Pro
            35                  40                  45

Leu Ala Glu Ala Arg Arg Glu Ala Arg Ser Ala Arg Arg Arg Arg Asp
            50                  55                  60

Arg Phe Ile Gly Arg Arg Ser Ala Leu Leu Asp Lys Leu Ile Ala Leu
65                  70                  75                  80

Gly Leu Leu Pro Gly Asp Pro Pro Ala Gly His Gly Arg Arg Arg Asn
                85                  90                  95

Gln Ala Leu Pro Asn Ala Glu Thr Lys Ala Leu Ala Asp Thr Asp Pro
                100                 105                 110

His Val Leu Arg Arg Arg Ala Leu Ser Glu Pro Leu Ser Pro His Glu
                115                 120                 125

Ile Gly Arg Ala Ile Phe His Leu Asn Thr Arg Gly Phe Lys Ser
                130                 135                 140

Asn Arg Lys Ala Asp Arg Gly Arg Asn Glu Pro Thr Gly Lys Ile
145                 150                 155                 160

Ala Thr Ala Gly Gln Ala Leu Asp Ala Leu Gly Lys Arg Thr Leu
                165                 170                 175

Gly Gln Phe Leu Ala Asp Arg Ile Asp Ala Gly Gln Pro Ala Arg Val
```

```
            180                 185                 190
Arg Met Gly Gly Glu Asn Gln Ala Tyr Asp Phe Tyr Pro Gln Arg Ser
            195                 200                 205
His Leu Glu Ala Glu Phe Ala Ala Ile Trp Glu Ala Gln Glu His His
            210                 215                 220
His Pro Glu Leu Leu Thr Asp Thr Ala Arg Thr Ala Ile His Arg Ile
225                 230                 235                 240
Leu Phe Phe Gln Arg Pro Leu Lys Thr Pro Glu Val Gly Phe Cys Thr
            245                 250                 255
Phe Ala Gly Met Ser Gly Val Pro His Asp Glu Arg Arg Leu Pro Lys
            260                 265                 270
Ala His Pro Leu Phe Gln Glu Arg Leu Tyr Glu Glu Val Asn Asn
            275                 280                 285
Leu Lys Val Val Ala Ala Gly Ala Ala Arg Asp Leu Thr Leu Asp
290                 295                 300
Glu Arg Asp Arg Leu Ile Leu Lys Leu Arg Asp Asn Lys Lys Val Thr
305                 310                 315                 320
Phe Ala Thr Leu Ala Lys Lys Val Leu Lys Leu Ala Glu Gly Glu Arg
            325                 330                 335
Phe Asn Lys Glu Ser Glu Ala Arg Lys Asp Leu Ala Gly Asp Glu Val
            340                 345                 350
Arg Ala Glu Met Ala Asp Lys Lys Arg Phe Gly Asn Arg Trp Thr His
            355                 360                 365
Phe Pro Leu Glu Arg Gln Leu Gln Ile Ile Asp Arg Val Gln Asn Glu
            370                 375                 380
Glu Asn Pro Asp Ile Leu Leu Ala Trp Leu Gln Ser Asp Cys Gly Leu
385                 390                 395                 400
Asp Lys Ala Ala Ala Val Ala Val Ala Arg Thr Asn Leu Pro Glu Gly
            405                 410                 415
His Gly Arg Phe Gly Glu Thr Ala Thr Arg Arg Leu Ile Ala Ala Leu
            420                 425                 430
Lys Ala Glu Val Val Thr Tyr Asp Lys Ala Ala Leu Ala Ala Gly Phe
            435                 440                 445
His His Ser Asp His Arg Thr Gly Glu Val Tyr Asp Leu Leu Pro Tyr
            450                 455                 460
Tyr Gly Glu Val Leu Thr Arg Glu Ile Ala Pro Gly Lys Ala Glu Tyr
465                 470                 475                 480
Gly Asp Pro Leu Glu Arg Gln Tyr Gly Lys Val Thr Asn Pro Thr Val
            485                 490                 495
His Ile Gly Leu Arg Gln Leu Gln Lys Leu Val Asn Ala Val Ile Ala
            500                 505                 510
Arg His Gly Arg Pro Asp Arg Ile Val Ile Glu Leu Ala Arg Glu Leu
            515                 520                 525
Lys Leu Asn Asp Lys Gln Lys Asp Glu His Gln Arg Arg Ile Arg Arg
            530                 535                 540
Asp Thr Glu Ala Ala Ile Arg Arg Gly Glu Lys Leu Val Glu Ala Gly
545                 550                 555                 560
Ile Ala Asp Thr Gly Ala Asn Arg Ala Leu Met Arg Gln Trp Glu Glu
            565                 570                 575
Leu Asn Pro Ser Asn Pro Leu Asp Arg Arg Cys Pro Tyr Cys Gly Glu
            580                 585                 590
Pro Ile Gly Met Ala Gln Ile Phe Asn Ser Leu Ala Asp Ile Asp His
            595                 600                 605
```

```
Ile Ile Pro Tyr Ser Arg Ser Leu Asp Asp Ser Pro Ala Asn Lys Val
        610                 615                 620

Leu Val His Arg Asn Cys Asn Arg Gln Lys Gly Asn Lys Thr Pro Trp
625                 630                 635                 640

Asp Arg Trp His Glu Asp Glu Ala Lys Trp Glu Ile Ile Ser Ala Gln
            645                 650                 655

Val Ala Arg Met His Pro Ser Lys Gln Trp Arg Phe Gly Pro Asp Ala
        660                 665                 670

Met Glu Arg Leu Glu Arg Asp Gly Phe Ala Ala Arg Gln Leu Thr
        675                 680                 685

Asp Thr Gln Tyr Leu Ala Arg Ile Ala Asp Lys Tyr Leu Arg Gly Leu
690                 695                 700

Tyr Pro Thr Ala Asp Glu Gly Arg Val Asp Val Ile Pro Gly Arg Met
705                 710                 715                 720

Thr Ala Met Leu Arg Arg Val Trp Gly Leu Asn Ser Leu Leu Pro Asp
                725                 730                 735

His Asn Phe Val Glu Asn Glu His Ser Ser Ala Pro Lys Asn Arg Leu
            740                 745                 750

Asp His Arg His His Ala Ile Asp Ala Thr Val Ala Ala Val Thr Ser
            755                 760                 765

Leu Ser Arg Met Gln Gln Ile Ala Ala Ala Ala Arg Ser Glu Glu
770                 775                 780

Lys Glu Leu Glu Arg Leu Phe Asp Asp Leu Pro His Pro Trp Asp Gly
785                 790                 795                 800

Phe Arg Glu Asp Leu Gly Ala Cys Leu Ala Arg Thr Val Ala Thr His
                805                 810                 815

Lys Pro Asp His Gly Arg Ser Ala Lys Pro Ser Arg His Arg Asp Val
            820                 825                 830

Thr Ala Gly Lys Leu His Asn Asp Thr Ala Tyr Gly Leu Thr Gly Leu
            835                 840                 845

Lys Thr Thr Asp Gly Lys Thr Pro Ile Val Val His Arg Val Leu Leu
850                 855                 860

Ala Ser Leu Lys Pro Thr Gln Ile Ala Asp Pro Asp Cys Ile Pro Asp
865                 870                 875                 880

Glu Thr Leu Arg Asn Ala Leu Trp Leu Ala Thr Arg Asp Cys Ser Gly
                885                 890                 895

Lys Ala Phe Asp Gln Ala Leu Ala Arg Phe Ala Lys Glu His Pro Val
            900                 905                 910

Phe Lys Gly Ile Arg Arg Val Arg Ile Arg Glu Pro Leu Asn Val Ile
            915                 920                 925

Pro Ile His Asp Arg Glu Gly Lys Pro Tyr Lys Ser Tyr Ala Gly Ala
930                 935                 940

Ser Asn Asp Arg Tyr Asn Val Trp Arg Met Pro Asp Ala Ser Trp Arg
945                 950                 955                 960

His Asp Val Val Ser Thr Phe Asn Ala His Arg Ser Asp Tyr Arg Asp
                965                 970                 975

Leu Arg Pro His Pro Ala Ala Lys Lys Val Leu Ser Leu Arg Gln Asn
            980                 985                 990

Asp Met Ile Ala Val Glu Arg Asn  Gly Gly Leu Arg Glu  Ile Met Arg
            995                 1000                1005

Val Val  Lys Phe Asn Gln Ala  Gly Arg Leu Thr Leu  Cys Pro Pro
    1010                1015                1020
```

```
Asn Glu Gly Gly Lys Leu Gln Asn Arg Asp Ala Ala Pro Asn Asp
    1025                1030                1035

Ala Asp Pro Phe Lys Tyr Thr Tyr Leu Ser Pro Ser Ser Leu Lys
    1040                1045                1050

Asn Ala Lys Ala Arg Gln Val Arg Ile Asp Pro Leu Gly Arg Val
    1055                1060                1065

Phe Asp Pro Gly Pro Arg Glu
    1070            1075

<210> SEQ ID NO 7
<211> LENGTH: 1045
<212> TYPE: PRT
<213> ORGANISM: Parvibium lacunae

<400> SEQUENCE: 7

Met Lys Asn Lys Met Gln Tyr Arg Leu Ala Leu Asp Leu Gly Thr Thr
1               5                   10                  15

Ser Leu Gly Trp Ala Met Leu Arg Val Lys Pro Asn Pro Glu Gly Arg
            20                  25                  30

Leu Glu Pro Phe Ala Val Val Lys Ala Gly Val Arg Ile Phe Ser Asp
        35                  40                  45

Gly Arg Asn Pro Lys Asp Gly Ser Ser Leu Ala Val Thr Arg Arg Glu
    50                  55                  60

Ala Arg Ala Met Arg Arg Arg Asp Arg Leu Leu Lys Arg Lys Ala
65              70                  75                  80

Arg Met Leu Gln Gln Leu Thr Ala Phe Gly Phe Pro Thr Asp Leu
                85                  90                  95

Ala Glu Arg Lys Ala Leu Glu Thr Leu Asn Pro Tyr Glu Leu Arg Ala
            100                 105                 110

Lys Gly Leu Asp Glu Pro Leu Ser Pro Tyr Gly Phe Gly Arg Ser Leu
        115                 120                 125

Phe His Ile Asn Gln Arg Arg Gly Phe Lys Ser Asn Arg Lys Thr Asp
    130                 135                 140

Lys Lys Glu Asn Asp Ser Ser Ala Leu Lys Ala Ala Ile Arg Arg Val
145                 150                 155                 160

Ala Ser Glu Ile Asp Gly Asn Gln Ala Arg Thr Val Gly Glu Trp Leu
                165                 170                 175

Tyr Lys Arg Met Leu Asn Gly Gln Pro Val Arg Gly Tyr Arg Glu
            180                 185                 190

Thr Lys Val Gln Lys Glu Asp Gly Lys Thr Lys Ile Asp Lys Ser Tyr
        195                 200                 205

Asp Leu Tyr Ile Asp Arg Ala Met Val Glu Ala Glu Phe Glu Ala Leu
    210                 215                 220

Trp Ala Lys Gln Ala Ser Leu Asn Pro Ala Val Tyr Ser Glu Gln Ala
225                 230                 235                 240

Lys Ala Thr Leu Lys Asp Val Leu Leu Phe Gln Arg Asn Leu Arg Pro
                245                 250                 255

Val Lys Pro Gly Arg Cys Thr Leu Ile Pro Thr Glu Glu Arg Ala Pro
            260                 265                 270

Leu Ala Leu Pro Ser Thr Gln Arg Phe Arg Ile Tyr Gln Glu Val Asn
        275                 280                 285

Asn Leu Arg Ile Leu Arg Glu Gly Leu Lys Asp Glu Ala Leu Thr Leu
    290                 295                 300

Val Gln Arg Asp Ala Leu Val Thr Ala Leu Glu Gln Asn Asn Lys Arg
305                 310                 315                 320
```

```
Thr Phe Ala Gln Ile Lys Lys Leu Leu Gly Leu Asp Gly Gln Thr Gln
                325                 330                 335

Phe Asn Phe Glu Asp Pro Lys Arg Gln Glu Leu Lys Gly Asn Thr Thr
            340                 345                 350

Ser Ala Ile Leu Ser His Pro Lys His Phe Gly Asp Ala Trp Phe Gly
                355                 360                 365

Phe Asp Glu Ala Lys Gln Asp Gly Ile Val Cys Gln Leu Leu Asn Glu
    370                 375                 380

Glu Asn Glu Ser Ala Leu Ile Arg Trp Leu Met Asp His Thr Gly Val
385                 390                 395                 400

Asp Glu Ala His Ala Glu Ala Ile Ala Asn Ala Ala Leu Pro Glu Gly
                405                 410                 415

Tyr Gly Ser Leu Ser Arg Ala Ala Leu Ala Lys Ile Leu Pro Glu Leu
                420                 425                 430

Arg Lys Ala Val Ile Thr Tyr Asp Lys Ala Ala Gln Ala Ala Gly Phe
                435                 440                 445

Asp His His Ser His Ile Ser Pro Ser Thr Thr Gly Glu Ile Leu Pro
    450                 455                 460

Glu Leu Pro Tyr Tyr Gly Glu Ala Leu Gln Arg His Val Gly Phe Gly
465                 470                 475                 480

Thr Gly Asn Pro Asp Asp Val Pro Glu Lys Arg Tyr Gly Lys Ile Ala
                485                 490                 495

Asn Pro Thr Val His Ile Gly Leu Asn Gln Val Arg Lys Val Val Asn
                500                 505                 510

Ala Leu Ile Lys Arg Tyr Gly His Pro Ser Glu Val Ile Val Glu Val
                515                 520                 525

Ala Arg Asp Leu Lys Gln Ser Lys Lys Gln Arg Asp Glu Glu Asn Lys
                530                 535                 540

Arg Gln Ala Glu Asn Gln Lys Arg Asn Glu Arg Ile Arg Gln Asp Ile
545                 550                 555                 560

Ala Ala Met Arg Pro Asp Arg Ser Glu Glu Arg Val Thr Arg Thr Asp
                565                 570                 575

Ile Gln Lys Trp Ile Leu Trp Glu Glu Leu Ser Phe Asp Pro Ala Asn
                580                 585                 590

Arg Cys Cys Pro Tyr Ser Gly Val Gln Ile Ser Ala Glu Met Leu Met
                595                 600                 605

Ser Asp Ala Val Glu Ile Glu His Ile Leu Pro Phe Ser Arg Thr Leu
    610                 615                 620

Asp Asp Ser Leu Asn Asn Lys Thr Val Ser Met Arg Gln Ala Asn Arg
625                 630                 635                 640

Ile Lys Gly Asn Gln Thr Pro Phe Glu Ala Phe Gly Lys Asp Asn Ala
                645                 650                 655

Leu Gly Val Asn Tyr Ser Asp Ile Leu Met Arg Ala Gln Gln Met Pro
                660                 665                 670

Lys Ala Lys Arg Lys Arg Phe Ala Glu Asn Ala Leu Glu Glu Trp Leu
                675                 680                 685

Gln Asn Glu Lys Asn Phe Leu Ala Arg Ala Leu Asn Asp Thr Arg Tyr
    690                 695                 700

Leu Ser Arg Val Ala Arg Glu Tyr Val Ser Leu Ile Cys Pro Gln Ala
705                 710                 715                 720

Thr Arg Val Ile Pro Gly Gln Met Thr Ala Gln Leu Arg Ala Lys Phe
                725                 730                 735
```

```
Gly Leu Asn Asp Ile Leu Gly Leu Asp Gly Glu Lys Asn Arg Asn Asp
                740                 745                 750

His Arg His His Ala Val Asp Ala Cys Val Ile Gly Val Thr Asp Gln
            755                 760                 765

Gly Leu Leu Gln Arg Phe Ala Tyr Ala Ser Ala Ser Ala Arg Ala Asn
        770                 775                 780

Gly Leu Ala Arg Leu Val Asp Thr Met Pro Asp Pro Trp Pro Ser Tyr
785                 790                 795                 800

Arg Gln His Val Gln Arg Ala Val Gln Asn Ile Tyr Val Ser His Lys
                805                 810                 815

Pro Asp His Ser His Glu Gly Ala Met Phe Asp Glu Thr Ile Tyr Ser
            820                 825                 830

Ala Thr Gly Lys Ser Arg Ser Ala Ala Lys Asp Arg Thr Val Ile Pro
        835                 840                 845

Phe Ile Ala Lys Asn Trp Ser His Pro Asp Asp His Asn Lys Gln Arg
850                 855                 860

Pro Phe Lys Gly Leu Ile Thr Asp Val Ser Gln Arg His Gln Asn Lys
865                 870                 875                 880

Pro Tyr Lys Gly Leu Leu Ser Asn Ser Asn Tyr Cys Ile Glu Ile Tyr
                885                 890                 895

Ser Asp Glu Ala Gly Trp Gly His Val Leu Lys Thr Phe Asp Ala
            900                 905                 910

Tyr Gln Ile Val Arg Ala His Lys Asn Ala Ser Glu Gly Met Gln Ala
        915                 920                 925

Leu Arg Asn Lys His Ser Ser Gln Asn Gly His Pro Leu Val Met Arg
    930                 935                 940

Leu Met Ile Gly Asp Tyr Ile Arg Ala Glu Ile Asp Gly Phe Leu Leu
945                 950                 955                 960

Leu Leu Gln Val Leu Lys Ile Asn Ser Ser Gly Ser Ile Thr Phe Ile
                965                 970                 975

Lys Pro Asn Glu Thr Asn Ile Ser Ala Arg Tyr Leu Ala Lys Leu Ala
            980                 985                 990

Ala Gln Lys Ala Gln Lys Glu Gly Lys Pro Phe Asp Asp Ile Ala Leu
        995                 1000                1005

Asn Asp Val Phe Phe Gln Lys Ala Ile Ser Ala Asp Ser Leu Arg
    1010                1015                1020

Leu Phe Lys Ala Arg Pro Val Thr Leu Ser Pro Ile Gly Glu Leu
    1025                1030                1035

Arg Asp Pro Gly Phe Lys Gly
    1040                1045

<210> SEQ ID NO 8
<211> LENGTH: 1071
<212> TYPE: PRT
<213> ORGANISM: Pelagicola sp. LXJ1103

<400> SEQUENCE: 8

Met Arg Leu Gly Leu Asp Ile Gly Thr Asn Ser Ile Gly Trp Trp Leu
1               5                   10                  15

Tyr Arg Thr Glu Asn Asp Gln Ile Thr Cys Val Val Asp Gly Gly Val
                20                  25                  30

Arg Val Phe Ser Asp Gly Arg Asp Pro Gln Ser Lys Glu Ser Leu Ala
            35                  40                  45

Val Asp Arg Arg Val Ala Arg Ala Gln Arg Arg Arg Asp Arg Tyr
        50                  55                  60
```

```
Leu Arg Arg Lys Ala Ala Leu Met Lys Arg Met Ala Glu Ala Gly Leu
 65                  70                  75                  80

Met Pro Ala Asp Pro Val Gln Ala Lys Ala Leu Gln Ala Leu Asp Pro
                 85                  90                  95

Tyr Asp Leu Arg Ala Arg Gly Leu Asp Glu Ala Leu Pro Leu Ala His
            100                 105                 110

Phe Gly Arg Ala Leu Phe His Leu Asn Gln Arg Gly Phe Lys Ser
        115                 120                 125

Asn Arg Lys Ala Asp Arg Gly Asp Asn Glu Ser Gly Lys Ile Lys Asp
    130                 135                 140

Ala Thr Ala Arg Leu Asp Trp Ala Met Arg Asp Ala Arg Ala Arg Thr
145                 150                 155                 160

Tyr Gly Glu Phe Leu His Met Arg Gln Asp Lys Ala Asp Asp Pro Arg
                165                 170                 175

Arg Val Pro Thr Val Arg Thr Arg Leu Ser Val Ala Arg Arg Asp Asn
            180                 185                 190

Ala Glu Lys Glu Glu Ala Gly Tyr Asp Phe Tyr Pro Asp Arg Arg His
        195                 200                 205

Leu Ser Glu Glu Phe Asp Ala Leu Trp Ala Ala Gln Ala Glu His His
    210                 215                 220

Thr Thr Leu Thr Asp Asp Leu Arg Asp Gln Ile Lys Thr Ile Ile Phe
225                 230                 235                 240

His Gln Arg Pro Leu Lys Ala Pro Glu Val Gly Leu Cys Leu Phe Thr
                245                 250                 255

Asp Glu Arg Arg Ile Pro Ser Ala His Pro Leu Asn Gln Arg Arg Ile
            260                 265                 270

Leu Leu Glu Thr Val Asn Gly Leu Arg Ile Val Ala Arg Gly Glu Ala
        275                 280                 285

Ala Arg Gly Leu Thr Arg Glu Glu Arg Asp Gln Ile Val His Gly Leu
    290                 295                 300

Asp Asn Lys Gly His Thr Lys Thr Leu Ser Gly Met Ser Met Lys Leu
305                 310                 315                 320

Arg Ala Ile Gly Lys Val Ile Lys Leu Arg Ser Asp Gln Ser Phe Thr
                325                 330                 335

Leu Glu Thr Ala Asn Arg Asp Ala Ile Ala Cys Asp Pro Val Arg Ala
            340                 345                 350

Ser Leu Ser His Pro Glu Arg Met Gly Gly Val Trp Thr Thr Leu Asp
        355                 360                 365

Glu Asp Ala Gln Trp Asp Val Val Gln Arg Leu Arg Ala Val Gln Ser
    370                 375                 380

Asp Thr Glu His Glu Ala Leu Val Asp Trp Leu Met Ala Thr His Gly
385                 390                 395                 400

Leu Gly Gln Asp Tyr Ala Gln Ala Thr Ala Asn Ala Pro Leu Pro Glu
                405                 410                 415

Gly Tyr Gly Arg Leu Gly Leu Thr Ala Thr Arg Lys Ile Leu Ala Ala
            420                 425                 430

Leu Glu Ala Asp Val Met Ser Tyr Ser Asp Ala Val Ala Ala Cys Gly
        435                 440                 445

Trp Ser His Ser Gly Pro Thr Gly Glu Val Leu Glu Ala Leu Pro
    450                 455                 460

Tyr Tyr Gly Glu Ile Leu Asp Arg His Val Ile Pro Gly Thr Gly Val
465                 470                 475                 480
```

```
Lys Thr Asp Glu Asp Val Lys Arg Phe Gly Arg Ile Thr Asn Pro Thr
                485                 490                 495

Val His Ile Gly Leu Asn Gln Ile Arg Arg Leu Val Asn Arg Ile Ile
            500                 505                 510

Cys Val His Gly Lys Pro Asp Gln Ile Val Glu Val Ala Arg Asp
        515                 520                 525

Leu Lys Asn Ser Glu Asp Gln Lys Arg Glu Ile Gln Lys Thr Ile Arg
    530                 535                 540

Lys Asn Thr Asp Asp Ala Ile Lys Arg Gly Lys Lys Leu Val Glu Glu
545                 550                 555                 560

Leu Gly Gln Lys Asp Thr Gly Ala Asn Arg Leu Ile Leu Arg Leu Trp
                565                 570                 575

Glu Asn Leu Gly Asn Asp Val Met Thr Arg Gln Cys Pro Tyr Ser Gly
            580                 585                 590

Lys Arg Ile Ser Ala Ala Met Leu Phe Asp Gly Ser Cys Asp Val Asp
        595                 600                 605

His Ile Leu Pro Phe Ser Arg Thr Leu Asp Asp Ser Ile Trp Asn Lys
    610                 615                 620

Thr Leu Cys Leu Lys Glu Asn Arg Lys Lys Ala Asn Lys Thr Pro
625                 630                 635                 640

Trp Glu Val Trp Gly Glu Thr Asp Gln Trp Asp Val Ile Val Ala Asn
                645                 650                 655

Leu Lys Asn Leu Asp Arg Lys Gln Ala Trp Arg Phe Ala Pro Asp Ala
            660                 665                 670

Val Glu Arg Phe Glu Gly Glu Asn Asp Phe Ser Ala Arg Ala Leu Lys
        675                 680                 685

Asp Thr Gln Tyr Leu Ser Arg Val Ala Arg Ala Tyr Leu Asp Ala Leu
    690                 695                 700

Tyr Asp Gly Ala Asp Gly Lys Ser His Val Trp Val Val Pro Gly Arg
705                 710                 715                 720

Leu Thr Glu Met Leu Arg Arg His Trp Gly Leu Asn Gly Ile Glu Val
                725                 730                 735

Leu Thr Asp Ser Asp Ala Gln Thr Val Lys Ser Lys Asn Arg Gln Asp
            740                 745                 750

His Arg His His Ala Ile Asp Ala Ala Val Val Ala Ala Thr Asp Arg
        755                 760                 765

Ser Leu Ile Gln Arg Ile Ser Lys Ile Ala Lys His Asp Glu Gln Ala
    770                 775                 780

Gly Ala Glu Gln Val Ala Arg Ser Val Pro Pro Trp Asp Gly Phe
785                 790                 795                 800

Arg Asp Asp Val Ala Gly Gln Ile Gly Arg Ile Ile Val Ser His Arg
                805                 810                 815

Ala Asp His Gly Arg Ile Asp Pro Thr Ala Arg Ala Gln Gly Ser Asp
            820                 825                 830

Thr Thr Ala Gly Gln Leu His Met Asp Thr Ala Tyr Gly Ile Val Asp
        835                 840                 845

Gly Gly His Val Val Ser Arg Lys Pro Leu Met Ser Leu Gly Ala Gly
    850                 855                 860

Asp Ile Arg Lys Ile Arg Asp Pro Asp Leu Gln Arg His Leu Thr Arg
865                 870                 875                 880

Val Thr Arg Gly Leu Asp Lys Lys Glu Phe Glu Gln Ala Leu Ala Ser
                885                 890                 895

Phe Ala Ala Ser Arg Lys Leu Pro Asp Gln Ser Glu Asn Pro Tyr Phe
```

```
                900             905             910
Gly Leu Arg Arg Val Arg Leu Leu Asp Ala Leu Gln Asp Ser Ala Arg
            915             920             925
Val Pro Val Arg Asn Ala Thr Gly Asn Ile Tyr Lys Ala Tyr Lys Ala
        930             935             940
Gly Ser Asn His Cys Tyr Glu Val Trp Arg Met Pro Asp Gly Lys Val
945             950             955             960
Lys Pro Trp Ala Ile Ser Thr Phe Glu Ala His Gln Ser Gly Asp Gly
                965             970             975
Ser Lys Pro His Pro Ala Ala Lys Arg Leu Leu Arg Val Phe Lys Arg
            980             985             990
Asp Met Val Val Ile Glu Arg Lys Gly Ile Thr Val Ile Cys Tyr Val
        995             1000            1005
Gln Lys Met Asp Val Ala Asn Gly Leu Phe Leu Val Pro His Thr
        1010            1015            1020
Glu Gly Asn Ala Asp Ala Arg Asn Arg Asp Lys Glu Asp Asp Phe
        1025            1030            1035
Lys Phe Ile Gln Met Ser Ala Ala Ser Leu Ile Lys Ala Arg Ile
        1040            1045            1050
Arg Arg Val His Val Asp Glu Met Gly Arg Met Arg Asp Pro Gly
        1055            1060            1065
Pro Pro Arg
        1070

<210> SEQ ID NO 9
<211> LENGTH: 3147
<212> TYPE: DNA
<213> ORGANISM: Comamonadaceae bacterium NML00-0135

<400> SEQUENCE: 9
atgaatgtgt ggaaagggac tggtttcgtg tcaagaaaaa gaaacatcat tcgttaccga       60
ctggctttgg atctgggctc cacctcgctg gctgggcca tcctgcgcct gaatgctgac       120
aaccagccca ccgccatcct caaggctggc gtgcgcatct tcagcgatgg ccgaaaccca       180
aaggatggct cctctctggc cgtgacccgc gcgccgccc gcgccatgcg ccgccgtcgc       240
gaccgcctgc tcaagcgcaa ggcgcgcatg ctggacaagc tgattgcaca tggcttcttc       300
ccacaggacg aggccgcgcg caaagcattg gaggtgctca atccctacca gttgcgcgcc       360
gagggcttgc agcgcgcact gatgccgggc gagttcgccc gcgcaatgtt tcatatcaac       420
cagcgccgcg gcttcaagag caaccgcaag accgacaaga agacagcga cagcggcgcc       480 ctcaaaaccg ccatcagcca actgcgccag caactgcaaa acgaaaacgc ccgcacggta       540
ggcgaatggc tgtggcaacg cctgcaagcc ggccaaggca cgcgtgcccg ctaccgggaa       600
acgcgcatcg ccaccgacac aggcaagggc aagatcgaca aaagctacga cctctatatc       660
gaccgccaga tggtggccga tgagttcgat gcgctgtggg ccgtgcaggc ggccttcaac       720
cccgtactgt tcaacgagca ggcacgggcc gaactgcgcg cacccctgct gcatcaacgc       780
ccgttgcgcc cggccaagcc agggcgctgc accttgctgc cggaagaaga gcgcgccccg       840
ctggccctgc ccagcacgca gcgttttcgc atcctgcaag aggtgaatca cctgcgcatt       900
ctgcacccag acttgcgtga agaagcattg acgctggatc ggcgcaatgc catcgtggcc       960
ttgctggaga acagggggaaa agtcacgttc caggccatgc gcagaacact caacctgggt      1020
gatgccgtgc aattcaattt ggaagacgcc aagcgccgtg aactcaaggg caatgccacc      1080
```

```
acggcggcac tgtcgaaaaa ggaactgttc ggggcagcgt ggcacgactt tgacgaagcc    1140
ttgcaggacg acatcgtgct gcgcctggtc acggaagaaa gcgaagccga actggtgcaa    1200
tggctgatcg aaaacactgg cgtggatgag gcacgcgcca cggccattgc caacactggc    1260
ctgccagaag gctacggcag cctcagccgc aaggcactgg cgcgcatcgt gcctgcgctg    1320
cgcgccgagg tcatcaccta cgacaaggcg gtgcaggccg ccggctttgc ccatcacagc    1380
gatttgcgat tcagtttcga gtacgacagc gccgatgtgg agcaggtggg agagcgtatc    1440
gacaaaacca ccggcgaaat cctgcctgtg tctgccttca gcagttgcc ctactacggc     1500 aaggcgctgc aacgtcacgt ggcctttggc agtggcaacc cgcaagaccc ggaagaaaaa    1560
cgctacggca agatcgccaa ccccaccgta catatcggcc tgaaccaggt gcgccgcgtg    1620
gtcaacgatt tgatccgacg ttatggccgg ccaaccgaaa tcgtggtgga actggcgcgc    1680
gagctcaagc aaagccgtga gcaaaagctg gaggcgcaac gcaagcaagc cgacaaccaa    1740
aagcgcaatg cgcgcattcg cgcggaaatt gcgcctatct tgggcatcag cgaagagcgg    1800
gtgaagcatg cagacattca gaatggatcc ctgtgggagg agttgagctt tgacgtcgcc    1860
gaccgccgct gcccctacag cggcgtgcag atcagcgcgc gcatgctgct cagcgatgag    1920
gtggaaatcg agcacatcct gcccttctct caaacgctgg atgacagcct gaacaacaaa    1980
accgtttcca tgcggcaagc caaccgcatc aaaggcaacc gcacgccttg cgaggcgcgg    2040
caggactttg aggcgcaggg ctggccgtac gagggcatgc agcaacgcgc cgaacgcatg    2100
ccccgcgcca aacgctaccg cttcgcgccc gatggttacg aacgctggct gggtgaggac    2160
caaggctttc tggcgcgcgc gctgaatgac acgcgctatc tctcgcgcat cgcccgggat    2220
tacctcaccc ttgtctgccc cggcggtgtg cgggtgattc cggggcggat gacggctttg    2280
ctgcgcgcca agttcggcct gaatgggggtc ttgagcctga gcggcgagaa aaaccgcgat    2340
gaccatcgtc accatgccgt ggacgcctgt gtcattggcg ttactgacca gggtctgttg    2400
cagcgctttg ccgaggccag cgcgatggct cgccagcaag gactggaaaa gctggtggaa    2460
acgatgccct gccttgggaa aacctaccca gcgcatgtgc agcgcgccgt acaaaacatc    2520
tgggtcagcc accgccccga ccatgggcat gagggcggca tgatggaaga gcttcctac    2580 ggcatcagca aggatgggcg catcaagcag cggcgcaagg ccgatggcag tcaagggcgt    2640
gagatcagca atctgatccg catcagcgaa ccaagccagc ccgagcgcca cggcgtagac    2700
gccgaaggcc agcctttgcc ctacaaaggc tatgtcggcg gcagcaacta ctgcatcgaa    2760
atcacgcgca tgacaaagg caaatgggag ggcgaagtga tctcgacctt ccgcgcctat    2820
caaatcgtgc gcaaacatgg cgtggcgcgc ctgcgacatc cagagatggc acagaacggg    2880
aaggcgctgg tgatgcgcct gatgattgac gactgcgtgc gcctagaatt ggacggacgg    2940
gaagagacga tgcgtgtggt ggtaattccc aggaacggac aggtcttcat ggcgccactg    3000
cacgaagcca atgtggatgc ccgcaaccgg gataagaatg atccgttctc ctatatctcg    3060
aagatggccg gctccttcct aaaagccaaa gcccgccaca tcaccatctc gcccatcggc    3120
gagctgcacg acccccggctt caagggc                                       3147
```

<210> SEQ ID NO 10
<211> LENGTH: 3063
<212> TYPE: DNA
<213> ORGANISM: Demequina sediminicola

<400> SEQUENCE: 10

```
atgactggca ctgacgccac agcacactcg cacacgccgt accgcctcgg gctcgatgta    60
```

-continued

```
gggacaggat ctttgggttg ggccgtcgtt gaactcgata ccgacggcaa tcctgtccgc    120
atcgtgcgca ccggctcgcg gatctatggg agcgggcgca aacccaagga cttttcatcg    180
ttagcggccg accggcgtgc cgcacgtcag atgcgcaagc aacgcgaccg ctatcttcaa    240
cgccgcacgc gcctcatgca tgaactggtg gccgccggtc tgatgcccga ggccgaggtg    300
gagcggcaga agctcaagga tctcaacccc tacctgctac gcgctcgtgg ggttaaagag    360
gaactgaccg cccacgaact tggcagggct ctctttcatc tccagcagcg ccgtggcttc    420
aagtcaaatc gcaagacaga ccgcaaggac gacgaccgca gcgcgatgaa gagcgccatc    480
gcatcgctcc aatccgactt gggcgacgac acccttggca cgtacatgtg aagcggatc     540 cagaacggcg aatctgtgcg gtcccgtccg cgaaaggtcg ggtcaaagaa cgagtacgac    600
ttttacgtga accgcgcgat ggtcgaggat gagttcaatc agttgtggga ctaccaaagc    660
cagtcccacg gcgacctcct cacggacgaa gcccgcatcc gcgttcatga cgccatcttt    720
agccaacgtc cgctcaagcc ggtggacccg ggcgctgca cgttcgaaac agatcagcga     780
cgcgcaccga aggcactccc gagctctcaa ctgttccgca tctaccaaga acttaacgcg    840
atcagagtga tcgatccgtt ctcatcgagc caagcagatc gacccctgac gcgtcaggag    900
cgcgatgccg gcgcatcgtt cctcctgggc agggtgaagg ccaccttccc tcaactcaag    960
aaggcgatgt ttgggcccac aaagctccaa ctctcacttg agtacggaga acgcaagaac   1020
atcctgggtg acgtcgtagg aagcgagttg cgcaaagcgc agcacatcgg cccagactgg   1080
gagacgtatg acctcgccac ccaggacctc atcgtgacga tcctgctcga ggcagacact   1140
gacgatgaag tgatcgagcg gcttcaggct gagtcgtcgc tatcgctcga tcaggtccac   1200
ggcgcgcttg aggcaccact cccggacgac tacctacggc tgagccatcg tgcgattggc   1260
aagatcctgc ctcatctcaa ggatgaatgg aatgaagagg gcaatgcacc ggtgatgtat   1320
gacgcggccg tccgtgccgc gggataccaa tcgcactcag agttccacag cggtgttctt   1380
gaagacacgc tccctatta cgggaaggtg ctgaagcgat acacgcaaga ggtctccggg    1440
agcagccaag ctgctacgaa ccctgacgaa tgggagttcg gcaagatcgc caatccgacc   1500
gtgcacatcg gcctcaatca gatccgcacc gtcgtgaact cactgattga ccgctacggc   1560
ctgcccacac agattcatgt cgaggtagcc cgcgacttgg gccagtcggc tgagggaagg   1620
cgtgaagcag cgtccaaccg tgccaagaat gaacgagcaa acgaagcgct caacgcccgc   1680
ctgaccgaac tgggacaacg caccaacttt gccaatcggg agcggctgcg cctctacgat   1740
gagatctcag tcctcaatca caggtgtgtc ctgacaggca tccccatcga gatgtcgcga   1800
ctgttcacca atgactatca ggttgaccac atcctgccgt tctcccggac cctggacgac   1860
tcgcgcggaa acaagattct ggttcaccac acggccaatc agttcaaggg cgcccggagc   1920
cccttcgagg catactcgga gacggcagac tgggatcaca tccttcaacg cgcaagcgat   1980
gcctttggcg ctacgagccc caagttcaag cgcttttctg ccgacgccat ggacaggtac   2040
tcgaacggcg agcaagactt catcgcccgc caactcaacg acaccagcta cctggcacga   2100
gtgacacgcg agtatctagg gagcatcgtg atcccgacc ggatcctagc cacaccgggc    2160
agacttactt cgctcttgcg ccaccactgg gggctcaatg gcctgctatc cgatgccgcg   2220
gagaagaacc gctcagatca ccggcaccac gccatcgatg cccttgtcgt tgcactcagt   2280
gagcgagtaa ctctaaaggc cgtcaccgac gccaaccgtc gtgccggtga ccaaggcatc   2340
gaacgcttgc tagtcgacct cccccagccg tgggagggct ttgcggatca tgcccgtgag   2400
```

| | |
|---|---:|
| tctgttgatc gcattgtggt gtctcacaag ccagatcaca atgagaaagg ccagctccac | 2460 |
| gaagagaccg cctatggagt cctggaaggg cccgacaaaa agggcaggtt cctcacccgc | 2520 |
| aagcgcatca cggaccctgc caaggtgtg gtaggcagtt gggagcaacc caagtggcgt | 2580 |
| gacgtcattc cgctgtacag gcgcggcgag gggccagact cgaccttcc ctacaaggct | 2640 |
| tacattggcg gctccaacta ctgcatcgag atcgtccgaa ctgccaaggg gaaatgggct | 2700 |
| ggggaggtag tctccacgca caccgccaac acggccgagt atcgcgcttt catggcagag | 2760 |
| ccgggcgcgt atcgcgccca gagttacgcc ggtggtgacc tcgtcatgcg gctcatcgcc | 2820 |
| aatgacacca tcgcaatcga agtcggcgat gcgggtcgcc agatcatgag gctgtgccag | 2880 |
| ttggagacgg tcggagctat gtacttcgca aatgtgcgtg aaggcaacgt cgcagcacgt | 2940 |
| tcacgggctc gagacaacga cttttcgttg ctcaagaagg cggcaagcac acttcagcca | 3000 |
| ctcaaggctc ggagagtctt tgttgatccc attggcaggg tttttgaccc tgatttcaag | 3060 |
| gag | 3063 |

<210> SEQ ID NO 11
<211> LENGTH: 3138
<212> TYPE: DNA
<213> ORGANISM: Fuerstia marisgermanicae

<400> SEQUENCE: 11

| | |
|---|---:|
| atgaactaca ttcttgggct ggatcttggt tccgcctcac ttggctgggc agttttggaa | 60 |
| tgcaccgaag tcgacggcag cctgcagccg actcgcatcg aacgcacggg tgtgcgaatt | 120 |
| ttcgaagccg cgctggaagg cgacatcgaa cagggccgcg acgcctctcg agcagccaaa | 180 |
| cggcgagaag ctcgtcaacc gcgtcgtcaa aactggcgga cgcagcaacg aaaacgcaaa | 240 |
| ctgttccgac tattacagca acacggactg ctgccggctt cagaaaagga cgacgcgatc | 300 |
| agccgcaaag ccgtgttcga tcaacttgac aaggaactga ccgaaaaaca catcacggaa | 360 |
| ggcgatcaca cagcccatca gcacctgccg tacctgctgc gaatgctggc atctggcgca | 420 |
| aaggtgaagc catttgaact tggacgagcg atctacagcc tcgctcagcg ccgtggcttt | 480 |
| ctcagcaacc gcaaagctga cacagatgaa aagaagacg gcgttgtcaa agcgagcatc | 540 |
| tccgaacttg gcggtcaaat agctggtcgc acgatcgctc agacgtttgt cgaagacatc | 600 |
| agtccggacc atgaagatcc tggtcgtcaa cgcatacggc aacgctacac agcccgtgag | 660 |
| atgtttcatg acgaattcaa tcgaattcga aaacagcagc aaccgcactt cgacctcgcg | 720 |
| gacaatgact gggataccgt ttataaaaca atcttctttc agcgtccgtt gaagtcgcag | 780 |
| cgtcaccgca tcggccgttg cgaaatcgat ggcggtcagc gttgtcttga tgctcttgat | 840 |
| gtctttcagc agtttcgtat ctggcacgcg gtgcagaatc tgcgactcgc ggacgcctac | 900 |
| agtttggggc gggacggtcg gctgacgctg gaagaacagc agaagattgt cgacgcattg | 960 |
| cagactcagg ccacgatgac gtggggaaaa gtcgttacgc tgctgggtct aaaacgcggc | 1020 |
| acgaagttca caattcagga atggaacacg aaagggctaa cagggcatcg caccaactct | 1080 |
| gcgatgatgc acgtcttcgg cgatgaatgg ctggacaggc cattggaaga acgagacgcc | 1140 |
| atcacaaagg aagtcgtcta cttccgcaaa ccatcagcga tgagaaaacg gggccaggaa | 1200 |
| gcatggggac tgtcagagga acaggccgcc ctgctaccgt caactcggct ggaagaagct | 1260 |
| cacgcccgac attccgccgc gacattggcc atctttgtcg aacgcatgag tcgtggcgaa | 1320 |
| gactattcca ccattcgcaa agacattacc ggcaaagacg acagcgaacc actcgaccag | 1380 |
| cttccaccgc tcagcaaagc cgggctggac atcaccaacc ccgccgtcat tcgtggcctg | 1440 |

```
acagaacttc gcaaggttgt gaacgaactg gtgcggcaat acggcaagcc catcggcatc   1500
cgcatcgaac tgtctcggtc gctaaagaat tcgcgagaca aacgcatcaa gctgcacaaa   1560
gataacgaag atcgtcgtaa gcgtcgcgag aaggcgatcg aaggtattct gaagcaaatc   1620
cctggccggt actcgggcaa cgatatcgaa aaatggctac tcgcagaaga atgcggctgg   1680
cactgtccgt acaccggaag accgatttcg ccttccacac tgcttgggtc gcaaccacaa   1740
ttcgacatcg agcacatttt cccgcgccga tatctcgaca acagcttcag caataagacg   1800
ttgtgctatc acgaattcaa tcgcaacgtc aaaaagaacc aaaccgcctt cgatgcgtgt   1860
tccggcctcg atagctggga cgaaatcctg cagcgtgtca acaactttga tgggccggtc   1920
gcagcattaa aacgtaaacg ctttctgacc gcagcgaaag aaattccgga cggtttcact   1980
tcaaaacacc tcaacgataa tcgctacaac gcagttgtcg cgaagaaata cgtggccatg   2040
ctgtatggcg ggctgtcaga cgcggatggt agtcagcgag tctttgctgt cacgggcgga   2100
cacacggcac tgctgcggcg agaatggggc ctgaattcga ttttaagcgg aaccgaagag   2160
aaaacacgag acgaccatcg gcaccacgcc gtcgatgcgg tggtgatcgc attgacagac   2220
ccggcaagaa ttcaggcttt ggtaaacgct gcagagcttg ccgaaaagaa agcgtctcgc   2280
cgcttttacg aagccgtcca ggacccgtgg ccgaagttca gcagcaaagt cgctgattca   2340
atcaatgaaa tagtggtttc ccaccgtccg accagaactc ttccgggagc tctgcatgcg   2400
gaatcgattt atagcaaacc gcacatcgac aaagacggca cacgaaccca tcgcattcgg   2460
aaacacatca ccaagctgtc tgcaaccgaa ttgaagaagg acaagattgt cgacccagcg   2520
attcgcgatc tggtgaaggc caaactgaaa gaactcggcg aatccaatcc ggcgaaagcc   2580
ttcgccgagg agaagaacca cccgttctta accgcaaaag acggtcgcaa ataccgatt    2640 cacaaagtgc gagtgtttgc cgacaagaaa cctcgggcaa tcgccaaaaa cgagcggcag   2700
cgctatgtcg ccagcggaaa agattccaac tttgcgtcca tgatttacgc cgtcgtcgac   2760
aaagacggcc acgaaatcaa atgggaacac aaagtcatca cccgcctgga ggcgcacgaa   2820
cgtaagactc gtaatcgtac ggtgaacgga gagaaagtgc tgctaccaga tcccaccgac   2880
ttcaacgacg acaagaagcg ggtcttcaaa ttcgcgttgt gtaagaacga tacagtgatg   2940
ctggaaggcc ccgacggaga cgacgtgatt tgtcggatac agaagatcag tcaagccgaa   3000
attcagctgt gtccactggc gacgccgtct gttcaaggaa aagctcgttc gaaatggaac   3060
caaatccaat caatcgacaa tctgcgaaaa tggaacctca aacggttct aatttctccg    3120 acgggtattg agcatagg                                                 3138
```

<210> SEQ ID NO 12
<211> LENGTH: 3108
<212> TYPE: DNA
<213> ORGANISM: Nitrosomonas sp. Nm33

<400> SEQUENCE: 12

```
atgctgcata agatgcgcta tcgactggca cttgatttag gatcaacttc actgggctgg   60
gcgatgatta gattagatgc caatcagcga ccctgtgcgg ttatcaaagc gggggtgcgt   120
attttttcga acggccgcaa tccgaaagat ggttcttctt tggctgtaac ccgcagagaa   180
gcccgcgcca tgcgtcgtcg tcgtgatcgt ctgctcaaac gcaaggcacg catgatgcgt   240
acactcatag aatatggctt ttttcctgcc gaagaagcgc agcggaaggc actagaaaca   300
ctcaatcctt ataaattacg tgctgatgga ttggataaag cactcactcc ggctgaattt   360
```

-continued

```
ggccgtgtat tgtttcacat caaccaacga cgcggattca agagtaaccg caaaactgat     420
aaaaaagata ctgatagtgg tgcgctaaaa accgctatca gcaaattgcg cgaaatactg     480
aaaacagaaa actgccgcac cgtgggtgaa tggctgcaca aacgcaatca agcaggtcaa     540
actgttcgcg ctcgctaccg ccaagacaaa actatcaagg atgatggcaa ggcaaaaatt     600
gacaagtatt acgatctcta tattgaccgc gccatgattg agcatgagtt taatgaatta     660
tggagaaagc aggcagaatt caatccagcc ctattcagca gtgcagccta caccgacttg     720
aaagacgtat tgttgtatca acgtccgctt aaacctgtca aacctgggcg ttgcacctttt    780 atgtccgatg aagaacgtgc accgttagca ttacctagca cccaacgctt ccgtatgtat     840
caggaggtta ataatctgcg tatcctgcgg gaaggcttga aggaagaacc tctgacattg     900
cagcaacgcg atgatctaat tgttgtgcta gaaagaaaca ataaacgcac ctttacgcaa     960
attaagaaat tgcttggcgt tggcggtgca gttcagttca actttgaaga tccgaaacgt    1020
gaggaactta aggtaatac caccaacgcc attcttggca aaaagaaca ttttggtgag      1080 gcttggattg cgttcgacga agctaaacaa gacgccattg tcatgcaatt aatcaaagag    1140
gaaaacgaag ctaaactcat ccagtggctg caagatgaaa ccggcattga ggaagaacgt    1200
gctgaaatca ttgccaatgt tggattaccg gaaggctatg gcagtttagg tacaaaggca    1260
ttagcacgaa ttctgccaga actgcgccgt gatgtggtga catacgacaa ggcggtacaa    1320
gctgcaggct tcgagcacca cagtaaactc aatcaaaata gaggaattcc cggcatcacg    1380
ttcaaaatcg aaagcattga tcaagatact ggtgagatca aagaatttca cattcacaag    1440
gaattgcctt attacggtga atatctgcaa cgccacgttg gatttggcag cggcaaaccg    1500
gaagatccca tcgaaaaacg atacggcaaa attgctaacc ccaccgtgca tatcgggtta    1560
aatcaggtac gccttgcagt aaacgcgctc attaagcgct acggtcatcc cagcgaagtc    1620
atagtcgagg tggcgcgtga cttgaaacaa agcaaagagc agcgcagcga agaaaataag    1680
cggcaagctg aaaatcagca acgcaacaat cggttacgca ctgaaattgc tagaattta    1740 cagattaatg aagagggcat ccgtcgcgac gacattgaga agatgattt atggatcgaa    1800 ctcagtgctg atgtcgctga ccggaaatgc ccttattcag gtgtaccgat cagcgcaacc    1860
atgctcctga gcgacgaagt ggaaattgag cacatttttgc ccttctcaca aacgctcgat    1920
gacagtctca acaacaaaac ggtggcgctc cgtaaagcca atcgcgttaa aggagaccgg    1980
acaccgtggg aagcacagca agattttgct gctcaaggct ggagctatgc ggatatcctc    2040
gccagggcag aaaacatgcg caaagaaaaa cgctatcgtt ttgccgaaga tggttataaa    2100
cgctggctga aggatgatgc gggattccta ccgcgcgcac tgaatgacac gcgctattta    2160
agcagagtgg cacgcgaata cctgcacctg atttgcccca atactcgtgt catccctggt    2220
cgcataaccg ccatgctgcg cagtcaattt ggtctcaaca aggtgctcgg cttgaacgga    2280
gaaaagaacc gcaatgacca ccgccaccac gcggtggatg cctgcgtaat tggcgtgact    2340
gatcagggtt tgttgcaaaa attcgcaaaa gccagtgcca gcgcgcgtga aaagcaactc    2400
aaccggctcg tggacaacat ggagtcaccg tggaaaaact accaagagca tgtacaacgc    2460
gccattgatg ctatttgggt tagccacaag ccggatcaca gccacgaagg cgcaatgcac    2520
aatgacacag cttatggctt gcgaggcaat ggcaaagtca gtttccataa aatgatggat    2580
ggtaagcgtg aatacattga agataatctc aaagtcattg aaattgccga tacaaaagct    2640
gcagaacgcc atggcttgtt gcccaatggt aaacctaaac cctataaagg ctacaaaggt    2700
gacagcaact actgcattga aattgttcgc aatgaaaaag gcagatggga aggagaggtt    2760
```

```
atttctacct tgaggctta tcagctcgtg cgtgaacagg gtgccgcaca gcttcggcat    2820
ccggctttgg gtatcagcgg gaaacctttg gtaatgcggt taatgattga tgacacagtt    2880
cgtttagatg ttgacggtca atcttgcaca atgcgaatag cgaaattaag tagtaatggg    2940
caaatattca tggcagacat atgtgaagca aacgttgatg caagaaatcg aaataaagaa    3000
gattcatttg cctacatttc caaaatggca ggttctcttc aaacagccaa agcacgccgc    3060
gtcaccattt ctccgattgg cgaactccgc gattccggtt tcaagggg              3108
```

<210> SEQ ID NO 13
<211> LENGTH: 3186
<212> TYPE: DNA
<213> ORGANISM: Novosphingobium sp. SYSU G00007

<400> SEQUENCE: 13

```
atggagaagc gcctgggact ggatatcggg acaaactcga tcggttggtg cctgtatgaa      60
ggcgacagca ttctcgatat cggcgtgaga atcttctcgg acggacgaga cccgaaatcc     120
ggggcaagtc ttgccgttga tcgccggaat gcgcgtgcca tgcgtcggcg ccgcgatcgt     180
tatcttggtc gtcgatccgc tctcatcaag gcgctcaaag cccatggcct tttccccgca     240
gaacaggatg cggcaaaggc gctcgaacgc gaggatccat acagcttgag ggttcgtgcg     300
ctcgatcatc ggctggatcc gcatcagatc ggcaggcga tctttcacct gaaccagcgt      360 cgtggttttcc gctctaaccg caaggccgac agggtattgg gcgatcagga agcggactg     420 atttccaccg ccactcgtgt tctggatgag gcgatggcca aaagcggcgc gcgcacccct    480
ggcgagtttc tcgcttcacg cgacacccgc agagtgcgca tgcggcctga cgtcaagggc    540
tatgatttct atcctaatcg gcaacactat ctcgaagagt tcgagaagat ctgggacgcg    600
caatcgcaat accaccccga tctgctgagc caacaggcga atccgccat ccaccgaatc     660 atctttcacc agcgcccgct taagccgcag gctgtcggca catgcacttt cgccgggtta    720
cacggcatcc ctggcgatga aacgcgcttg cccaaagccc atccctgtt ccagcagcgc     780 aggctttacg aggaagtcaa ccagcttgag atcgtttgtg caagcgcccc tgcccgcaag    840
ctgacgcgcg acgaacgcga tgccctcatc ctcaagctgc aggacaaaaa gaaggtcact    900
ttctccaccc tcgcgcgcac cataagattg aaggagggtg aacgcttcaa caaggaaagc    960
gagaaccgga aggatctggc aggcgacgaa gtgcgtgccg atgagtgaa caagacgcg    1020 tttggcaggc gatggtttca cctttcccctt gatgagcagt ggtctgttat cgaccgcttg    1080
ctgaacgagg aaagcaccga agacctgctg gcctggctcg aaaaggaatg gtcgctgccc    1140
agcgatgtcg ccgaggcagt agccaatgcg catctgccag acggccatgg caggtttggc    1200
cttactgcca ccgttcgcct gttggaacac ctcaaggctg acgtggtgac ttatgccgaa    1260
gcagcaagac gtgcaggctt ccaccacagc gactttcgcg atggcgcgtg ctacgatgag    1320
cttccctact acggggagat actttcccgc gagatcgcgc caggcaagga cgaatacggc    1380
gatccgctgg aacggcaatg gggcaagatt accaatccca ccgttcacat cggactgaac    1440
cagttgcgac ggctgatcaa cgcgcttgtc agacggcacg tcgtcccga tttcatttc     1500 gtcgaactgg cgcgtgagct gaagctgaac gaaaagcaga aggccgacca aagcgccgg    1560 atcaagcaga caaccgatgc cgcccgcgcc agggcagaaa agctgcgcga tcggccag     1620 cgcgacagtg gcagcaaccg gatgctcctg cgcatatggg aagaactgaa tccctccaat    1680
ccacttgacc ggcggtgccc ctattgcgcc gaacccattt cgatcgagat gctgatgagc    1740
```

-continued

```
ggatcagccg atatcgatca cattgttccc tattcgcgtt gccttgatga cagcgccgcg   1800
aacaaggttg tcgcgcataa ccactgcaat cggcagaaag gaaaccgcac cccatgggaa   1860
caatggggc aaacgacgcg ctggcccttg atccaggagc aggtcgctcg catgcatcgg    1920
tccaagcaat ggcgctttgg ccccgatgcg atggaacggg tggaccggga tggtggcttc   1980
atcgctcgcc agcttaccga cacccagtat ctttcgcgca ttgcggcgca gtatctttcc   2040
gctctctata cacccgatga gggacggcgg gtctatgccg tgactggccg gttgacggcg   2100
atgctccgcc gactgtgggg actgaatgac atcctgcccg atcacaactg ggttctgaac   2160
ccgcacagca acgcacccaa gaaccggctt gatcaccgcc accatgccat tgatgctgcg   2220
gtggttggtg ccacaactcc ggcaatgatc cagcaggttg ctagagcggc agcacgcgcg   2280
gaagagcagg atcttgaccg gctctttgcc gatctgccac cgccatggcc aggcttccgc   2340
gaggaactgc agggccgcat catggccgct gttgtcagtc acaagccgga tcatgggcgc   2400
aaggggcgtc cccttccagg gcgagacagc acctcaggcc gcctgcacaa cgatacggcc   2460
tatggcttca ccggaaggcg caatgccaag ggcatgccga tcgtggtcac gcgaaagccg   2520
ctgctggccc tcaagcccga agacctgacc gatccggaaa gaatacccga cccggcactg   2580
cagggcgcgt tgtttgaagc cacgcggggc gcaaccggca aggactttga aaaggcgctg   2640
cgcgactttt cgcgaaggga cggcccttat cagggcatcc ggcgcatacg gttgaccgaa   2700
gcgctcaacg tgattccgat ccgtgatcga acaggacacg cctataaggg tgtaaagggc   2760
gatgccaatg cgcgtttcga tgtctggcgg cttcctgatg gcaaatggat cacgcggtgg   2820
aaggaccggg acggcatcga acattccggc atagtatcgc tgttcgatgc acatcagccg   2880
agccaagtct atcaccgccc ccaccctgcc gcgaagaagg tgcttagcct gcggcagaat   2940
gatctcgttg cggttgaaca cgatggcgac ccaggcaaga tcatgcgtgt ggtcaagttt   3000
tctgccaatg gctcgatcac cttcgcccca cataacgaag ccgggccgct aaagacgcgt   3060
gataccgacc ctgccgatcc gttccgttat gtcaccactg ttgcgagcgg actgaagaag   3120
atgcgcgcgc ggcaggtgcg gatcgacgaa ctaggaaaag tccacgatcc ggggccgcgc   3180
gaagac                                                              3186
```

<210> SEQ ID NO 14
<211> LENGTH: 3225
<212> TYPE: DNA
<213> ORGANISM: Paracoccus bengalensis

<400> SEQUENCE: 14

```
atgaccacta cactcggcat tgatcttggc acgtcgtcgt tgggctggtg tctcatcgaa     60
gacgaacacc gcatcctcga tctcggcgtg atcatcttca gcgccgccgc cggtgccggg    120
cgcgacccgc aatcgggcgc acccctcgcc gaagcgcggg gcgaggcccg ttcggcgcgg    180
cggcggcggg acaggttcat cggtcgccgc tcggctcttc tggacaagct gatcgcgctc    240
ggcctgctgc ccgagaccc gcccgcgggc catgggcggc ggcgcaacca ggcgctgccg    300
aatgccgaga cgaaggcgct ggccgacacc gatccccatg tcctgcgccg ccgggctttg    360
tcggagccac tttcgccgca cgagatcggc cgggcgatct tccacctcaa cacccggcgc    420
ggcttcaagt cgaaccgtaa ggccgaccgg ggccgaaacg agcccgaaac cggcaagatc    480
gccaccgccg gccaggcgct ggacgcggcc ttgggcaagc gcaccctcgg ccaatttctg    540
gccgaccgga tcgacgccgg gcaaccgcg cgggtgcgga tgggtggcga gaaccaggcc    600
tatgatttct atccccagcg cagccatctc gaggcggagt tcgcggcgat ctgggaggcg    660
```

-continued

```
caggaacacc accaccccga gttgctgacc gacacggccc ggaccgcgat ccatcgcatc    720
ctgttctttc agcgcccgct gaaaacgccc gaggtgggtt tttgcacctt cgccggcatg    780
agcggtgtgc ctcacgacga gcgccggctg ccaaaggcgc atccgctgtt ccaggaacgg    840
cggctctacg aggaggtgaa caacctcaag gtagtcgccg ccggagccgc tgcgcgcgac    900
ctgacgctgg atgaacggga ccggctgatc ctcaagttgc gcgacaacaa gaaagtcacc    960
ttcgccactt tggccaagaa ggtgctgaaa ctggccgagg cgagcggtt caacaaggaa   1020 agcgaagccc gcaaggacct ggcgggcgac gaggtccggg ccgagatggc ggacaagaag   1080
cgcttcggca atcgctggac gcatttcccg ctggagcgga agttgcagat catcgaccgt   1140
gtgcagaacg aggaaaatcc cgatatcctg ctggcctggc tgcaatccga ctgcgggctg   1200
gacaaggcgc cggcggtcgc ggtggccagg acgaacctgc ccgaggggca cggccgcttc   1260
ggcgagaccg cgaccggcg gctgatcgcg gctctaaagg ccgaggtcgt tacctatgac   1320
aaggccgcgc tggcggcagg gttccaccat agcgatcacc ggacgggcga ggtttacgac   1380
ctcctgccct attacggcga ggtcctgacc cgtgagatcg cgcccggcaa ggcggagtac   1440
ggcgatccgc tcgaacgcca atatggcaag gtcaccaatc ccaccgtcca tattggcctg   1500
cgccagttgc aaaagctggt gaatgcggtg atcgcccggc atggcaggcc cgaccggatc   1560
gtcatcgaac tcgcccgcga actgaagctc aatgacaagc agaaggacga gcatcagcga   1620
cggatcaggc gggataccga ggcggcgatc cgcaggggcg agaagcttgt tgaggcgggt   1680
attgccgata ccggcgccaa ccgcgccctg atgcggcaat gggaggagct gaacccgtcg   1740 aacccctcg accgtcgctg cccctactgc ggcgagccga ttggcatggc gcagattttc   1800
aatagcctag cggatatcga ccatatcatc ccctattcca ggtcgctcga cgacagcccg   1860
gcgaacaaag ttttggtcca tcgcaactgc aaccgccaga agggcaacaa gacgccctgg   1920
gatcggtggc acgaggacga ggcgaaatgg gaaatcatct cggcccaggt tgcgcggatg   1980 caccttcga aacaatggcg ctttggcccc gacgcgatga gcggctgga acgcgacggc   2040 ggcttcgccg cccgccaact gactgatacc cagtatctgg cgcggatcgc ggacaaatac   2100
ctgcgcggcc tttatccgac tgctgatgag ggccgggtcg atgtcatccc cgggcgcatg   2160
accgcgatgc tgcgccgggt ctggggcctg aacagcctgc tgcccgacca taacttcgtc   2220
gagaacgaac attccagcgc accgaagaac cggctggatc accgccacca tgcgattgac   2280
gccacggtcg cggcggtgac atctctgtcc cggatgcagc agatcgcagc cgcagcggcc   2340
cggtcggagg aaaaggaatt ggagcgcctg ttcgacgatc tgccgcatcc ttgggacggc   2400
ttccgcgagg acctgggcgc gtgccttgcc cgcacagtcg ccacgcacaa gcccgatcat   2460
ggacgcagcg cgaaaccctc gcgccaccgc gatgtgacgg cgggcaagct gcacaacgac   2520
accgcctatg gcctgaccgg cctgaagacc accgatggca agacccctat cgtcgtgcac   2580
cgcgttctcc tggcctcgct gaagcccacg cagatcgccg accccgactg tattcccgac   2640
gaaaccctcc gcaacgccct gtggctcgcc acccgggact gttccggcaa ggccttcgat   2700
caggccctag cgcgcttcgc caaggagcat ccggtgttca agggcatccg ccgggtgagg   2760
atacgcgagc cgctgaacgt catcccgatc cacgacaggg aaggaaaacc ttacaaaagc   2820
tatgccgggg cgtccaacga ccgatacaat gtctggcgga tgcccgacgc ttcctggcgg   2880
catgatgttg tgtccacctt caacgcgcac cggagcgatt atcgcgacct cgcccgcac   2940 ccagcggcga aaaggttttt atcgctacgc cagaacgata tgatcgcggt ggagcgtaat   3000
```

```
ggtgggcttc gggagattat gcgggtcgtt aagttcaacc aagccgggcg gctgactctt    3060
tgtccgccga acgagggcgg caagcttcag aaccgggacg cggcaccgaa cgacgccgat    3120
ccgttcaaat acacttatct ttctcccagc tccctaaaaa acgccaaggc ccgtcaggtc    3180
cgcatcgatc cactcggtcg cgtcttcgat cccggcccac gcgaa                   3225

<210> SEQ ID NO 15
<211> LENGTH: 3135
<212> TYPE: DNA
<213> ORGANISM: Parvibium lacunae

<400> SEQUENCE: 15
atgaaaaaca aaatgcaata ccgtttggcc cttgatttag caccacctc acttggctgg     60 gccatgcttc gtgtaaaacc caatcccgaa ggccgtttag agccttttgc cgtcgtaaaa    120
gcaggtgtgc gaatcttttc agatggccgc aacccgaaag atggttcctc attagccgtg    180
acccgccgcg aagcgcgtgc catgcgccgc gccgcgacc gcttactgaa acgcaaagca     240
cgtatgctgc aacagctcac tgcctttggc ttttcccca ccgatctggc cgagcgcaaa     300
gcactggaaa cgctcaaccc ctacgaactc cgcgccaaag gcctagatga accactcagc    360
ccttatgagt ttggccggtc gctcttccac attaaccaac gccgtggctt aaaagtaac     420 cgcaaaaccg acaaaaaaga aaacgatagc agcgccctca agccgccat cggcgtgtg     480 gcgagcgaaa tcgacggcaa tcaggcgcgt accgtcggcg aatggctcta caagcggatg    540
ctcaatggtc agcccgtaag aggtcggtat cgcgaaacca aggtacaaaa agaagacggc    600
aaaaccaaaa tcgataaaag ctacgatctc tacatcgacc gcgccatggt agaggccgaa    660
tttgaagcgc tctgggccaa gcaagcctcg ctaaatcccg ccgtctacag cgagcaagcc    720
aaggccacgc taaagatgt tttactgttc caacgcaatt tgcgcccagt aaacctggc     780 cgctgcacac tgattcccac tgaagaacgt gcgccactgg ccctaccgag tacgcaacgc    840 tttcggatt atcaagaagt aaataacctg cgcatactac gtgaaggttt aaaagacgaa     900
gcacttacac tggtgcagcg tgatgcgctc gtcaccgcgc tggaacagaa caacaagcgg    960 actttgctc aaattaaaaa attgctcggt cttgatgggc aaacccaatt taattttgaa    1020
gaccccaaac gccaagaact caaaggcaat accaccagcg ctattctgag ccaccccaaa    1080
cattttggtg acgcttggtt tggttttgat gaagccaagc aagacgggat tgtgtgtcag    1140
cttctcaacg aagaaaacga aagcgcgctg attcgctggc tgatggatca cacaggggtg    1200
gatgaggccc atgccgaagc tattgccaat gcggcactcc ccgaaggcta tggctcgctc    1260
agccgcgctg ccctcgccaa gattctgccc gagctccgca aagcggtgat tacctatgac    1320
aaagcggcgc aagccgccgg gtttgaccac cacagccaca ttagccccag taccaccggc    1380
gaaattttgc ccgaacttcc ctattacggc gaggcgctgc aacgccatgt gggctttggc    1440
acgggcaacc ccgatgatgt gcctgaaaaa cgctacggca aatcgccaa ccccaccgta    1500 cacattggtt taaccaagt gcgcaaggtg gtgaatgcgc tcattaaacg ctatgggcac    1560
cccagcgagg tgattgtaga agtggcacgc gacctcaagc aaagcaaaaa gcagcgcgat    1620
gaagaaaaca acgccaggc cgaaaaccaa aaacgtaatg agcggattcg tcaagatatt    1680
gccgccatgc gtcctgatag aagtgaagag cgcgtgaccc gtacagatat tcaaaaatgg    1740
atcttatggg aagagctaag cttttgatcca gcgaatcgat gctgtcccta ctcgggcgta    1800
caaatcagcg ctgaaatgct aatgagtgat gcggtgaaa tcgaacacat cttgcccttc    1860
tctcgcacct tggatgacag cctgaataac aaaacggtgt ccatgcgcca agccaaccgc    1920
```

| | | |
|---|---|---|
| attaaaggca accaaacacc ctttgaggcc tttggtaaag acaatgctct gggcgtgaac | 1980 |
| tacagcgaca ttctgatgcg cgcgcagcag atgcccaaag ccaagcgcaa acgtttcgct | 2040 |
| gaaaatgctt tggaagaatg gctgcaaaat gaaaaaaatt ttcttgcccg cgcgctgaac | 2100 |
| gacacccgct acctcagccg cgtggcacgc gaatacgtca gcctgatttg cccacaagcc | 2160 |
| acacgcgtga ttccgggaca aatgacggca cagctccgcg ccaaatttgg cctgaatgac | 2220 |
| atactcggtt tagatggcga aaagaaccgc aacgatcacc gccaccatgc cgttgatgcc | 2280 |
| tgcgtgattg gcgtcaccga ccaaggcttg ctccagcgat ttgcctatgc cagcgccagc | 2340 |
| gcccgcgcaa atggactagc gcgtttggta gacaccatgc ctgacccttg cccagctac | 2400 |
| cgccagcacg tacaacgggc ggtacaaaat atttatgtca gccacaaacc cgaccacagc | 2460 |
| catgaaggcg caatgtttga cgaaaccatc tacagcgcca ctgggaaaag tcgcagcgca | 2520 |
| gctaaagatc gcacagtcat tccttttatt gctaaaaatt ggagccatcc tgacgaccac | 2580 |
| aacaaacagc gtccgttcaa gggcttgata acagatgttt ctcaacggca tcaaaacaaa | 2640 |
| ccctacaaag gattactatc aaacagcaat tactgcatcg aaatttattc ggatgaagca | 2700 |
| ggctggggtg gcatgtgtact caaaactttt gatgcctatc aaatcgtcag gcacacaaa | 2760 |
| aatgctagtg agggtatgca agcgctacgt aataaacata gcagccagaa tgggcaccca | 2820 |
| ctagttatgc gtttgatgat cggggactac attcgcgcag aaatagatgg tttcttattg | 2880 |
| ctgctccaag tacttaaaat caatagttca ggctcgatca ccttcattaa gccgaatgaa | 2940 |
| accaatatca gcgcacggta cttagcaaag ctagcagcac aaaaagctca aaaagaaggt | 3000 |
| aagccattcg atgacattgc gctgaatgat gttttcttc agaaagcaat atctgccgat | 3060 |
| agtttacggt tatttaaagc taggcctgtc accctctccc ccatcggtga gctacgcgac | 3120 |
| cccggcttta aaggc | 3135 |

<210> SEQ ID NO 16
<211> LENGTH: 3213
<212> TYPE: DNA
<213> ORGANISM: Pelagicola sp. LXJ1103

<400> SEQUENCE: 16

| | | |
|---|---|---|
| atgcgacttg gccttgatat tggaacgaac tccatcggct ggtggcttta ccggacggaa | 60 |
| aatgaccaga taacgtgcgt cgtcgatggc ggagtgaggg ttttctcgga tgggcgggat | 120 |
| ccgcagtcaa aggagtcgct ggccgtcgat aggcgcgtgg cccgtgcgca cgccgtcgc | 180 |
| cgtgacagat acttgcgccg caaggctgct ttgatgaaac ggatggctga ggcaggcttg | 240 |
| atgccagccg atcccgtgca ggccaaagcg ttgcaagctc ttgatcccta tgaccttcgg | 300 |
| gcacgggggc tcgatgaggc tttgccgctg gcgcatttcg gcggggcgct gtttcacctc | 360 |
| aaccagcgac gtgggttcaa atccaatcga aaggccgacc gcggcgataa cgaaagtggt | 420 |
| aagatcaagg atgcgactgc acggctggat tgggcgatgc gcgatgcacg cgcacgcacc | 480 |
| tatggcgagt ttctgcatat gcggcaggac aaggccgatg atccgcgtcg cgtcccgacg | 540 |
| gtgcgcacgc gcttgtccgt ggcgcggcgt gacaatgccg aaaaagagga ggcagggtat | 600 |
| gatttttacc ccgaccggcg gcacctgtca gaggagtttg acgcgctatg ggccgcacag | 660 |
| gcggaacatc acaccaccct gacggacgat ctgcgcgacc agatcaagac gatcatcttt | 720 |
| caccagcgcc ccctgaaggc gcctgaggtc ggtctgtgtc tattcacgga tgaacggcgt | 780 |
| attccgtctg cgcatcccct tgaaccagcg gcggatcctgt tggagacggt gaatgggctg | 840 |

```
cgaattgttg cgcgagggga ggcggcacgt gggttgactc gtgaagaacg tgaccagatc    900
gttcatgggc tagataacaa aggacatacg aaaaccctgt cgggaatgtc gatgaaactc    960
agggcaattg gcaaggtgat caaacttagg agtgaccaaa gtttcacgtt ggagactgcc   1020
aaccgggatg ccattgcctg cgaccccgtc cgtgctagcc tgtcgcatcc agaaaggatg   1080
ggcggggtct ggaccacact ggacgaagac gctcaatggg acgtggtgca acgcctccgt   1140
gcggtgcaga gtgataccga gcatgaggcg ctggttgatt ggttgatggc cacccacggg   1200
cttggccagg attatgcgca agcaacggcg aatgcgccgc tgcccgaagg ttacggacgg   1260
cttgggctga cggcaacgcg caagattctg cgggcattgg aggctgatgt gatgtcctat   1320
agcgatgctg tggccgcctg tggttggtcc cattctggcg gaccaacggg tgaggtgttg   1380
gaggctctgc catactacgg tgaaattctg gaccggcatg taatcccggg aacaggtgtg   1440
aaaactgacg aggacgtcaa acgcttcggt cgtattacca accctacggt ccatatcggg   1500
ttgaaccaga tcaggcgact ggtgaaccgg atcatttgtg tgcacggcaa gccggaccag   1560
atcgtggtgg aggttgcccg cgacctaaag aactccgagg atcaaaagcg tgagattcag   1620
aagacgatca ggaaaaatac ggatgacgcg atcaagcgcg gcaaaaagct ggttgaagaa   1680
ctggggcaaa aagacacagg cgcaaaccgg ttaatcctgc ggctgtggga aaaccttggc   1740
aatgacgtta tgacccgcca atgccsctat tctggcaagc gtatcagtgc ggcgatgttg   1800
tttgacgggt cgtgtgatgt tgatcatatc cttcctttct cacgtacgtt ggatgatagc   1860
atttggaaca agaccctatg cttgaaagag gaaaatcgga aaaaggctaa caagacgccg   1920
tgggaggtct gggcgaaac agaccagtgg gacgtgatcg tcgccaacct caagaatctt   1980
gatagaaagc aggcatggcg cttttgccccc gatgcggtgg aacggtttga gggcgagaac   2040
gacttttccg cccgtgcact aaaagatacc caatacctgt ctcgtgtggc acgggcttat   2100
ctggatgcgt tgtatgacgg ggcggacggc aaatcccatg tttgggttgt gccgggccgg   2160
ttgacggaaa tgctgcgccg ccattggggg ttgaacggga tcgaggtgct gacggacagc   2220
gacgcgcaaa ccgtgaaatc caagaaccgg caggaccacc ggcatcacgc catcgacgcc   2280
gccgtggtcg cagccaccga ccgcagcctg atccagcgga tcagcaagat agccaagcac   2340
gacgaacagg cgggcgccga acaggtcgcg cggtccgtcc cgccgccttg ggacggtttc   2400
cgtgatgatg tcgccggaca gatcgggcgg atcatcgtca gccacagggc agatcacggg   2460
cgcattgatc cgaccgcgcg cgcacaaggc agtgacacga cagcggggca gttgcatatg   2520
gatacggctt acgggatcgt tgacggtggg catgtggtca gccgcaaacc gctgatgtcg   2580
cttggtgcag gtgatatcag gaaaatccgc gatcccgatt tgcagcgtca tctcacgcgt   2640
gtcacgcgcg gtttggacaa gaaggaattt gaacaggctc tggcctcttt tgcggcgtcg   2700
cgcaaactgc cggaccaaag cgaaaaccct tatttcgggc tgcgacgtgt gcggcttctg   2760
gatgccttgc aagacagtgc ccgtgtgccg gttagaaacg ccacaggcaa tatctacaag   2820
gcctacaagg caggtagcaa ccattgctac gaggtgtggg ggatgcctga tggcaaggtc   2880
aagccttggg caatctcaac gtttgaggcg caccaatccg gcgatgggtc caagccccat   2940
ccggctgcaa aacggctctt gcgggtgttc aagcgggata tggtggtaat tgaacgtaaa   3000
gggataacgg tgatctgcta cgtccagaaa atggacgttg ccaacggcct gtttctggtg   3060
ccgcataccg aggggaatgc cgatgcgcgc aaccgcgaca aggaggatga tttcaaattc   3120
atccagatgt ctgcggcgtc tttgattaag gccagaatcc gccgcgttca cgttgatgaa   3180
atgggccgga tgcgcgaccc gggcccgccc cgt                                3213
```

<210> SEQ ID NO 17
<211> LENGTH: 3144
<212> TYPE: DNA
<213> ORGANISM: Artificial Sequence
<220> FEATURE:
<223> OTHER INFORMATION: OMNI-59 DNA optimized for expression in human
      cells

<400> SEQUENCE: 17

| | |
|---|---|
| aacgtgtgga aaggcaccgg cttcgtgtcc cggaagcgga acatcatcag atacagactg | 60 |
| gccctggatc tgggcagcac atctcttgga tgggccatcc tgagactgaa cgccgataat | 120 |
| cagcccaccg ccattctgaa agccggcgtg cggatcttca gcgacggcag aaatcctaag | 180 |
| gatggcagca gcctggccgt gactagaagg gctgctagag ccatgcggcg gagaagagac | 240 |
| agactgctga agcggaaggc ccggatgctg gataagctga tcgcccacgg attcttccca | 300 |
| caagacgaag ccgccagaaa ggccctggaa gtgctgaacc cttatcagct gagagccgag | 360 |
| ggactgcaga gggctcttat gcctggcgaa tttgccagcc catgttcca catcaaccag | 420 |
| cggagaggct tcaagagcaa cagaaagacc gacaagaagg acagcgactc tggcgccctg | 480 |
| aaaacagcca ttagccagct gagacagcag ctgcagaacg agaatgccag aacagttggc | 540 |
| gagtggctgt ggcagagact gcaagctgga cagggcacca gagccagata cagggaaacc | 600 |
| agaatcgcca ccgataccgg caagggcaag atcgacaaga gctacgacct gtacatcgac | 660 |
| cggcagatgg tggccgatga gtttgatgct ctgtgggccg tgcaggccgc cttcaatcct | 720 |
| gtgctgttta atgagcaggc cagagccgag ctgagagaca ctctgctgca tcagaggcca | 780 |
| ctgaggcctg ccaagcctgg aagatgtaca ctgctgcccg aggaagaaag agccccactg | 840 |
| gctctgccta gcacacagcg gttcagaatc ctgcaagaag tgaaccacct gaggattctg | 900 |
| caccccgacc tgagagaaga ggccctgaca ctggatcgga gaaatgccat gtgtggccctg | 960 |
| ctggaaaacc ggggcaaagt gacattccag gccatgcgga gaacactgaa cctgggagat | 1020 |
| gccgtgcagt tcaacctcga ggacgccaag agaagagagc tgaagggcaa cgccacaacc | 1080 |
| gccgctctga gcaagaaaga actgtttgga gccgcctggc acgacttcga tgaagccctg | 1140 |
| caggatgaca tcgtgctgag actggtcaca gaggaatctg aggccgaact ggtgcagtgg | 1200 |
| ctgatcgaga atactggcgt ggacgaagcc agagctaccg ccattgctaa taccggcctg | 1260 |
| cctgaaggct acggcagcct gtctagaaaa gccctggcca gaatcgtgcc agctctgagg | 1320 |
| gccgaagtga tcacctacga taaggctgtg caggcagccg gctttgccca ccactctgat | 1380 |
| ctgagattca gcttcgagta cgacagcgcc gacgtggaac aagtgggcga gagaatcgat | 1440 |
| aagaccaccg cgagattct gcccgtgtcc gcctttaagc agctgcctta ttatggcaag | 1500 |
| gccctgcaga gacacgtggc ctttggatct ggaaaccctc aggacccga ggaaaagaga | 1560 |
| tacggcaaga ttgccaatcc taccgtgcac atcggcctga atcaagtgcg agagtggtc | 1620 |
| aacgacctga tcagaagata tggcagaccc accgagatcg tggtggaact ggccagagaa | 1680 |
| ctgaagcaga gcagagagca gaagctggaa gcccagagaa agcaggccga caaccagaag | 1740 |
| agaaacgcca gaatcagggc cgagatcgcc cctatcctgg gcatctctga ggaaagagtg | 1800 |
| aagcacgccg acatccaaaa gtggattctc tgggaagaac tgagcttcga cgtggccgac | 1860 |
| agaagatgtc cttacagcgg agtgcagatc agcgccagaa tgctgctgag cgacgaggtg | 1920 |
| gaaatcgagc acatcctgcc tttcagccag acactggacg acagcctgaa caacaagacc | 1980 |
| gtgtccatgc ggcaggccaa ccggatcaag ggcaatagaa caccctggca ggccaggcag | 2040 |

```
gattttgaag cccaaggctg gccttacgag ggaatgcagc aacgggccga agaatgccc   2100 agagccaaga gatacagatt cgcccctgac ggctatgagc ggtggctggg agaagatcag  2160
ggattcctgg ctagagccct gaacgacacc agatacctga ccggatcgc cagagactac   2220 ctgacacttg tgtgtcctgg cggcgttaga gtgatccctg aagaatgac agccctgctg   2280 agggctaagt ttggcctgaa tggcgtgctg agcctgtccg gcgagaagaa tagagatgac  2340
cacagacacc acgccgtgga tgcctgtgtg attggagtga ctgatcaggg cctgctgcag  2400
agatttgccg aagcctctgc catggccaga cagcagggac tcgagaagct ggtggaaacc  2460
atgcctctgc cttgggagac ataccccgct catgtgcaga gagctgtgca gaacatctgg  2520
gtgtcccaca gaccagatca cggccacgaa gcggcatga tggaagagac aagctacggc  2580
atcagcaagg acggcaggat caagcagaga agaaaggccg atggcagcca gggcagagag  2640
atcagcaacc tgattcggat cagcgagccc tctcagcctg aaagacatgg cgttgacgcc  2700
gaaggccaac cactgcctta caagggctat gtcggcggca gcaactactg catcgagatc  2760
acccggaacg acaaaggcaa gtgggaaggc gaagtgatta gcaccttccg ggcctaccag  2820
attgtgcgga acatggcgt ggccagactg aggcatcccg agatggctca gaatgggaaa   2880
gccctcgtga tgcggctgat gatcgatgac tgcgtgcggc tggaactgga tggccgggaa  2940
gaaaccatga gagtggttgt gatccccaga aacggccagg tgttcatggc ccctctgcac  3000
gaagccaacg tggacgccag aaacagagac aagaacgacc ctttcagcta catctccaag  3060
atggccggca gcttcctgaa ggccaaagcc aggcacatca caatcagccc tatcggcgag  3120
ctgcacgacc ctggctttaa aggc                                         3144
```

<210> SEQ ID NO 18
<211> LENGTH: 3060
<212> TYPE: DNA
<213> ORGANISM: Artificial Sequence
<220> FEATURE:
<223> OTHER INFORMATION: OMNI-61 DNA optimized for expression in human
      cells

<400> SEQUENCE: 18

```
accggaacag atgccaccgc tcacagccac acaccttaca gactgggcct cgatgtcggc   60
acaggatctc ttggatgggc cgtcgtggaa ctggacaccg atggaaatcc tgtgcggatc   120
gtgcggaccg gcagcagaat ctatggcagc ggcagaaagc ccaaggactt tagctctctg   180
gccgccgata aagggccgc cagacagatg agaaagcagc gggatagata cctgcagcgg   240
cggacaagac tgatgcatga actggtggct gccggactga tgcctgaggc tgaggtggaa  300
agacagaagc tgaaggatct gaaccctac ctgctgagag ccagaggcgt gaaagaagaa   360
ctgacagccc acgaactggg cagagccctg tttcatctgc aacagcggag aggcttcaag  420
agcaacagaa agaccgaccg gaaggacgac gacagatccg ccatgaagtc tgccattgcc  480
agcctgcagt ctgacctggg agatgataca ctgggcacct acatgtggaa gagaatccag  540
aatggcgaga gcgtgcggag cagacctaga aaagtgggca gcaagaacga gtacgacttc  600
tacgtgaacc gcgccatggt ggaagatgag ttcaaccagc tgtgggacta ccagagccag  660
tctcacggcg atctgctgac cgatgaggcc agaattagag tgcacgacgc catctttagc  720
cagcggcctc tgaagcctgt ggaccctggc agatgcacct tcgagacaga tcagagaagg  780
gcccctaagg ctctgcctag cagccagctg ttccggatct accaagagct gaacgccatc  840
agagtgatcg accccttag cagcgaccag gccgatagac tctgaccag acaagaaaga   900
```

```
gatgccggcg ctagtttcct gctgggaaga gtgaaggcca cctttccaca gctgaagaaa      960
gccatgttcg gccccaccaa actgcagctg tctctggaat acggcgagcg gaagaatatc     1020
ctgggcgacg ttgtgggctc tgagctgaga aaagcccagc acatcggccc cgactgggag     1080
acatatgatc tggccactca ggacctgatc gtgaccatcc tgctggaagc cgacaccgac     1140
gacgaagtga ttgaaaggct gcaggccgag agcagcctgt cactggatca agttcatggc     1200
gccctggaag cccctctgcc tgatgattat ctgagactga ccacagagc catcggcaag      1260 atcctgcctc acctgaagga cgagtggaac aagagggca cgcccctgt gatgtatgat       1320 gccgctgtta gagccgccgg atatcagagc acagcgagt tcatagcgg cgtgctggaa       1380 gatacctgc cttactacgg caaggtgctg aagcggtaca cacaagaggt gtccggatct      1440
tcccaggccg ccacaaatcc tgatgagtgg agtttggca agatcgccaa tcctaccgtg      1500
cacatcggac tgaaccagat cagaaccgtg gtcaacagcc tgatcgacag atacggcctg     1560
cctacacaga ttcacgtcga ggtggcaaga gatctgggcc agtctgccga gggaagaaga     1620
gaggctgcca gcaacagagc caagaatgag agagccaacg aggccctgaa tgccagactg     1680
acagagctgg gccagcgcac caatttcgcc aacagagaga gactgcggct gtacgacgag     1740
atcagcgtgc tgaatcacag atgcgtgctg acaggcatcc ccatcgagat gagcagactg     1800
ttcaccaacg actaccaggt ggaccacatc ctgcctttca gcagaaccct ggacgacagc     1860
cggggcaaca agattctggt gcatcacacc gccaaccagt tcaagggcgc cagatctcca     1920
ttcgaggcct actctgagac agccgattgg gatcacattc tgcagagagc ctctgacgcc     1980
tttggcgcca cctctcctaa gttcaagaga ttcagcgccg acgccatgga cagatacagc     2040
aacggcgagc aggactttat cgccaggcag ctgaacgaca ccagctacct ggccagagtg     2100
acaagagagt acctgggcag catcgtggac cccgacagaa tccttgctac acctggcaga     2160
ctgactagcc tgctgaggca ccattgggc ctgaatggac tgctgtctga cgccgccgag      2220
aagaacagaa gcgatcacag acaccacgcc atcgatgctc tggtggtggc cctgtctgag     2280
agagtgacac tgaaagccgt gaccgacgct aatcggagag ccggcgatca gggaatcgaa     2340
agactgctgg ttgacctgcc tcagccttgg gagggattg ccgatcacgc cagagaaagc      2400
gtggaccgga ttgtggtgtc ccacaagcct gaccacaacg agaaaggcca gctgcacgaa     2460
gagacagcct atggcgttct ggaaggcccc gacaagaagg gcagattcct gaccagaaag     2520
cggatcaccg atcctgccaa gggcgttgtc ggatcttggg aacagcctaa gtggcgggac     2580
gtgatcccac tgtatagaag aggcgagggc cctgacagca cactgcctta caaggcctac     2640
atcggcggca gcaactactg catcgaaatt gtgcggacag ccaaaggcaa gtgggctggc    2700
gaagtggtgt ctaccatac agccaacaca gccgagtacc gggcctttat ggctgagcct     2760
ggtgcctaca gagcccagtc ttatgctggc ggcgatctcg tgatgaggct gatcgccaac    2820
gacacaatcg ccatcgaagt gggagatgct ggccggcaga tcatgagact gtgtcagctg     2880
gaaaccgtgg agccatgta cttcgccaac gttcgcgagg gaaacgtggc cgcaagaagc     2940
agagccaggg acaacgattt cagtctgctg aagaaggccg cctccacact gcagccactg     3000
aaggctagaa gagtgtttgt ggaccccatc ggcagagtgt tcgatcccga cttcaaagag     3060
```

<210> SEQ ID NO 19
<211> LENGTH: 3135
<212> TYPE: DNA
<213> ORGANISM: Artificial Sequence
<220> FEATURE:

<223> OTHER INFORMATION: OMNI-67 DNA optimized for expression in human cells

<400> SEQUENCE: 19

```
aactacatcc tgggcctcga tctgggatct gcctctcttg gatgggccgt gctggaatgt      60
accgaggttg acgaagcct gcagcctacc agaatcgaaa gaaccggcgt gcggatcttt     120
gaagccggcg tggaaggcga tatcgagcag ggaagagatg cctctagagc cgccaagaga     180
agagaggcca gacagcccag acggcagaat tggagaaccc agcagcggaa gcggaagctg     240
tttagactgc tgcaacagca cggactgctg cccgcctctg agaaggatga tgccatcagc     300
agaaaggccg tgttcgacca gctggacaaa gagctgaccg agaagcacat caccgagggc     360
gatcacacag cccaccagca tctgccttac ctgctgagaa tgctggcctc cggcgccaaa     420
gtgaagcctt ttgaactggg cagagccatc tacagcctgg ctcagagaag aggcttcctg     480
agcaatagga aggccgacac cgacgagaaa gaggatggcg tcgtcaaggc ctctatcagc     540
gaactcggag acagatcgc cggcagaaca atcgcccaga ccttcgtgga agatatcagc     600
cccgatcacg aggaccccgg cagacagaga atcagacaga ggtacaccgc cagagagatg     660
ttccacgacg agttcaaccg gatcagaaag cagcagcagc ccacttcgac ctggccgac     720
aatgattggg acaccgtgta caagaccatc ttcttccagc ggcctctgaa gtcccagcgg     780
cacagaatcg aagatgcga gatcgatggc ggccagagat gtctggatgc cctggatgtg     840
ttccagcagt tcagaatctg gcacgccgtg cagaacctga actggccga tgcctattct     900
ctggggagag atggcagact gacccctggaa gaacagcaga aaatcgtgga cgccctgcag     960
acccaggcca ccatgacatg gggaaaagtg gttaccctgc tgggcctgaa gcggggcacc    1020
aagtttacaa tccaagagtg gaacaccaag ggcctgaccg ccacagaac aaactctgcc    1080
atgatgcacg tgttcggcga cgagtggctg acagacctc tggaagagag ggacgccatc    1140
accaaagaag tggtgtactt cagaaagccc agcgccatga aaagcgggg acaagaagct    1200
tggggcctgt ctgaagaaca ggccgctctg ctgcctagca ccagacttga agaagcccac    1260
gccagacatt ctgctgccac actggccatc tttgtggaac ggatgagcag aggcgaggac    1320
tacagcacca tcagaaagga catcaccggc aaggacgaca gcgagcctct tgatcaactg    1380
cctcctctga gcaaggccgg actggatatc accaatcctg ccgtgatcag aggcctgaca    1440
gagctgagaa aggtggtcaa cgaactcgtg cggcagtacg gcaagcctat cggaatcaga    1500
atcgagctga gcagaagcct gaagaactcc cgggacaagc ggatcaagct gcacaaggac    1560
aacgaggacc gcagaaagcg gagagagaag gccatcgagg gaatcctgaa gcagatccct    1620
ggcagataca gcggcaacga catcgagaaa tggctgctgg ccgaggaatg tggctggcac    1680
tgtccttata ccggcagacc tatcagccct agcacactgc tgggcagcca gcctcagttt    1740
gacatcgagc acatcttccc tcggcgctac ctggacaaca gcttcagcaa caagaccctg    1800
tgctaccacg agtttaatcg aacgtgaag aagaaccaga ccgccttcga tgcctgtagc    1860
ggcctggatt cttgggacga gatcctgcag agagtgaaca acttcgacgg acccgtggct    1920
gccctgaaga gaaagagatt tctgaccgcc gccaaagaga tccccgacgg ctttaccagc    1980
aagcacctga cgacaaccg gtacaacgcc gtggtggcca gaaatacgt ggccatgctg    2040
tatggcggcc tgtccgatgc tgatggatct cagagagtgt ttgccgtcac cggcggacat    2100
acagcactgc ttagaagaga gtggggcctg aacagcatcc tgagcggcac cgaagagaaa    2160
accagggacg atcacagaca ccacgccgtg gatgccgtgg ttattgccct gacagatcct    2220
```

```
gccaggattc aggccctggt taatgccgcc gagctggccg aaaagaaggc cagcagacgg   2280 tttttatgagg ccgtgcagga cccctggcct aagtttagct ctaaggtggc cgacagcatc   2340
aacgagattg tggtgtccca ccggcctaca agaacactgc ctggtgctct gcacgccgag   2400
agcatctact ccaagcctca catcgacaag gacggcaaca ccaaccacag gattcggaag   2460
cacattacca agctgtccgc caccgagctg aagaaagaca agatcgtgga ccccgccatc   2520
agggacctcg tgaaggccaa actgaaagag ctgggcgaga gcaaccctgc caaggccttt   2580
gccgaggaaa agaatcaccc atttctgaca gccaaggatg gccggaagat ccccattcac   2640
aaagtgcggg tgttcgccga taagaagcct cgggccattg ccaagaacga gcggcagaga   2700
tatgtggcca gcggcaagga tagcaacttc gccagcatga tctacgctgt ggtggataag   2760
gacggccacg agatcaagtg ggagcacaaa gtgatcaccc ggctggaagc ccatgagaga   2820
aagacccgga acagaaccgt gaacggcgag aaggtgctgc tgcctgatcc taccgacttc   2880
aacgacgaca gaaacggggt gttcaagttc gccctgtgca agaacgacac cgtgatgctg   2940
gaaggcccag atggcgacga cgtgatctgc agaatccaga gatcagcca ggccgagatc   3000 cagctgtgtc ctctggctac acctagcgtg cagggcaaag ccagatccaa gtggaaccag   3060
atccagagca tcgacaacct gcggaagtgg aatctgcgga ccgtgctgat ctctcccacc   3120
ggaattgagc acaga                                                     3135
```

<210> SEQ ID NO 20
<211> LENGTH: 3105
<212> TYPE: DNA
<213> ORGANISM: Artificial Sequence
<220> FEATURE:
<223> OTHER INFORMATION: OMNI-76 DNA optimized for expression in human
      cells

<400> SEQUENCE: 20

```
ctgcacaaga tgagatacag actggccctg gatctgggca gcacatctct cggatgggcc    60
atgatcagac tggacgccaa tcagaggcct tgcgccgtga ttaaggccgg cgtgcggatc   120
ttcagcaacg gcagaaatcc taaggacggc agcagcctgg ccgtgactag aagagaagcc   180
agagccatgc ggcggagaag agacagactg ctgaagcgga aggcccggat gatgagaacc   240
ctgatcgagt acggattctt cccagccgag gaagcccaga gaaaggccct ggaaacactg   300
aacccctaca gctgagagc cgacggcctg ataaggctc tgacaccagc cgagttcggc   360
agagtgctgt ccacatcaa ccagcggaga ggcttcaaga gcaacagaaa gaccgacaag   420
aaggacaccg actctggcgc cctgaaaacc gccatcagca gctgcgcga gatcctgaaa   480 acagagaact gcagaaccgt cggcgagtgg ctgcacaaaa gaaatcaggc cggccagaca   540
gtgcgggcca gatatagaca ggacaagacc atcaaggacg acggcaaggc caagatcgac   600
aagtactacg acctgtacat cgaccgcgcc atgatcgagc acgagttcaa tgagctgtgg   660
cggaagcagg ccgagttcaa ccctgctctg tttagcagcg ccgcctacac cgatctgaag   720
gacgttctgc tgtaccagcg gcctctgaag cctgtgaagc ccggcagatg taccttcatg   780
agcgacgagg aaagagcccc tctggctctg cctagcacac agcggttccg gatgtaccaa   840
gaagtgaaca acctgagaat cctgcgcgag ggactgaaag aggaacccct gacactgcag   900
cagagggacg atctgatcgt ggtgctggaa cggaacaaca gcggaccttt cacacagatc   960
aagaagctgc tcgagttgg cggagccgtg cagttcaatt tcgaggaccc caagagagag  1020
gaactgaagg gcaacaccac caacgccatc ctgggcaaga aagagcactt tggagaggcc  1080
```

```
tggatcgcct tcgatgaggc caaacaggat gccatcgtga tgcagctgat caaagaggaa    1140
aacgaggcca agctgatcca gtggctccag gacgagacag gcattgagga agagagagcc    1200
gagatcattg ccaacgtggg cctgcctgaa ggctatggct ctctgggaac aaaggctctg    1260
gccaggattc tgcccgagct gagaagagat gtggtcacct acgataaggc cgtgcaggct    1320
gccggatttg agcaccactc caagctgaat cagaaccggg gcatcccgg catcaccttc    1380 aagatcgaga gcatcgatca ggacaccggc gaaatcaaag agtttcacat ccacaaagag    1440 ctgcccctact acggcgagta cctgcagaga cacgttggct ttggcagcgg aaagcctgag    1500
gaccctatcg agaaaagata cggcaagatc gccaatccta ccgtgcacat cggcctgaat    1560
caagtgcggc tggctgtgaa cgccctgatc aagagatacg gacaccccag cgaagtgatc    1620
gtggaagtgg ccagagatct gaagcagagc aaagagcagc ggagcgaaga gaacaagaga    1680
caggccgaga accagcagcg gaacaatcgg ctgagaaccg agattgcccg catcctgcag    1740
atcaacgagg aaggcatcag acgggacgac atcgagaaga tgatcctgtg gatcgagctg    1800
agcgccgatg tggccgatag aaagtgtcct tacagcggcg tgccaatcag cgccaccatg    1860
ctgctgtctg acgaggtgga aatcgagcac atcctgcctt tcagccagac actggacgac    1920
agcctgaaca caaaaacagt ggccctgaga aaagccaaca gagtgaaggg cgacagaacc    1980
ccttgggaag ctcagcagga ttttgccgct caaggctggt cctacgccga cattctggct    2040
cgggccgaga atatgcggaa agagaagcgg tacagattcg ccgaggacgg ctacaagaga    2100
tggctgaagg atgacgccgg cttcctgcct agagcactga acgataccag atacctgagc    2160
agagtggccc gggaatacct gcacctgatc tgccccaata ccagagtgat ccctggcaga    2220
atcaccgcca tgctgagatc ccagttcgga ctgaacaagg tgctgggcct gaacggcgag    2280
aagaaccgga tgatcacag acaccacgcc gtggatgcct gtgtgatcgg agttacagat    2340
cagggcctgc tgcagaagtt tgccaaggct tctgccagcg ccagagagaa gcagctgaac    2400
agactggtgg acaacatgga aagcccttgg aagaactacc aagagcacgt gcagagggcc    2460
atcgatgcca tctgggtgtc ccacaagcct gatcattctc acgagggcgc catgcacaat    2520
gataccgcct atggcctgag aggcaacggc aaggtgtcct tcacaaaaat gatggacggc    2580
aaacgcgagt acatcgagga caacctgaaa gtgatcgaga tcgccgatac caaggccgcc    2640
gaaagacacg gactgctgcc taatggcaag cccaagcctt acaagggcta caaaggcgac    2700
agcaactact gcatcgagat tgtgcggaac gagaaaggca gatgggaggg cgaagtcatc    2760 agcaccttg aggcctacca gctcgttaga gaacagggcg ctgcacagct gagacaccca    2820
gctctgggaa tctctggcaa gcctctggtc atgcggctga tgatcgatga caccgtcagg    2880
ctggatgtgg acggcagag ctgtaccatg agaatcgcca agctgtcctc caacggccag    2940
atcttcatgg ccgacatctg cgaggccaat gtggacgccc ggaacagaaa caaagaggac    3000
tccttcgcct acatctccaa gatggccggc tctctgcaga ccgccaaggc cagaagagtg    3060
acaatctctc ccatcggaga gctgagagac agcggcttca aaggc                   3105
```

<210> SEQ ID NO 21
<211> LENGTH: 3183
<212> TYPE: DNA
<213> ORGANISM: Artificial Sequence
<220> FEATURE:
<223> OTHER INFORMATION: OMNI-79 DNA optimized for expression in human
      cells

<400> SEQUENCE: 21

-continued

```
gagaagagac tgggcctcga catcggcaca aatagcatcg gctggtgcct gtacgagggc      60
gactctatcc tggatatcgg cgtgcggatc ttcagcgacg gcagagatcc taaatctggc    120
gcctctctgg ccgtggacag acggaatgct agagccatgc ggcggagaag ggatagatac    180
ctgggaagaa gaagcgccct gatcaaggcc ctgaaggccc atggactgtt tccagccgaa    240
caggatgccg ccaaggctct ggaaagagag gacccttaca gcctgagagt cagagccctg    300
gatcacagac tggaccctca tcagatcggc agagccatct tccacctgaa ccagcggaga    360
ggcttcagaa gcaacagaaa ggccgacaga gtgctgggcg atcaagagag cggactgatc    420
agcacagcca ccagagttct ggacgaagcc atggccaaaa gcggcgctag aacactggga    480
gagtttctgg ccagccggga cactagaaga gtgcggatga ggcctgacgt gaagggctac    540
gacttctacc ccaaccggca gcactacctg gaagagttcg agaagatctg ggacgcccag    600
agccagtatc accctgatct gctgtctcag caggccaaga gcgccatcca ccggatcatt    660
tttcaccaga ggccactgaa gccacaggcc gtgggaacat gtacatttgc cggactgcat    720
ggcatccccg gcgacgagac aagactgcct aaagctcacc ctctgttcca gcagcggcgg    780
ctgtatgagg aagtgaacca gtggaaaatc gtgtgcgcca gcgctcctgc cagaaagctg    840
accagagatg agagagatgc cctgatcctg aagctgcagg acaagaaaaa agtgaccttc    900
agcacactgg cccggaccat cagactgaaa gagggcgaga gattcaacaa agagagcgag    960
aaccggaagg acctggctgg ggatgaagtg cgggccgaga tgagcgataa gaccagattc   1020
ggcagacggt ggtttcacct gagcctggat gagcagtggt ccgtgatcga cagactgctg   1080
aacgaggaaa gcaccgagga tctgctggcc tggctgaaaa agagtggtc cctgccttct   1140
gatgtggccg aagccgtggc taatgcccat ctgcctgatg ccacggaag atttggcctg   1200
acagccaccg ttagactgct cgaacacctg aaagccgacg tggtcacata tgccgaagct   1260
gctcggagag ccggcttcca ccactctgat ttcagagatg cgcctgcta cgacgagctg   1320
ccttactatg gcgagatcct gagcagagag atcgcccctg aaaggacga gtacggcgat   1380
ccactggaaa acagtgggg caagatcaca accccaccg tgcacatcgg cctgaatcag   1440
ctgagaaggc tgattaacgc cctcgtgcgg agacacggca gacccgatttt catcttcgtg   1500
gaactggccc gcgagctgaa gctgaatgag aagcagaagg ccgaccacaa gcggcggatc   1560
aagcagacaa cagatgccgc tagagctaga gccgagaagc tgagagaaat cggacagaga   1620
gacagcggct ccaaccggat gctgctgcgg atttgggaag aactgaaccc cagcaatccc   1680
ctggacagaa gatgccccta ttgcgccgag cctatctcca tcgagatgct gatgagcggc   1740
agcgccgaca tcgatcacat cgtgccttac agcagatgcc tggacgatag cgccgccaac   1800
aaagtggtgg cccacaacca ctgcaacaga cagaagggca cagaaccccc ttgggagcag   1860
tggggacaga ccacaagatg gcccctgatt caagaacagg tggcccggat gcacagatcc   1920
aaacaatggc gcttcggccc cgacgccatg aacgagttg atcgagatgg cggctttatc   1980
gcccggcagc tgacagatac ccagtacctg tctagaatcg ccgcacagta cctgagcgcc   2040
ctgtacacac ctgatgaagg cagacgggtg tacgccgtga caggcagact gactgctatg   2100
cttagacggg tgtggggcct gaacgacatc ctgcctgatc acaactgggt gctgaacct   2160
cacagcaacg cccctaagaa caggctggat catagacacc acgccatcga tgccgccgtt   2220
gtgggagcta caaacacccgc catgattcag caggttgcca gagctgctgc aagagccgag   2280
gaacaggacc tggatagact gttcgctgac ctgcctccte catggccagg ctttagagag   2340
gaactgcagg gcagaattat ggccgctgtg gtgtctcaca gcccgacca tggaagaaag   2400
```

```
ggcagaccac tgcctggcag agatagcaca tccggcagac tgcacaatga caccgcctac    2460
ggctttactg gccgcagaaa tgccaagggc atgcctatcg tggtcaccag aaaacccctg    2520
ctggccctga aacctgagga cctgacagac cccgagagaa tcccagatcc tgctctgcag    2580
ggcgcactgt ttgaagccac tagaggcgct accggcaagg acttcgagaa agccctgcgg    2640
gacttcagca aagagatgg cccttaccag ggcatcagac ggattagact gaccgaggct    2700
ctgaacgtga tccccatcag agatagaacc ggccacgcct acaaaggcgt gaaaggcgac    2760
gccaacgcca gattcgatgt tggagactg cccgacggca gtggatcac cagatggaag    2820 gatagagatg gcatcgagca cagcggcatc gtgtccctgt ttgatgctca ccagcctagc    2880
caggtgtacc acagacctca tcctgccgcc aaaaaggtgc tgagcctgag acagaatgac    2940
ctggtggcag tggaacacga tggcgacccc ggaaagatca tgcgggtcgt gaagtttagc    3000
gccaacggca gcatcacatt cgccccacat aatgaggccg acctctgaa aacccgggac    3060 accgatcctg ccgatccttt cagatacgtg acaacagtgg ccagcggcct gaagaagatg    3120
agagccagac aagtgcggat cgatgagctg ggcaaagtgc acgatcccgg acctagagag    3180
gat                                                                 3183

<210> SEQ ID NO 22
<211> LENGTH: 3222
<212> TYPE: DNA
<213> ORGANISM: Artificial Sequence
<220> FEATURE:
<223> OTHER INFORMATION: OMNI-80 DNA optimized for expression in human
      cells

<400> SEQUENCE: 22
accaccacac tgggcatcga tctgggcaca tcttctctcg gctggtgcct gatcgaggac      60
gagcacagaa tcctggacct gggcgtgatc atttttttctg ccgctgccgg cgctggaaga    120
gatcctcaat ctggtgctcc tctggccgag gccagaagag aagccagaag cgctcggcgg    180
agaagagaca gattcatcgg cagaagaagc gccctgctgg acaagctgat tgctctggga    240
cttctgcctg gcgatccacc agctggacac ggaagaagaa gaaatcaggc cctgcctaac    300
gccgagacaa aggcccttgc cgatacagat ccccacgtgc tgagaagaag ggctctgtct    360
gaacctctga gccctcacga gatcggcaga gccatcttcc acctgaacac agacgggc      420 ttcaagagca acagaaaggc cgacagaggc cggaatgagc ccgagacagg caaaattgct    480
acagccggac aggccctgga tgccgctctg ggaaaaagaa cactgggcca gtttctggcc    540
gatcggattg atgctggaca gcctgccaga gttagaatgg gcggcgagaa tcaggcctac    600
gacttctatc ctcagcggag ccacctgaa gccgagtttg ctgccatttg ggaagcccaa    660
gagcaccacc atcctgagct gctgaccgat acagccagaa ccgccatcca ccgcatcctg    720
ttcttccaga ggccactgaa aaccctgaa gtgggcttct gcacctttgc cggaatgtct    780
ggcgtgcccc atgatgagag aaggctgcct aaggctcacc tctgttcca agagcggaga    840 ctgtacgagg aagtgaacaa cctgaaagtg gtggccgctg gcgctgccgc tagagatctt    900
acactggacg agcgggacag actgatcctg aagctgcggg acaacaagaa agtgaccttc    960
gccacactgg ccaagaaggt gctgaagctg gccgaaggcg agcggttcaa caaagagagc   1020
gaggctagaa aggacctggc tgggatgaa gtgcgggccg aaatggccga taagaagaga   1080
ttcggcaacc ggtggaccca ctttccactc gagagacagc tgcagatcat cgaccgggtg   1140
cagaacgagg aaaaccccga tattctgctg gcctggctgc agagcgattg cggacttgat   1200
```

```
aaggctgctg ctgtggccgt ggccaggaca atcttcctg aaggccacgg cagattcggc    1260
gagacagcca caagaaggct gatcgccgct ctgaaggccg aggtggtcac atatgataag    1320
gccgcactgg ctgccggctt ccaccactct gatcatagaa ccggcgaggt gtacgacctg    1380
ctgccttatt atggcgaggt gctgaccaga gagatcgccc tggaaaagc cgagtatggc    1440 gaccctctgg aacggcagta cggcaaagtg accaatccta ccgtgcacat cggcctgagg    1500
cagctccaga aactcgtgaa tgccgtgatc gccagacacg gcagaccga cagaattgtg    1560 attgagctgg cccgggaact gaagctgaac gacaagcaga aagacgagca ccagcggcgg    1620
atcagaagag ataccgaggc cgccattaga cggggcgaga actggttgaa gccggaatt     1680 gctgacaccg gcgccaatag agcactgatg agacagtggg aagaactgaa ccccagcaat    1740
cccctggaca aagatgtcc ttactgcggc gagcctatcg gcatgcccca gatctttaac     1800
agcctggccg acatcgacca catcatccct tacagcagaa gcctggacga cagccccgct    1860
aacaaagtgc tggtgcaccg gaactgcaac cggcagaagg gaaacaagac cccttgggac    1920
agatggcacg aggatgaggc caagtgggag atcatttctg cccaggtggc cagaatgcac    1980
cctagcaaac aatggcgctt cggcccccgat gccatgaaaa gacttgagag agatggcggc    2040
tttgccgcca gacagctgac cgacacacag tacctggctc ggatcgccga caagtacctg    2100
agaggactgt accctacagc cgacgagggc agagtggatg tgatccctgg aagaatgacc    2160
gccatgctgc gaagagtgtg gggcctcaat tctctgctgc ccgaccacaa cttcgtggaa    2220
aacgagcact ctagcgcccc taagaaccgg ctggatcaca gacaccacgc cattgatgct    2280
acagtggccg ccgtgacaag cctgagcaga atgcaacaga ttgccgccgc agccgccaga    2340
tccgaggaaa aagagctgga aaggctgttc gacgatctgc cccatccttg ggacggcttt    2400
agagaggatc tgggcgcctg tctggctaga acagtggcca cacacaagcc cgatcacgga    2460
agatctgcca agccaagcag acacagagat gtgacagccg gcaagctgca caatgatacc    2520
gcctatggcc tgaccggcct gaaaaccacc gatggcaaga cacccatcgt ggtgcataga    2580
gtgctgctgg cttccctgaa gcctacacag atcgccgatc ctgactgcat ccccgacgag    2640
acactgagaa atgccctgtg gctggccaca agagattgca gcggcaaggc ttttgaccag    2700
gcactggcca gattcgccaa agaacacccc gtgttcaagg gcattagaag agtgcggatc    2760
agggaaccac tgaacgtgat ccccatccac gacagagagg gcaagcccta caaaagctac    2820
gctggcgcct ccaacgacag atacaatgtg tggcggatgc ccgacgcctc ttggagacac    2880
gatgtcgtgt ccaccttcaa cgcccacaga agcgactaca gagatctgag ccacatcct     2940 gccgccaaaa aagtgctgtc cctgcggcag aacgacatga tcgccgtgga aagaaacggc    3000
ggcctgcgcg agatcatgcg ggtcgtgaag tttaatcagg ccggcagact gacccctgtgt   3060 cctcctaatg aaggcggaaa gctgcagaac agggacgccg ctccaaacga cgccgatcca   3120
ttcaagtaca cctatctgag ccccagcagc ctgaagaacg ccaaagccag acaagtgcgc   3180
atcgacccac tgggaagagt gttcgatccc ggacctagag ag                      3222
```

<210> SEQ ID NO 23
<211> LENGTH: 3132
<212> TYPE: DNA
<213> ORGANISM: Artificial Sequence
<220> FEATURE:
<223> OTHER INFORMATION: OMNI-81 DNA optimized for expression in human cells

<400> SEQUENCE: 23

```
aagaacaaga tgcagtaccg gctggccctg gatctgggca caacatctct tggatgggcc    60
atgctgagag tgaagcccaa tcctgagggc agactggaac cttttgccgt ggttaaggcc   120
ggcgtgcgga tcttctctga cggcagaaat cctaaggacg cagcagcct ggccgtgact    180
agaagagaag ccagagccat gcggcggaga agagacagac tgctgaagcg aaagcccgg   240
atgctgcaac agctgaccgc cttcggcttc tttcctaccg atctggccga gcggaaggcc   300
ctggaaacac tgaatcctta cgagctgaga gccaaaggcc tggacgagcc tctgagccct   360
tacgagtttg cagaagcct gttccacatc aaccagcgga gaggcttcaa gagcaaccgc    420
aagaccgaca gaaagagaa cgacagctct gccctgaagg ccgccattag aagagtggcc    480
agcgagatcg atggcaacca ggccagaaca gtcggcgagt ggctgtacaa gagaatgctg   540
aacggccagc ctgtgcgggg cagatacaga gaaacaaagg tgcagaaaga ggacggcaag   600
accaagatcg acaagtccta cgacctgtac atcgatagag ccatggtgga agccgagttt   660
gaggccctgt gggctaagca ggcttctctg aatcctgccg tgtacagcga gcaggccaag   720
gccacactga aggatgtgct gctgttccag agaaacctgc ggcctgtgaa gcctggcaga   780
tgcacactga tccccacaga ggaaagagcc cctctggctc tgcctagcac acagcggttc   840
cggatctacc aagaagtgaa caacctgaga atcctgagag agggcctgaa ggacgaagcc   900
ctgacactgg ttcagagaga tgccctggtt acagccctgg aacagaacaa caagcggaca   960
ttcgcccaga tcaagaagct gctgggactc gacggccaga cacagttcaa cttcgaggac  1020
cccaagcggc aagagctgaa gggcaatacc acaagcgcca tcctgtctca ccctaagcac  1080
ttcggcgacg cttggtttgg cttcgacgag gccaagcagg atggcatcgt gtgccagctg  1140
ctgaacgagg aaaatgagag cgccctgatc cggtggctga tggatcatac aggcgtggac  1200
gaagctcacg ccgaggctat tgctaatgcc gctctgccag aaggctacgg ctctctgtct  1260
agagctgccc tggccaagat tctgcctgag ctgagaaagg ccgtgatcac ctacgataag  1320
gctgccagg ccgctggctt tgatcaccac tctcacatca gccctagcac acaggcgag   1380
atcctgccag agctgcctta ttatggcgag gccctgcaga gacacgttgg ctttggaacc  1440
ggcaatcccg acgatgtgcc tgagaagaga tacggcaaga tcgccaatcc aaccgtgcac  1500
atcggcctga tcaagtgcg gaaggtggtc aatgccctga tcaagagata tggacacccc  1560
agcgaagtga tcgtggaagt ggccagagat ctgaagcaga caagaagca gcgcgacgaa  1620
gagaacaaga gacaggccga gaaccagaag cggaacgagc ggatcagaca ggatattgcc  1680
gccatgagc ccgacagatc cgaagagaga gtgacccgga ccgacatcca gaatggat    1740
ctgtgggaag aactgagctt cgaccccgcc aacagatgct gtccttactc tggcgtgcag  1800
atcagcgccg agatgctgat gtctgacgcc gtggaaatcg agcacattct gccttcagc   1860
agaaccctgg acgacagcct gaacaacaaa accgtgtcca tgaggcaggc caatcggatc  1920
aagggcaatc agacccctttt cgaggccttc ggcaaggata cgccctggg cgtgaactac  1980
agcgacatcc tgatgagagc ccagcagatg cccaaggcca agagaaagag attcgccgag  2040
aacgccctcg aggaatggct gcagaacgag aagaacttcc tggctagagc cctgaacgac  2100
accagatacc tttccagagt ggcccgggaa tacgtgtccc tgatctgtcc tcaagccacc  2160
agagtgatcc ctggccagat gacagcacag ctgagggcca gtttggccct gaacgatatc  2220
ctcgcctgg atggcgagaa gaatcggaac gatcacagac accatgccgt ggatgcctgt  2280
gtgatcggag tgacagatca aggcctgctg cagagatttg cctacgcctc tgccagcgcc  2340
```

| | |
|---|---:|
| agagctaatg gactggctag actggtggac acaatgcccg atccttggcc tagctacaga | 2400 |
| cagcacgtgc agagggccgt gcagaacatc tatgtgtccc acaagcctga ccacagccac | 2460 |
| gagggcgcca tgttcgatga caatctacc agcgccaccg gcaagtctag aagcgccgcc | 2520 |
| aaggatagaa cagtgatccc ctttatcgcc aagaactggt cacaccccga cgaccacaac | 2580 |
| aagcagaggc cttttaaggg cctgatcacc gacgtgtccc agagacacca gaacaagcct | 2640 |
| tacaagggcc tgctgagcaa cagcaactac tgcatcgaga tctactccga tgaggccgga | 2700 |
| tggggcggac acgtgctgaa acattcgac gcctatcaga tcgtgcgggc ccacaagaat | 2760 |
| gcctctgagg gaatgcaggc cctgcggaac aagcacagca gccagaatgg ccatcctctg | 2820 |
| gtcatgagac tgatgatcgg cgactacatc cgggccgaga ttgatggctt tctgctgctg | 2880 |
| ctccaagtgc tgaagatcaa cagcagcggc agcatcacct tcatcaagcc caacgagaca | 2940 |
| aacatcagcg cccggtatct ggccaagctg gctgctcaga aagcccagaa agaaggcaag | 3000 |
| cccttcgacg atatcgccct gaatgacgtg ttctttcaga aggccatctc cgccgatagc | 3060 |
| ctgcggctgt ttaaagccag acctgtgaca ctgagcccca tcggcgaact gagagatccc | 3120 |
| ggctttaaag gc | 3132 |

<210> SEQ ID NO 24
<211> LENGTH: 3210
<212> TYPE: DNA
<213> ORGANISM: Artificial Sequence
<220> FEATURE:
<223> OTHER INFORMATION: OMNI-82 DNA optimized for expression in human cells

<400> SEQUENCE: 24

| | |
|---|---:|
| agactgggcc tcgatatcgg caccaattct atcggctggt ggctgtacag aaccgagaac | 60 |
| gaccagatca cctgtgtggt ggatggcgga gtgcgggtgt tctctgatgg cagagatccc | 120 |
| cagagcaaag aaagcctggc cgtggacaga gagtggcta gagcccagcg gcggagaaga | 180 |
| gacagatacc tgagaagaaa ggccgctctg atgaagagaa tggccgaggc tggactgatg | 240 |
| cctgctgatc ctgttcaggc caaagctctg caggctctgg accctatga tctgagagcc | 300 |
| agaggactgg atgaagccct gccactggct catttcggca gagccctgtt ccacctgaac | 360 |
| cagagaagag gcttcaagag caaccggaag gccgacagag gcgacaatga gagcggaaag | 420 |
| atcaaggacg ccaccgccag actggactgg gccatgagag atgccagagc cagaacctac | 480 |
| ggcgagttcc tgcacatgag acaggacaag gccgacgatc ctagaagagt gcctaccgtg | 540 |
| cggaccagac tgtctgtggc cagaagagat aacgccgaga agaggaagc cggctacgac | 600 |
| ttctacccg acagaaggca cctgagcgaa gagtttgatg ccctgtgggc cgctcaggcc | 660 |
| gaacaccata caaccctgac cgacgacctg cgggatcaga tcaagaccat catcttccac | 720 |
| cagcggcctc tgaaggctcc tgaagtgggc ctgtgtctgt tcaccgacga gaagaatc | 780 |
| cccagcgctc acccctctgaa ccagcggaga atcctgctgg aaaccgtgaa cggcctgaga | 840 |
| atcgtggcaa gaggcgaagc cgctagaggc ctgacaagag aggaacgcga tcagatcgtg | 900 |
| cacggcctgg ataacaaggg ccacacaaag acactgagcg gcatgagcat gaagctgcgc | 960 |
| gccatcggca aagtgatcaa gctgagatcc gaccagagct tcacccctgga aacagccaac | 1020 |
| agggacgcca ttgcttgcga tcctgtcaga gcctctctgt ctcaccctga gaatgggc | 1080 |
| ggagtgtgga caaactgga tgaggatgcc cagtgggacg tcgtgcagag actgagagct | 1140 |
| gtgcagagcg atacagagca cgaagccctg gtggattggc tgatggccac acacggactc | 1200 |

```
ggacaggatt atgcccaggc cacagctaat gcccctctgc ctgaaggata tggcagactg    1260
ggactgaccg ccaccagaaa gattctggct gccctggaag ccgacgtgat gagctattct    1320
gatgccgtgg ctgcctgtgg atggtccat tctggtggac ctacaggcga agtgctggaa    1380
gctctgccct actatggcga gatcctggac agacacgtga tccctggcac cggcgtgaaa    1440
accgacgagg atgtgaagag attcggccgg atcacaaacc ccacagtgca catcggactg    1500
aatcagatcc ggcggctggt caacagaatc atctgtgtgc acggcaagcc tgaccagatc    1560
gtggtggaag tggccaggga cctgaagaac agcgaggatc agaagagaga gatccagaaa    1620
accatccgga gaacaccga cgacgccatc aagagaggca agaagctggt tgaggaactg    1680
ggccagaagg acaccggcgc caatagactg attctgcggc tgtgggagaa cctgggcaac    1740
gatgtgatga ccagacagtg cccctacagc ggcaagagaa ttagcgccgc catgctgttc    1800
gacggcagct gtgatgtgga ccacattctg cccttcagca gaaccctgga cgacagcatc    1860
tggaacaaga ccctgtgcct gaaagaagag aatcgcaaga aggccaacaa gacaccctgg    1920
gaagtgtggg gcgagacaga ccagtgggat gtgatcgtgg ccaatctgaa gaacctggac    1980
cggaagcagg cttggagatt tgcccctgac gccgtggaaa gattcgaggg cgagaacgat    2040
ttcagcgctc gggccctgaa agacacccag tacctgtcta gagtggctcg ggcctatctg    2100
gacgctctgt atgatggcgc cgatggcaag tctcacgtgt gggttgtgcc aggcagactg    2160
accgaaatgc tgaagggca ctggggcctg aatggcatcg aggtgctgac agactctgac    2220
gcccagaccg tgaagtccaa gaacagacag gaccacagac accacgccat tgatgctgct    2280
gtggtggccg ctaccgatcg gagcctgatc cagaggatct ccaagatcgc caagcacgat    2340
gaacaggctg gcgccgaaca ggtggcaaga tctgttcctc ctccttggga cggcttcaga    2400
gatgatgtgg ccggacagat cggcaggatc attgtgtctc acagagccga ccacggcaga    2460
atcgatccta cagccagagc acagggcagc gatacaacag ccggacagct gcacatggat    2520
accgcctatg gaattgtgga cggcggccac gtcgtgtcca gaaagcctct tatgtctctc    2580
ggagccggcg acatcagaaa gatcagagat cctgacctgc agcggcatct gaccagagtg    2640
acacgcggac tggacaagaa agagttcgaa caggccctgg cctccttcgc cgcttctaga    2700
aaactgcccg atcagagcga gaacccctac ttcggactgc ggagagttag actgctggac    2760
gcactgcagg atagcgccag agtgcctgtt agaaacgcca ccggcaacat ctacaaggcc    2820
tataaggccg gcagcaacca ctgctacgaa gtgtggcgga tgcccgacgg aaaagtgaag    2880
ccttgggcca tctctaccct tgaggcccac cagagcggag atggctctaa acctcatcct    2940
gccgccaagc ggctgctgag agtgttcaag cgcgatatgg tggtcatcga gcggaagggc    3000
atcaccgtga tctgctacgt gcagaaaatg gacgtggcca acggcctgtt tctggtgcct    3060
cacacagagg gcaacgccga cgccagaaat agggacaaag gaggacgactt caagttcatc    3120 cagatgagcg ccgcctctct gatcaaggcc agaattagaa gggtgcacgt ggacgagatg    3180
ggaagaatga gagatcccgg acctcctcgg                                     3210
```

<210> SEQ ID NO 25
<211> LENGTH: 10
<212> TYPE: RNA
<213> ORGANISM: Artificial Sequence
<220> FEATURE:
<223> OTHER INFORMATION: OMNI-59 crRNA (Repeat)

<400> SEQUENCE: 25
guuccgguca                                                           10

<210> SEQ ID NO 26
<211> LENGTH: 11
<212> TYPE: RNA
<213> ORGANISM: Artificial Sequence
<220> FEATURE:
<223> OTHER INFORMATION: OMNI-59 tracrRNA (Antirepeat)

<400> SEQUENCE: 26
uggucgcuaa c                                                              11

<210> SEQ ID NO 27
<211> LENGTH: 34
<212> TYPE: RNA
<213> ORGANISM: Artificial Sequence
<220> FEATURE:
<223> OTHER INFORMATION: OMNI-59 TracrRNA Portion 1

<400> SEQUENCE: 27
aagcugaugc uuuuguagcu agaugcaaaa aaug                                     34

<210> SEQ ID NO 28
<211> LENGTH: 31
<212> TYPE: RNA
<213> ORGANISM: Artificial Sequence
<220> FEATURE:
<223> OTHER INFORMATION: OMNI-59 TracrRNA Portion 2

<400> SEQUENCE: 28
gaaagccggg caugcccggc uuucggcuuu u                                        31

<210> SEQ ID NO 29
<211> LENGTH: 90
<212> TYPE: RNA
<213> ORGANISM: Artificial Sequence
<220> FEATURE:
<223> OTHER INFORMATION: OMNI-59 sgRNA Scaffold V1

<400> SEQUENCE: 29
guuccgguca gaauggucg cuaacaagcu gaugcuuuug uagcuagaug caaaaaaugg          60
aaagccgggc augcccggcu uucggcuuuu                                          90

<210> SEQ ID NO 30
<211> LENGTH: 15
<212> TYPE: RNA
<213> ORGANISM: Artificial Sequence
<220> FEATURE:
<223> OTHER INFORMATION: OMNI-61 crRNA (Repeat)

<400> SEQUENCE: 30
guugcggcca gagcu                                                          15

<210> SEQ ID NO 31
<211> LENGTH: 12
<212> TYPE: RNA
<213> ORGANISM: Artificial Sequence
<220> FEATURE:
<223> OTHER INFORMATION: OMNI-61 Partial crRNA 2

<400> SEQUENCE: 31
guugcggcca ga                                                             12

<210> SEQ ID NO 32
<211> LENGTH: 10
<212> TYPE: RNA

<213> ORGANISM: Artificial Sequence
<220> FEATURE:
<223> OTHER INFORMATION: OMNI-61 Partial crRNA 3

<400> SEQUENCE: 32
guugcggcca                                                           10

<210> SEQ ID NO 33
<211> LENGTH: 15
<212> TYPE: RNA
<213> ORGANISM: Artificial Sequence
<220> FEATURE:
<223> OTHER INFORMATION: OMNI-61 tracrRNA (Antirepeat)

<400> SEQUENCE: 33
ggcucugccg cuaac                                                     15

<210> SEQ ID NO 34
<211> LENGTH: 12
<212> TYPE: RNA
<213> ORGANISM: Artificial Sequence
<220> FEATURE:
<223> OTHER INFORMATION: OMNI-61 Partial tracrRNA 2

<400> SEQUENCE: 34
ucugccgcua ac                                                        12

<210> SEQ ID NO 35
<211> LENGTH: 10
<212> TYPE: RNA
<213> ORGANISM: Artificial Sequence
<220> FEATURE:
<223> OTHER INFORMATION: OMNI-61 Partial tracrRNA 3

<400> SEQUENCE: 35
ugccgcuaac                                                           10

<210> SEQ ID NO 36
<211> LENGTH: 35
<212> TYPE: RNA
<213> ORGANISM: Artificial Sequence
<220> FEATURE:
<223> OTHER INFORMATION: OMNI-61 TracrRNA Portion 1

<400> SEQUENCE: 36
aaggagaaac uuguuggauc aggacuccac aagau                               35

<210> SEQ ID NO 37
<211> LENGTH: 15
<212> TYPE: RNA
<213> ORGANISM: Artificial Sequence
<220> FEATURE:
<223> OTHER INFORMATION: OMNI-61 tracrRNA Portion 1-partial

<400> SEQUENCE: 37
aaggagaaac uuguu                                                     15

<210> SEQ ID NO 38
<211> LENGTH: 27
<212> TYPE: RNA
<213> ORGANISM: Artificial Sequence
<220> FEATURE:
<223> OTHER INFORMATION: OMNI-61 TracrRNA Portion 2

<400> SEQUENCE: 38
gagacggcuc ccucgugggg ccguuuu                                        27

```
<210> SEQ ID NO 39
<211> LENGTH: 96
<212> TYPE: RNA
<213> ORGANISM: Artificial Sequence
<220> FEATURE:
<223> OTHER INFORMATION: OMNI-61 sgRNA Scaffold V1

<400> SEQUENCE: 39
guugcggcca gagcugaaag gcucugccgc uaacaaggag aaacuuguug gaucaggacu        60
ccacaagaug agacggcucc cucguggggc cguuuu                                  96

<210> SEQ ID NO 40
<211> LENGTH: 16
<212> TYPE: RNA
<213> ORGANISM: Artificial Sequence
<220> FEATURE:
<223> OTHER INFORMATION: OMNI-67 crRNA (Repeat)

<400> SEQUENCE: 40
gcugugguuc gucggg                                                        16

<210> SEQ ID NO 41
<211> LENGTH: 15
<212> TYPE: RNA
<213> ORGANISM: Artificial Sequence
<220> FEATURE:
<223> OTHER INFORMATION: OMNI-67 Partial crRNA 1

<400> SEQUENCE: 41
gcugugguuc gucgg                                                         15

<210> SEQ ID NO 42
<211> LENGTH: 12
<212> TYPE: RNA
<213> ORGANISM: Artificial Sequence
<220> FEATURE:
<223> OTHER INFORMATION: OMNI-67 Partial crRNA 2

<400> SEQUENCE: 42
gcugugguuc gu                                                            12

<210> SEQ ID NO 43
<211> LENGTH: 10
<212> TYPE: RNA
<213> ORGANISM: Artificial Sequence
<220> FEATURE:
<223> OTHER INFORMATION: OMNI-67 Partial crRNA 3

<400> SEQUENCE: 43
gcugugguuc                                                               10

<210> SEQ ID NO 44
<211> LENGTH: 16
<212> TYPE: RNA
<213> ORGANISM: Artificial Sequence
<220> FEATURE:
<223> OTHER INFORMATION: OMNI-67 tracrRNA (Antirepeat)

<400> SEQUENCE: 44
ccugacuuau cacagu                                                        16

<210> SEQ ID NO 45
<211> LENGTH: 15
<212> TYPE: RNA
```

```
<213> ORGANISM: Artificial Sequence
<220> FEATURE:
<223> OTHER INFORMATION: OMNI-67 Partial tracrRNA 1

<400> SEQUENCE: 45
cugacuuauc acagu                                                     15

<210> SEQ ID NO 46
<211> LENGTH: 12
<212> TYPE: RNA
<213> ORGANISM: Artificial Sequence
<220> FEATURE:
<223> OTHER INFORMATION: OMNI-67 Partial tracrRNA 2

<400> SEQUENCE: 46
acuuaucaca gu                                                        12

<210> SEQ ID NO 47
<211> LENGTH: 10
<212> TYPE: RNA
<213> ORGANISM: Artificial Sequence
<220> FEATURE:
<223> OTHER INFORMATION: OMNI-67 Partial tracrRNA 3

<400> SEQUENCE: 47
uuaucacagu                                                           10

<210> SEQ ID NO 48
<211> LENGTH: 15
<212> TYPE: RNA
<213> ORGANISM: Artificial Sequence
<220> FEATURE:
<223> OTHER INFORMATION: OMNI-67 TracrRNA Portion 1

<400> SEQUENCE: 48
aagguucucu accgc                                                     15

<210> SEQ ID NO 49
<211> LENGTH: 11
<212> TYPE: RNA
<213> ORGANISM: Artificial Sequence
<220> FEATURE:
<223> OTHER INFORMATION: OMNI-67 tracrRNA Portion 1-partial

<400> SEQUENCE: 49
gguucucuac c                                                         11

<210> SEQ ID NO 50
<211> LENGTH: 25
<212> TYPE: RNA
<213> ORGANISM: Artificial Sequence
<220> FEATURE:
<223> OTHER INFORMATION: OMNI-67 TracrRNA Portion 2

<400> SEQUENCE: 50
acggcaaugu guuuacacau ccguu                                          25

<210> SEQ ID NO 51
<211> LENGTH: 28
<212> TYPE: RNA
<213> ORGANISM: Artificial Sequence
<220> FEATURE:
<223> OTHER INFORMATION: OMNI-67 TracrRNA Portion 3

<400> SEQUENCE: 51
aaggacgguc cuggaccguc cuuuuuuu                                       28
```

<210> SEQ ID NO 52
<211> LENGTH: 104
<212> TYPE: RNA
<213> ORGANISM: Artificial Sequence
<220> FEATURE:
<223> OTHER INFORMATION: OMNI-67 sgRNA Scaffold V1

<400> SEQUENCE: 52
gcugugguuc gucggggaaa ccugacuuau cacaguaagg uucucuaccg cacggcaaug    60
uguuuacaca uccguuaagg acguccugg accguccuuu uuuu    104

<210> SEQ ID NO 53
<211> LENGTH: 13
<212> TYPE: RNA
<213> ORGANISM: Artificial Sequence
<220> FEATURE:
<223> OTHER INFORMATION: OMNI-76 crRNA (Repeat)

<400> SEQUENCE: 53
guuccggcua gag    13

<210> SEQ ID NO 54
<211> LENGTH: 12
<212> TYPE: RNA
<213> ORGANISM: Artificial Sequence
<220> FEATURE:
<223> OTHER INFORMATION: OMNI-76 Partial crRNA 2

<400> SEQUENCE: 54
guuccggcua ga    12

<210> SEQ ID NO 55
<211> LENGTH: 10
<212> TYPE: RNA
<213> ORGANISM: Artificial Sequence
<220> FEATURE:
<223> OTHER INFORMATION: OMNI-76 Partial crRNA 3

<400> SEQUENCE: 55
guuccggcua    10

<210> SEQ ID NO 56
<211> LENGTH: 14
<212> TYPE: RNA
<213> ORGANISM: Artificial Sequence
<220> FEATURE:
<223> OTHER INFORMATION: OMNI-76 tracrRNA (Antirepeat)

<400> SEQUENCE: 56
cucuggacgc uaac    14

<210> SEQ ID NO 57
<211> LENGTH: 13
<212> TYPE: RNA
<213> ORGANISM: Artificial Sequence
<220> FEATURE:
<223> OTHER INFORMATION: OMNI-76 Partial tracrRNA 2

<400> SEQUENCE: 57
ucuggacgcu aac    13

<210> SEQ ID NO 58
<211> LENGTH: 11
<212> TYPE: RNA

```
<213> ORGANISM: Artificial Sequence
<220> FEATURE:
<223> OTHER INFORMATION: OMNI-76 Partial tracrRNA 3

<400> SEQUENCE: 58
uggacgcuaa c                                                           11

<210> SEQ ID NO 59
<211> LENGTH: 24
<212> TYPE: RNA
<213> ORGANISM: Artificial Sequence
<220> FEATURE:
<223> OTHER INFORMATION: OMNI-76 TracrRNA Portion 1

<400> SEQUENCE: 59
aagcugaaag augcaccaaa ugau                                             24

<210> SEQ ID NO 60
<211> LENGTH: 12
<212> TYPE: RNA
<213> ORGANISM: Artificial Sequence
<220> FEATURE:
<223> OTHER INFORMATION: OMNI-76 tracrRNA Portion 1-partial

<400> SEQUENCE: 60
gcugaaagau gc                                                          12

<210> SEQ ID NO 61
<211> LENGTH: 25
<212> TYPE: RNA
<213> ORGANISM: Artificial Sequence
<220> FEATURE:
<223> OTHER INFORMATION: OMNI-76 TracrRNA Portion 2

<400> SEQUENCE: 61
agggucgcua uaggcgaccc uuuuu                                            25

<210> SEQ ID NO 62
<211> LENGTH: 80
<212> TYPE: RNA
<213> ORGANISM: Artificial Sequence
<220> FEATURE:
<223> OTHER INFORMATION: OMNI-76 sgRNA Scaffold V1

<400> SEQUENCE: 62
guuccggcua gaggaaacuc uggacgcuaa caagcugaaa gaugcaccaa augauagggu      60
cgcuauaggc gacccuuuuu                                                  80

<210> SEQ ID NO 63
<211> LENGTH: 12
<212> TYPE: RNA
<213> ORGANISM: Artificial Sequence
<220> FEATURE:
<223> OTHER INFORMATION: OMNI-79-1 crRNA (Repeat)

<400> SEQUENCE: 63
guugccgcug ga                                                          12

<210> SEQ ID NO 64
<211> LENGTH: 10
<212> TYPE: RNA
<213> ORGANISM: Artificial Sequence
<220> FEATURE:
<223> OTHER INFORMATION: OMNI-79-1 Partial crRNA 3

<400> SEQUENCE: 64
```

```
guugccgcug                                                              10

<210> SEQ ID NO 65
<211> LENGTH: 13
<212> TYPE: RNA
<213> ORGANISM: Artificial Sequence
<220> FEATURE:
<223> OTHER INFORMATION: OMNI-79-1 tracrRNA (Antirepeat)

<400> SEQUENCE: 65
uccaguuguu aac                                                          13

<210> SEQ ID NO 66
<211> LENGTH: 11
<212> TYPE: RNA
<213> ORGANISM: Artificial Sequence
<220> FEATURE:
<223> OTHER INFORMATION: OMNI-79-1 Partial tracrRNA 3

<400> SEQUENCE: 66
caguuguuaa c                                                            11

<210> SEQ ID NO 67
<211> LENGTH: 22
<212> TYPE: RNA
<213> ORGANISM: Artificial Sequence
<220> FEATURE:
<223> OTHER INFORMATION: OMNI-79-1 TracrRNA Portion 1

<400> SEQUENCE: 67
aagcagcuug acugcaccaa au                                                22

<210> SEQ ID NO 68
<211> LENGTH: 13
<212> TYPE: RNA
<213> ORGANISM: Artificial Sequence
<220> FEATURE:
<223> OTHER INFORMATION: OMNI-79-1 tracrRNA Portion 1-partial

<400> SEQUENCE: 68
gcagcuugac ugc                                                          13

<210> SEQ ID NO 69
<211> LENGTH: 29
<212> TYPE: RNA
<213> ORGANISM: Artificial Sequence
<220> FEATURE:
<223> OTHER INFORMATION: OMNI-79-1 TracrRNA Portion 2

<400> SEQUENCE: 69
aaggcggggg cugcggcccu cgcuuuuuu                                         29

<210> SEQ ID NO 70
<211> LENGTH: 80
<212> TYPE: RNA
<213> ORGANISM: Artificial Sequence
<220> FEATURE:
<223> OTHER INFORMATION: OMNI-79-1 sgRNA Scaffold V1

<400> SEQUENCE: 70
guugccgcug gagaaaucca guuguuaaca agcagcuuga cugcaccaaa uaaggcgggg       60
gcugcggccc ucgcuuuuuu                                                   80

<210> SEQ ID NO 71
```

```
<211> LENGTH: 15
<212> TYPE: RNA
<213> ORGANISM: Artificial Sequence
<220> FEATURE:
<223> OTHER INFORMATION: OMNI-79-2 crRNA (Repeat)

<400> SEQUENCE: 71
guugccgcug gaccg                                                          15

<210> SEQ ID NO 72
<211> LENGTH: 12
<212> TYPE: RNA
<213> ORGANISM: Artificial Sequence
<220> FEATURE:
<223> OTHER INFORMATION: OMNI-79-2 Partial crRNA 2

<400> SEQUENCE: 72
guugccgcug ga                                                             12

<210> SEQ ID NO 73
<211> LENGTH: 10
<212> TYPE: RNA
<213> ORGANISM: Artificial Sequence
<220> FEATURE:
<223> OTHER INFORMATION: OMNI-79-2 Partial crRNA 3

<400> SEQUENCE: 73
guugccgcug                                                                10

<210> SEQ ID NO 74
<211> LENGTH: 16
<212> TYPE: RNA
<213> ORGANISM: Artificial Sequence
<220> FEATURE:
<223> OTHER INFORMATION: OMNI-79-2 tracrRNA (Antirepeat)

<400> SEQUENCE: 74
cggucuggca guuaac                                                         16

<210> SEQ ID NO 75
<211> LENGTH: 13
<212> TYPE: RNA
<213> ORGANISM: Artificial Sequence
<220> FEATURE:
<223> OTHER INFORMATION: OMNI-79-2 Partial tracrRNA 2

<400> SEQUENCE: 75
ucuggcaguu aac                                                            13

<210> SEQ ID NO 76
<211> LENGTH: 11
<212> TYPE: RNA
<213> ORGANISM: Artificial Sequence
<220> FEATURE:
<223> OTHER INFORMATION: OMNI-79-2 Partial tracrRNA 3

<400> SEQUENCE: 76
uggcaguuaa c                                                              11

<210> SEQ ID NO 77
<211> LENGTH: 21
<212> TYPE: RNA
<213> ORGANISM: Artificial Sequence
<220> FEATURE:
<223> OTHER INFORMATION: OMNI-79-2 TracrRNA Portion 1

<400> SEQUENCE: 77
```
aagugucagu acgcaacaga u                                             21

<210> SEQ ID NO 78
<211> LENGTH: 12
<212> TYPE: RNA
<213> ORGANISM: Artificial Sequence
<220> FEATURE:
<223> OTHER INFORMATION: OMNI-79-2 tracrRNA Portion 1-partial

<400> SEQUENCE: 78
gugucaguac gc                                                       12

<210> SEQ ID NO 79
<211> LENGTH: 29
<212> TYPE: RNA
<213> ORGANISM: Artificial Sequence
<220> FEATURE:
<223> OTHER INFORMATION: OMNI-79-2 TracrRNA Portion 2

<400> SEQUENCE: 79
aagggcgacg cuccggcguc gccuuuuuu                                     29

<210> SEQ ID NO 80
<211> LENGTH: 85
<212> TYPE: RNA
<213> ORGANISM: Artificial Sequence
<220> FEATURE:
<223> OTHER INFORMATION: OMNI-79-2 sgRNA Scaffold V1

<400> SEQUENCE: 80
guugccgcug gaccggaaac ggucuggcag uuaacaagug ucaguacgca acagauaagg   60
gcgacgcucc ggcgucgccu uuuu                                          85

<210> SEQ ID NO 81
<211> LENGTH: 13
<212> TYPE: RNA
<213> ORGANISM: Artificial Sequence
<220> FEATURE:
<223> OTHER INFORMATION: OMNI-79-3 crRNA (Repeat)

<400> SEQUENCE: 81
guugccgcug gac                                                      13

<210> SEQ ID NO 82
<211> LENGTH: 12
<212> TYPE: RNA
<213> ORGANISM: Artificial Sequence
<220> FEATURE:
<223> OTHER INFORMATION: OMNI-79-3 Partial crRNA 2

<400> SEQUENCE: 82
guugccgcug ga                                                       12

<210> SEQ ID NO 83
<211> LENGTH: 10
<212> TYPE: RNA
<213> ORGANISM: Artificial Sequence
<220> FEATURE:
<223> OTHER INFORMATION: OMNI-79-3 Partial crRNA 3

<400> SEQUENCE: 83
guugccgcug                                                          10

<210> SEQ ID NO 84

-continued

```
<211> LENGTH: 14
<212> TYPE: RNA
<213> ORGANISM: Artificial Sequence
<220> FEATURE:
<223> OTHER INFORMATION: OMNI-79-3 tracrRNA (Antirepeat)

<400> SEQUENCE: 84
gucuggcggu uaac                                                        14

<210> SEQ ID NO 85
<211> LENGTH: 13
<212> TYPE: RNA
<213> ORGANISM: Artificial Sequence
<220> FEATURE:
<223> OTHER INFORMATION: OMNI-79-3 Partial tracrRNA 2

<400> SEQUENCE: 85
ucuggcgguu aac                                                         13

<210> SEQ ID NO 86
<211> LENGTH: 11
<212> TYPE: RNA
<213> ORGANISM: Artificial Sequence
<220> FEATURE:
<223> OTHER INFORMATION: OMNI-79-3 Partial tracrRNA 3

<400> SEQUENCE: 86
uggcgguuaa c                                                           11

<210> SEQ ID NO 87
<211> LENGTH: 22
<212> TYPE: RNA
<213> ORGANISM: Artificial Sequence
<220> FEATURE:
<223> OTHER INFORMATION: OMNI-79-3 TracrRNA Portion 1

<400> SEQUENCE: 87
aagcagccag ucugcaccag au                                               22

<210> SEQ ID NO 88
<211> LENGTH: 13
<212> TYPE: RNA
<213> ORGANISM: Artificial Sequence
<220> FEATURE:
<223> OTHER INFORMATION: OMNI-79-3 tracrRNA Portion 1-partial

<400> SEQUENCE: 88
gcagccaguc ugc                                                         13

<210> SEQ ID NO 89
<211> LENGTH: 29
<212> TYPE: RNA
<213> ORGANISM: Artificial Sequence
<220> FEATURE:
<223> OTHER INFORMATION: OMNI-79-3 TracrRNA Portion 2

<400> SEQUENCE: 89
aagggcggcg cuccggcgcc gccuuuuuu                                        29

<210> SEQ ID NO 90
<211> LENGTH: 82
<212> TYPE: RNA
<213> ORGANISM: Artificial Sequence
<220> FEATURE:
<223> OTHER INFORMATION: OMNI-79-3 sgRNA Scaffold V1

<400> SEQUENCE: 90
```
guugccgcug gacgaaaguc uggcgguuaa caagcagcca gucugcacca gauaagggcg    60
gcgcuccggc gccgccuuuu uu    82

<210> SEQ ID NO 91
<211> LENGTH: 11
<212> TYPE: RNA
<213> ORGANISM: Artificial Sequence
<220> FEATURE:
<223> OTHER INFORMATION: OMNI-80 crRNA (Repeat)

<400> SEQUENCE: 91
guugcgguug g    11

<210> SEQ ID NO 92
<211> LENGTH: 10
<212> TYPE: RNA
<213> ORGANISM: Artificial Sequence
<220> FEATURE:
<223> OTHER INFORMATION: OMNI-80 Partial crRNA 3

<400> SEQUENCE: 92
guugcgguug    10

<210> SEQ ID NO 93
<211> LENGTH: 12
<212> TYPE: RNA
<213> ORGANISM: Artificial Sequence
<220> FEATURE:
<223> OTHER INFORMATION: OMNI-80 tracrRNA (Antirepeat)

<400> SEQUENCE: 93
cuggcuguua ac    12

<210> SEQ ID NO 94
<211> LENGTH: 11
<212> TYPE: RNA
<213> ORGANISM: Artificial Sequence
<220> FEATURE:
<223> OTHER INFORMATION: OMNI-80 Partial tracrRNA 3

<400> SEQUENCE: 94
uggcuguuaa c    11

<210> SEQ ID NO 95
<211> LENGTH: 22
<212> TYPE: RNA
<213> ORGANISM: Artificial Sequence
<220> FEATURE:
<223> OTHER INFORMATION: OMNI-80 TracrRNA Portion 1

<400> SEQUENCE: 95
aagcagcuug acugcaccaa au    22

<210> SEQ ID NO 96
<211> LENGTH: 13
<212> TYPE: RNA
<213> ORGANISM: Artificial Sequence
<220> FEATURE:
<223> OTHER INFORMATION: OMNI-80 tracrRNA Portion 1-partial

<400> SEQUENCE: 96
gcagcuugac ugc    13

<210> SEQ ID NO 97

```
<211> LENGTH: 27
<212> TYPE: RNA
<213> ORGANISM: Artificial Sequence
<220> FEATURE:
<223> OTHER INFORMATION: OMNI-80 TracrRNA Portion 2

<400> SEQUENCE: 97
aagggcaggg cugcggcccu gccuuuu                                          27

<210> SEQ ID NO 98
<211> LENGTH: 76
<212> TYPE: RNA
<213> ORGANISM: Artificial Sequence
<220> FEATURE:
<223> OTHER INFORMATION: OMNI-80 sgRNA Scaffold V1

<400> SEQUENCE: 98
guugcgguug ggaaacuggc uguuaacaag cagcuugacu gcaccaaaua agggcagggc      60
ugcggcccug ccuuuu                                                     76

<210> SEQ ID NO 99
<211> LENGTH: 13
<212> TYPE: RNA
<213> ORGANISM: Artificial Sequence
<220> FEATURE:
<223> OTHER INFORMATION: OMNI-81 crRNA (Repeat)

<400> SEQUENCE: 99
guuccggcua gag                                                        13

<210> SEQ ID NO 100
<211> LENGTH: 12
<212> TYPE: RNA
<213> ORGANISM: Artificial Sequence
<220> FEATURE:
<223> OTHER INFORMATION: OMNI-81 Partial crRNA 2

<400> SEQUENCE: 100
guuccggcua ga                                                         12

<210> SEQ ID NO 101
<211> LENGTH: 10
<212> TYPE: RNA
<213> ORGANISM: Artificial Sequence
<220> FEATURE:
<223> OTHER INFORMATION: OMNI-81 Partial crRNA 3

<400> SEQUENCE: 101
guuccggcua                                                            10

<210> SEQ ID NO 102
<211> LENGTH: 14
<212> TYPE: RNA
<213> ORGANISM: Artificial Sequence
<220> FEATURE:
<223> OTHER INFORMATION: OMNI-81 tracrRNA (Antirepeat)

<400> SEQUENCE: 102
cucuagacgc uaac                                                       14

<210> SEQ ID NO 103
<211> LENGTH: 13
<212> TYPE: RNA
<213> ORGANISM: Artificial Sequence
<220> FEATURE:
<223> OTHER INFORMATION: OMNI-81 Partial tracrRNA 2
```

<400> SEQUENCE: 103
ucuagacgcu aac                                                               13

<210> SEQ ID NO 104
<211> LENGTH: 11
<212> TYPE: RNA
<213> ORGANISM: Artificial Sequence
<220> FEATURE:
<223> OTHER INFORMATION: OMNI-81 Partial tracrRNA 3

<400> SEQUENCE: 104
uagacgcuaa c                                                                 11

<210> SEQ ID NO 105
<211> LENGTH: 22
<212> TYPE: RNA
<213> ORGANISM: Artificial Sequence
<220> FEATURE:
<223> OTHER INFORMATION: OMNI-81 TracrRNA Portion 1

<400> SEQUENCE: 105
aagcugaaag augcaccaaa ug                                                     22

<210> SEQ ID NO 106
<211> LENGTH: 12
<212> TYPE: RNA
<213> ORGANISM: Artificial Sequence
<220> FEATURE:
<223> OTHER INFORMATION: OMNI-81 tracrRNA Portion 1-partial

<400> SEQUENCE: 106
gcugaaagau gc                                                                12

<210> SEQ ID NO 107
<211> LENGTH: 30
<212> TYPE: RNA
<213> ORGANISM: Artificial Sequence
<220> FEATURE:
<223> OTHER INFORMATION: OMNI-81 TracrRNA Portion 2

<400> SEQUENCE: 107
gaaagccgcu auaugcggcu uucgucuuuu                                             30

<210> SEQ ID NO 108
<211> LENGTH: 83
<212> TYPE: RNA
<213> ORGANISM: Artificial Sequence
<220> FEATURE:
<223> OTHER INFORMATION: OMNI-81 sgRNA Scaffold V1

<400> SEQUENCE: 108
guuccggcua gaggaaacuc uagacgcuaa caagcugaaa gaugcaccaa auggaaagcc            60
gcuauaugcg gcuuucgucu uuu                                                    83

<210> SEQ ID NO 109
<211> LENGTH: 16
<212> TYPE: RNA
<213> ORGANISM: Artificial Sequence
<220> FEATURE:
<223> OTHER INFORMATION: OMNI-82 crRNA (Repeat)

<400> SEQUENCE: 109
guugcggcug gaccgc                                                            16

```
<210> SEQ ID NO 110
<211> LENGTH: 15
<212> TYPE: RNA
<213> ORGANISM: Artificial Sequence
<220> FEATURE:
<223> OTHER INFORMATION: OMNI-82 Partial crRNA 1

<400> SEQUENCE: 110
guugcggcug gaccg                                                        15

<210> SEQ ID NO 111
<211> LENGTH: 12
<212> TYPE: RNA
<213> ORGANISM: Artificial Sequence
<220> FEATURE:
<223> OTHER INFORMATION: OMNI-82 Partial crRNA 2

<400> SEQUENCE: 111
guugcggcug ga                                                           12

<210> SEQ ID NO 112
<211> LENGTH: 10
<212> TYPE: RNA
<213> ORGANISM: Artificial Sequence
<220> FEATURE:
<223> OTHER INFORMATION: OMNI-82 Partial crRNA 3

<400> SEQUENCE: 112
guugcggcug                                                              10

<210> SEQ ID NO 113
<211> LENGTH: 17
<212> TYPE: RNA
<213> ORGANISM: Artificial Sequence
<220> FEATURE:
<223> OTHER INFORMATION: OMNI-82 tracrRNA (Antirepeat)

<400> SEQUENCE: 113
gcggucgagc uguuaac                                                      17

<210> SEQ ID NO 114
<211> LENGTH: 16
<212> TYPE: RNA
<213> ORGANISM: Artificial Sequence
<220> FEATURE:
<223> OTHER INFORMATION: OMNI-82 Partial tracrRNA 1

<400> SEQUENCE: 114
cggucgagcu guuaac                                                       16

<210> SEQ ID NO 115
<211> LENGTH: 13
<212> TYPE: RNA
<213> ORGANISM: Artificial Sequence
<220> FEATURE:
<223> OTHER INFORMATION: OMNI-82 Partial tracrRNA 2

<400> SEQUENCE: 115
ucgagcuguu aac                                                          13

<210> SEQ ID NO 116
<211> LENGTH: 11
<212> TYPE: RNA
<213> ORGANISM: Artificial Sequence
<220> FEATURE:
<223> OTHER INFORMATION: OMNI-82 Partial tracrRNA 3
```

```
<400> SEQUENCE: 116
gagcuguuaa c                                                           11

<210> SEQ ID NO 117
<211> LENGTH: 22
<212> TYPE: RNA
<213> ORGANISM: Artificial Sequence
<220> FEATURE:
<223> OTHER INFORMATION: OMNI-82 TracrRNA Portion 1

<400> SEQUENCE: 117
aagcauucga uugcaccaca uu                                               22

<210> SEQ ID NO 118
<211> LENGTH: 12
<212> TYPE: RNA
<213> ORGANISM: Artificial Sequence
<220> FEATURE:
<223> OTHER INFORMATION: OMNI-82 tracrRNA Portion 1-partial

<400> SEQUENCE: 118
gcauucgauu gc                                                          12

<210> SEQ ID NO 119
<211> LENGTH: 28
<212> TYPE: RNA
<213> ORGANISM: Artificial Sequence
<220> FEATURE:
<223> OTHER INFORMATION: OMNI-82 TracrRNA Portion 2

<400> SEQUENCE: 119
gaagcgcagg gccacggccc ugcguuuu                                         28

<210> SEQ ID NO 120
<211> LENGTH: 87
<212> TYPE: RNA
<213> ORGANISM: Artificial Sequence
<220> FEATURE:
<223> OTHER INFORMATION: OMNI-82 sgRNA Scaffold V1

<400> SEQUENCE: 120
guugcggcug gaccgcgaaa gcggucgagc uguuaacaag cauucgauug caccacauug      60
aagcgcaggg ccacggcccu gcguuuu                                          87

<210> SEQ ID NO 121
<211> LENGTH: 6616
<212> TYPE: DNA
<213> ORGANISM: Artificial Sequence
<220> FEATURE:
<223> OTHER INFORMATION: pbNNC-3

<400> SEQUENCE: 121
gttgtgccac gcggttggga atgtaattca gctccgccat cgccgcttcc acttttccc       60 gcgttttcgc agaaacgtgg ctggcctggt tcaccacgcg ggaaacggtc tgataagaga     120
caccggcata tctctgcgac atcgtataac gttactggtt tcacattcac cccctgaatt    180
gactctcttc cgggcgctat catgccatac cgcgaaaggt tttgcgccat tcgatggtgt    240
cgggatctcg acgctaaatt aatacgactc actataggg aattgtgagc ggataacaat     300
tcccctgtag aaataatttt gtttaactaa agaggagaaa tttcatatgt acccatacga    360
tgtgccagat tacgctggca ccgagctcgg taccgagaag agactgggcc tcgacatcgg    420
```

```
cacaaatagc atcggctggt gcctgtacga gggcgactct atcctggata tcggcgtgcg    480
gatcttcagc gacggcagag atcctaaatc tggcgcctct ctggccgtgg acagacggaa    540
tgctagagcc atgcggcgga aagggatag atacctggga agaagaagcg ccctgatcaa     600
ggccctgaag gccatggac tgtttccagc cgaacaggat gccgccaagg ctctggaaag     660
agaggaccct tacagcctga gagtcagagc cctggatcac agactggacc ctcatcagat    720
cggcagagcc atcttccacc tgaaccagcg gagaggcttc agaagcaaca gaaaggccga    780
cagagtgctg ggcgatcaag agagcggact gatcagcaca gccaccagag ttctggacga    840
agccatggcc aaaagcggcg ctagaacact gggagagttt ctggccagcc gggacactag    900
aagagtgcgg atgaggcctg acgtgaaggg ctacgacttc taccccaacc ggcagcacta    960
cctggaagag ttcgagaaga tctgggacgc ccagagccag tatcaccctg atctgctgtc   1020
tcagcaggcc aagagcgcca tccaccggat cattttcac cagaggccac tgaagccaca    1080
ggccgtggga acatgtacat tgccggact gcatggcatc cccggcgacg agacaagact    1140
gcctaaagct caccctctgt tccagcagcg gcggctgtat gaggaagtga accagctgga   1200
aatcgtgtgc gccagcgctc ctgccagaaa gctgaccaga gatgagagag atgccctgat   1260
cctgaagctg caggacaaga aaaaagtgac cttcagcaca ctggcccgga ccatcagact   1320
gaaagagggc gagagattca caaagagag cgagaaccgg aaggacctgg ctggggatga   1380
agtgcgggcc gagatgagcg ataagaccag attcggcaga cggtggtttc acctgagcct   1440
ggatgagcag tggtccgtga tcgacagact gctgaacgag gaaagcaccg aggatctgct   1500
ggcctggctg gaaaaagagt ggtccctgcc ttctgatgtg gccgaagccg tggctaatgc   1560
ccatctgcct gatggccacg gaagatttgg cctgacagcc accgttagac tgctcgaaca   1620
cctgaaagcc gacgtggtca catatgccga agctgctcgg agagccggct ccaccactc   1680
tgatttcaga gatggcgcct gctacgacga gctgccttac tatggcgaga tcctgagcag   1740
agagatcgcc cctggaaagg acgagtacg cgatccactg gaaagacagt ggggcaagat   1800
cacaaacccc accgtgcaca tcggcctgaa tcagctgaga aggctgatta acgccctcgt   1860
gcggagacac ggcagacccg atttcatctt cgtggaactg gcccgcgagc tgaagctgaa   1920
tgagaagcag aaggccgacc acaagcggcg gatcaagcag acaacagatg ccgctagagc   1980
tagagccgag aagctgagag aaatcggaca gagagacagc ggctccaacc ggatgctgct   2040
gcggatttgg gaagaactga accccagcaa tccctggac agaagatgcc cttattgcgc   2100
cgagcctatc tccatcgaga tgctgatgag cggcagcgcc gacatcgatc acatcgtgcc   2160
ttacagcaga tgcctggacg atagcgccgc caacaaagtg gtggcccaca accactgcaa   2220
cagacagaag gcaacagaa cccttgggga gcagtgggga cagaccacaa gatggcccct   2280
gattcaagaa caggtggccc ggatgcacag atccaaacaa tggcgcttcg ccccgacgc   2340
catggaacga gttgatcgag atggcggctt tatcgcccgg cagctgacag atacccagta   2400
cctgtctaga atcgccgcac agtacctgag cgccctgtac acacctgatg aaggcagacg   2460
ggtgtacgcc gtgacaggca gactgactgc tatgcttaga cggctgtggg gcctgaacga   2520
catcctgcct gatcacaact gggtgctgaa ccctcacagc aacgcccta agaacaggct   2580
ggatcataga caccacgcca tcgatgccgc cgttgtggga gctacaacac ccgccatgat   2640
tcagcaggtt gccagagctg ctgcaagagc cgaggaacag gacctggata gactgttcgc   2700
tgacctgcct cctccatggc caggcttag agaggaactg caggcagaa ttatggccgc    2760
tgtggtgtct cacaagcccg accatggaag aaagggcaga ccactgcctg cagagatag    2820
```

```
cacatccggc agactgcaca atgacaccgc ctacggcttt actggccgca gaaatgccaa    2880
gggcatgcct atcgtggtca ccagaaaacc cctgctggcc ctgaaacctg aggacctgac    2940
agaccccgag agaatcccag atcctgctct gcagggcgca ctgtttgaag ccactagagg    3000
cgctaccggc aaggacttcg agaaagccct gcgggacttc agcagaagag atggccctta    3060
ccagggcatc agacggatta gactgaccga ggctctgaac gtgatcccca tcagagatag    3120
aaccggccac gcctacaaag gcgtgaaagg cgacgccaac gccagattcg atgtttggag    3180
actgcccgac ggcaagtgga tcaccagatg aaggataga gatggcatcg agcacagcgg    3240
catcgtgtcc ctgtttgatg ctcaccagcc tagccaggtg taccacagac tcatcctgc     3300 cgccaaaaag gtgctgagcc tgagacagaa tgacctggtg gcagtggaac acgatggcga    3360
ccccggaaag atcatgcggg tcgtgaagtt tagcgccaac ggcagcatca cattcgcccc    3420
acataatgag gccggacctc tgaaaacccg ggacaccgat cctgccgatc ctttcagata    3480
cgtgacaaca gtggccagcg gcctgaagaa gatgagagcc agacaagtgc ggatcgatga    3540
gctgggcaaa gtgcacgatc ccggacctag agaggatgga tccccaaaaa agaaaagaaa    3600
agttgctgcc gcactcgagc atcatcacca tcaccatcat cattaagcgg ccgcctagca    3660
taaccccttg gggcctctaa acgggtcttg aggggttttt tgacctaggc tagggatat    3720 attccgcttc ctcgctcact gactcgctac gctcggtcgt tcgactgcgg cgagcggaaa    3780
tggcttacga acgggcgga gatttcctgg aagatgccag gaagatactt aacagggaag    3840
tgagagggcc gcggcaaagc cgttttttcca taggctccgc ccccctgaca agcatcacga    3900
aatctgacgc tcaaatcagt ggtggcgaaa cccgacagga ctataaagat accaggcgtt    3960 tcccctggc ggctccctcg tgcgctctcc tgttcctgcc tttcggttta ccggtgtcat     4020
tccgctgtta tggccgcgtt tgtctcattc cacgcctgac actcagttcc gggtaggcag    4080
ttcgctccaa gctggactgt atgcacgaac ccccgttca gtccgaccgc tgcgccttat     4140
ccggtaacta tcgtcttgag tccaacccgg aaagacatgc aaaagcacca ctggcagcag    4200
ccactggtaa ttgatttaga ggagttagtc ttgaagtcat gcgccggtta aggctaaact    4260
gaaaggacaa gttttggtga ctgcgctcct ccaagccagt tacctcggtt caaagagttg    4320
gtagctcaga gaaccttcga aaaaccgccc tgcaaggcgg ttttttcgtt ttcagagcaa    4380
gagattacgc gcagaccaaa acgatctcaa gaagatcatc ttattaatca gataaaatat    4440
ttctagattt cagtgcaatt tatctcttca aatgtagcac ctgaagtcag ccccatacga    4500
tataagttgt tactagtgct tggattctca ccaataaaaa acgcccggcg caaccgagc     4560 gttctgaaca aatccagatg gagttctgag gtcattactg gatctatcaa caggagtcca    4620
agcgagctcg taaacttggt ctgacagtta ccaatgctta atcagtgagg cacctatctc    4680
agcgatctgt ctatttcgtt catccatagt tgcctgactc cccgtcgtgt agataactac    4740
gatacgggag ggcttaccat ctggccccag tgctgcaatg ataccgcggg agccacgctc    4800
accggctcca gatttatcag caataaacca gccagccgga agggccgagc gcagaagtgg    4860
tcctgcaact ttatccgcct ccatccagtc tattaattgt tgccgggaag ctagagtaag    4920
tagttcgcca gttaatagtt tgcgcaacgt tgttgccatt gctacaggca tcgtggtgtc    4980
acgctcgtcg tttggtatgg cttcattcag ctccggttcc caacgatcaa ggcgagttac    5040
atgatccccc atgttgtgca aaaaagcggt tagctccttc ggtcctccga tcgttgtcag    5100
aagtaagttg gccgcagtgt tatcactcat ggttatggca gcactgcata attctcttac    5160
```

```
tgtcatgcca tccgtaagat gcttttctgt gactggtgag tactcaacca agtcattctg    5220
agaatagtgt atgcggcgac cgagttgctc ttgcccggcg tcaatacggg ataataccgc    5280
gccacatagc agaactttaa aagtgctcat cattggaaaa cgttcttcgg ggcgaaaact    5340
ctcaaggatc ttaccgctgt tgagatccag ttcgatgtaa cccactcgtg cacccaactg    5400
atcttcagca tcttttactt tcaccagcgt ttctgggtga gcaaaacag gaaggcaaaa     5460 tgccgcaaaa aagggaataa gggcgacacg gaaatgttga atactcatac tcttcctttt    5520
tcaatattat tgaagcattt atcagggtta ttgtctcatg agcggataca tatttgaatg    5580
tatttagaaa aataaacaaa tagggggttcc gcgcacattt ccccgaaaag tgccacctga    5640
cgtcctcgag tcccggtgcc taatgagtga gctaacttac attaattgcg ttgcgctcac    5700
tgcccgcttt ccagtcggga aacctgtcgt gccagctgca ttaatgaatc ggccaacgcg    5760
cggggagagg cggtttgcgt attgggcgcc agggtggttt tcttttcac cagtgacacg      5820 ggcaacagct gattgccctt caccgcctgg ccctgagaga gttgcagcaa gcggtccacg    5880
ctggtttgcc ccagcaggcg aaaatcctgt ttgatggtgg ttaacggcgg gatataacat    5940
gagctgtctt cggtatcgtc gtatcccact accgagatgt ccgcaccaac gcgcagcccg    6000
gactcggtaa tggcgcgcat gccgcccagc gccatcgat cgttggcaac cagcatcgca      6060
gtgggaacga tgccctcatt cagcatttgc atggtttgtt gaaaaccgga catggcactc    6120
cagtcgcctt cccgttccgc tatcggctga atttgattgc gagtgagata tttatgccag    6180
ccagccagac gcagacgcgc cgagacagaa cttaatgggc ccgctaacag cgcgatttgc    6240
tggtgaccca atgcgaccag atgctccacg cccagtcgcg taccgtcttc atgggagaaa    6300
ataatactgt tgatgggtgt ctggtcagag acatcaagaa ataacgccgg aacattagtg    6360
caggcagctt ccacagcaat ggcatcctgg tcatccagcg gatagttaat gatcagccca    6420
ctgacgcgtt gcgcgagaag attgtgcacc gccgctttac aggcttcgac gccgcttcgt    6480
tctaccatcg acaccaccac gctggcaccc agttgatcgg cgcgagattt aatcgccgcg    6540
acaatttgcg acggcgcgtg cagggccaga ctggaggtgg caacgccaat cagcaacgac    6600
tgtttgcccg ccagtt                                                    6616
```

<210> SEQ ID NO 122
<211> LENGTH: 2549
<212> TYPE: DNA
<213> ORGANISM: Artificial Sequence
<220> FEATURE:
<223> OTHER INFORMATION: Artificial Sequence

<400> SEQUENCE: 122

```
gcataaccaa gcctatgcct acagcatcca gggtgacggt gccgaggatg acgatgagcg      60
cattgttaga tttcatacac ggtgcctgac tgcgttagca atttaactgt gataaactac     120
cgcattaaag cttatcgatg ataagctgtc aacacatttc cccgaaaagt gccacctgac     180
gtcctcgagt cccgcataat cgaaattaat acgactcact atagggaaga gcagagcctt    240
ggtctcgttg ccgctggaga atccagttg ttaacaagca gcttgactgc accaaataag     300 gcggggggctg cggccctcgc ttttttgaat tcttccgctg agcaataact agcataaccc    360 cttgggggcct ctaaacgggt cttgagggggt ttttgacct aggctagggg atatattccg     420
cttcctcgcg gtaccccgct tcctcgctca ctgactcgct acgctcggtc gttcgactgc     480
ggcgagcgga aatggcttac gaacgggcg gagatttcct ggaagatgcc aggaagatac       540
ttaacaggga agtgagaggg ccgcggcaaa gccgtttttc cataggctcc gccccctga      600
```

```
caagcatcac gaaatctgac gctcaaatca gtggtggcga aacccgacag gactataaag    660
ataccaggcg tttcccctg gcggctccct cgtgcgctct cctgttcctg cctttcggtt    720
taccggtgtc attccgctgt tatggccgcg tttgtctcat tccacgcctg acactcagtt    780
ccgggtaggc agttcgctcc aagctggact gtatgcacga accccccgtt cagtccgacc    840
gctgcgcctt atccggtaac tatcgtcttg agtccaaccc ggaaagacat gcaaaagcac    900
cactggcagc agccactggt aattgattta gaggagttag tcttgaagtc atgcgccggt    960
taaggctaaa ctgaaaggac aagttttggt gactgcgctc ctccaagcca gttacctcgg   1020
ttcaaagagt tggtagctca gagaaccttc gaaaaaccgc cctgcaaggc ggttttttcg   1080
ttttcagagc aagagattac gcgcagacca aaacgatctc aagaagatca tcttattaat   1140
cagataaaat atttctagat ttcagtgcaa tttatctctt caaatgtagc acctgaagtc   1200
agccccatac gatataagtt gttactagtg cttggattct caccaataaa aaacgcccgg   1260
cggcaaccga gcgttctgaa caaatccaga tggagttctg aggtcattac tggatctatc   1320
aacaggagtc caagcgagaa gggttggttt gcgcattcac agttctccgc aagaattgat   1380
tggctccaat tcttggagtg gtgaatccgt tagcgaggtg ccgccggctt ccattcaggt   1440
cgaggtggcc cggctccatg caccgcgacg caacgcgggg aggcagacaa ggtatagggc   1500
ggcgcctaca atccatgcca acccgttcca tgtgctcgcc gaggcggcat aaatcgccgt   1560
gacgatcagc ggtccaatga tcgaagttag gctggtaaga gccgcgagcg atccttgaag   1620
ctgtccctga tggtcgtcat ctacctgcct ggacagcatg gcctgcaacg cgggcatccc   1680
gatgccgccg gaagcgagaa gaatcataat ggggaaggcc atccagcctc gcgtcgcgaa   1740
cgccagcaag acgtagccca gcgcgtcggc cgccatgccg gcgataatgg cctgcttctc   1800
gccgaaacgt ttggtggcgg gaccagtgac gaaggcttga gcgagggcgt gcaagattcc   1860
gaataccgca agcgacaggc cgatcatcgt cgcgctccag cgaaagcggt cctcgccgaa   1920
aatgacccag agcgctgccg gcacctgtcc tacgagttgc atgataaaga agacagtcat   1980
aagtgcggcg acgatagtca tgccccgcgc ccaccggaag gagctgactg ggttgaaggc   2040
tctcaagggc atcggtcgac gctctcccctt atgcgactcc tgcattagga agcagccag    2100 tagtaggttg aggccgttga gcaccgccgc cgcaaggaat ggtgcatgca aggagatggc   2160
gcccaacagt cccccggcca cggggcctgc caccatacc acgccgaaac aagcgctcat    2220
gagcccgaag tggcgagccc gatcttcccc atcggtgatg tcggcgatat aggcgccagc   2280
aaccgcacct gtggcgccgg tgatgccggc cacgatgcgt ccggcgtaga ggatccacag   2340
gacgggtgtg gtcgccatga tcgcgtagtc gatagtggct ccaagtagcg aagcgagcag   2400
gactgggcgc cggccaaagc ggtcggacag tgctccgaga acgggtgcgc atagaaattg   2460
catcaacgca tatagcgcta gcagcacgcc atagtgactg gcgatgctgt cggaatggac   2520
gatatcccgc aagaggcccg gcagtaccg                                    2549
```

<210> SEQ ID NO 123
<211> LENGTH: 5009
<212> TYPE: DNA
<213> ORGANISM: Artificial Sequence
<220> FEATURE:
<223> OTHER INFORMATION: pbPOS T2 library
<220> FEATURE:
<221> NAME/KEY: misc_feature
<222> LOCATION: (3040)..(3047)
<223> OTHER INFORMATION: n is a, c, g, or t

<400> SEQUENCE: 123

```
tcgagtcttt acactttatg cttccggctc gtatgttgtg tggaattgtg agcggataac      60
aatttcacac atgattacgg attcaacgtc gtgactggta aaacccgggc gttacccaac     120
ttaatcgcct tgcagcacat ccccctttcg ccagcaggcg taataaggaa aggattcatg     180
tactatttga aaacacaaa cttttggatg ttcggtttat tcttttttctt ttactttttt     240
atcatgggag cctacttccc gttttttccg atttggctac atgatatcaa ccatatcagc     300
aaaagtgata cgggtattat ttttgccgct atttctctgt tctcgctatt attccaaccg     360
ctgtttggtc tgcttcctga caaactcggt ctacgcaaat acctgctgtg gattattacc     420
ggcatgttag tgatgtttgc gccgttcttt attttatct tcgggccact gctgcagtac      480
aacattttag tagggtcgat tgttggtggt atttatctag gctttagttt taacgccggt     540
gcgccagcag tagaggcatt tattgagaaa gtcagccggc gcagtaattt cgaatttggt     600
cgcgcgcgga tgtttggcag tgttggctgg gcgctggttg cctcgattgt cgggatcatg     660
ttcaccatta ataatcagtt tgttttctgg ctgggctctg gcagttgtct catcctcgcc     720
gttttactct ttttcgccaa aacggacgcg ccctcaagtg ccacggttgc caatgcggta     780
ggtgccaacc attcggcatt tagccttaag ctggcactgg aactgttcag acagccaaaa     840
ctgtggtttt tgtcactgta tgttattggc gtttcctcca cctacgatgt ttttgaccaa     900
cagtttgcta atttctttac ttcgttcttt gctaccggtg aacagggtac ccgcgtattt     960
ggctacgtaa cgacaatggg cgaattactt aacgcctcga ttatgttctt tgcgccactg    1020
atcattaatc gcatcggtgg gaagaatgcc ctgctgctgg ctggcactat tatgtctgta    1080
cgtattattg gctcatcgtt cgccacctca gcgctggaag tggttattct gaaaacgctg    1140
catatgtttg aagtaccgtt cctgctggtg ggctccttta aatatattac tagtcagttt    1200
gaagtgcgtt tttcagcgac gatttatctg gtcagtttca gcttctttaa gcaactggcg    1260
atgattttta tgtctgtact ggcgggcaat atgtatgaaa gcataggttt ccaaggcgct    1320
tatctggtgc tgggtctggt ggcgctgggc ttcaccttaa tttccgtgtt cacgcttagc    1380
ggcccgggcc cgctttccct gctgcgtcgt caggtgaatg aagtcgctta aaggcctcga    1440
tgcagctagc atgctaatct gattcgttac caattatgac aacttgacgg ctacatcatt    1500
cactttttct tcacaaccgg cacgaactc gctcgggctg ccccggtgc atttttaaa      1560
tacccgcgag aaatagagtt gatcgtcaaa accaacattg cgaccgacgg tggcgatagg    1620
catccggtg gtgctcaaaa gcagcttcgc ctggctgata cgttggtcct cgcgccagct    1680
taagacgcta atccctaact gctggcggaa aagatgtgac agacgcgacg gcgacaagca    1740
aacatgctgt gcgacgctgg cgatatcaaa attgctgtct gccaggtgat cgctgatgta    1800
ctgacaagcc tcgcgtaccc gattatccat cggtggatgg agcgactcgt taatcgcttc    1860
catgcgccgc agtaacaatt gctcaagcag atttatcgcc agcagctccg aatagcgccc    1920
ttccccttgc ccggcgttaa tgatttgccc aaacaggtcg ctgaaatgcg gctggtgcgc    1980
ttcatccggg cgaaagaacc ccgtattggc aaatattgac ggccagttaa gccattcatg    2040
ccagtaggcg cgcggacgaa agtaaaccca ctggtgatac cattcgcgag cctccggatg    2100
acgaccgtag tgatgaatct ctcctggcgg gaacagcaaa atatcacccg gtcggcaaac    2160
aaattctcgt ccctgatttt tcaccacccc ctgaccgcga atggtgagat tgagaatata    2220
accttctcatt cccagcggtc ggtcgataaa aaatcgaga taaccgttgg cctcaatcgg    2280
cgttaaaccc gccaccagat gggcattaaa cgagtatccc ggcagcaggg gatcattttg    2340
```

```
cgcttcagcc atactttca tactcccgcc attcagagaa gaaaccaatt gtccatattg    2400
catcagacat tgccgtcact gcgtcttta ctggctcttc tcgctaacca aaccggtaac    2460
cccgcttatt aaaagcattc tgtaacaaag cgggaccaaa gccatgacaa aaacgcgtaa    2520
caaaagtgtc tataatcacg gcagaaaagt ccacattgat tatttgcacg gcgtcacact    2580
ttgctatgcc atagcatttt tatccataag attagcggat cctacctgac gcttttatc    2640 gcaactctct actgtttctc catacccgtt ttttggggt agcgattgaa aacgatgcag    2700
tttaaggttt acacctataa agagagagc cgttatcgtc tgtttgtgga tgtacagagt    2760
gatattattg acacgcccgg gcgacggatg gtgatccccc tggccagtgc acgtctgctg    2820
tcagataaag tctcccgtga actttacccg gtggtgcata tcggggatga agctggcgc    2880 atgatgacca ccgatatggc cagtgtgccg gtctccgtta tcggggaaga agtggctgat    2940
ctcagccacc gcgaaaatga catcaaaaac gccattaacc tgatgttttg gggaatataa    3000
tcttctagac atacaatgga agagcagagc cttggtctcn nnnnnnaag cttgatatcg    3060 aattcctgca gcccggggga tcccatggta cgcgtgctag aggcatcaaa taaaacgaaa    3120
ggctcagtcg aaagactggg cctttcgttt tatctgttgt ttgtcggtga acgctctcct    3180
gagtaggaca atccgccgc cctagaccta ggcgttcggc tgcggcgagc ggtatcagct    3240
cactcaaagg cggtaatacg gttatccaca gaatcagggg ataacgcagg aaagaacatg    3300
tgagcaaaag gccagcaaaa ggccaggaac cgtaaaaagg ccgcgttgct ggcgtttttc    3360
cataggctcc gcccccctga cgagcatcac aaaaatcgac gctcaagtca gaggtggcga    3420
aacccgacag gactataaag ataccaggcg tttccccctg gaagctccct cgtgcgctct    3480
cctgttccga ccctgccgct taccggatac ctgtccgcct ttctcccttc gggaagcgtg    3540
gcgctttctc aatgctcacg ctgtaggtat ctcagttcgg tgtaggtcgt tcgctccaag    3600
ctgggctgtg tgcacgaacc ccccgttcag cccgaccgct gcgccttatc cggtaactat    3660
cgtcttgagt ccaacccggt aagacacgac ttatcgccac tggcagcagc cactggtaac    3720
aggattagca gagcgaggta tgtaggcggt gctacagagt tcttgaagtg gtggcctaac    3780
tacggctaca ctagaaggac agtatttggt atctgcgctc tgctgaagcc agttaccttc    3840
ggaaaaagag ttggtagctc ttgatccggc aaacaaacca ccgctggtag cggtggtttt    3900
tttgtttgca agcagcagat tacgcgcaga aaaaaaggat ctcaagaaga tcctttgatc    3960
ttttctacgg ggtctgacgc tcagtggaac gaaaactcac gttaagggat tttggtcatg    4020
actagtgctt ggattctcac caataaaaaa cgcccggcgg caaccgagcg ttctgaacaa    4080
atccagatgg agttctgagg tcattactgg atctatcaac aggagtccaa gcgagctcga    4140
tatcaaatta cgcccgccc tgccactcat cgcagtactg ttgtaattca ttaagcattc    4200
tgccgacatg gaagccatca cagacggcat gatgaacctg aatcgccagc ggcatcagca    4260
ccttgtcgcc ttgcgtataa tatttgccca tggtgaaaac ggggcgaag aagttgtcca    4320 tattggccac gtttaaatca aaactggtga aactcaccca gggattggct gagacgaaaa    4380
acatattctc aataaaccct ttagggaaat aggccaggtt ttcaccgtaa cacgccacat    4440
cttgcgaata tatgtgtaga aactgccgga atcgtcgtg gtattcactc cagagcgatg    4500
aaaacgtttc agtttgctca tggaaaacgg tgtaacaagg gtgaacacta tcccatatca    4560
ccagctcacc gtctttcatt gccatacgga attccggatg agcattcatc aggcgggcaa    4620
gaatgtgaat aaaggccgga taaaacttgt gcttattttt ctttacggtc tttaaaaagg    4680
```

-continued

```
ccgtaatatc cagctgaacg gtctggttat aggtacattg agcaactgac tgaaatgcct    4740
caaaatgttc tttacgatgc cattgggata tatcaacggt ggtatatcca gtgattttt    4800 tctccatttt agcttcctta gctcctgaaa atctcgataa ctcaaaaaat acgcccggta    4860
gtgatcttat ttcattatgg tgaaagttgg aacctcttac gtgccgatca acgtctcatt    4920
ttcgccagat atcgacgtct aagaaaccat tattatcatg acattaacct ataaaaatag    4980
gcgtatcacg aggccctttc gtcttcacc                                      5009
```

<210> SEQ ID NO 124
<211> LENGTH: 5515
<212> TYPE: DNA
<213> ORGANISM: Artificial Sequence
<220> FEATURE:
<223> OTHER INFORMATION: pET9a

<400> SEQUENCE: 124

```
taatacgact cactataggg agaccacaac ggtttccctc tagagagaca ataaccctga      60
taatgcttca ataatattga aaaggaaga gtatgcctaa gaagaagaga aaggtgggta     120
ccgagaagag actgggcctc gacatcggca caaatagcat cggctggtgc ctgtacgagg     180
gcgactctat cctggatatc ggcgtgcgga tcttcagcga cggcagagat cctaaatctg     240
gcgcctctct ggccgtggac agacggaatg ctagagccat gcggcggaga agggatagat     300
acctgggaag aagaagcgcc ctgatcaagg ccctgaaggc ccatggactg tttccagccg     360
aacaggatgc cgccaaggct ctggaaagag aggacccctta cagcctgaga gtcagagccc     420
tggatcacag actggaccct catcagatcg gcagagccat cttccacctg aaccagcgga     480
gaggcttcag aagcaacaga aaggccgaca gagtgctggg cgatcaagag agcggactga     540
tcagcacagc caccagagtt ctggacgaag ccatggccaa aagcggcgct agaacactgg     600
gagagtttct ggccagccgg gacactagaa gagtgcggat gaggcctgac gtgaagggct     660
acgacttcta ccccaaccgg cagcactacc tggaagagtt cgagaagatc tgggacgccc     720
agagccagta tcaccctgat ctgctgtctc agcaggccaa gagcgccatc caccggatca     780 ttttttcacca gaggccactg aagccacagg ccgtgggaac atgtacattt gccggactgc     840
atggcatccc cggcgacgag acaagactgc ctaaagctca ccctctgttc cagcagcggc     900
ggctgtatga ggaagtgaac cagctggaaa tcgtgtgcgc cagcgctcct gccagaaagc     960
tgaccagaga tgagagagat gccctgatcc tgaagctgca ggacaagaaa aaagtgacct    1020
tcagcacact ggcccggacc atcagactga aagaggcga gagattcaac aaagagagcg    1080
agaaccggaa ggacctggct ggggatgaag tgcgggccga tgagcgat aagaccagat    1140 tcggcagacg gtggtttcac ctgagcctgg atgagcagtg gtccgtgatc gacagactgc    1200
tgaacgagga aagcaccgag gatctgctgg cctggctgga aaagagtgg tccctgcctt    1260 ctgatgtggc cgaagccgtg gctaatgccc atctgcctga tggccacgga agatttggcc    1320
tgacagccac cgttagactg ctcgaacacc tgaaagccga cgtggtcaca tatgccgaag    1380
ctgctcggag agccggcttc accactctg atttcagaga tggcgcctgc tacgacgagc    1440
tgccttacta tggcgagatc ctgagcagag agatcgcccc tggaaaggac gagtacggcg    1500
atccactgga aagacagtgg ggcaagatca caaacccac cgtgcacatc ggcctgaatc    1560
agctgagaag gctgattaac gcccctcgtgc ggagacacgg cagacccgat ttcatcttcg    1620
tggaactggc ccgcgagctg aagctgaatg agaagcagaa ggccgaccac aagcggcgga    1680
tcaagcagac aacagatgcc gctagagcta gagccgagaa gctgagagaa atcggacaga    1740
```

```
gagacagcgg ctccaaccgg atgctgctgc ggatttggga agaactgaac cccagcaatc   1800
ccctggacag aagatgccct tattgcgccg agcctatctc catcgagatg ctgatgagcg   1860
gcagcgccga catcgatcac atcgtgcctt acagcagatg cctggacgat agcgccgcca   1920
acaaagtggt ggcccacaac cactgcaaca gacagaaggg caacgaaacc ccttgggagc   1980
agtggggaca gaccacaaga tggcccctga ttcaagaaca ggtggcccgg atgcacagat   2040
ccaaacaatg gcgcttcggc cccgacgcca tggaacgagt tgatcgagat ggcggcttta   2100
tcgcccggca gctgacagat acccagtacc tgtctagaat cgccgcacag tacctgagcg   2160
ccctgtacac acctgatgaa ggcagacggg tgtacgccgt gacaggcaga ctgactgcta   2220
tgcttagacg gctgtggggc ctgaacgaca tcctgcctga tcacaactgg gtgctgaacc   2280
ctcacagcaa cgcccctaag aacaggctgg atcatagaca ccacgccatc gatgccgccg   2340
ttgtgggagc tacaacaccc gccatgattc agcaggttgc cagagctgct gcaagagccg   2400
aggaacagga cctggataga ctgttcgctg acctgcctcc tccatggcca ggctttagag   2460
aggaactgca gggcagaatt atggccgctg tggtgtctca caagcccgac catggaagaa   2520
agggcagacc actgcctggc agagatagca catccggcag actgcacaat gacaccgcct   2580
acggctttac tggccgcaga aatgccaagg gcatgcctat cgtggtcacc agaaaacccc   2640
tgctggccct gaaacctgag gacctgacag accccgagag aatccagat cctgctctgc   2700
agggcgcact gtttgaagcc actagaggcg ctaccggcaa ggacttcgag aaagccctgc   2760
gggacttcag cagaagagat ggcccttacc agggcatcag acggattaga ctgaccgagg   2820
ctctgaacgt gatccccatc agagatagaa ccggccacgc ctacaaaggc gtgaaggcg   2880
acgccaacgc cagattcgat gtttggagac tgcccgacgg caagtggatc accagatgga   2940
aggatagaga tggcatcgag cacagcggca tcgtgtccct gtttgatgct caccagccta   3000
gccaggtgta ccacagacct catcctgccg ccaaaaaggt gctgagcctg agacagaatg   3060
acctggtggc agtggaacac gatggcgacc ccggaaagat catgcgggtc gtgaagttta   3120
gcgccaacgg cagcatcaca ttcgccccac ataatgaggc cggacctctg aaaacccggg   3180
acaccgatcc tgccgatcct ttcagatacg tgacaacagt ggccagcggc ctgaagaaga   3240
tgagagccag acaagtgcgg atcgatgagc tgggcaaagt gcacgatccc ggacctagag   3300
aggatggatc ctacccatac gatgttccag attacgcggc cgctccaaaa agaaaaagaa   3360
aagttgcggc tagccatcat caccatcacc atcatcatta aggctgctaa caaagcccga   3420
aaggaagctg agttggctgc tgccaccgct gagcaataac tagcataacc ccttggggcc   3480
tctaaacggg tcttgagggg ttttttgctg aaaggaggaa ctatatccgg atatccacag   3540
gacgggtgtg gtcgccatga tcgcgtagtc gatagtggct ccaagtagcg aagcgagcag   3600
gactgggcgg cggccaaagc ggtcggacag tgctccgaga acgggtgcgc atagaaattg   3660
catcaacgca tatagcgcta gcagcacgcc atagtgactg gcgatgctgt cggaatggac   3720
gatatcccgc aagaggcccg gcagtaccgg cataaccaag cctatgccta cagcatccag   3780
ggtgacggtg ccgaggatga cgatgagcgc attgttagat tcatacacg gtgcctgact   3840
gcgttagcaa tttaactgtg ataaactacc gcattaaagc ttatcgatga taagctgtca   3900
aacatgagaa ttcttagaaa aactcatcga gcatcaaatg aaactgcaat ttattcatat   3960
caggattatc aataccatat ttttgaaaaa gccgtttctg taatgaagga gaaaactcac   4020
cgaggcagtt ccataggatg gcaagatcct ggtatcggtc tgcgattccg actcgtccaa   4080
```

| | |
|---|---|
| catcaataca acctattaat ttcccctcgt caaaaataag gttatcaagt gagaaatcac | 4140 |
| catgagtgac gactgaatcc ggtgagaatg gcaaaagctt atgcatttct ttccagactt | 4200 |
| gttcaacagg ccagccatta cgctcgtcat caaaatcact cgcatcaacc aaaccgttat | 4260 |
| tcattcgtga ttgcgcctga gcgagacgaa atacgcgatc gctgttaaaa ggacaattac | 4320 |
| aaacaggaat cgaatgcaac cggcgcagga acactgccag cgcatcaaca atattttcac | 4380 |
| ctgaatcagg atattcttct aatacctgga atgctgtttt cccggggatc gcagtggtga | 4440 |
| gtaaccatgc atcatcagga gtacggataa aatgcttgat ggtcggaaga ggcataaatt | 4500 |
| ccgtcagcca gtttagtctg accatctcat ctgtaacatc attggcaacg ctacctttgc | 4560 |
| catgtttcag aaacaactct ggcgcatcgg gcttcccata caatcgatag attgtcgcac | 4620 |
| ctgattgccc gacattatcg cgagcccatt tatacccata taaatcagca tccatgttgg | 4680 |
| aatttaatcg cggcctcgag caagacgttt cccgttgaat atggctcata cacccccttg | 4740 |
| tattactgtt tatgtaagca gacagttttta ttgttcatga ccaaaatccc ttaacgtgag | 4800 |
| ttttcgttcc actgagcgtc agacccccgta gaaaagatca aaggatcttc ttgagatcct | 4860 |
| ttttttctgc gcgtaatctg ctgcttgcaa acaaaaaaac caccgctacc agcggtggtt | 4920 |
| tgtttgccgg atcaagagct accaactctt tttccgaagg taactggctt cagcagagcg | 4980 |
| cagataccaa atactgtcct tctagtgtag ccgtagttag gccaccactt caagaactct | 5040 |
| gtagcaccgc ctacatacct cgctctgcta atcctgttac cagtggctgc tgccagtggc | 5100 |
| gataagtcgt gtcttaccgg gttggactca agacgatagt taccggataa ggcgcagcgg | 5160 |
| tcgggctgaa cggggggttc gtgcacacag cccagcttgg agcgaacgac ctacaccgaa | 5220 |
| ctgagatacc tacagcgtga gctatgagaa agcgccacgc ttcccgaagg gagaaaggcg | 5280 |
| gacaggtatc cggtaagcgg cagggtcgga acaggagagc gcacgaggga gcttccaggg | 5340 |
| ggaaacgcct ggtatcttta tagtcctgtc gggtttcgcc acctctgact tgagcgtcga | 5400 |
| ttttgtgat gctcgtcagg ggggcggagc ctatggaaaa acgccagcaa cgcggccttt | 5460 |
| ttacggttcc tggccttttg ctggccttttt gctcacatgt tcgatcccgc gaaat | 5515 |

<210> SEQ ID NO 125
<211> LENGTH: 9428
<212> TYPE: DNA
<213> ORGANISM: Artificial Sequence
<220> FEATURE:
<223> OTHER INFORMATION: pmOMNI

<400> SEQUENCE: 125

| | |
|---|---|
| gacggatcgg gagatctccc gatccccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |

```
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttgcca ccatgcctaa gaagaagaga aaggtgggta ccgagaagag      960
actgggcctc gacatcggca caaatagcat cggctggtgc ctgtacgagg gcgactctat     1020
cctggatatc ggcgtgcgga tcttcagcga cggcagagat cctaaatctg cgcctctct     1080 ggccgtggac agacggaatg ctagagccat gcggcgagaa agggatagat acctgggaag     1140
aagaagcgcc ctgatcaagg ccctgaaggc ccatggactg tttccagccg aacaggatgc     1200
cgccaaggct ctggaaagag aggaccctta cagcctgaga gtcagagccc tggatcacag     1260
actggaccct catcagatcg gcagagccat cttccacctg aaccagcgga gaggcttcag     1320
aagcaacaga aaggccgaca gagtgctggg cgatcaagag agcggactga tcagcacagc     1380
caccagagtt ctggacgaag ccatggccaa aagcggcgct agaacactgg gagagtttct     1440
ggccagccgg gacactagaa gagtgcggat gaggcctgac gtgaagggct acgacttcta     1500
ccccaaccgg cagcactacc tggaagagtt cgagaagatc tgggacgccc agagccagta     1560
tcaccctgat ctgctgtctc agcaggccaa gagcgccatc caccggatca ttttcacca     1620 gaggccactg aagccacagg ccgtgggaac atgtacattt gccggactgc atggcatccc     1680
cggcgacgag acaagactgc ctaaagctca ccctctgttc cagcagcggc ggctgtatga     1740
ggaagtgaac cagctggaaa tcgtgtgcgc cagcgctcct gccagaaagc tgaccagaga     1800
tgagagagat gccctgatcc tgaagctgca ggacaagaaa aaagtgacct tcagcacact     1860
ggcccggacc atcagactga agagggcga gagattcaac aaagagagcg agaaccggaa     1920
ggacctggct ggggatgaag tgcgggccga gatgagcgat aagaccagat cggcagacg     1980 gtggtttcac ctgagcctgg atgagcagtg gtccgtgatc gacagactgc tgaacgagga     2040
aagcaccgag gatctgctgg cctggctgga aaaagagtgg tccctgcctt ctgatgtggc     2100
cgaagccgtg gctaatgccc atctgcctga tggccacgga gatttggcc tgacagccac     2160 cgttagactg ctcgaacacc tgaaagccga cgtggtcaca tatgccgaag ctgctcggag     2220
agccggcttc caccactctg atttcagaga tggcgcctgc tacgacgagc tgccttacta     2280
tggcgagatc ctgagcagag atcgcccc tggaaaggac gagtacggcg atccactgga     2340
aagacagtgg ggcaagatca caaaccccac cgtgcacatc ggcctgaatc agctgagaag     2400
gctgattaac gccctcgtgc ggagacacgg cagacccgat ttcatcttcg tggaactggc     2460
ccgcgagctg aagctgaatg agaagcagaa ggccgaccac aagcggcgga tcaagcagac     2520
aacagatgcc gctagagcta gagccgagaa gctgagagaa atcggacaga gacagcgg     2580 ctccaaccgg atgctgctgc ggatttggga agaactgaac cccagcaatc ccctggacag     2640
aagatgccct tattgcgccg agcctatctc catcgagatg ctgatgagcg cagcgccga     2700 catcgatcac atcgtgcctt acagcagatg cctggacgat agcgccgcca acaaagtggt     2760
ggcccacaac cactgcaaca gacagaaggg caacagaacc ccttgggagc agtggggaca     2820
gaccacaaga tggcccctga ttcaagaaca ggtggcccgg atgcacagat ccaaacaatg     2880
gcgcttcggc cccgacgcca tggaacgagt tgatcgagat ggcggcttta tcgcccggca     2940
gctgacagat acccagtacc tgtctagaat cgccgcacag tacctgagcg ccctgtacac     3000
```

```
acctgatgaa ggcagacggg tgtacgccgt gacaggcaga ctgactgcta tgcttagacg    3060
gctgtgdggc ctgaacgaca tcctgcctga tcacaactgg gtgctgaacc ctcacagcaa    3120
cgccccctaag aacaggctgg atcatagaca ccacgccatc gatgccgccg ttgtgggagc   3180
tacaacaccc gccatgattc agcaggttgc cagagctgct gcaagagccg aggaacagga    3240
cctggataga ctgttcgctg acctgcctcc tccatggcca ggctttagag aggaactgca    3300
gggcagaatt atggccgctg tggtgtctca caagcccgac catggaagaa agggcagacc    3360
actgcctggc agagatagca catccggcag actgcacaat gacaccgcct acggctttac    3420
tggccgcaga aatgccaagg gcatgcctat cgtggtcacc agaaaacccc tgctggccct    3480
gaaacctgag gacctgacag accccgagag aatcccagat cctgctctgc agggcgcact    3540
gtttgaagcc actagaggcg ctaccggcaa ggacttcgag aaagccctgc gggacttcag    3600
cagaagagat ggcccttacc agggcatcag acggattaga ctgaccgagg ctctgaacgt    3660
gatccccatc agagatagaa ccggccacgc ctacaaaggc gtgaaaggcg acgccaacgc    3720
cagattcgat gtttggagac tgcccgacgg caagtggatc accagatgga aggatagaga    3780
tggcatcgag cacagcggca tcgtgtccct gtttgatgct caccagccta gccaggtgta    3840
ccacagacct catcctgccg ccaaaaaggt gctgagcctg agacagaatg acctggtggc    3900
agtggaacac gatggcgacc ccggaaagat catgcgggtc gtgaagttta gcgccaacgg    3960
cagcatcaca ttcgccccac ataatgaggc cggacctctg aaaacccggg acaccgatcc    4020
tgccgatcct ttcagatacg tgacaacagt ggccagcggc ctgaagaaga tgagagccag    4080
acaagtgcgg atcgatgagc tgggcaaagt gcacgatccc ggacctagag aggatggatc    4140
ctacccatac gatgttccag attacgcggc cgctccaaaa agaaaagaa aagttgaatt    4200
cggcggcagc ggcgccacca acttcagcct gctgaagcag gccggcgacg tggaggagaa    4260
ccccggcccc atggtgagca agggcgagga ggataacatg gccatcatca aggagttcat    4320
gcgcttcaag gtgcacatgg agggctccgt gaacggccac gagttcgaga tcgagggcga    4380
gggcgagggc cgcccctacg agggcaccca gaccgccaag ctgaaggtga ccaagggtgg    4440
ccccctgccc ttcgcctggg acatcctgtc ccctcagttc atgtacggct ccaaggccta    4500
cgtgaagcac cccgccgaca tccccgacta cttgaagctg tccttcccccg agggcttcaa    4560
gtgggagcgc gtgatgaact tcgaggacgg cggcgtggtg accgtgaccc aggactcctc    4620
cctgcaggac ggcgagttca tctacaaggt gaagctgcgc ggcaccaact tccctctcga    4680
cggccccgta atgcagaaga gaccatgggg ctgggaggcc tcctccgagc ggatgtaccc    4740
cgaggacggc gccctgaagg gcgagatcaa gcagaggctg aagctgaagg acggcggcca    4800
ctacgacgct gaggtcaaga ccaccctaca aggccaagaag cccgtgcagc tgcccggcgc    4860
ctacaacgtc aacatcaagt tggacatcac ctcccacaac gaggactaca ccatcgtgga    4920
acagtacgaa cgcgccgagg ccgccactc caccggcggc atggacgagc tgtacaagta    4980
gctcgagtct agagggcccg tttaaacccg ctgatcagcc tcgactgtgc cttctagttg    5040
ccagccatct gttgtttgcc cctccccgt gccttccttg accctggaag gtgccactcc    5100
cactgtcctt tcctaataaa atgaggaaat tgcatcgcat tgtctgagta ggtgtcattc    5160
tattctgggg ggtgggtgg ggcaggacag caaggggag gattgggaag acaatagcag    5220
gcatgctggg gatgcggtgg gctctatggc ttctgaggcg gaaagaacca gctggggctc    5280
tagggggtat ccccacgcgc cctgtagcgg cgcattaagc gcggcgggtg tggtggttac    5340
gcgcagcgtg accgctacac ttgccagcgc cctagcgccc gctccttttcg ctttcttccc    5400
```

```
ttcctttctc gccacgttcg ccggctttcc ccgtcaagct ctaaatcggg ggctcccttt    5460
agggttccga tttagtgctt tacggcacct cgaccccaaa aaacttgatt agggtgatgg    5520
ttcacgtagt gggccatcgc cctgatagac ggttttccgc cctttgacgt tggagtccac    5580 gttcttttaat agtggactct tgttccaaac tggaacaaca ctcaaccta tctcggtcta    5640 ttcttttgat ttataaggga ttttgccgat ttcggcctat tggttaaaaa atgagctgat    5700
ttaacaaaaa tttaacgcga attaattctg tggaatgtgt gtcagttagg gtgtggaaag    5760
tccccaggct ccccagcagg cagaagtatg caaagcatgc atctcaatta gtcagcaacc    5820
aggtgtggaa agtccccagg ctccccagca ggcagaagta tgcaaagcat gcatctcaat    5880
tagtcagcaa ccatagtccc gcccctaact ccgcccatcc cgcccctaac tccgcccagt    5940
tccgcccatt ctccgcccca tggctgacta attttttttta tttatgcaga ggccgaggcc    6000
gcctctgcct ctgagctatt ccagaagtag tgaggaggct ttttttggagg cctaggcttt    6060 tgcaaaaagc tcccgggagc ttgtatatcc attttcggat ctgatcaaga gacaggatga    6120
ggatcgtttc gcatgattga acaagatgga ttgcacgcag gttctccggc cgcttgggtg    6180
gagaggctat tcggctatga ctgggcacaa cagacaatcg gctgctctga tgccgccgtg    6240
ttccggctgt cagcgcaggg gcgcccggtt ctttttgtca agaccgacct gtccggtgcc    6300
ctgaatgaac tgcaggacga ggcagcgcgg ctatcgtggc tggccacgac gggcgttcct    6360
tgcgcagctg tgctcgacgt tgtcactgaa gcgggaaggg actggctgct attgggcgaa    6420
gtgccggggc aggatctcct gtcatctcac cttgctcctg ccgagaaagt atccatcatg    6480
gctgatgcaa tgcggcggct gcatacgctt gatccggcta cctgcccatt cgaccaccaa    6540
gcgaaacatc gcatcgagcg agcacgtact cggatggaag ccggtcttgt cgatcaggat    6600
gatctggacg aagagcatca ggggctcgcg ccagccgaac tgttcgccag gctcaaggcg    6660
cgcatgcccg acggcgagga tctcgtcgtg acccatggcg atgcctgctt gccgaatatc    6720
atggtggaaa atggccgctt ttctggattc atcgactgtg gccggctggg tgtggcggac    6780
cgctatcagg acatagcgtt ggctacccgt gatattgctg aagagcttgg cggcgaatgg    6840
gctgaccgct tcctcgtgct ttacggtatc gccgctcccg attcgcagcg catcgccttc    6900
tatcgccttc ttgacgagtt cttctgagcg ggactctggg gttcgaaatg accgaccaag    6960
cgacgcccaa cctgccatca cgagatttcg attccaccgc cgccttctat gaaaggttgg    7020
gcttcggaat cgttttccgg gacgccggct ggatgatcct ccagcgcggg gatctcatgc    7080
tggagttctt cgcccacccc aacttgttta ttgcagctta atggttac aaataaagca    7140 atagcatcac aaatttcaca aataaagcat ttttttcact gcattctagt tgtggttgt    7200 ccaaactcat caatgtatct tatcatgtct gtataccgtc gacctctagc tagagcttgg    7260
cgtaatcatg gtcatagctg tttcctgtgt gaaattgtta tccgctcaca attccacaca    7320
acatacgagc cggaagcata aagtgtaaag cctggggtgc ctaatgagtg agctaactca    7380
cattaattgc gttgcgctca ctgcccgctt tccagtcggg aaacctgtcg tgccagctgc    7440
attaatgaat cggccaacgc gcggggagag gcggtttgcg tattgggcgc tcttccgctt    7500
cctcgctcac tgactcgctg cgctcggtcg ttcggctgcg gcgagcggta tcagctcact    7560
caaaggcggt aatacggtta tccacagaat caggggataa cgcaggaaag aacatgtgag    7620
caaaaggcca gcaaaaggcc aggaaccgta aaaaggccgc gttgctggcg tttttccata    7680
ggctccgccc ccctgacgag catcacaaaa atcgacgctc aagtcagagg tggcgaaacc    7740
```

```
cgacaggact ataaagatac caggcgtttc ccctggaag ctccctcgtg cgctctcctg    7800
ttccgaccct gccgcttacc ggatacctgt ccgccttct cccttcggga agcgtggcgc    7860
tttctcatag ctcacgctgt aggtatctca gttcggtgta ggtcgttcgc tccaagctgg    7920
gctgtgtgca cgaacccccc gttcagcccg accgctgcgc cttatccggt aactatcgtc    7980
ttgagtccaa cccggtaaga cacgacttat cgccactggc agcagccact ggtaacagga    8040
ttagcagagc gaggtatgta ggcggtgcta cagagttctt gaagtggtgg cctaactacg    8100
gctacactag aagaacagta tttggtatct gcgctctgct gaagccagtt accttcggaa    8160
aaagagttgg tagctcttga tccggcaaac aaaccaccgc tggtagcggt ggttttttg     8220 tttgcaagca gcagattacg cgcagaaaaa aaggatctca agaagatcct ttgatctttt    8280
ctacggggtc tgacgctcag tggaacgaaa actcacgtta agggattttg gtcatgagat    8340
tatcaaaaag gatcttcacc tagatccttt taaattaaaa atgaagtttt aaatcaatct    8400
aaagtatata tgagtaaact tggtctgaca gttaccaatg cttaatcagt gaggcaccta    8460
tctcagcgat ctgtctattt cgttcatcca tagttgcctg actccccgtc gtgtagataa    8520
ctacgatacg ggagggctta ccatctggcc ccagtgctgc aatgataccg cgagacccac    8580
gctcaccggc tccagattta tcagcaataa accagccagc cggaagggcc gagcgcagaa    8640
gtggtcctgc aactttatcc gcctccatcc agtctattaa ttgttgccgg gaagctagag    8700
taagtagttc gccagttaat agtttgcgca acgttgttgc cattgctaca ggcatcgtgg    8760
tgtcacgctc gtcgtttggt atggcttcat tcagctccgg ttcccaacga tcaaggcgag    8820
ttacatgatc ccccatgttg tgcaaaaaag cggttagctc cttcggtcct ccgatcgttg    8880
tcagaagtaa gttggccgca gtgttatcac tcatggttat ggcagcactg cataattctc    8940
ttactgtcat gccatccgta agatgctttt ctgtgactgg tgagtactca accaagtcat    9000
tctgagaata gtgtatgcgg cgaccgagtt gctcttgccc ggcgtcaata cgggataata    9060
ccgcgccaca tagcagaact ttaaaagtgc tcatcattgg aaaacgttct cggggcgaa     9120 aactctcaag gatcttaccg ctgttgagat ccagttcgat gtaacccact cgtgcaccca    9180
actgatcttc agcatctttt actttcacca gcgtttctgg gtgagcaaaa acaggaaggc    9240
aaaatgccgc aaaaaaggga ataagggcga cacggaaatg ttgaatactc atactcttcc    9300
tttttcaata ttattgaagc atttatcagg gttattgtct catgagcgga tacatatttg    9360
aatgtattta gaaaaataaa caaatagggg ttccgcgcac atttccccga aaagtgccac    9420
ctgacgtc                                                           9428
```

<210> SEQ ID NO 126
<211> LENGTH: 2726
<212> TYPE: DNA
<213> ORGANISM: Artificial Sequence
<220> FEATURE:
<223> OTHER INFORMATION: pmGuide T2/Endogenic site

<400> SEQUENCE: 126

```
ggaagagcag agccttggtc tcgttccggc tagaggaaac tctggacgct aacaagctga      60
aagatgcacc aaatgatagg gtcgctatag gcgacccttt ttgaattctt ccgctgagca    120
ataactagca taaccccttg gggcctctaa acgggtcttg aggggttttt tgacctaggc    180
taggggatat attccgcttc ctcgcggtac cccgcttcct cgctcactga ctcgctacgc    240
tcggtcgttc gactgcggcg agcggaaatg cttacgaac ggggcggaga tttcctggaa     300
gatgccagga agatacttaa caggaagtg agagggccgc ggcaaagccg tttttccata     360
```

```
ggctccgccc ccctgacaag catcacgaaa tctgacgctc aaatcagtgg tggcgaaacc      420
cgacaggact ataaagatac caggcgtttc ccctggcgg ctccctcgtg cgctctcctg      480
ttcctgcctt tcggtttacc ggtgtcattc cgctgttatg gccgcgtttg tctcattcca      540
cgcctgacac tcagttccgg gtaggcagtt cgctccaagc tggactgtat gcacgaaccc      600
cccgttcagt ccgaccgctg cgccttatcc ggtaactatc gtcttgagtc caacccggaa      660
agacatgcaa aagcaccact ggcagcagcc actggtaatt gatttagagg agttagtctt      720
gaagtcatgc gccggttaag gctaaactga aggacaagt tttggtgact gcgctcctcc      780
aagccagtta cctcggttca aagagttggt agctcagaga accttcgaaa accgccctg      840 caaggcggtt ttttcgtttt cagagcaaga gattacgcgc agaccaaaac gatctcaaga      900
agatcatctt attaatcaga taaaatattt ctagatttca gtgcaattta tctcttcaaa      960
tgtagcacct gaagtcagcc ccatacgata taagttgtta ctagtgcttg gattctcacc     1020
aataaaaaac gcccggcggc aaccgagcgt tctgaacaaa tccagatgga gttctgaggt     1080
cattactgga tctatcaaca ggagtccaag cgagaagggt tggtttgcgc attcacagtt     1140
ctccgcaaga attgattggc tccaattctt ggagtggtga atccgttagc gaggtgccgc     1200
cggcttccat tcaggtcgag gtggcccggc tccatgcacc gcgacgcaac gcggggaggc     1260
agacaaggta tagggcggcg cctacaatcc atgccaaccc gttccatgtg ctcgccgagg     1320
cggcataaat cgccgtgacg atcagcggtc caatgatcga agttaggctg gtaagagccg     1380
cgagcgatcc ttgaagctgt ccctgatggt cgtcatctac ctgcctggac agcatggcct     1440
gcaacgcggg catcccgatg ccgccggaag cgagaagaat cataatgggg aaggccatcc     1500
agcctcgcgt cgcgaacgcc agcaagacgt agcccagcgc gtcggccgcc atgcggcga      1560 taatggcctg cttctcgccg aaacgtttgg tggcgggacc agtgacgaag gcttgagcga     1620
gggcgtgcaa gattccgaat accgcaagcg acaggccgat catcgtcgcg ctccagcgaa     1680
agcggtcctc gccgaaaatg acccagagcg ctgccggcac ctgtcctacg agttgcatga     1740
taaagaagac agtcataagt gcggcgacga tagtcatgcc ccgcgcccac cggaaggagc     1800
tgactgggtt gaaggctctc aagggcatcg gtcgacgctc tcccttatgc gactcctgca     1860
ttaggaagca gcccagtagt aggttgaggc cgttgagcac cgccgccgca aggaatggtg     1920
catgcaagga gatggcgccc aacagtcccc cggccacggg gcctgccacc atacccacgc     1980
cgaaacaagc gctcatgagc ccgaagtggc gagcccgatc ttccccatcg gtgatgtcgg     2040
cgatataggc gccagcaacc gcacctgtgg cgccggtgat gccggccacg atgcgtccgg     2100
cgtagaggat ccacaggacg ggtgtggtcg ccatgatcgc gtagtcgata gtggctccaa     2160
gtagcgaagc gagcaggact gggcggcggc caaagcggtc ggacagtgct ccgagaacgg     2220
gtgcgcatag aaattgcatc aacgcatata gcgctagcag cacgccatag tgactggcga     2280
tgctgtcgga atggacgata tcccgcaaga ggcccggcag taccggcata accaagccta     2340
tgcctacagc atccagggtg acggtgccga ggatgacgat gagcgcattg ttagatttca     2400
tacacggtgc ctgactgcgt tagcaattta actgtgataa actaccgcat taaagcttat     2460
cgatgataag ctgtcaagag ggcctatttc ccatgattcc ttcatatttg catatacgat     2520
acaaggctgt tagagagata attagaatta atttgactgt aaacacaaag atattagtac     2580
aaaatacgtg acgtagaaag taataatttc ttgggtagtt tgcagtttta aaattatgtt     2640
ttaaaatgga ctatcatatg cttaccgtaa cttgaaagta tttcgatttc ttggctttat     2700
```
atatcttgtg gaaaggacga aacacc 2726

<210> SEQ ID NO 127
<211> LENGTH: 4194
<212> TYPE: DNA
<213> ORGANISM: Artificial Sequence
<220> FEATURE:
<223> OTHER INFORMATION: pPML3.1
<220> FEATURE:
<221> NAME/KEY: misc_feature
<222> LOCATION: (2256)..(2261)
<223> OTHER INFORMATION: n is a, c, g, or t

<400> SEQUENCE: 127

| | | |
|---|---|---|
| gggtctctct ggttagacca gatctgagcc tgggagctct ctggctaact agggaaccca | 60 |
| ctgcttaagc ctcaataaag cttgccttga gtgcttcaag tagtgtgtgc ccgtctgttg | 120 |
| tgtgactctg gtaactagag atccctcaga cccttttagt cagtgtggaa aatctctagc | 180 |
| agtggcgccc gaacagggac ttgaaagcga aagggaaacc agaggagctc tctcgacgca | 240 |
| ggactcggct tgctgaagcg cgcacggcaa gaggcgaggg gcggcgactg gtgagtacgc | 300 |
| caaaaatttt gactagcgga ggctagaagg agagagatgg gtgcgagagc gtcagtatta | 360 |
| agcggggggag aattagatcg cgatgggaaa aaattcggtt aaggccaggg ggaaagaaaa | 420 |
| aatataaatt aaaacatata gtatgggcaa gcagggagct agaacgattc gcagttaatc | 480 |
| ctggcctgtt agaaacatca gaaggctgta gacaaatact gggacagcta caaccatccc | 540 |
| ttcagacagg atcagaagaa cttagatcat tatataatac agtagcaacc ctctattgtg | 600 |
| tgcatcaaag gatagagata aaagacacca aggaagcttt agacaagata gaggaagagc | 660 |
| aaaacaaaag taagaccacc gcacagcaag cggccgctga tcttcagacc tggaggagga | 720 |
| gatatgaggg acaattggag aagtgaatta tataaatata agtagtaaaa aattgaacca | 780 |
| ttaggagtag cacccaccaa ggcaaagaga agagtggtgc agagagaaaa aagagcagtg | 840 |
| ggaataggag ctttgttcct tgggttcttg ggagcagcag gaagcactat gggcgcagcg | 900 |
| tcaatgacgc tgacggtaca ggccagacaa ttattgtctg gtatagtgca gcagcagaac | 960 |
| aatttgctga gggctattga ggcgcaacag catctgttgc aactcacagt ctggggcatc | 1020 |
| aagcagctcc aggcaagaat cctggctgtg gaaagatacc taaaggatca acagctcctg | 1080 |
| gggatttggg gttgctctgg aaaactcatt tgcaccactg ctgtgccttg gaatgctagt | 1140 |
| tggagtaata aatctctgga acagatttgg aatcacacga cctggatgga gtgggacaga | 1200 |
| gaaattaaca attacacaag cttaatacac tccttaattg aagaatcgca aaaccagcaa | 1260 |
| gaaaagaatg aacaagaatt attggaatta gataaatggg caagtttgtg gaattggttt | 1320 |
| aacataacaa attggctgtg gtatataaaa ttattcataa tgatagtagg aggcttggta | 1380 |
| ggtttaagaa tagttttttgc tgtactttct atagtgaata gagttaggca gggatattca | 1440 |
| ccattatcgt ttcagaccca cctcccaacc ccgaggggac ccgacaggcc cgaaggaata | 1500 |
| gaagaagaag gtggagagag agacagagac agatccattc gattagtgaa cggatctcga | 1560 |
| cggtatcgat aagcttggga gttccgcgtt acataactta cggtaaatgg cccgcctggc | 1620 |
| tgaccgccca acgaccccg cccattgacg tcaataatga cgtatgttcc catagtaacg | 1680 |
| ccaatagga cttttccattg acgtcaatgg gtggagtatt tacggtaaac tgcccacttg | 1740 |
| gcagtacatc aagtgtatca tatgccaagt acgccccta ttgacgtcaa tgacggtaaa | 1800 |
| tggcccgcct ggcattatgc ccagtacatg acctttatggg actttcctac ttggcagtac | 1860 |
| atctacgtat tagtcatcgc tattaccatg gtgatgcggt tttggcagta catcaatggg | 1920 |

```
cgtggatagc ggtttgactc acggggattt ccaagtctcc accccattga cgtcaatggg    1980
agtttgtttt ggcaccaaaa tcaacgggac tttccaaaat gtcgtaacaa ctccgcccca    2040
ttgacgcaaa tgggcggtag gcgtgtacgg tgggaggtct atataagcag agctcgttta    2100
gtgaaccgtc agatcgcctg gagacgccat ccacgctgtt ttgacctcca tagaagacac    2160
cgactctaga ggatccacta gtccagtgtg gtggaattct gcagatatca aagcttgcca    2220
ccatgcatac aatggaagag cagagccttg gtctcnnnnn ngcgggtctg gtggcgctag    2280
cgtgtccaag ggcgaggagc tgttcaccgg cgtggtgccc atcctggtgg agctggacgg    2340
cgacgtgaac ggccacaagt tcagcgtgag cggcgagggc gaaggggacg ctacttacgg    2400
caaactgact ctcaagttta tctgtactac cgggaagctc cctgtcccct ggcctacact    2460
ggtcacaact ctcacatatg gggtccagtg cttcagcaga tacccccgacc acatgaagca    2520
gcacgacttc ttcaagagcg ccatgcccga gggctacgtg caggagagaa ccatcttctt    2580
caaggacgac ggcaactaca agaccagagc tgaggtcaag tttgagggtg acaccctggt    2640
gaacagaatc gagctgaagg gcatcgactt caaggaggac ggcaacatcc tgggccacaa    2700
gctggagtac aactacaaca gccacaacgt gtacatcatg gctgataaac agaagaatgg    2760
gattaaggtg aacttcaaga tcagacacaa catcgaggac ggcagcgtgc agctggccga    2820
ccactaccag cagaacaccc ccatcggcga cggccccgtg ctgctgcccg acaaccacta    2880
cctgagcacc cagagcgctc tcagtaagga ccctaatgag aagagagacc acatggtgct    2940
gctggagttc gtgaccgccg ccggcatcac cctgggcatg gacgagctgt acaagtgagg    3000
gcctaatgag tttggaatta attctgtgga atgtgtgtca gttagggtgt ggaaagtccc    3060
caggctcccc agcaggcaga agtatgcaaa gcatgcatct caattagtca gcaaccaggt    3120
gtggaaagtc cccaggctcc ccagcaggca gaagtatgca aagcatgcat ctcaattagt    3180
cagcaaccat agtcccgccc ctaactccgc ccatcccgcc cctaactccg cccagttccg    3240
cccattctcc gccccatggc tgactaattt tttttattta tgcagaggcc gaggccgcct    3300
ctgcctctga gctattccag aagtagtgag gaggcttttt tggaggccta ggcttttgca    3360
aaaagctccc gggagcttgt atatccattt tcggatctga tcagcacgtg ttgacaatta    3420
atcatcggca tagtatatcg gcatagtata atacgacaag gtgaggaact aaaccatggc    3480
caagcctttg tctcaagaag aatccaccct cattgaaaga gcaacggcta caatcaacag    3540
catccccatc tctgaagact acagcgtcgc cagcgcagct ctctctagcg acggccgcat    3600
cttcactggt gtcaatgtat atcatttac tgggggaccc tgtgcagaac tcgtggtgct    3660
gggcactgct gctgctgcgg cagctggcaa cctgacttgt atcgtcgcga tcggaaatga    3720
gaacaggggc atcttgagcc cctgcggacg gtgccgacag gtgcttctcg atctgcatcc    3780
tgggatcaaa gccatagtga aggacagtga tggacagccg acggcagttg ggattcgtga    3840
attgctgccc tctggttatg tgtgggaggg ctaagcacaa ttcgagctcg gtaccttta    3900
gaccaatgac ttacaaggca gctgtagatc ttagccactt tttaaaagaa aaggggggac    3960
tggaagggct aattcactcc caacgaagac aagatctgct ttttgcttgt actgggtctc    4020
tctggttaga ccagatctga gcctgggagc tctctggcta actagggaac ccactgctta    4080
agcctcaata aagcttgcct tgagtgcttc aagtagtgtg tgcccgtctg ttgtgtgact    4140
ctggtaacta gagatccctc agaccctttt agtcagtgtg gaaaatctct agca          4194
```

<210> SEQ ID NO 128

<211> LENGTH: 4566
<212> TYPE: DNA
<213> ORGANISM: Artificial Sequence
<220> FEATURE:
<223> OTHER INFORMATION: AAV

<400> SEQUENCE: 128

| | |
|---|---|
| tctagacaac tttgtataga aaagttggag ggcctatttc ccatgattcc ttcatatttg | 60 |
| catatacgat acaaggctgt tagagagata attggaatta atttgactgt aaacacaaag | 120 |
| atattagtac aaaatacgtg acgtagaaag taataatttc ttgggtagtt tgcagtttta | 180 |
| aaattatgtt ttaaaatgga ctatcatatg cttaccgtaa cttgaaagta tttcgatttc | 240 |
| ttggctttat atatcttgtg gaaaggacga acaccggtg gaccaggtga ccaccgtgag | 300 |
| ttgccgctgg agaaatccag ttgttaacaa gcagcttgac tgcaccaaat aaggcgggg | 360 |
| ctgcggccct cgcttttca gtttgtaca aaaaagcagg cttagttatt aatagtaatc | 420 |
| aattacgggg tcattagttc atagcccata tatggagttc cgcgttacat aacttacggt | 480 |
| aaatggcccg cctggctgac cgcccaacga cccccgccca ttgacgtcaa taatgacgta | 540 |
| tgttcccata gtaacgccaa tagggacttt ccattgacgt caatgggtgg agtatttacg | 600 |
| gtaaactgcc cacttggcag tacatcaagt gtatcatatg ccaagtacgc ccctattga | 660 |
| cgtcaatgac ggtaaatggc ccgcctggca ttatgcccag tacatgacct tatgggactt | 720 |
| tcctacttgg cagtacatct acgtattagt catcgctatt accatggtga tgcggttttg | 780 |
| gcagtacatc aatgggcgtg atagcggtt tgactcacgg ggatttccaa gtctccaccc | 840 |
| cattgacgtc aatgggagtt tgttttggca ccaaaatcaa cgggactttc caaaatgtcg | 900 |
| taacaactcc gccccattga cgcaaatggg cggtaggcgt gtacggtggg aggtctatat | 960 |
| aagcagagct ggtttagtga accgtcagat cacccagctt tcttgtacaa agtgggccac | 1020 |
| catggcccct aagaagaaga gaaaggtggg taccgagaag agactgggcc tcgacatcgg | 1080 |
| cacaaatagc atcggctggt gcctgtacga gggcgactct atcctggata tcggcgtgcg | 1140 |
| gatcttcagc gacggcagag atcctaaatc tggcgcctct ctggccgtgg acagacggaa | 1200 |
| tgctagagcc atgcggcgga gaagggatag atacctggga agaagaagcg ccctgatcaa | 1260 |
| ggccctgaag gcccatggac tgtttccagc cgaacaggat gccgccaagg ctctggaaag | 1320 |
| agaggaccct tacagcctga gagtcagagc cctggatcac agactggacc tcatcagat | 1380 |
| cggcagagcc atcttccacc tgaaccagcg gagaggcttc agaagcaaca gaaaggccga | 1440 |
| cagagtgctg ggcgatcaag agagcggact gatcagcaca gccaccagag ttctggacga | 1500 |
| agccatggcc aaaagcggcg ctagaacact gggagagttt ctggcagcc gggacactag | 1560 |
| aagagtgcgg atgaggcctg acgtgaaggg ctacgacttc taccccaacc ggcagcacta | 1620 |
| cctggaagag ttcgagaaga tctgggacgc ccagagccag tatcaccctg atctgctgtc | 1680 |
| tcagcaggcc aagagcgcca tccaccggat cattttcac cagaggccac tgaagccaca | 1740 |
| ggccgtggga acatgtacat tgccggact gcatggcatc cccggcgacg agacaagact | 1800 |
| gcctaaagct caccctctgt tccagcagcg gcggctgtat gaggaagtga accagctgga | 1860 |
| aatcgtgtgc gccagcgctc ctgccagaaa gctgaccaga gatgagagag atgccctgat | 1920 |
| cctgaagctg caggacaaga aaaagtgac cttcagcaca ctggccaga ccatcagact | 1980 |
| gaaagagggc gagagattca caaagagag cgagaaccgg aaggacctgg ctggggatga | 2040 |
| agtgcgggcc gagatgagcg ataagaccag attcggcaga cggtggtttc acctgagcct | 2100 |
| ggatgagcag tggtccgtga tcgacagact gctgaacgag gaaagcaccg aggatctgct | 2160 |

```
ggcctggctg gaaaaagagt ggtccctgcc ttctgatgtg gccgaagccg tggctaatgc    2220
ccatctgcct gatggccacg gaagatttgg cctgacagcc accgttagac tgctcgaaca    2280
cctgaaagcc gacgtggtca catatgccga agctgctcgg agagccggct tccaccactc    2340
tgatttcaga gatggcgcct gctacgacga gctgccttac tatggcgaga tcctgagcag    2400
agagatcgcc cctggaaagg acgagtacgg cgatccactg aaagacagt ggggcaagat     2460
cacaaacccc accgtgcaca tcggcctgaa tcagctgaga aggctgatta acgccctcgt    2520
gcggagacac ggcagacccg atttcatctt cgtggaactg gcccgcgagc tgaagctgaa    2580
tgagaagcag aaggccgacc acaagcggcg gatcaagcag acaacagatg ccgctagagc    2640
tagagccgag aagctgagag aaatcggaca gagagacagc ggctccaacc ggatgctgct    2700
gcggatttgg gaagaactga accccagcaa tcccctggac agaagatgcc cttattgcgc    2760
cgagcctatc tccatcgaga tgctgatgag cggcagcgcc gacatcgatc acatcgtgcc    2820
ttacagcaga tgcctggacg atagcgccgc caacaaagtg gtgcccaca accactgcaa     2880
cagacagaag ggcaacagaa cccccttggga gcagtgggga cagaccacaa gatggcccct   2940
gattcaagaa caggtggccc ggatgcacag atccaaacaa tggcgcttcg gccccgacgc    3000
catggaacga gttgatcgag atggcggctt tatcgcccgg cagctgacag atacccagta    3060
cctgtctaga atcgccgcac agtacctgag cgccctgtac acacctgatg aaggcagacg    3120
ggtgtacgcc gtgacaggca gactgactgc tatgcttaga cggctgtggg gcctgaacga    3180
catcctgcct gatcacaaact gggtgctgaa ccctcacagc aacgcccta agaacaggct    3240
ggatcataga caccacgcca tcgatgccgc cgttgtggga gctacaacac ccgccatgat    3300
tcagcaggtt gccagagctg ctgcaagagc cgaggaacag gacctggata gactgttcgc    3360
tgacctgcct cctccatggc caggctttag agaggaactg caggggcagaa ttatggccgc    3420
tgtggtgtct cacaagcccg accatggaag aaagggcaga ccactgcctg gcagagatag    3480
cacatccggc agactgcaca atgacaccgc ctacggcttt actggccgca gaaatgccaa    3540
gggcatgcct atcgtggtca ccagaaaacc cctgctggcc ctgaaacctg aggacctgac    3600
agaccccgag agaatcccag atcctgctct gcagggcgca ctgtttgaag ccactagagg    3660
cgctaccggc aaggacttcg agaaagccct gcgggacttc agcagaagag atggccctta    3720
ccagggcatc agacggatta gactgaccga ggctctgaac gtgatcccca tcagagatag    3780
aaccggccac gcctacaaag gcgtgaaagg cgacgccaac gccagattcg atgtttggag    3840
actgcccgac ggcaagtgga tcaccagatg gaaggataga gatggcatcg agcacagcgg    3900
catcgtgtcc ctgtttgatg ctcaccagcc tagccaggtg taccacagac ctcatcctgc    3960
cgccaaaaag gtgctgagcc tgagacagaa tgacctggtg gcagtggaac acgatggcga    4020
ccccggaaag atcatgcggg tcgtgaagtt tagcgccaac ggcagcatca cattcgcccc    4080
acataatgag gccggacctc tgaaaacccg ggacaccgat cctgccgatc ctttcagata    4140
cgtgacaaca gtggccagcg gcctgaagaa gatgagagcc agacaagtgc ggatcgatga    4200
gctgggcaaa gtgcacgatc ccggacctag agaggatgga tcctacccat acgatgttcc    4260
agattacgcg gccgctccaa aaaagaaaag aaaagtttga caactttatt atacatagtt    4320
ggaattccta gagctcgctg atcagcctcg actgtgcctt ctagttgcca gccatctgtt    4380
gtttgcccct cccccgtgcc ttccttgacc ctggaaggtg ccactcccac tgtccttttcc   4440
taataaaatg aggaaattgc atcgcattgt ctgagtaggt gtcattctat tctggggggt    4500
```

```
ggggtggggc aggacagcaa gggggaggat tgggaagaga atagcaggca tgctggggag    4560
ggccgc                                                               4566
```

<210> SEQ ID NO 129
<211> LENGTH: 9
<212> TYPE: PRT
<213> ORGANISM: Artificial Sequence
<220> FEATURE:
<223> OTHER INFORMATION: HA-tag

<400> SEQUENCE: 129

```
Tyr Pro Tyr Asp Val Pro Asp Tyr Ala
1               5
```

<210> SEQ ID NO 130
<211> LENGTH: 7
<212> TYPE: PRT
<213> ORGANISM: Artificial Sequence
<220> FEATURE:
<223> OTHER INFORMATION: NLS

<400> SEQUENCE: 130

```
Pro Lys Lys Lys Arg Lys Val
1               5
```

<210> SEQ ID NO 131
<211> LENGTH: 19
<212> TYPE: PRT
<213> ORGANISM: Artificial Sequence
<220> FEATURE:
<223> OTHER INFORMATION: P2A

<400> SEQUENCE: 131

```
Ala Thr Asn Phe Ser Leu Leu Lys Gln Ala Gly Asp Val Glu Glu Asn
1               5                   10                  15

Pro Gly Pro
```

<210> SEQ ID NO 132
<211> LENGTH: 236
<212> TYPE: PRT
<213> ORGANISM: Artificial Sequence
<220> FEATURE:
<223> OTHER INFORMATION: mCherry

<400> SEQUENCE: 132

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125
```

```
Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 133
<211> LENGTH: 27
<212> TYPE: DNA
<213> ORGANISM: Artificial Sequence
<220> FEATURE:
<223> OTHER INFORMATION: HA-tag

<400> SEQUENCE: 133
tacccatacg atgttccaga ttacgct                                    27

<210> SEQ ID NO 134
<211> LENGTH: 21
<212> TYPE: DNA
<213> ORGANISM: Artificial Sequence
<220> FEATURE:
<223> OTHER INFORMATION: NLS

<400> SEQUENCE: 134
ccaaaaaaga aagaaaagt t                                           21

<210> SEQ ID NO 135
<211> LENGTH: 57
<212> TYPE: DNA
<213> ORGANISM: Artificial Sequence
<220> FEATURE:
<223> OTHER INFORMATION: P2A

<400> SEQUENCE: 135
gccaccaact tcagcctgct gaagcaggcc ggcgacgtgg aggagaaccc cggcccc    57

<210> SEQ ID NO 136
<211> LENGTH: 711
<212> TYPE: DNA
<213> ORGANISM: Artificial Sequence
<220> FEATURE:
<223> OTHER INFORMATION: mCherry

<400> SEQUENCE: 136
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctgtc cctcagttc atgtacggct ccaaggccta cgtgaagcac   240
cccgccgaca tccccgacta cttgaagctg tccttcccg agggcttcaa gtgggagcgc   300
gtgatgaact tcgaggacgg cggcgtggtg accgtgaccc aggactcctc cctgcaggac   360

-continued

```
ggcgagttca tctacaaggt gaagctgcgc ggcaccaact tcccctccga cggcccgta    420 atgcagaaga agaccatggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg ccgccactc caccggcggc atggacgagc tgtacaagta g              711
```

```
<210> SEQ ID NO 137
<211> LENGTH: 22
<212> TYPE: DNA
<213> ORGANISM: Artificial Sequence
<220> FEATURE:
<223> OTHER INFORMATION: OMNI59_CXCR4_S1

<400> SEQUENCE: 137
agcgcccgct tggggagga gg                                              22

<210> SEQ ID NO 138
<211> LENGTH: 22
<212> TYPE: DNA
<213> ORGANISM: Artificial Sequence
<220> FEATURE:
<223> OTHER INFORMATION: OMNI59_CXCR4_S2

<400> SEQUENCE: 138
caatataccc caagcaccga ag                                             22

<210> SEQ ID NO 139
<211> LENGTH: 22
<212> TYPE: DNA
<213> ORGANISM: Artificial Sequence
<220> FEATURE:
<223> OTHER INFORMATION: OMNI59_PDCD1_S1

<400> SEQUENCE: 139
taagaaccat cctggccgcc ag                                             22

<210> SEQ ID NO 140
<211> LENGTH: 22
<212> TYPE: DNA
<213> ORGANISM: Artificial Sequence
<220> FEATURE:
<223> OTHER INFORMATION: OMNI59_PDCD1_S2

<400> SEQUENCE: 140
gtaccagttt agcacgaagc tc                                             22

<210> SEQ ID NO 141
<211> LENGTH: 22
<212> TYPE: DNA
<213> ORGANISM: Artificial Sequence
<220> FEATURE:
<223> OTHER INFORMATION: OMNI59_TRAC_S1

<400> SEQUENCE: 141
ctggaataat gctgttgttg aa                                             22

<210> SEQ ID NO 142
<211> LENGTH: 22
<212> TYPE: DNA
<213> ORGANISM: Artificial Sequence
<220> FEATURE:
<223> OTHER INFORMATION: OMNI59_TRAC_S2
```

<400> SEQUENCE: 142
tgatgtcaag ctggtcgaga aa                                          22

<210> SEQ ID NO 143
<211> LENGTH: 22
<212> TYPE: DNA
<213> ORGANISM: Artificial Sequence
<220> FEATURE:
<223> OTHER INFORMATION: OMNI67_CXCR4_S3

<400> SEQUENCE: 143
cgccaagtga taaacacgag ga                                          22

<210> SEQ ID NO 144
<211> LENGTH: 22
<212> TYPE: DNA
<213> ORGANISM: Artificial Sequence
<220> FEATURE:
<223> OTHER INFORMATION: OMNI67_CXCR4_S4

<400> SEQUENCE: 144
ttgggcggga gtgtcagaaa at                                          22

<210> SEQ ID NO 145
<211> LENGTH: 22
<212> TYPE: DNA
<213> ORGANISM: Artificial Sequence
<220> FEATURE:
<223> OTHER INFORMATION: OMNI67_PDCD1_S3

<400> SEQUENCE: 145
atcctggccg ccagcccagt tg                                          22

<210> SEQ ID NO 146
<211> LENGTH: 22
<212> TYPE: DNA
<213> ORGANISM: Artificial Sequence
<220> FEATURE:
<223> OTHER INFORMATION: OMNI67_PDCD1_S4

<400> SEQUENCE: 146
taaactggta ccgcatgagc cc                                          22

<210> SEQ ID NO 147
<211> LENGTH: 22
<212> TYPE: DNA
<213> ORGANISM: Artificial Sequence
<220> FEATURE:
<223> OTHER INFORMATION: OMNI67_TRAC_S3

<400> SEQUENCE: 147
agctgagaga ctctaaatcc ag                                          22

<210> SEQ ID NO 148
<211> LENGTH: 22
<212> TYPE: DNA
<213> ORGANISM: Artificial Sequence
<220> FEATURE:
<223> OTHER INFORMATION: OMNI67_TRAC_S4

<400> SEQUENCE: 148
gacttcaaga gcaacagtgc tg                                          22

<210> SEQ ID NO 149

```
<211> LENGTH: 22
<212> TYPE: DNA
<213> ORGANISM: Artificial Sequence
<220> FEATURE:
<223> OTHER INFORMATION: OMNI79_CXCR4_S25

<400> SEQUENCE: 149
tggcaagaga cccacacacc gg                                          22

<210> SEQ ID NO 150
<211> LENGTH: 22
<212> TYPE: DNA
<213> ORGANISM: Artificial Sequence
<220> FEATURE:
<223> OTHER INFORMATION: OMNI79_CXCR4_S26

<400> SEQUENCE: 150
acacaccgga ggagcgcccg ct                                          22

<210> SEQ ID NO 151
<211> LENGTH: 22
<212> TYPE: DNA
<213> ORGANISM: Artificial Sequence
<220> FEATURE:
<223> OTHER INFORMATION: OMNI79_g58_Ref

<400> SEQUENCE: 151
cagctgcggg aaagggattc cc                                          22

<210> SEQ ID NO 152
<211> LENGTH: 22
<212> TYPE: DNA
<213> ORGANISM: Artificial Sequence
<220> FEATURE:
<223> OTHER INFORMATION: OMNI79_g35

<400> SEQUENCE: 152
gcagtccggg ctgggagcgg gt                                          22

<210> SEQ ID NO 153
<211> LENGTH: 22
<212> TYPE: DNA
<213> ORGANISM: Artificial Sequence
<220> FEATURE:
<223> OTHER INFORMATION: OMNI81_CXCR4_S6

<400> SEQUENCE: 153
gggtatattg ggcgggagtg tc                                          22

<210> SEQ ID NO 154
<211> LENGTH: 22
<212> TYPE: DNA
<213> ORGANISM: Artificial Sequence
<220> FEATURE:
<223> OTHER INFORMATION: OMNI81_CXCR4_S7

<400> SEQUENCE: 154
ccactacaag ttgcttgaag cc                                          22

<210> SEQ ID NO 155
<211> LENGTH: 22
<212> TYPE: DNA
<213> ORGANISM: Artificial Sequence
<220> FEATURE:
<223> OTHER INFORMATION: OMNI81_PDCD1_S7

<400> SEQUENCE: 155
```
ggtcaccacg agcagggctg gg                                              22

<210> SEQ ID NO 156
<211> LENGTH: 22
<212> TYPE: DNA
<213> ORGANISM: Artificial Sequence
<220> FEATURE:
<223> OTHER INFORMATION: OMNI81_PDCD1_S8

<400> SEQUENCE: 156
cacgaagctc tccgatgtgt tg                                              22

<210> SEQ ID NO 157
<211> LENGTH: 22
<212> TYPE: DNA
<213> ORGANISM: Artificial Sequence
<220> FEATURE:
<223> OTHER INFORMATION: OMNI81_TRAC_S6

<400> SEQUENCE: 157
ttactttgtg acacatttgt tt                                              22

<210> SEQ ID NO 158
<211> LENGTH: 22
<212> TYPE: DNA
<213> ORGANISM: Artificial Sequence
<220> FEATURE:
<223> OTHER INFORMATION: OMNI81_TRAC_S7

<400> SEQUENCE: 158
ggctggggaa gaaggtgtct tc                                              22

<210> SEQ ID NO 159
<211> LENGTH: 331
<212> TYPE: DNA
<213> ORGANISM: Artificial Sequence
<220> FEATURE:
<223> OTHER INFORMATION: OMNI59_CXCR4_S1 3' (PAM containing) genomic seq

<400> SEQUENCE: 159
gccaagtgat aaacacgagg atggcaagag acccacacac cggaggagcg cccgcttggg      60
ggaggaggtg ccgtttgttc attttctgac actcccgccc aatataccccc aagcaccgaa    120 gggccttcgt tttaagaccg cattctcttt acccactaca agttgcttga agcccagaat    180
ggtttgtatt taggcaggcg tgggaaaatt aagttttttgc gctttaggag aatgagtctt    240
tgcaacgccc ccgccctccc ccgtgatcc tccttctcc ctcttcccct ccctgggcga      300
aaaacttctt acaaaaagtt aatcactgcc c                                   331

<210> SEQ ID NO 160
<211> LENGTH: 331
<212> TYPE: DNA
<213> ORGANISM: Artificial Sequence
<220> FEATURE:
<223> OTHER INFORMATION: OMNI59_CXCR4_S2 3' (PAM containing) genomic seq

<400> SEQUENCE: 160
gccaagtgat aaacacgagg atggcaagag acccacacac cggaggagcg cccgcttggg      60
ggaggaggtg ccgtttgttc attttctgac actcccgccc aatataccccc aagcaccgaa    120 gggccttcgt tttaagaccg cattctcttt acccactaca agttgcttga agcccagaat    180
ggtttgtatt taggcaggcg tgggaaaatt aagttttttgc gctttaggag aatgagtctt    240

```
tgcaacgccc cgccctccc cccgtgatcc tcccttctcc cctcttccct ccctgggcga    300
aaaacttctt acaaaaagtt aatcactgcc c                                 331
```

<210> SEQ ID NO 161
<211> LENGTH: 370
<212> TYPE: DNA
<213> ORGANISM: Artificial Sequence
<220> FEATURE:
<223> OTHER INFORMATION: OMNI59_PDCD1_S1 3' (PAM containing) genomic seq

<400> SEQUENCE: 161

```
gctgctccag gcatgcagat cccacaggcg ccctggccag tcgtctgggc ggtgctacaa    60
ctgggctggc ggccaggatg gttcttaggt aggtggggtc ggcggtcagg tgtcccagag   120
ccaggggtct ggagggacct tccaccctca gtccctggca ggtcgggggg tgctgaggcg   180
ggcctggccc tggcagccca ggggtcccgg agcgaggggt ctggagggac ctttcactct   240
cagtccctgg caggtcgggg ggtgctgtgg caggcccagc cttggccccc agctctgccc   300
cttaccctga gctgtgtggc tttgggcagc tcgaactcct gggttcctct ctgggcccca   360
actcctcccc                                                          370
```

<210> SEQ ID NO 162
<211> LENGTH: 494
<212> TYPE: DNA
<213> ORGANISM: Artificial Sequence
<220> FEATURE:
<223> OTHER INFORMATION: OMNI59_PDCD1_S2 3' (PAM containing) genomic seq

<400> SEQUENCE: 162

```
ccctgctcgt ggtgaccgaa ggggacaacg ccaccttcac ctgcagcttc tccaacacat    60
cggagagctt cgtgctaaac tggtaccgca tgagccccag caaccagacg acaagctgg   120 ccgccttccc cgaggaccgc agccagcccg ccaggactg ccgcttccgt gtcacacaac   180
tgcccaacgg gcgtgacttc cacatgagcg tggtcagggc ccggcgcaat gacagcggca   240
cctacctctg tggggccatc tccctggccc caaggcgca gatcaaagag agcctgcggg   300
cagagctcag ggtgacaggt gcggcctcgg aggccccggg gcaggggtga gctgagccgg   360
tcctggggtg ggtgtcccct cctgcacagg atcaggagct ccagggtcgt agggcaggga   420
ccccccagct ccagtccagg gctctgtcct gcacctgggg aatggtgacc ggcatctctg   480
tcctctagct ctgg                                                     494
```

<210> SEQ ID NO 163
<211> LENGTH: 429
<212> TYPE: DNA
<213> ORGANISM: Artificial Sequence
<220> FEATURE:
<223> OTHER INFORMATION: OMNI59_TRAC_S1 3' (PAM containing) genomic seq

<400> SEQUENCE: 163

```
gtggcctgga gcaacaaatc tgactttgca tgtgcaaacg ccttcaacaa cagcattatt    60
ccagaagaca ccttcttccc cagcccaggt aagggcagct ttggtgcctt cgcaggctgt   120
ttccttgctt caggaatggc caggttctgc ccagagctct ggtcaatgat gtctaaaact   180
cctctgattg gtggtctcgg ccttatccat gccaccaaa ccctctttt tactaagaaa    240 cagtgagcct tgttctggca gtccagagaa tgacacggga aaaaagcaga tgaagagaag   300
gtggcaggag agggcacgtg gcccagcctc agtctctcca actgagttcc tgcctgcctg   360
cctttgctca gactgtttgc cccttactgc tcttctaggc ctcattctaa gccccttctc   420
```

-continued

```
caagttgcc                                                           429

<210> SEQ ID NO 164
<211> LENGTH: 447
<212> TYPE: DNA
<213> ORGANISM: Artificial Sequence
<220> FEATURE:
<223> OTHER INFORMATION: OMNI59_TRAC_S2 3' (PAM containing) genomic seq

<400> SEQUENCE: 164
gcctgctctg gatgctgaaa gaatgtctgt tttcccttt agaaagttcc tgtgatgtca    60
agctggtcga gaaaagcttt gaaacaggta agacaggggt ctagcctggg tttgcacagg  120
attgcggaag tgatgaaccc gcaataaccc tgcctggatg agggagtggg aagaaattag  180
tagatgtggg aatgaatgat gaggaatgga acagcggtt caagacctgc ccagagctgg   240
gtggggtctc tcctgaatcc ctctcaccat ctctgacttt ccattctaag cactttgagg  300
atgagtttct agcttcaata gaccaaggac tctctcctag gcctctgtat tccttttcaac 360 agctccactg tcaagagagc cagagagagc ttctgggtgg cccagctgtg aaatttctga  420
gtcccttagg gatagcccta aacgaac                                      447

<210> SEQ ID NO 165
<211> LENGTH: 421
<212> TYPE: DNA
<213> ORGANISM: Artificial Sequence
<220> FEATURE:
<223> OTHER INFORMATION: OMNI67_CXCR4_S3 3' (PAM containing) genomic seq

<400> SEQUENCE: 165
ggaaatgaaa cttggggcga ggaccacggg tgcagacccc gttaccttct ccacccagga   60
aaatgccccg ctccctaacg tcccaaacgc gccaagtgat aaacacgagg atggcaagag  120
acccacacac cggaggagcg cccgcttggg ggaggaggtg ccgtttgttc attttctgac  180
actcccgccc aatataccc aagcaccgaa gggccttcgt tttaagaccg cattctcttt   240
acccactaca agttgcttga agcccagaat ggtttgtatt taggcaggcg tgggaaaatt  300 aagttttgc gctttaggag aatgagtctt tgcaacgccc ccgccctccc ccgtgatcc   360 tcccttctcc cctcttccct ccctgggcga aaaacttctt acaaaaagtt aatcactgcc  420
c                                                                  421

<210> SEQ ID NO 166
<211> LENGTH: 439
<212> TYPE: DNA
<213> ORGANISM: Artificial Sequence
<220> FEATURE:
<223> OTHER INFORMATION: OMNI67_CXCR4_S4 3' (PAM containing) genomic seq

<400> SEQUENCE: 166
gatggcaaga gacccacaca ccggaggagc gcccgcttgg gggaggaggt gccgtttgtt   60
cattttctga cactcccgcc caatataccc caagcaccga agggccttcg ttttaagacc  120
gcattctctt tacccactac aagttgcttg aagcccagaa tggtttgtat ttaggcaggc  180
gtgggaaaat taagtttttg cgctttagga gaatgagtct ttgcaacgcc ccgccctcc   240 ccccgtgatc ctcccttctc ccctcttccc tccctgggcg aaaaacttct acaaaaagt   300 taatcactgc ccctcctagc agcacccacc ccacccccca cgccgcctgg gagtggcctc  360
tttgtgtgta tttttttttt cctcctaagg aaggtttttt ttcttccctc tagtgggcgg  420
```

```
ggcagaggag ttagccaag                                                    439
```

```
<210> SEQ ID NO 167
<211> LENGTH: 386
<212> TYPE: DNA
<213> ORGANISM: Artificial Sequence
<220> FEATURE:
<223> OTHER INFORMATION: OMNI67_PDCD1_S3 3' (PAM containing) genomic seq

<400> SEQUENCE: 167
gctcacctcc gcctgagcag tggagaaggc ggcactctgg tggggctgct ccaggcatgc        60
agatcccaca gcgccctgg ccagtcgtct gggcggtgct acaactgggc tgcggccag         120 gatggttctt aggtaggtgg ggtcggcggt caggtgtccc agagccaggg gtctggaggg       180
accttccacc ctcagtccct ggcaggtcgg ggggtgctga ggcgggcctg gcctggcag        240 cccaggggtc ccggagcgag gggtctggag ggacctttca ctctcagtcc ctggcaggtc       300 gggggggtgct gtggcaggcc cagccttggc ccccagctct gccccttacc ctgagctgtg     360
tggctttggg cagctcgaac tcctgg                                            386
```

```
<210> SEQ ID NO 168
<211> LENGTH: 494
<212> TYPE: DNA
<213> ORGANISM: Artificial Sequence
<220> FEATURE:
<223> OTHER INFORMATION: OMNI67_PDCD1_S4 3' (PAM containing) genomic seq

<400> SEQUENCE: 168
ccctgctcgt ggtgaccgaa ggggacaacg ccaccttcac ctgcagcttc tccaacacat        60
cggagagctt cgtgctaaac tggtaccgca tgagccccag caaccagacg gacaagctgg       120
ccgccttccc cgaggaccgc agccagcccg gccaggactg ccgcttccgt gtcacacaac       180
tgcccaacgg gcgtgacttc cacatgagcg tggtcagggc ccggcgcaat gacagcggca       240
cctacctctg tggggccatc tccctggccc caaggcgca gatcaaagag agcctgcggg        300
cagagctcag ggtgacaggt gcggcctcgg aggccccggg gcaggggtga gctgagccgg       360
tcctggggtg ggtgtcccct cctgcacagg atcaggagct ccagggtcgt agggcaggaa      420 cccccccagct ccagtccagg gctctgtcct gcacctgggg aatggtgacc ggcatctctg     480
tcctctagct ctgg                                                         494
```

```
<210> SEQ ID NO 169
<211> LENGTH: 463
<212> TYPE: DNA
<213> ORGANISM: Artificial Sequence
<220> FEATURE:
<223> OTHER INFORMATION: OMNI67_TRAC_S3 3' (PAM containing) genomic seq

<400> SEQUENCE: 169
cctgggttgg ggcaaagagg gaaatgagat catgtcctaa ccctgatcct cttgtcccac        60
agatatccag aaccctgacc ctgccgtgta ccagctgaga gactctaaat ccagtgacaa       120
gtctgtctgc ctattcaccg attttgattc tcaaacaaat gtgtcacaaa gtaaggattc      180
tgatgtgtat atcacagaca aaactgtgct agacatgagg tctatggact tcaagagcaa       240
cagtgctgtg gcctggagca acaaatctga ctttgcatgt gcaaacgcct tcaacaacag       300
cattattcca gaagacacct tcttccccag cccaggtaag ggcagctttg gtgccttcgc      360
aggctgtttc cttgcttcag gaatggccag gttctgccca gagctctggt caatgatgtc      420
taaaactcct ctgattggtg gtctcggcct tatccattgc cac                         463
```

<210> SEQ ID NO 170
<211> LENGTH: 463
<212> TYPE: DNA
<213> ORGANISM: Artificial Sequence
<220> FEATURE:
<223> OTHER INFORMATION: OMNI67_TRAC_S4 3' (PAM containing) genomic seq

<400> SEQUENCE: 170

```
cctgggttgg ggcaaagagg gaaatgagat catgtcctaa ccctgatcct cttgtcccac        60
agatatccag aaccctgacc ctgccgtgta ccagctgaga gactctaaat ccagtgacaa       120
gtctgtctgc ctattcaccg attttgattc tcaaacaaat gtgtcacaaa gtaaggattc       180
tgatgtgtat atcacagaca aaactgtgct agacatgagg tctatggact tcaagagcaa       240
cagtgctgtg gcctggagca acaaatctga ctttgcatgt gcaaacgcct tcaacaacag       300
cattattcca gaagacacct tcttccccag cccaggtaag ggcagctttg gtgccttcgc       360
aggctgtttc cttgcttcag gaatggccag gttctgccca gagctctggt caatgatgtc       420
taaaactcct ctgattggtg gtctcggcct tatccattgc cac                         463
```

<210> SEQ ID NO 171
<211> LENGTH: 421
<212> TYPE: DNA
<213> ORGANISM: Artificial Sequence
<220> FEATURE:
<223> OTHER INFORMATION: OMNI79_CXCR4_S25 3' (PAM containing) genomic
      seq

<400> SEQUENCE: 171

```
ggaaatgaaa cttggggcga ggaccacggg tgcagacccc gttaccttct ccacccagga        60
aaatgccccg ctccctaacg tcccaaacgc gccaagtgat aaacacgagg atggcaagag       120
acccacacac cggaggagcg cccgcttggg ggaggaggtg ccgtttgttc attttctgac       180
actcccgccc aatataccc aagcaccgaa gggccttcgt tttaagaccg cattctcttt        240
acccactaca agttgcttga agcccagaat ggtttgtatt taggcaggcg tgggaaaatt       300
aagttttgc gctttaggag aatgagtctt tgcaacgccc cgccctccc ccgtgatcc         360
tccctttctcc cctcttccct ccctgggcga aaaacttctt acaaaaagtt aatcactgcc       420
c                                                                       421
```

<210> SEQ ID NO 172
<211> LENGTH: 382
<212> TYPE: DNA
<213> ORGANISM: Artificial Sequence
<220> FEATURE:
<223> OTHER INFORMATION: OMNI79_CXCR4_S26 3' (PAM containing) genomic
      seq

<400> SEQUENCE: 172

```
cgttaccttc tccacccagg aaaatgcccc gctccctaac gtcccaaacg cgccaagtga        60
taaacacgag gatggcaaga gacccacaca ccggaggagc gcccgcttgg gggaggaggt       120
gccgtttgtt catttctga cactcccgcc aatataccc caagcaccga agggccttcg        180
ttttaagacc gcattctctt tacccactac aagttgcttg agcccagaa tggtttgtat        240
ttaggcaggc gtgggaaaat taagttttg cgctttagga gaatgagtct tgcaacgcc         300
cccgccctcc cccgtgatc ctcccttctc cctcttcccc tccctgggcg aaaaacttct        360
tacaaaaagt taatcactgc cc                                                382
```

<210> SEQ ID NO 173
<211> LENGTH: 350
<212> TYPE: DNA
<213> ORGANISM: Artificial Sequence
<220> FEATURE:
<223> OTHER INFORMATION: OMNI79_g58_Ref 3' (PAM containing) genomic seq

<400> SEQUENCE: 173

```
agggccattg tctccctaac ccgagagcca tgggggtcca cttgcctgtg gtcacgtcag      60
gactccagcc tggcccaggc tctgcgtgtc cccgggtgcc ctcgcccgc ctattcctgg     120 agacaggccc gttggttccc ttcccctccc cttgtcctgg agccaggagg acgttggttc    180
ttgcgacagc cttggcccgg ccgttgcagc tggaacatcg tgggggagat gggaagagga    240
acggggcccg gagcccgggg ctgggtcctg ggaatcccctt tcccgcagct gggactccag   300
ctcccctgcc agttcctcca ggcggaagcc ctcaggcttg gtcctcactc                350
```

<210> SEQ ID NO 174
<211> LENGTH: 443
<212> TYPE: DNA
<213> ORGANISM: Artificial Sequence
<220> FEATURE:
<223> OTHER INFORMATION: OMNI79_g35 3' (PAM containing) genomic seq

<400> SEQUENCE: 174

```
ggcgtctgtt tcgtacgtgc cctgggtgtc cctctgctcc ccacccgctc ccagcccgga     60
ctgcagcaac aggcaccgtg gctagaccct aggagggact tcccaaccct gacaggcggc    120
gggcaggtgg gcagggcctc gcagtccagc ttccccacct tgtctgcctc cacaggggga   180
ctccggcagc cccttggtct gcaacgggct aatccacgga attgcctcct tcgtccgggg   240
aggctgcgcc tcagggctct accccgatgc ctttgccccg gtggcacagt ttgtaaactg    300
gatcgactct atcatccaac gctccgagga caacccctgt ccccaccccc gggacccgga   360
cccggccagc aggacccact gagaagggct gcccgggtca cctcagctgc ccacacccac   420
actctccagc atctggcaca ata                                            443
```

<210> SEQ ID NO 175
<211> LENGTH: 439
<212> TYPE: DNA
<213> ORGANISM: Artificial Sequence
<220> FEATURE:
<223> OTHER INFORMATION: OMNI81_CXCR4_S6 3' (PAM containing) genomic seq

<400> SEQUENCE: 175

```
gatggcaaga gacccacaca ccggaggagc gcccgcttgg gggaggaggt gccgtttgtt     60
cattttctga cactcccgcc caatataccc caagcaccga agggccttcg ttttaagacc    120
gcattctctt tacccactac aagttgcttg aagcccagaa tggtttgtat ttaggcaggc    180
gtgggaaaat taagtttttg cgctttagga gaatgagtct ttgcaacgcc cccgccctcc    240
ccccgtgatc ctcccttctc ccctcttccc tccctgggcg aaaaacttct tacaaaaagt   300
taatcactgc ccctcctagc agcacccacc ccaccccca gccgcctgg gagtggcctc     360 tttgtgtgta tttttttttt cctcctaagg aaggtttttt ttcttccctc tagtgggcgg    420
ggcagaggag ttagccaag                                                 439
```

<210> SEQ ID NO 176
<211> LENGTH: 422
<212> TYPE: DNA
<213> ORGANISM: Artificial Sequence
<220> FEATURE:
<223> OTHER INFORMATION: OMNI81_CXCR4_S7 3' (PAM containing) genomic seq

<400> SEQUENCE: 176

```
ggaggaggtg ccgtttgttc attttctgac actcccgccc aatataccccc aagcaccgaa      60
gggccttcgt tttaagaccg cattctcttt acccactaca agttgcttga agcccagaat     120
ggtttgtatt taggcaggcg tgggaaaatt aagttttttgc gctttaggag aatgagtctt    180
tgcaacgccc ccgccctccc cccgtgatcc tcccttctcc cctcttccct ccctgggcga     240
aaaacttctt acaaaaagtt aatcactgcc cctcctagca gcacccaccc cacccccccac   300
gccgcctggg agtggcctct ttgtgtgtat ttttttttttc ctcctaagga aggtttttttt  360
tcttccctct agtgggcggg gcagaggagt tagccaagat gtgactttga aaccctcagc    420
gt                                                                   422
```

<210> SEQ ID NO 177
<211> LENGTH: 435
<212> TYPE: DNA
<213> ORGANISM: Artificial Sequence
<220> FEATURE:
<223> OTHER INFORMATION: OMNI81_PDCD1_S7 3' (PAM containing) genomic seq

<400> SEQUENCE: 177

```
cccttcctca cctctctcca tctctcagac tccccagaca ggccctggaa ccccccccacc    60
ttctccccag ccctgctcgt ggtgaccgaa ggggacaacg ccaccttcac ctgcagcttc    120
tccaacacat cggagagctt cgtgctaaac tggtaccgca tgagcccccag caaccagacg   180
gacaagctgg ccgccttccc cgaggaccgc agccagcccg gccaggactg ccgcttccgt    240
gtcacacaac tgcccaacgg gcgtgacttc cacatgagcg tggtcagggc ccggcgcaat    300
gacagcggca cctacctctg tggggccatc tccctggccc caaggcgca gatcaaagag    360
agcctgcggg cagagctcag ggtgacaggt gcggcctcgg aggcccccggg gcaggggtga  420
gctgagccgg tcctg                                                    435
```

<210> SEQ ID NO 178
<211> LENGTH: 494
<212> TYPE: DNA
<213> ORGANISM: Artificial Sequence
<220> FEATURE:
<223> OTHER INFORMATION: OMNI81_PDCD1_S8 3' (PAM containing) genomic seq

<400> SEQUENCE: 178

```
ccctgctcgt ggtgaccgaa ggggacaacg ccaccttcac ctgcagcttc tccaacacat     60
cggagagctt cgtgctaaac tggtaccgca tgagcccccag caaccagacg gacaagctgg  120
ccgccttccc cgaggaccgc agccagcccg gccaggactg ccgcttccgt gtcacacaac   180
tgcccaacgg gcgtgacttc cacatgagcg tggtcagggc ccggcgcaat gacagcggca   240
cctacctctg tggggccatc tccctggccc caaggcgca gatcaaagag agcctgcggg    300
cagagctcag ggtgacaggt gcggcctcgg aggcccccggg gcaggggtga gctgagccgg  360
tcctggggtg ggtgtcccct cctgcacagg atcaggagct ccagggtcgt agggcaggga   420
cccccccagct ccagtccagg gctctgtcct gcacctgggg aatggtgacc ggcatctctg  480
tcctctagct ctgg                                                     494
```

<210> SEQ ID NO 179
<211> LENGTH: 463
<212> TYPE: DNA

```
<213> ORGANISM: Artificial Sequence
<220> FEATURE:
<223> OTHER INFORMATION: OMNI81_TRAC_S6 3' (PAM containing) genomic seq

<400> SEQUENCE: 179
cctgggttgg ggcaaagagg gaaatgagat catgtcctaa ccctgatcct cttgtcccac      60
agatatccag aaccctgacc ctgccgtgta ccagctgaga gactctaaat ccagtgacaa     120
gtctgtctgc ctattcaccg attttgattc tcaaacaaat gtgtcacaaa gtaaggattc     180
tgatgtgtat atcacagaca aaactgtgct agacatgagg tctatggact tcaagagcaa     240
cagtgctgtg gcctggagca acaaatctga ctttgcatgt gcaaacgcct tcaacaacag     300
cattattcca gaagacacct tcttccccag cccaggtaag ggcagctttg gtgccttcgc     360
aggctgtttc cttgcttcag gaatggccag gttctgccca gagctctggt caatgatgtc     420
taaaactcct ctgattggtg gtctcggcct tatccattgc cac                       463

<210> SEQ ID NO 180
<211> LENGTH: 429
<212> TYPE: DNA
<213> ORGANISM: Artificial Sequence
<220> FEATURE:
<223> OTHER INFORMATION: OMNI81_TRAC_S7 3' (PAM containing) genomic seq

<400> SEQUENCE: 180
gtggcctgga gcaacaaatc tgactttgca tgtgcaaacg ccttcaacaa cagcattatt      60
ccagaagaca ccttcttccc cagcccaggt aagggcagct ttggtgcctt cgcaggctgt     120
ttccttgctt caggaatggc caggttctgc ccagagctct ggtcaatgat gtctaaaact     180
cctctgattg gtggtctcgg ccttatccat tgccaccaaa accctctttt tactaagaaa     240
cagtgagcct tgttctggca gtccagagaa tgacacggga aaaaagcaga tgaagagaag     300
gtggcaggag agggcacgtg gcccagcctc agtctctcca actgagttcc tgcctgcctg     360
cctttgctca gactgtttgc cccttactgc tcttctaggc ctcattctaa gccccttctc     420
caagttgcc                                                             429

<210> SEQ ID NO 181
<211> LENGTH: 22
<212> TYPE: DNA
<213> ORGANISM: Artificial Sequence
<220> FEATURE:
<223> OTHER INFORMATION: OMNI79_PDCD1_S24

<400> SEQUENCE: 181
gtcgtctggg cggtgctaca ac                                               22

<210> SEQ ID NO 182
<211> LENGTH: 22
<212> TYPE: DNA
<213> ORGANISM: Artificial Sequence
<220> FEATURE:
<223> OTHER INFORMATION: OMNI79_PDCD1_S25

<400> SEQUENCE: 182
tgctacaact gggctggcgg cc                                               22

<210> SEQ ID NO 183
<211> LENGTH: 22
<212> TYPE: DNA
<213> ORGANISM: Artificial Sequence
<220> FEATURE:
<223> OTHER INFORMATION: OMNI79_TRAC_S21
```

-continued

<400> SEQUENCE: 183
actgtgctag acatgaggtc ta                                          22

<210> SEQ ID NO 184
<211> LENGTH: 22
<212> TYPE: DNA
<213> ORGANISM: Artificial Sequence
<220> FEATURE:
<223> OTHER INFORMATION: OMNI79_TRAC_S24

<400> SEQUENCE: 184
ggccactttc aggaggagga tt                                          22

<210> SEQ ID NO 185
<211> LENGTH: 22
<212> TYPE: DNA
<213> ORGANISM: Artificial Sequence
<220> FEATURE:
<223> OTHER INFORMATION: OMNI79_EMX_S2

<400> SEQUENCE: 185
cttctgtgaa tgttagaccc at                                          22

<210> SEQ ID NO 186
<211> LENGTH: 22
<212> TYPE: DNA
<213> ORGANISM: Artificial Sequence
<220> FEATURE:
<223> OTHER INFORMATION: OMNI79_EMX_S3

<400> SEQUENCE: 186
acccatggga gcagctggtc ag                                          22

<210> SEQ ID NO 187
<211> LENGTH: 22
<212> TYPE: DNA
<213> ORGANISM: Artificial Sequence
<220> FEATURE:
<223> OTHER INFORMATION: OMNI79_SAMD9_rs070_1

<400> SEQUENCE: 187
ttagagtaga aatcgtctca tt                                          22

<210> SEQ ID NO 188
<211> LENGTH: 22
<212> TYPE: DNA
<213> ORGANISM: Artificial Sequence
<220> FEATURE:
<223> OTHER INFORMATION: OMNI79_SAMD9_rs070_2

<400> SEQUENCE: 188
gtagaaatcg tctcatttgg tg                                          22

<210> SEQ ID NO 189
<211> LENGTH: 22
<212> TYPE: DNA
<213> ORGANISM: Artificial Sequence
<220> FEATURE:
<223> OTHER INFORMATION: OMNI79_SAMD9_rs201_alt

<400> SEQUENCE: 189
tttaatctgg aagtaatcat at                                          22

<210> SEQ ID NO 190

```
<210> SEQ ID NO 190
<211> LENGTH: 22
<212> TYPE: DNA
<213> ORGANISM: Artificial Sequence
<220> FEATURE:
<223> OTHER INFORMATION: OMNI79_SAMD9_rs499_1

<400> SEQUENCE: 190
ggatctcttg ggtcatccac ag                                              22

<210> SEQ ID NO 191
<211> LENGTH: 22
<212> TYPE: DNA
<213> ORGANISM: Artificial Sequence
<220> FEATURE:
<223> OTHER INFORMATION: OMNI79_SAMD9_rs499_2

<400> SEQUENCE: 191
gtatttctat tactgtcctc tg                                              22

<210> SEQ ID NO 192
<211> LENGTH: 22
<212> TYPE: DNA
<213> ORGANISM: Artificial Sequence
<220> FEATURE:
<223> OTHER INFORMATION: OMNI79_SAMD9L_rs532_1

<400> SEQUENCE: 192 cttttttgatc attacattga ag                                             22

<210> SEQ ID NO 193
<211> LENGTH: 22
<212> TYPE: DNA
<213> ORGANISM: Artificial Sequence
<220> FEATURE:
<223> OTHER INFORMATION: OMNI79_SAMD9L_rs532_2

<400> SEQUENCE: 193
attacattga agtggtcaat ga                                              22

<210> SEQ ID NO 194
<211> LENGTH: 22
<212> TYPE: DNA
<213> ORGANISM: Artificial Sequence
<220> FEATURE:
<223> OTHER INFORMATION: OMNI79_Serpina_S12

<400> SEQUENCE: 194
gtggaccagg tgaccaccgt ga                                              22

<210> SEQ ID NO 195
<211> LENGTH: 22
<212> TYPE: DNA
<213> ORGANISM: Artificial Sequence
<220> FEATURE:
<223> OTHER INFORMATION: OMNI79_Serpina_S13

<400> SEQUENCE: 195
cacggtggtc acctggtcca cg                                              22

<210> SEQ ID NO 196
<211> LENGTH: 22
<212> TYPE: DNA
<213> ORGANISM: Artificial Sequence
<220> FEATURE:
<223> OTHER INFORMATION: OMNI79_Serpina_S14

<400> SEQUENCE: 196
```
aggcaccttc acggtggtca cc                                                   22

<210> SEQ ID NO 197
<211> LENGTH: 22
<212> TYPE: DNA
<213> ORGANISM: Artificial Sequence
<220> FEATURE:
<223> OTHER INFORMATION: OMNI79_Serpina_S22

<400> SEQUENCE: 197
gactccaaaa cctgctctct cc                                                   22

<210> SEQ ID NO 198
<211> LENGTH: 22
<212> TYPE: DNA
<213> ORGANISM: Artificial Sequence
<220> FEATURE:
<223> OTHER INFORMATION: OMNI79_Serpina_S23

<400> SEQUENCE: 198
gttttggagt cctgatgtta ta                                                   22

<210> SEQ ID NO 199
<211> LENGTH: 22
<212> TYPE: DNA
<213> ORGANISM: Artificial Sequence
<220> FEATURE:
<223> OTHER INFORMATION: OMNI79_Serpina_S32

<400> SEQUENCE: 199
attgcaaaac tgatactgat tc                                                   22

<210> SEQ ID NO 200
<211> LENGTH: 22
<212> TYPE: DNA
<213> ORGANISM: Artificial Sequence
<220> FEATURE:
<223> OTHER INFORMATION: OMNI79_Serpina_S33

<400> SEQUENCE: 200
cagttttgca atctgaaaga cc                                                   22

<210> SEQ ID NO 201
<211> LENGTH: 22
<212> TYPE: DNA
<213> ORGANISM: Artificial Sequence
<220> FEATURE:
<223> OTHER INFORMATION: OMNI79_Serpina_S34

<400> SEQUENCE: 201
agttttgcaa tctgaaagac ct                                                   22

<210> SEQ ID NO 202
<211> LENGTH: 22
<212> TYPE: DNA
<213> ORGANISM: Artificial Sequence
<220> FEATURE:
<223> OTHER INFORMATION: OMNI79_Serpina_S38

<400> SEQUENCE: 202
acagcagcac caccacacgt tc                                                   22

<210> SEQ ID NO 203
<211> LENGTH: 22
<212> TYPE: DNA

```
<213> ORGANISM: Artificial Sequence
<220> FEATURE:
<223> OTHER INFORMATION: OMNI79_Serpina_S39

<400> SEQUENCE: 203
ttggttctgc cagaacgtgt gg                                              22

<210> SEQ ID NO 204
<211> LENGTH: 25
<212> TYPE: DNA
<213> ORGANISM: Artificial Sequence
<220> FEATURE:
<223> OTHER INFORMATION: OMNI79_Serpina_S40

<400> SEQUENCE: 204
tttttggttc tgccagaacg tgtgg                                           25

<210> SEQ ID NO 205
<211> LENGTH: 22
<212> TYPE: DNA
<213> ORGANISM: Artificial Sequence
<220> FEATURE:
<223> OTHER INFORMATION: OMNI79_Serpina_S49

<400> SEQUENCE: 205
acacaaaagc ctcagccttt ca                                              22

<210> SEQ ID NO 206
<211> LENGTH: 22
<212> TYPE: DNA
<213> ORGANISM: Artificial Sequence
<220> FEATURE:
<223> OTHER INFORMATION: OMNI79_Serpina_S50

<400> SEQUENCE: 206
gctgaggctt ttgtgttgct ct                                              22

<210> SEQ ID NO 207
<211> LENGTH: 22
<212> TYPE: DNA
<213> ORGANISM: Artificial Sequence
<220> FEATURE:
<223> OTHER INFORMATION: OMNI79_Serpina_S51

<400> SEQUENCE: 207
aggcttttgt gttgctcttg gt                                              22

<210> SEQ ID NO 208
<211> LENGTH: 22
<212> TYPE: DNA
<213> ORGANISM: Artificial Sequence
<220> FEATURE:
<223> OTHER INFORMATION: OMNI81_EMX_S11

<400> SEQUENCE: 208
gctcccatgg gtctaacatt ca                                              22

<210> SEQ ID NO 209
<211> LENGTH: 22
<212> TYPE: DNA
<213> ORGANISM: Artificial Sequence
<220> FEATURE:
<223> OTHER INFORMATION: OMNI81_EMX_S12

<400> SEQUENCE: 209
tacaaacggc agaagctgga gg                                              22
```

<210> SEQ ID NO 210
<211> LENGTH: 22
<212> TYPE: DNA
<213> ORGANISM: Artificial Sequence
<220> FEATURE:
<223> OTHER INFORMATION: OMNI81_B2M_S8

<400> SEQUENCE: 210
cggcccgaat gctgtcagct tc                                             22

<210> SEQ ID NO 211
<211> LENGTH: 22
<212> TYPE: DNA
<213> ORGANISM: Artificial Sequence
<220> FEATURE:
<223> OTHER INFORMATION: OMNI81_B2M_S9

<400> SEQUENCE: 211
actacactga attcaccccc ac                                             22

<210> SEQ ID NO 212
<211> LENGTH: 14
<212> TYPE: DNA
<213> ORGANISM: Artificial Sequence
<220> FEATURE:
<223> OTHER INFORMATION: OMNI79_SAMD9_rs070_1 3' (PAM containing)
      genomic seq

<400> SEQUENCE: 212
tggtgtggtt ttct                                                      14

<210> SEQ ID NO 213
<211> LENGTH: 19
<212> TYPE: DNA
<213> ORGANISM: Artificial Sequence
<220> FEATURE:
<223> OTHER INFORMATION: OMNI79_SAMD9_rs070_2 3' (PAM containing)
      genomic seq

<400> SEQUENCE: 213
tggttttctg ttctacata                                                 19

<210> SEQ ID NO 214
<211> LENGTH: 19
<212> TYPE: DNA
<213> ORGANISM: Artificial Sequence
<220> FEATURE:
<223> OTHER INFORMATION: OMNI79_SAMD9_rs201_alt 3' (PAM containing)
      genomic seq

<400> SEQUENCE: 214
tggcattcag agaactgtg                                                 19

<210> SEQ ID NO 215
<211> LENGTH: 19
<212> TYPE: DNA
<213> ORGANISM: Artificial Sequence
<220> FEATURE:
<223> OTHER INFORMATION: OMNI79_SAMD9_rs499_1 3' (PAM containing)
      genomic seq

<400> SEQUENCE: 215
aggacagtaa tagaaatac                                                 19

<210> SEQ ID NO 216

```
<211> LENGTH: 18
<212> TYPE: DNA
<213> ORGANISM: Artificial Sequence
<220> FEATURE:
<223> OTHER INFORMATION: OMNI79_SAMD9_rs499_2 3' (PAM containing)
      genomic seq

<400> SEQUENCE: 216
tggatgaccc aagagatc                                                 18

<210> SEQ ID NO 217
<211> LENGTH: 18
<212> TYPE: DNA
<213> ORGANISM: Artificial Sequence
<220> FEATURE:
<223> OTHER INFORMATION: OMNI79_SAMD9L_rs532_1 3' (PAM containing)
      genomic seq

<400> SEQUENCE: 217
tggtcaatga aggcagcc                                                 18

<210> SEQ ID NO 218
<211> LENGTH: 18
<212> TYPE: DNA
<213> ORGANISM: Artificial Sequence
<220> FEATURE:
<223> OTHER INFORMATION: OMNI79_SAMD9L_rs532_2 3' (PAM containing)
      genomic seq

<400> SEQUENCE: 218
aggcagcctt actggtga                                                 18

<210> SEQ ID NO 219
<211> LENGTH: 17
<212> TYPE: DNA
<213> ORGANISM: Artificial Sequence
<220> FEATURE:
<223> OTHER INFORMATION: OMNI79_Serpina_S12 3' (PAM containing)
      genomic seq

<400> SEQUENCE: 219
aggtgcctat gatgaag                                                  17

<210> SEQ ID NO 220
<211> LENGTH: 20
<212> TYPE: DNA
<213> ORGANISM: Artificial Sequence
<220> FEATURE:
<223> OTHER INFORMATION: OMNI79_Serpina_S13 3' (PAM containing) genomic
      seq

<400> SEQUENCE: 220
tggaagtcct cttcctcggt                                               20

<210> SEQ ID NO 221
<211> LENGTH: 21
<212> TYPE: DNA
<213> ORGANISM: Artificial Sequence
<220> FEATURE:
<223> OTHER INFORMATION: OMNI79_Serpina_S14 3' (PAM containing) genomic
      seq

<400> SEQUENCE: 221
tggtccacgt ggaagtcctc t                                             21

<210> SEQ ID NO 222
<211> LENGTH: 14
```

```
<212> TYPE: DNA
<213> ORGANISM: Artificial Sequence
<220> FEATURE:
<223> OTHER INFORMATION: OMNI79_Serpina_S22 3' (PAM containing) genomic
      seq

<400> SEQUENCE: 222
tggcccttct atca                                                         14

<210> SEQ ID NO 223
<211> LENGTH: 17
<212> TYPE: DNA
<213> ORGANISM: Artificial Sequence
<220> FEATURE:
<223> OTHER INFORMATION: OMNI79_Serpina_S23 3' (PAM containing) genomic
      seq

<400> SEQUENCE: 223
aggaacagct tgggagg                                                      17

<210> SEQ ID NO 224
<211> LENGTH: 19
<212> TYPE: DNA
<213> ORGANISM: Artificial Sequence
<220> FEATURE:
<223> OTHER INFORMATION: OMNI79_Serpina_S32 3' (PAM containing) genomic
      seq

<400> SEQUENCE: 224
tgggacacta gagtcgtgt                                                    19

<210> SEQ ID NO 225
<211> LENGTH: 18
<212> TYPE: DNA
<213> ORGANISM: Artificial Sequence
<220> FEATURE:
<223> OTHER INFORMATION: OMNI79_Serpina_S33 3' (PAM containing) genomic
      seq

<400> SEQUENCE: 225
tgggttcaaa tcctgcct                                                     18

<210> SEQ ID NO 226
<211> LENGTH: 18
<212> TYPE: DNA
<213> ORGANISM: Artificial Sequence
<220> FEATURE:
<223> OTHER INFORMATION: OMNI79_Serpina_S34 3' (PAM containing) genomic
      seq

<400> SEQUENCE: 226
gggttcaaat cctgcctc                                                     18

<210> SEQ ID NO 227
<211> LENGTH: 20
<212> TYPE: DNA
<213> ORGANISM: Artificial Sequence
<220> FEATURE:
<223> OTHER INFORMATION: OMNI79_Serpina_S38 3' (PAM containing) genomic
      seq

<400> SEQUENCE: 227
tggcagaacc aaaaaggaac                                                   20

<210> SEQ ID NO 228
<211> LENGTH: 23
<212> TYPE: DNA
```

```
<213> ORGANISM: Artificial Sequence
<220> FEATURE:
<223> OTHER INFORMATION: OMNI79_Serpina_S39 3' (PAM containing) genomic
      seq

<400> SEQUENCE: 228
tggtgctgct gtccctgccc tgg                                             23

<210> SEQ ID NO 229
<211> LENGTH: 20
<212> TYPE: DNA
<213> ORGANISM: Artificial Sequence
<220> FEATURE:
<223> OTHER INFORMATION: OMNI79_Serpina_S40 3' (PAM containing) genomic
      seq

<400> SEQUENCE: 229
tggtggtgct gctgtccctg                                                 20

<210> SEQ ID NO 230
<211> LENGTH: 20
<212> TYPE: DNA
<213> ORGANISM: Artificial Sequence
<220> FEATURE:
<223> OTHER INFORMATION: OMNI79_Serpina_S49 3' (PAM containing) genomic
      seq

<400> SEQUENCE: 230
aggagcactt ggggtgtttg                                                 20

<210> SEQ ID NO 231
<211> LENGTH: 20
<212> TYPE: DNA
<213> ORGANISM: Artificial Sequence
<220> FEATURE:
<223> OTHER INFORMATION: OMNI79_Serpina_S50 3' (PAM containing) genomic
      seq

<400> SEQUENCE: 231
tggttggatt attcacaggc                                                 20

<210> SEQ ID NO 232
<211> LENGTH: 16
<212> TYPE: DNA
<213> ORGANISM: Artificial Sequence
<220> FEATURE:
<223> OTHER INFORMATION: OMNI79_Serpina_S51 3' (PAM containing) genomic
      seq

<400> SEQUENCE: 232
tggattattc acaggc                                                     16

<210> SEQ ID NO 233
<211> LENGTH: 19
<212> TYPE: RNA
<213> ORGANISM: Artificial Sequence
<220> FEATURE:
<223> OTHER INFORMATION: ELANE g35 19nt

<400> SEQUENCE: 233
guccgggcug ggagcgggu                                                  19

<210> SEQ ID NO 234
<211> LENGTH: 20
<212> TYPE: RNA
<213> ORGANISM: Artificial Sequence
<220> FEATURE:
```

```
<223> OTHER INFORMATION: ELANE g35 20nt

<400> SEQUENCE: 234
aguccgggcu gggagcgggu                                                    20

<210> SEQ ID NO 235
<211> LENGTH: 21
<212> TYPE: RNA
<213> ORGANISM: Artificial Sequence
<220> FEATURE:
<223> OTHER INFORMATION: ELANE g35 21nt

<400> SEQUENCE: 235
caguccgggc ugggagcggg u                                                  21

<210> SEQ ID NO 236
<211> LENGTH: 22
<212> TYPE: RNA
<213> ORGANISM: Artificial Sequence
<220> FEATURE:
<223> OTHER INFORMATION: ELANE g35 22nt

<400> SEQUENCE: 236
gcaguccggg cugggagcgg gu                                                 22

<210> SEQ ID NO 237
<211> LENGTH: 23
<212> TYPE: RNA
<213> ORGANISM: Artificial Sequence
<220> FEATURE:
<223> OTHER INFORMATION: ELANE g35 23nt

<400> SEQUENCE: 237
ugcaguccgg gcugggagcg ggu                                                23

<210> SEQ ID NO 238
<211> LENGTH: 24
<212> TYPE: RNA
<213> ORGANISM: Artificial Sequence
<220> FEATURE:
<223> OTHER INFORMATION: ELANE g35 24nt

<400> SEQUENCE: 238
cugcaguccg ggcugggagc gggu                                               24

<210> SEQ ID NO 239
<211> LENGTH: 25
<212> TYPE: RNA
<213> ORGANISM: Artificial Sequence
<220> FEATURE:
<223> OTHER INFORMATION: ELANE g35 25nt

<400> SEQUENCE: 239
gcugcagucc gggcugggag cgggu                                              25

<210> SEQ ID NO 240
<211> LENGTH: 26
<212> TYPE: RNA
<213> ORGANISM: Artificial Sequence
<220> FEATURE:
<223> OTHER INFORMATION: ELANE g35 26nt

<400> SEQUENCE: 240
ugcugcaguc cgggcuggga gcgggu                                             26
```

```
<210> SEQ ID NO 241
<211> LENGTH: 80
<212> TYPE: RNA
<213> ORGANISM: Artificial Sequence
<220> FEATURE:
<223> OTHER INFORMATION: OMNI-79 scaffold sequence

<400> SEQUENCE: 241
guugccgcug gagaaaucca guuguuaaca agcagcuuga cugcaccaaa uaaggcgggg      60
gcugcggccc ucgcuuuuuu                                                 80

<210> SEQ ID NO 242
<211> LENGTH: 22
<212> TYPE: DNA
<213> ORGANISM: Artificial Sequence
<220> FEATURE:
<223> OTHER INFORMATION: T1 sequence

<400> SEQUENCE: 242
ggtgcggttc accagggtgt cg                                              22

<210> SEQ ID NO 243
<211> LENGTH: 22
<212> TYPE: DNA
<213> ORGANISM: Artificial Sequence
<220> FEATURE:
<223> OTHER INFORMATION: T2 sequence

<400> SEQUENCE: 243
ggaagagcag agccttggtc tc                                              22
```

OMNI-59, 61, 67, 76, 79, 80, 81, AND 82 CRISPR NUCLEASES

CROSS-REFERENCE TO RELATED APPLICATIONS

This application is a § 371 national stage of PCT International Application No. PCT/US2021/035928, filed Jun. 4, 2021, claiming the benefit of U.S. Provisional Application Nos. 63/122,564, filed Dec. 8, 2020, and 63/034,610, filed Jun. 4, 2020, the contents of each of which are hereby incorporated by reference into the appliation.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide sequences which are present in the file named "220902_91412-A-PCT-US_Substitute_Sequence_Listing_AWG.txt", which is 252,678 bytes in size, and which was created on Jun. 2, 2021 in the IBM-PC machine format, having an operating system compatibility with MS-Windows, which is contained in the text file filed Jun. 4, 2021 as part of this application.

FIELD OF THE INVENTION

The present invention is directed to, inter alia, composition and methods for genome editing.

BACKGROUND OF THE INVENTION

The Clustered Regularly Interspaced Short Palindromic Repeat (CRISPR) systems of bacterial and archaeal adaptive immunity show extreme diversity of protein composition and genomic loci architecture. The CRISPR systems have become important tools for research and genome engineering. Nevertheless, many details of CRISPR systems have not been determined and the applicability of CRISPR nucleases may be limited by sequence specificity requirements, expression, or delivery challenges. Different CRISPR nucleases have diverse characteristics such as: size, PAM site, on target activity, specificity, cleavage pattern (e.g. blunt, staggered ends), and prominent pattern of indel formation following cleavage. Different sets of characteristics may be useful for different applications. For example, some CRISPR nucleases may be able to target particular genomic loci that other CRISPR nucleases cannot due to limitations of the PAM site. In addition, some CRISPR nucleases currently in use exhibit pre-immunity, which may limit in vivo applicability. See Charlesworth et al., Nature Medicine (2019) and Wagner et al., Nature Medicine (2019). Accordingly, discovery, engineering, and improvement of novel CRISPR nucleases is of importance.

SUMMARY OF THE INVENTION

Disclosed herein are compositions and methods that may be utilized for genomic engineering, epigenomic engineering, genome targeting, genome editing of cells, and/or in vitro diagnostics.

The disclosed compositions may be utilized for modifying genomic DNA sequences. As used herein, genomic DNA refers to linear and/or chromosomal DNA and/or plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at predetermined target sites in a genomic DNA sequence, resulting in mutation, insertion, and/or deletion of a DNA sequence at the target site(s) in a genome.

Accordingly, in some embodiments, the compositions comprise a Clustered Regularly Interspaced Short Palindromic Repeat (CRISPR) nucleases. In some embodiments, the CRISPR nuclease is a CRISPR-associated protein.

In some embodiments, the compositions comprise a Clustered Regularly Interspaced Short Palindromic Repeats (CRISPR) nuclease having 100%, 99%, 98%, 97%, 96%, 95%, 94%, 93%, 92%, 91%, 90%, 85% identity to CRISPR nucleases derived from *Acetobacterium* sp. KB-1, *Alistipes* sp. An54, *Bartonella apis*, *Blastopirellula marina*, *Bryobacter aggregatus* MPL3, *Algoriphagus marinus*, *Butyrivibrio* sp. AC2005, bacterium LF-3, *Aliiarcobacter faecis*, *Caviibacter abscessus*, *Arcobacter* sp. SM1702, *Arcobacter mytili*, *Arcobacter thereius*, *Carnobacterium funditum*, *Peptoniphilus obesi* ph1, *Carnobacterium iners*, *Lactobacillus allii*, *Bacteroides coagulans*, *Butyrivibrio* sp. NC3005, *Clostridium* sp. AF02-29 or *Algoriphagus antarcticus*. Each possibility represents a separate embodiment.

OMNI CRISPR Nucleases

Embodiments of the present invention provide for CRISPR nucleases designated as an "OMNI" nuclease as provided in Tables 1a-1b.

This invention provides a method of modifying a nucleotide sequence at a target site in the genome of a mammalian cell comprising introducing into the cell (i) a composition comprising a CRISPR nuclease having at least 95% identity to an amino acid sequence selected from the group consisting of SEQ ID NOs: 1-8 or a nucleic acid molecule comprising a sequence encoding a CRISPR nuclease which sequence has at least 95% identity to a nucleic acid sequence selected from the group consisting of SEQ ID NOs: 9-24 and (ii) a DNA-targeting RNA molecule, or a DNA polynucleotide encoding a DNA-targeting RNA molecule, comprising a nucleotide sequence that is complementary to a sequence in the target DNA.

This invention also provides a non-naturally occurring composition comprising a CRISPR associated system comprising:
  a) one or more RNA molecules comprising a guide sequence portion linked to a direct repeat sequence, wherein the guide sequence is capable of hybridizing with a target sequence, or one or more nucleotide sequences encoding the one or more RNA molecules; and
  b) an CRISPR nuclease comprising an amino acid sequence having at least 95% identity to the amino acid sequence selected from the group consisting of SEQ ID NOs: 1-8 or a nucleic acid molecule comprising a sequence encoding the CRISPR nuclease; and
wherein the one or more RNA molecules hybridize to the target sequence, wherein the target sequence is adjacent to the 3' end of a complimentary sequence of a Protospacer Adjacent Motif (PAM), and the one or more RNA molecules form a complex with the RNA-guided nuclease.

This invention also provides a non-naturally occurring composition comprising:
a) a CRISPR nuclease comprising a sequence having at least 95% identity to the amino acid sequence selected from the group consisting of SEQ ID NOs: 1-8 or a nucleic acid molecule comprising a sequence encoding the CRISPR nuclease; and
b) one or more RNA molecules, or one or more DNA polynucleotide encoding the one or more RNA molecules, comprising at least one of:
 i) a nuclease-binding RNA nucleotide sequence capable of interacting with/binding to the CRISPR nuclease; and
 ii) a DNA-targeting RNA nucleotide sequence comprising a sequence complementary to a sequence in a target DNA sequence,
wherein the CRISPR nuclease is capable of complexing with the one or more RNA molecules to form a complex capable of hybridizing with the target DNA sequence.

BRIEF DESCRIPTION OF THE DRAWINGS

FIG. 1A: The native pre-mature crRNA-tracrRNA duplex. FIG. 1B: Example of V1 sgRNA design with the duplex shortening (indicated by triangles in A) compared with the native. FIG. 1C: Example of V2 sgRNA design with the duplex shortening (indicated by triangles in A) compared with the native.

FIGS. 2A-2H: In-vitro PAM Depletion by TXTL results for OMNI nucleases. The PAM logo is a schematic representation of the ratio of the depleted site. A condensed 4N window library of all possible PAM locations along an 8 bp sequence for each OMNI nuclease in a cell-free in vitro TXTL system is shown. Sequence motifs generated for in vitro PAM sites are based on depletion assay results. Activity estimated based on the average of the two most depleted sequences and was calculated as: 1—Depletion score. In vitro PAM depletion results for OMNI-59 sgRNA v1 and v2 (FIG. 2A); OMNI-61 sgRNA v1, and v2 (FIG. 2B); OMNI-67 sgRNA v1, and v2 (FIG. 2C); OMNI-76 sgRNA v1 and v2 (FIG. 2D); OMNI-79 sgRNA v1 and v2 (FIG. 2E); OMNI-80 sgRNA v1 and v2 (FIG. 2F); OMNI-81 sgRNA v1 and v2 (FIG. 2G); and OMNI-82 sgRNA v1 and v2 (FIG. 2H) are depicted.

FIG. 4A: The predicted secondary structure of a single-guide RNA (sgRNA) (crRNA-tracrRNA) scaffolds from Novosphingobium sp. SYSU G00007 (OMNI-79) and two other sgRNA scaffolds, SpSpCAP1 and SpSaNXO2, are presented. FIG. 4B: HeLa cells were transfected with gRNA molecules composed of spacers directed to CXCR4, TRAC, or ELANE genes, and either an OMNI-79 native scaffold, a SpSpCAP1 scaffold, or a SpSaNXO2 scaffold. Editing activity of OMNI-79 nuclease with each RNA molecule was determined using amplicon-based next-generation sequencing (NGS) measuring indel frequency.

FIG. 5A: HeLa cells were infected using AAV particles bearing OMNI-79 CRISPR nuclease under a CMV promoter and a gRNA molecule targeting CXCR4, ELANE, or A1AT genes and under a U6 promoter. Editing activity was determined using amplicon-based next-generation sequencing (NGS) measuring indel frequency. FIG. 5B: HepG2 cells were infected with OMNI-79 CRISPR nuclease and a A1AT-targeting gRNA molecule with or without bortezomib (BTZ). Editing activity was determined using amplicon-based next-generation sequencing (NGS) measuring indel frequency.

DETAILED DESCRIPTION

Figure 1A:
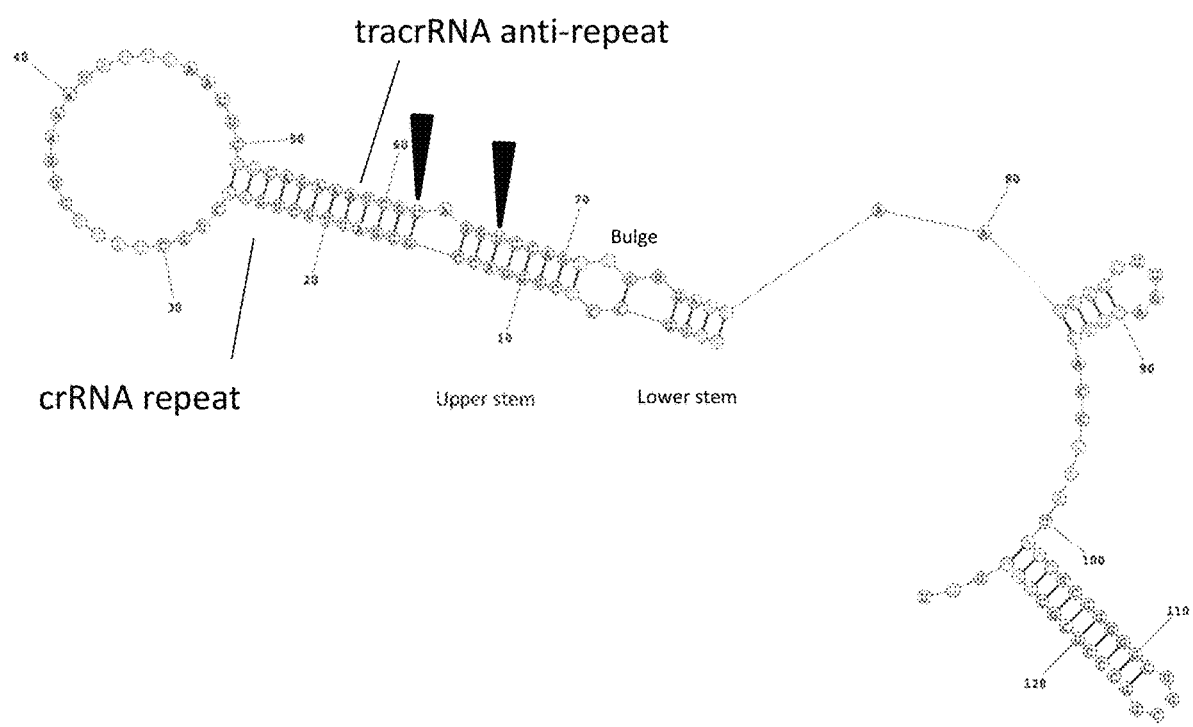
FIGS. 1A-1C: The predicted secondary structure of a single guide RNA (sgRNA) (crRNA-tracrRNA) from Novosphingobium sp. SYSU G00007 (OMNI-79) comprising a guide sequence portion and a sequence selected from the group consisting of SEQ ID Nos: 63-90: The crRNA and tracrRNA portions of the sgRNA are noted.
Figure 1B:
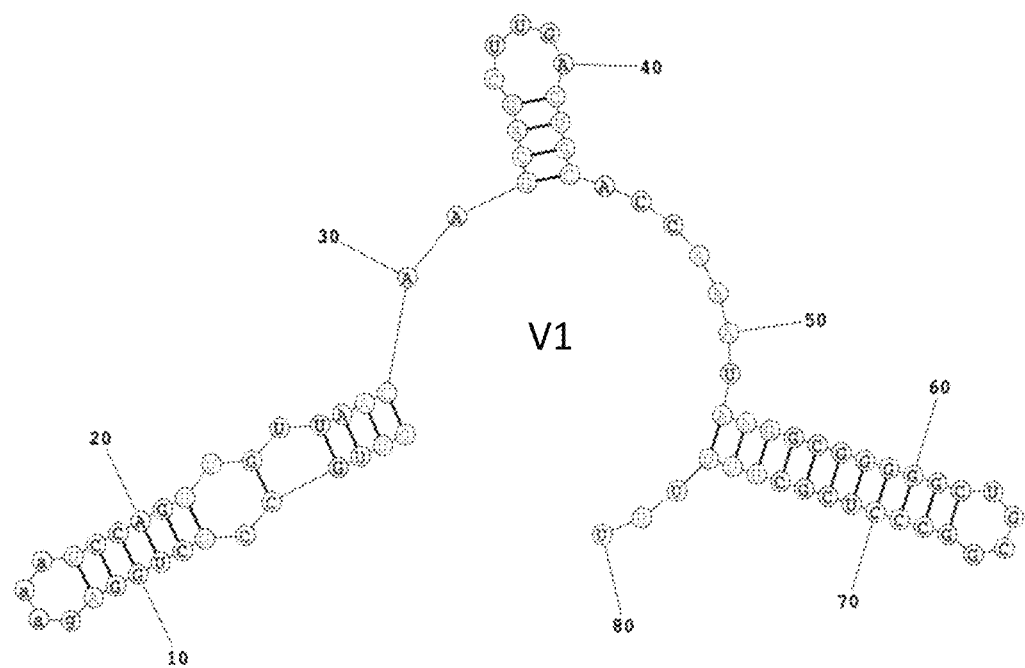

According to embodiments of the present invention, there is provided a non-naturally occurring composition comprising a CRISPR nuclease comprising a sequence having at least 90% identity to the amino acid sequence selected from the group consisting of SEQ ID NOs: 1-8, or a nucleic acid molecule comprising a sequence encoding the CRISPR nuclease.

In some embodiments, the composition further comprises one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site. In some embodiments, the target site is genomic DNA target site in a eukaryotic cell. In some embodiments, the RNA molecule or molecules are modified to have a 2'-O-methyl 3'-phosphorothioate at its 3' end, 5' end, or at both ends.

In some embodiments, the CRISPR nuclease comprises a sequence having at least 90% identity to the amino acid sequence set forth in SEQ ID NO: 5, and at least one RNA molecule comprises a sequence selected from the group consisting of SEQ ID NOs: 63-90.

In some embodiments, the CRISPR nuclease comprises a sequence having at least 90% identity to the amino acid sequence set forth in SEQ ID NO: 5 and at least one RNA molecule is a CRISPR RNA (crRNA) molecule comprising a guide sequence portion and a sequence selected from the group consisting of SEQ ID NOs: 63, 64, 71-73, and 81-83.

In some embodiments, the composition further comprises a transactivating CRISPR RNA (tracrRNA) molecule comprising a sequence set forth in the group consisting of SEQ ID NOs: 65-69, 74-79, and 84-89.

In some embodiments, the CRISPR nuclease comprises a sequence having at least 90% identity to the amino acid sequence set forth in SEQ ID NO: 5 and at least one RNA molecule is a single-guide RNA (sgRNA) molecule comprising a guide sequence portion and a sequence selected from the group consisting of SEQ ID NOs: 63-90.

In some embodiments, the guide sequence portion is 25 or 26 nucleotides in length.

In some embodiments, the CRISPR nuclease comprises a sequence having at least 90% identity to the amino acid sequence of SEQ ID NO: 5, and wherein the CRISPR nuclease is a nickase formed by an amino acid substitution at D8, E502, H735 or D738 of SEQ ID NO: 5.

In some embodiments, the CRISPR nuclease comprises a sequence having at least 90% identity to the amino acid sequence of SEQ ID NO: 5, and wherein the CRISPR nuclease is a nickase formed by an amino acid substitution at D586, H587 or N610 of SEQ ID NO: 5.

In some embodiments, the CRISPR nuclease comprises a sequence having at least 90% identity to the amino acid sequence of SEQ ID NO: 5, and wherein the CRISPR nuclease is a catalytically inactive nuclease formed by an amino acid substitution at D8, E502, H735 or D738 of SEQ ID NO: 5, and an amino acid substitution at D586, H587 or N610 of SEQ ID NO: 5.

In some embodiments, the CRISPR nuclease comprises a sequence having at least 90% identity to the amino acid sequence of SEQ ID NO: 5, and the CRISPR nuclease comprises a Domain A comprising a sequence having at least 90% identity to the amino acid sequence of at least 90% sequence identity to amino acids 1 to 40 of SEQ ID NO: 5.

In some embodiments, the CRISPR nuclease comprises a sequence having at least 90% identity to the amino acid sequence of SEQ ID NO: 5, and the CRISPR nuclease comprises a Domain B comprising a sequence having at least 90% identity to the amino acid sequence of at least 90% sequence identity to amino acids 41 to 76 of SEQ ID NO: 5.

In some embodiments, the CRISPR nuclease comprises a sequence having at least 90% identity to the amino acid sequence of SEQ ID NO: 5, and the CRISPR nuclease comprises a Domain C comprising a sequence having at least 90% identity to the amino acid sequence of at least 90% sequence identity to amino acids 77 to 228 of SEQ ID NO: 5.

In some embodiments, the CRISPR nuclease comprises a sequence having at least 90% identity to the amino acid sequence of SEQ ID NO: 5, and the CRISPR nuclease comprises a Domain D comprising a sequence having at least 90% identity to the amino acid sequence of at least 90% sequence identity to amino acids 229 to 446 of SEQ ID NO: 5.

In some embodiments, the CRISPR nuclease comprises a sequence having at least 90% identity to the amino acid sequence of SEQ ID NO: 5, and the CRISPR nuclease comprises a Domain E comprising a sequence having at least 90% identity to the amino acid sequence of at least 90% sequence identity to amino acids 447 to 507 of SEQ ID NO: 5.

In some embodiments, the CRISPR nuclease comprises a sequence having at least 90% identity to the amino acid sequence of SEQ ID NO: 5, and the CRISPR nuclease comprises a Domain F comprising a sequence having at least 90% identity to the amino acid sequence of at least 90% sequence identity to amino acids 539 to 648 of SEQ ID NO: 5.

In some embodiments, the CRISPR nuclease comprises a sequence having at least 90% identity to the amino acid sequence of SEQ ID NO: 5, and the CRISPR nuclease comprises a Domain G comprising a sequence having at least 90% identity to the amino acid sequence of at least 90% sequence identity to amino acids 655 to 822 of SEQ ID NO: 5.

In some embodiments, the CRISPR nuclease comprises a sequence having at least 90% identity to the amino acid sequence of SEQ ID NO: 5, and the CRISPR nuclease comprises a Domain H comprising a sequence having at least 90% identity to the amino acid sequence of at least 90% sequence identity to amino acids 823 to 921 of SEQ ID NO: 5.

In some embodiments, the CRISPR nuclease comprises a sequence having at least 90% identity to the amino acid sequence of SEQ ID NO: 5, and the CRISPR nuclease comprises a Domain I comprising a sequence having at least 90% identity to the amino acid sequence of at least 90% sequence identity to amino acids 922 to 1062 of SEQ ID NO: 5.

In some embodiments, the CRISPR nuclease comprises a sequence having at least 90% identity to the amino acid sequence set forth in SEQ ID NO: 1, and at least one RNA molecule comprises a sequence selected from the group consisting of SEQ ID NOs: 25-29.

In some embodiments, the CRISPR nuclease comprises a sequence having at least 90% identity to the amino acid sequence set forth in SEQ ID NO: 1 and at least one RNA molecule is a CRISPR RNA (crRNA) molecule comprising a guide sequence portion and a sequence set forth in SEQ ID NO: 25.

In some embodiments, the composition further comprises a transactivating CRISPR RNA (tracrRNA) molecule comprising a sequence set forth in the group consisting of SEQ ID NOs: 26-28.

In some embodiments, the CRISPR nuclease comprises a sequence having at least 90% identity to the amino acid sequence set forth in SEQ ID NO: 1 and at least one RNA molecule is a single-guide RNA (sgRNA) molecule comprising a guide sequence portion and a sequence selected from the group consisting of SEQ ID NOs: 25-29.

In some embodiments, the CRISPR nuclease comprises a sequence having at least 90% identity to the amino acid sequence of SEQ ID NO: 1, and wherein the CRISPR nuclease is a nickase formed by an amino acid substitution at D24, E557, H785 or D788 of SEQ ID NO: 1.

In some embodiments, the CRISPR nuclease comprises a sequence having at least 90% identity to the amino acid sequence of SEQ ID NO: 1, and wherein the CRISPR nuclease is a nickase formed by an amino acid substitution at E644, H645 or N668 of SEQ ID NO: 1.

In some embodiments, the CRISPR nuclease comprises a sequence having at least 90% identity to the amino acid sequence of SEQ ID NO: 1, and wherein the CRISPR nuclease is a catalytically inactive nuclease formed by an amino acid substitution at D24, E557, H785 or D788 of SEQ ID NO: 1, and an amino acid substitution at E644, H645 or N668 of SEQ ID NO: 1.

In some embodiments, the CRISPR nuclease comprises a sequence having at least 90% identity to the amino acid sequence set forth in SEQ ID NO: 2, and at least one RNA molecule comprises a sequence selected from the group consisting of SEQ ID NOs: 30-39.

In some embodiments, the CRISPR nuclease comprises a sequence having at least 90% identity to the amino acid sequence set forth in SEQ ID NO: 2 and at least one RNA molecule is a CRISPR RNA (crRNA) molecule comprising a guide sequence portion and a sequence selected from the group consisting of SEQ ID NOs: 30-32.

In some embodiments, the composition further comprises a transactivating CRISPR RNA (tracrRNA) molecule comprising a sequence set forth in the group consisting of SEQ ID NOs: 33-38.

In some embodiments, the CRISPR nuclease comprises a sequence having at least 90% identity to the amino acid sequence set forth in SEQ ID NO: 2 and at least one RNA molecule is a single-guide RNA (sgRNA) molecule comprising a guide sequence portion and a sequence selected from the group consisting of SEQ ID NOs: 30-39.

In some embodiments, the CRISPR nuclease comprises a sequence having at least 90% identity to the amino acid sequence of SEQ ID NO: 2, and wherein the CRISPR nuclease is a nickase formed by an amino acid substitution at D19, E528, H750 or D753 of SEQ ID NO: 2.

In some embodiments, the CRISPR nuclease comprises a sequence having at least 90% identity to the amino acid sequence of SEQ ID NO: 2, and wherein the CRISPR nuclease is a nickase formed by an amino acid substitution at D609, H610 or N633 of SEQ ID NO: 2.

In some embodiments, the CRISPR nuclease comprises a sequence having at least 90% identity to the amino acid sequence of SEQ ID NO: 2, and wherein the CRISPR nuclease is a catalytically inactive nuclease formed by an amino acid substitution at D19, E528, H750 or D753 of SEQ ID NO: 2, and an amino acid substitution at D609, H610 or N633 of SEQ ID NO: 2.

In some embodiments, the CRISPR nuclease comprises a sequence having at least 90% identity to the amino acid sequence set forth in SEQ ID NO: 3, and at least one RNA molecule comprises a sequence selected from the group consisting of SEQ ID NOs: 40-52

In some embodiments, the CRISPR nuclease comprises a sequence having at least 90% identity to the amino acid sequence set forth in SEQ ID NO: 3 and at least one RNA molecule is a CRISPR RNA (crRNA) molecule comprising a guide sequence portion and a sequence selected from the group consisting of SEQ ID NOs: 40-43.

In some embodiments, the composition further comprises a transactivating CRISPR RNA (tracrRNA) molecule comprising a sequence set forth in the group consisting of SEQ ID NOs: 44-51.

In some embodiments, the CRISPR nuclease comprises a sequence having at least 90% identity to the amino acid sequence set forth in SEQ ID NO: 3 and at least one RNA molecule is a single-guide RNA (sgRNA) molecule comprising a guide sequence portion and a sequence selected from the group consisting of SEQ ID NOs: 40-52.

In some embodiments, the CRISPR nuclease comprises a sequence having at least 90% identity to the amino acid sequence of SEQ ID NO: 3, and wherein the CRISPR nuclease is a nickase formed by an amino acid substitution at D8, E503, H729 or D732 of SEQ ID NO: 3.

In some embodiments, the CRISPR nuclease comprises a sequence having at least 90% identity to the amino acid sequence of SEQ ID NO: 3, and wherein the CRISPR nuclease is a nickase formed by an amino acid substitution at E584, H585 or N607 of SEQ ID NO: 3.

In some embodiments, the CRISPR nuclease comprises a sequence having at least 90% identity to the amino acid sequence of SEQ ID NO: 3, and wherein the CRISPR nuclease is a catalytically inactive nuclease formed by an amino acid substitution at D8, E503, H729 or D732 of SEQ ID NO: 1, and an amino acid substitution at E584, H585 or N607 of SEQ ID NO: 3.

In some embodiments, the CRISPR nuclease comprises a sequence having at least 90% identity to the amino acid sequence set forth in SEQ ID NO: 4, and at least one RNA molecule comprises a sequence selected from the group consisting of SEQ ID NOs: 53-62.

In some embodiments, the CRISPR nuclease comprises a sequence having at least 90% identity to the amino acid sequence set forth in SEQ ID NO: 4 and at least one RNA molecule is a CRISPR RNA (crRNA) molecule comprising a guide sequence portion and a sequence selected from the group consisting of SEQ ID NOs: 53-55.

In some embodiments, the composition further comprises a transactivating CRISPR RNA (tracrRNA) molecule comprising a sequence set forth in the group consisting of SEQ ID NOs: 56-61.

In some embodiments, the CRISPR nuclease comprises a sequence having at least 90% identity to the amino acid sequence set forth in SEQ ID NO: 4 and at least one RNA molecule is a single-guide RNA (sgRNA) molecule comprising a guide sequence portion and a sequence selected from the group consisting of SEQ ID NOs: 53-62.

In some embodiments, the CRISPR nuclease comprises a sequence having at least 90% identity to the amino acid sequence of SEQ ID NO: 4, and wherein the CRISPR nuclease is a nickase formed by an amino acid substitution at D12, E543, H770 or D773 of SEQ ID NO: 4.

In some embodiments, the CRISPR nuclease comprises a sequence having at least 90% identity to the amino acid sequence of SEQ ID NO: 4, and wherein the CRISPR nuclease is a nickase formed by an amino acid substitution at E630, H631 or N654 of SEQ ID NO: 4.

In some embodiments, the CRISPR nuclease comprises a sequence having at least 90% identity to the amino acid sequence of SEQ ID NO: 4, and wherein the CRISPR nuclease is a catalytically inactive nuclease formed by an amino acid substitution at D12, E543, H770 or D773 of SEQ ID NO: 4, and an amino acid substitution at E630, H631 or N654 of SEQ ID NO: 4.

In some embodiments, the CRISPR nuclease comprises a sequence having at least 90% identity to the amino acid sequence set forth in SEQ ID NO: 6, and at least one RNA molecule comprises a sequence selected from the group consisting of SEQ ID NOs: 91-98.

In some embodiments, the CRISPR nuclease comprises a sequence having at least 90% identity to the amino acid sequence set forth in SEQ ID NO: 6 and at least one RNA molecule is a CRISPR RNA (crRNA) molecule comprising a guide sequence portion and a sequence selected from the group consisting of SEQ ID NOs: 91 and 92.

In some embodiments, the composition further comprises a transactivating CRISPR RNA (tracrRNA) molecule comprising a sequence set forth in the group consisting of SEQ ID NOs: 93-97.

In some embodiments, the CRISPR nuclease comprises a sequence having at least 90% identity to the amino acid sequence set forth in SEQ ID NO: 6 and at least one RNA molecule is a single-guide RNA (sgRNA) molecule comprising a guide sequence portion and a sequence selected from the group consisting of SEQ ID NOs: 91-98.

In some embodiments, the CRISPR nuclease comprises a sequence having at least 90% identity to the amino acid sequence of SEQ ID NO: 6, and wherein the CRISPR nuclease is a nickase formed by an amino acid substitution at D8, E523, H757 or D760 of SEQ ID NO: 6.

In some embodiments, the CRISPR nuclease comprises a sequence having at least 90% identity to the amino acid sequence of SEQ ID NO: 6, and wherein the CRISPR nuclease is a nickase formed by an amino acid substitution at D607, H608 or N631 of SEQ ID NO: 6.

In some embodiments, the CRISPR nuclease comprises a sequence having at least 90% identity to the amino acid sequence of SEQ ID NO: 6, and wherein the CRISPR nuclease is a catalytically inactive nuclease formed by an amino acid substitution at D8, E523, H757 or D760 of SEQ ID NO: 6, and an amino acid substitution at D607, H608 or N631 of SEQ ID NO: 6.

In some embodiments, the CRISPR nuclease comprises a sequence having at least 90% identity to the amino acid sequence set forth in SEQ ID NO: 7, and at least one RNA molecule comprises a sequence selected from the group consisting of SEQ ID NOs: 99-108.

In some embodiments, the CRISPR nuclease comprises a sequence having at least 90% identity to the amino acid sequence set forth in SEQ ID NO: 7 and at least one RNA molecule is a CRISPR RNA (crRNA) molecule comprising a guide sequence portion and a sequence selected from the group consisting of SEQ ID NOs: 99-101.

In some embodiments, the composition further comprises a transactivating CRISPR RNA (tracrRNA) molecule comprising a sequence set forth in the group consisting of SEQ ID NOs: 102-107.

T In some embodiments, the CRISPR nuclease comprises a sequence having at least 90% identity to the amino acid sequence set forth in SEQ ID NO: 7 and at least one RNA molecule is a single-guide RNA (sgRNA) molecule comprising a guide sequence portion and a sequence selected from the group consisting of SEQ ID NOs: 99-108.

In some embodiments, the CRISPR nuclease comprises a sequence having at least 90% identity to the amino acid sequence of SEQ ID NO: 7, and wherein the CRISPR nuclease is a nickase formed by an amino acid substitution at D12, E527, H756 or D759 of SEQ ID NO: 7.

In some embodiments, the CRISPR nuclease comprises a sequence having at least 90% identity to the amino acid sequence of SEQ ID NO: 7, and wherein the CRISPR nuclease is a nickase formed by an amino acid substitution at E615, H616 or N639 of SEQ ID NO: 7.

In some embodiments, the CRISPR nuclease comprises a sequence having at least 90% identity to the amino acid sequence of SEQ ID NO: 7, and wherein the CRISPR nuclease is a catalytically inactive nuclease formed by an amino acid substitution at D12, E527, H756 or D759 of SEQ ID NO: 7, and an amino acid substitution at E615, H616 or N639 of SEQ ID NO: 7.

In some embodiments, the CRISPR nuclease comprises a sequence having at least 90% identity to the amino acid sequence set forth in SEQ ID NO: 8, and at least one RNA molecule comprises a sequence selected from the group consisting of SEQ ID NOs: 109-120.

In some embodiments, the CRISPR nuclease comprises a sequence having at least 90% identity to the amino acid sequence set forth in SEQ ID NO: 8 and at least one RNA molecule is a CRISPR RNA (crRNA) molecule comprising a guide sequence portion and a sequence selected from the group consisting of SEQ ID NOs: 109-112.

In some embodiments, the composition further comprises a transactivating CRISPR RNA (tracrRNA) molecule comprising a sequence set forth in the group consisting of SEQ ID NOs: 113-119.

In some embodiments, the CRISPR nuclease comprises a sequence having at least 90% identity to the amino acid sequence set forth in SEQ ID NO: 8 and at least one RNA molecule is a single-guide RNA (sgRNA) molecule comprising a guide sequence portion and a sequence selected from the group consisting of SEQ ID NOs: 109-120.

In some embodiments, the CRISPR nuclease comprises a sequence having at least 90% identity to the amino acid sequence of SEQ ID NO: 8, and wherein the CRISPR nuclease is a nickase formed by an amino acid substitution at D6, E524, H756 or D759 of SEQ ID NO: 8.

In some embodiments, the CRISPR nuclease comprises a sequence having at least 90% identity to the amino acid sequence of SEQ ID NO: 8, and wherein the CRISPR nuclease is a nickase formed by an amino acid substitution at D608, H609 or N632 of SEQ ID NO: 8.

In some embodiments, the CRISPR nuclease comprises a sequence having at least 90% identity to the amino acid sequence of SEQ ID NO: 8, and wherein the CRISPR nuclease is a catalytically inactive nuclease formed by an amino acid substitution at D6, E524, H756 or D759 of SEQ ID NO: 8, and an amino acid substitution at D608, H609 or N632 of SEQ ID NO: 8.

According to embodiments of the present invention, there is provided a non-naturally occurring composition comprising a CRISPR nuclease, wherein the CRISPR nuclease comprises an amino acid sequence corresponding to the amino acid sequence of at least one of Domain A, Domain B, Domain C, Domain D, Domain E, Domain F, Domain G, Domain H, or Doman I of OMNI-79 CRISPR nuclease (SEQ ID NO: 5).

In some embodiments, the CRISPR nuclease comprises a Domain A having at least 97% sequence identity to amino acids 1 to 40 of SEQ ID NO: 5.

In some embodiments, the CRISPR nuclease comprises a Domain B having at least 97% sequence identity to amino acids 41 to 76 of SEQ ID NO: 5.

In some embodiments, the CRISPR nuclease comprises a Domain C having at least 97% sequence identity to amino acids 77 to 228 of SEQ ID NO: 5.

In some embodiments, the CRISPR nuclease comprises a Domain D having at least 97% sequence identity to amino acids 229 to 446 of SEQ ID NO: 5.

In some embodiments, the CRISPR nuclease comprises a Domain E having at least 97% sequence identity to amino acids 447 to 507 of SEQ ID NO: 5.

In some embodiments, the CRISPR nuclease comprises a Domain F having at least 97% sequence identity to amino acids 539 to 648 of SEQ ID NO: 5.

In some embodiments, the CRISPR nuclease comprises a Domain G having at least 97% sequence identity to amino acids 665 to 822 of SEQ ID NO: 5.

In some embodiments, the CRISPR nuclease comprises a Domain H having at least 97% sequence identity to amino acids 823 to 921 of SEQ ID NO: 5.

In some embodiments, the CRISPR nuclease comprises a Domain I having at least 97% sequence identity to amino acids 922 to 1062 of SEQ ID NO: 5.

In some embodiments, the CRISPR nuclease sequence is at least 100-250, 250-500, 500-1000, or 1000-2000 amino acids in length.

A non-naturally occurring composition comprising a peptide, or a polynucleotide encoding the peptide, wherein the peptide comprises an amino acid sequence having at least 97% sequence identity to the amino acid sequence of at least one of Domain A, Domain B, Domain C, Domain D, Domain E, Domain F, Domain G, Domain H, or Doman I of OMNI-79 CRISPR nuclease.

According to embodiments of the present invention, there is provided a composition of an engineered, non-naturally occurring composition comprising a CRISPR associated system comprising:

one or more RNA molecules, or one or more nucleotide sequences encoding the one or more RNA molecules, the one or more RNA molecules comprising a guide sequence portion linked to a direct repeat sequence, wherein the guide sequence portion is capable of hybridizing with a target sequence; and a CRISPR nuclease comprising an amino acid sequence having at least 90% identity to the amino acid sequence selected from the group consisting of SEQ ID NOs: 1-8 or a nucleic acid molecule comprising a sequence encoding the CRISPR nuclease; and wherein the one or more RNA molecules hybridize to the target sequence, wherein the target sequence is adjacent to the 3' end of a complimentary sequence of a Protospacer Adjacent Motif (PAM), and the one or more RNA molecules form a complex with the CRISPR nuclease.

According to embodiments of the present invention, there is provided a method of modifying a nucleotide sequence at a target site in a cell-free system or the genome of a cell comprising introducing into the cell any one of the compositions described herein.

In some embodiments, the cell is a eukaryotic cell or a prokaryotic cell.

In some embodiments, the eukaryotic cell is a mammalian cell.

In some embodiments, the mammalian cell is a human cell.

In some embodiments, the CRISPR nuclease forms a complex with the at least one RNA molecule or RNA molecules, and effects a DNA break in a DNA strand adjacent to a protospacer adjacent motif (PAM) sequence, and/or effects a DNA break in a DNA strand adjacent to a sequence that is complementary to the PAM sequence.

In some embodiments, the CRISPR nuclease comprises a sequence having at least 90% identity to SEQ ID NO: 1 and the PAM site is NGCNNT.

In some embodiments, the CRISPR nuclease is a nickase formed by an amino acid substitution at D24, E557, H785 or D788 of SEQ ID NO: 1, and effects a DNA break in a DNA strand adjacent to a PAM sequence.

In some embodiments, the CRISPR nuclease is a nickase formed by an amino acid substitution at E644, H645 or N668 of SEQ ID NO: 1, and effects a DNA break in a DNA strand adjacent to a sequence that is complementary to the PAM sequence.

In some embodiments, the CRISPR nuclease comprises a sequence having at least 90% identity to SEQ ID NO: 2 and the PAM sequence is NSHNAC.

In some embodiments, the CRISPR nuclease is a nickase formed by an amino acid substitution at D19, E528, H750 or D753 of SEQ ID NO: 2, and effects a DNA break in a DNA strand adjacent to a PAM sequence.

In some embodiments, the CRISPR nuclease is a nickase formed by an amino acid substitution at D609, H610 or N633 of SEQ ID NO: 2, and effects a DNA break in a DNA strand adjacent to a sequence that is complementary to the PAM sequence.

In some embodiments, the CRISPR nuclease comprises a sequence having at least 90% identity to SEQ ID NO: 3 and the PAM sequence is NRRCM.

In some embodiments, the CRISPR nuclease is a nickase formed by an amino acid substitution at D8, E503, H729 or D732 of SEQ ID NO: 3, and effects a DNA break in a DNA strand adjacent to a PAM sequence.

In some embodiments, the CRISPR nuclease is a nickase formed by an amino acid substitution at E584, H585 or N607 of SEQ ID NO: 3, and effects a DNA break in a DNA strand adjacent to a sequence that is complementary to the PAM sequence.

In some embodiments, the CRISPR nuclease comprises a sequence having at least 90% identity to SEQ ID NO: 4 and the PAM sequence is NGSNNT.

In some embodiments, the CRISPR nuclease is a nickase formed by an amino acid substitution at D12, E543, H770 or D773 of SEQ ID NO: 4, and effects a DNA break in a DNA strand adjacent to a PAM sequence.

In some embodiments, the CRISPR nuclease is a nickase formed by an amino acid substitution at E630, H631 or N654 of SEQ ID NO: 4, and effects a DNA break in a DNA strand adjacent to a sequence that is complementary to the PAM sequence.

In some embodiments, the CRISPR nuclease comprises a sequence having at least 90% identity to SEQ ID NO: 5 and the PAM sequence is NGR or NGG.

In some embodiments, the CRISPR nuclease is a nickase formed by an amino acid substitution at D8, E502, H735 or D738 of SEQ ID NO: 5, and effects a DNA break in a DNA strand adjacent to the PAM sequence.

In some embodiments, the CRISPR nuclease is a nickase formed by an amino acid substitution at D586, H587 or N610 of SEQ ID NO: 5, and effects a DNA break in a DNA strand adjacent to a sequence that is complementary to the PAM sequence.

In some embodiments, the CRISPR nuclease comprises a sequence having at least 90% identity to SEQ ID NO: 6 and the PAM sequence is NNRGAY.

In some embodiments, the CRISPR nuclease is a nickase formed by an amino acid substitution at D8, E523, H757 or D760 of SEQ ID NO: 6, and effects a DNA break in a DNA strand adjacent to the PAM sequence.

In some embodiments, the CRISPR nuclease is a nickase formed by an amino acid substitution at D607, H608 or N631 of SEQ ID NO: 6, and effects a DNA break in a DNA strand adjacent to a sequence that is complementary to the PAM sequence.

In some embodiments, the CRISPR nuclease comprises a sequence having at least 90% identity to SEQ ID NO: 7 and the PAM sequence is NRRAA.

In some embodiments, the CRISPR nuclease is a nickase formed by an amino acid substitution at D12, E527, H756 or D759 of SEQ ID NO: 7, and effects a DNA break in a DNA strand adjacent to the PAM sequence.

In some embodiments, the CRISPR nuclease is a nickase formed by an amino acid substitution at E615, H616 or N639 of SEQ ID NO: 7, and effects a DNA break in a DNA strand adjacent to a sequence that is complementary to the PAM sequence.

In some embodiments, the CRISPR nuclease comprises a sequence having at least 90% identity to SEQ ID NO: 8 and the PAM sequence is NRRNTT.

In some embodiments, the CRISPR nuclease is a nickase formed by an amino acid substitution at D6, E524, H756 or D759 of SEQ ID NO: 8, and effects a DNA break in a DNA strand adjacent to the PAM sequence.

In some embodiments, the CRISPR nuclease is a nickase formed by an amino acid substitution at D608, H609 or N632 of SEQ ID NO: 8, and effects a DNA break in a DNA strand adjacent to a sequence that is complementary to the PAM sequence.

According to some aspects of the invention, the disclosed compositions comprise a Clustered Regularly Interspaced Short Palindromic Repeats (CRISPR) nuclease and/or a nucleic acid molecule comprising a sequence encoding the same.

Tables 1a-1b list novel CRISPR nucleases, as well as substitutions at one or more positions within each nuclease which convert the nuclease to a nickase or catalytically dead nuclease.

Tables 2a-2d provide crRNA, tracrRNA, and single-guide RNA (sgRNA) sequences, and portions of crRNA, tracrRNA, and sgRNA sequences, that are compatible with each listed CRISPR nuclease. Accordingly, a crRNA molecule capable of binding and targeting an OMNI nuclease listed in Tables 2a-2d as part of a crRNA:tracrRNA complex may comprise any crRNA sequence listed in Tables 2a-2d. Similarly, a tracrRNA molecule capable of binding and targeting an OMNI nuclease listed in Tables 2a-2d as part of a crRNA:tracrRNA complex may comprise any tracrRNA sequence listed in Tables 2a-2d. Also, a single-guide RNA molecule capable of binding and targeting an OMNI nuclease listed in Tables 2a-2d may comprise any sequence listed in Tables 2a-2d.

For example, a crRNA molecule of OMNI-61 nuclease (SEQ ID NO: 2) may comprise a sequence of SEQ ID NOs: 30-32; a tracrRNA molecule of OMNI-61 nuclease may comprise a sequence of any one of SEQ ID NOs: 33-38; and a sgRNA molecule of OMNI-62 nuclease may comprise a sequence of any one of SEQ ID NOs: 30-39. Other crRNA molecules, tracrRNA molecules, or sgRNA molecules for each OMNI nuclease may be derived from the sequences listed in Tables 2a-2d in the same manner.

In some embodiments, the CRISPR nuclease comprises an amino acid sequence having at least 100%, 99%, 98%, 97%, 96%, 95%, 94%, 93%, 92%, 91%, 90%, 89%, 88%, 87%, 86%, 85%, 84%, 83%, or 82% amino acid sequence identity to a CRISPR nuclease as set forth in any of SEQ ID NOs: 1-8. In an embodiment the sequence encoding the CRISPR nuclease has at least 95% identity to a nucleic acid sequence selected from the group consisting of SEQ ID NOs: 9-24.

In some embodiments, the CRISPR nuclease comprises an amino acid sequence having at least 100%, 99%, 98%, 97%, 96%, 95%, 94%, 93%, 92%, 91%, 90%, 89%, 88%, 87%, 86%, 85%, 84%, 83%, 82%, 81%, 80%, 75% amino acid sequence identity to a CRISPR nucleases derived from Comamonadaceae bacterium NML00-0135, *Demequina sediminicola, Fuerstia marisgermanicae, Nitrosomonas* sp. Nm33, *Novosphingobium* sp. SYSU G00007, *Paracoccus bengalensis*, Parvibium *lacunae*, or *Pelagicola* sp. LXJ1103. Each possibility represents a separate embodiment.

In some embodiments, the CRISPR nuclease is a nickase having an inactivated RuvC domain created by an amino acid substitution at a position provided for the CRISPR nuclease in Tables 1a-1b.

In some embodiments, the CRISPR nuclease is a nickase having an inactivated HNH domain created by an amino acid substitution at a position provided for the CRISPR nuclease in Tables 1a-1b.

In some embodiments, the CRISPR nuclease is a catalytically dead nuclease having an inactivated RuvC domain and an inactivated HNH domain created by substitutions at the positions provided for the CRISPR nuclease in Tables 1a-1b.

For example, a nickase may be generated for the OMNI-59 nuclease by inactivating its RuvC domain by substituting an aspartic acid residue (D) in position 24 of the amino acid sequence of OMNI-59 (SEQ ID NO: 1) for another amino acid e.g. alanine (A). Substitution to any other amino acid is permissible for each of the amino acid positions indicated in Tables 1a-1b, except if the amino acid position is followed by an asterisk, which indicates that any substitution other than aspartic acid (D) to glutamic acid (E) or glutamic acid (E) to aspartic acid (D) results in inactivation. For example, a nickase may be generated for the OMNI-79 nuclease (SEQ ID NO: 5) by inactivating its HNH domain by substituting an aspartic acid residue (D) in position 586 of the amino acid sequence of OMNI-79 for an amino acid other than glutamic acid (E), e.g. for alanine (A). Other nickases or catalytically dead nucleases can be generated using the same notation in Tables 1a-1b.

In some embodiments, the CRISPR nuclease utilizes a protospacer adjacent motif (PAM) sequence provided for the CRISPR nuclease in Tables 3a-3c.

According to some aspects of the invention, the disclosed method provide a method of modifying a nucleotide sequence at a DNA target site in a cell-free system or the genome of a cell comprising introducing into the cell any one of the CRISPR nucleases and a suitable crRNA:tracrRNA complex or sgRNA molecule.

In some embodiments, the CRISPR nuclease effects a DNA break in a DNA strand adjacent to a protospacer adjacent motif (PAM) sequence provided for the CRISPR nuclease in Tables 3a-3c, and effects a DNA break in a DNA strand adjacent to a sequence that is complementary to the PAM sequence. For example, the OMNI-79 nuclease with the appropriate targeting sgRNA molecule or crRNA:tracrRNA complex is capable of forming a DNA break in strand adjacent to a NGR or NGG sequence and in a DNA strand adjacent to a sequence that is complementary to a NGR or NGG sequence. In some embodiments, the DNA strand is within a nucleus of a cell.

According to some aspects of the invention, the disclosed compositions comprise DNA constructs or a vector system comprising nucleotide sequences that encode the CRISPR nuclease or variant CRISPR nuclease. In some embodiments, the nucleotide sequence that encode the CRISPR nuclease or variant CRISPR nuclease is operably linked to a promoter that is operable in the cells of interest. In some embodiments, the cell of interest is a eukaryotic cell. In some embodiments the cell of interest is a mammalian cell. In some embodiments, the nucleic acid sequence encoding the engineered CRISPR nuclease is codon optimized for use in cells from a particular organism. In some embodiments, the nucleic acid sequence encoding the nuclease is codon optimized for *E. coli*. In some embodiments, the nucleic acid sequence encoding the nuclease is codon optimized for eukaryotic cells. In some embodiments, the nucleic acid sequence encoding the nuclease is codon optimized for mammalian cells.

In some embodiments, the composition comprises a recombinant nucleic acid, comprising a heterologous promoter operably linked to a polynucleotide encoding a CRISPR enzyme having at least 100%, 99%, 98%, 97%, 96%, 95%, 94%, 93%, 92%, 91%, 90% identity to any of SEQ ID NOs: 1-8. Each possibility represents a separate embodiment.

In an embodiment of the composition, the CRISPR nuclease has at least 75%, 80%, 85, 90%, 95%, or 97% identity to the amino acid sequence as set forth in SEQ ID NO: 1 or the sequence encoding the CRISPR nuclease has at least a 75%, 80%, 85, 90%, 95%, or 97% sequence identity to a nucleotide sequence selected from the group consisting of SEQ ID NOs: 9 and 17.

In an embodiment of the composition, the CRISPR nuclease has at least 75%, 80%, 85, 90%, 95%, or 97% identity to the amino acid sequence as set forth in SEQ ID NO: 2 or the sequence encoding the CRISPR nuclease has at least a 75%, 80%, 85, 90%, 95%, or 97% sequence identity to a nucleotide sequence selected from the group consisting of SEQ ID NOs: 10 and 18.

In an embodiment of the composition, the CRISPR nuclease has at least 75%, 80%, 85, 90%, 95%, or 97% identity to the amino acid sequence as set forth in SEQ ID NO: 3 or the sequence encoding the CRISPR nuclease has at least a 75%, 80%, 85, 90%, 95%, or 97% sequence identity to a nucleotide sequence selected from the group consisting of SEQ ID NOs: 11 and 19.

In an embodiment of the composition, the CRISPR nuclease has at least 75%, 80%, 85, 90%, 95%, or 97% identity to the amino acid sequence as set forth in SEQ ID NO: 4 or the sequence encoding the CRISPR nuclease has at least a 75%, 80%, 85, 90%, 95%, or 97% sequence identity to a nucleotide sequence selected from the group consisting of SEQ ID NOs: 12 and 20.

In an embodiment of the composition, the CRISPR nuclease has at least 75%, 80%, 85, 90%, 95%, or 97% identity to the amino acid sequence as set forth in SEQ ID NO: 5 or the sequence encoding the CRISPR nuclease has at least a 75%, 80%, 85, 90%, 95%, or 97% sequence identity to a nucleotide sequence selected from the group consisting of SEQ ID NOs: 13 and 21.

In an embodiment of the composition, the CRISPR nuclease has at least 75%, 80%, 85, 90%, 95%, or 97% identity to the amino acid sequence as set forth in SEQ ID NO: 6 or the sequence encoding the CRISPR nuclease has at least a 75%, 80%, 85, 90%, 95%, or 97% sequence identity to a nucleotide sequence selected from the group consisting of SEQ ID NOs: 14 and 22.

In an embodiment of the composition, the CRISPR nuclease has at least 75%, 80%, 85, 90%, 95%, or 97% identity to the amino acid sequence as set forth in SEQ ID NO: 7 or the sequence encoding the CRISPR nuclease has at least a 75%, 80%, 85, 90%, 95%, or 97% sequence identity to a nucleotide sequence selected from the group consisting of SEQ ID NOs: 15 and 23.

In an embodiment of the composition, the CRISPR nuclease has at least 75%, 80%, 85, 90%, 95%, or 97% identity to the amino acid sequence as set forth in SEQ ID NO: 8 or the sequence encoding the CRISPR nuclease has at least a 75%, 80%, 85, 90%, 95%, or 97% sequence identity to a nucleotide sequence selected from the group consisting of SEQ ID NOs: 16 and 24.

According to some embodiments, there is provided an engineered or non-naturally occurring composition comprising a CRISPR nuclease comprising a sequence having at least 100%, 99%, 98%, 97%, 96%, 95%, 94%, 93%, 92%, 91%, 90%, 85%, 80% identity to the amino acid sequence selected from the group consisting of SEQ ID NOs: 1-8 or a nucleic acid molecule comprising a sequence encoding the CRISPR nuclease. Each possibility represents a separate embodiment.

In an embodiment, the CRISPR nuclease is engineered or non-naturally occurring. The CRISPR nuclease may also be recombinant. Such CRISPR nucleases are produced using laboratory methods (molecular cloning) to bring together genetic material from multiple sources, creating sequences that would not otherwise be found in biological organisms.

In an embodiment, the CRISPR nuclease of the invention exhibits increased specificity to a target site compared to a SpCas9 nuclease when complexed with the one or more RNA molecules.

In an embodiment, the complex of the CRISPR nuclease of the invention and one or more RNA molecules exhibits at least maintained on-target editing activity of the target site and reduced off-target activity compared to SpCas9 nuclease.

In an embodiment, the CRISPR nuclease further comprises an RNA-binding portion capable of interacting with a DNA-targeting RNA molecule (gRNA) and an activity portion that exhibits site-directed enzymatic activity.

In an embodiment, the composition further comprises a DNA-targeting RNA molecule or a DNA polynucleotide encoding a DNA-targeting RNA molecule, wherein the DNA-targeting RNA molecule comprises a nucleotide sequence that is complementary to a sequence in a target region, wherein the DNA-targeting RNA molecule and the CRISPR nuclease do not naturally occur together.

In an embodiment, the DNA-targeting RNA molecule further comprises a nucleotide sequence that can form a complex with a CRISPR nuclease.

This invention also provides a non-naturally occurring composition comprising a CRISPR associated system comprising:
  a) one or more RNA molecules comprising a guide sequence portion linked to a direct repeat sequence, wherein the guide sequence is capable of hybridizing with a target sequence, or one or more nucleotide sequences encoding the one or more RNA molecules; and
  b) a CRISPR nuclease comprising an amino acid sequence having at least 95% identity to the amino acid sequence selected from the group consisting of SEQ ID NOs: 1-8 or a nucleic acid molecule comprising a sequence encoding the CRISPR nuclease;
    wherein the one or more RNA molecules hybridize to the target sequence, wherein the target sequence is adjacent to the 3' end of a complimentary sequence of a Protospacer Adjacent Motif (PAM), and the one or more RNA molecules form a complex with the RNA-guided nuclease.

In an embodiment, the composition further comprises an RNA molecule comprising a nucleotide sequence that can form a complex with a CRISPR nuclease (tracrRNA) or a DNA polynucleotide comprising a sequence encoding an RNA molecule that can form a complex with the CRISPR nuclease.

In an embodiment, the composition further comprises a donor template for homology directed repair (HDR).

In an embodiment, the composition is capable of editing the target region in the genome of a cell.

In an embodiment of the composition:
  a) the CRISPR nuclease has at least 100%, 99%, 98%, 97%, 96%, 95%, 94%, 93%, 92%, 91%, 90%, 85%, 80% identity to SEQ ID NO: 1, and the RNA molecule comprises a sequence selected from SEQ ID NOs: 25-29;
  b) the CRISPR nuclease has at least 100%, 99%, 98%, 97%, 96%, 95%, 94%, 93%, 92%, 91%, 90%, 85%, 80% identity to SEQ ID NO: 2, and the RNA molecule comprises a sequence selected from SEQ ID NOs: 30-39;
  c) the CRISPR nuclease has at least 100%, 99%, 98%, 97%, 96%, 95%, 94%, 93%, 92%, 91%, 90%, 85%, 80% identity to SEQ ID NO: 3, and the RNA molecule comprises a sequence selected from SEQ ID NOs: 40-52;

d) the CRISPR nuclease has at least 100%, 99%, 98%, 97%, 96%, 95%, 94%, 93%, 92%, 91%, 90%, 85%, 80% identity to SEQ ID NO: 4, and the RNA molecule comprises a sequence selected from SEQ ID NOs: 53-62;

e) the CRISPR nuclease has at least 100%, 99%, 98%, 97%, 96%, 95%, 94%, 93%, 92%, 91%, 90%, 85%, 80% identity to SEQ ID NO: 5, and the RNA molecule comprises a sequence selected from SEQ ID NOs: 63-90;

f) the CRISPR nuclease has at least 100%, 99%, 98%, 97%, 96%, 95%, 94%, 93%, 92%, 91%, 90%, 85%, 80% identity to SEQ ID NO: 6, and the RNA molecule comprises a sequence selected from SEQ ID NOs: 91-98;

g) the CRISPR nuclease has at least 100%, 99%, 98%, 97%, 96%, 95%, 94%, 93%, 92%, 91%, 90%, 85%, 80% identity to SEQ ID NO: 7, and the RNA molecule comprises a sequence selected from SEQ ID NOs: 99-108; or h) the CRISPR nuclease has at least 100%, 99%, 98%, 97%, 96%, 95%, 94%, 93%, 92%, 91%, 90%, 85%, 80% identity to SEQ ID NO: 8, and the RNA molecule comprises a sequence selected from SEQ ID NOs: 109-120.

According to some embodiments, there is provided a non-naturally occurring composition comprising:
(a) a CRISPR nuclease, or a polynucleotide encoding the CRISPR nuclease, comprising:
an RNA-binding portion; and
an activity portion that exhibits site-directed enzymatic activity, wherein the CRISPR nuclease has at least 100%, 99%, 98%, 97%, 96%, 95%, 94%, 93%, 92%, 91%, 90%, 85%, 80% identity to any of SEQ ID NOs: 1-8; and
(b) one or more RNA molecules or a DNA polynucleotide encoding the one or more RNA molecules comprising:
i) a DNA-targeting RNA sequence, comprising a nucleotide sequence that is complementary to a sequence in a target DNA sequence; and
ii) a protein-binding RNA sequence, capable of interacting with the RNA-binding portion of the CRISPR nuclease,
wherein the DNA targeting RNA sequence and the CRISPR nuclease do not naturally occur together. Each possibility represents a separate embodiment.

In some embodiments, there is provided a single RNA molecule comprising the DNA-targeting RNA sequence and the protein-binding RNA sequence, wherein the RNA molecule can form a complex with the CRISPR nuclease and serve as the DNA targeting module. In some embodiments, the RNA molecule has a length of up to 1000 bases, 900 bases, 800 bases, 700 bases, 600 bases, 500 bases, 400 bases, 300 bases, 200 bases, 100 bases, 50 bases. Each possibility represents a separate embodiment. In some embodiments, a first RNA molecule comprising the DNA-targeting RNA sequence and a second RNA molecule comprising the protein-binding RNA sequence interact by base pairing or alternatively fused together to form one or more RNA molecules that complex with the CRISPR nuclease and serve as the DNA targeting module.

In some embodiments, the CRISPR nuclease has at least 100%, 99%, 98%, 97%, 96%, 95%, 94%, 93%, 92%, 91%, 90%, 85%, 80% identity to SEQ ID NO: 1, and the RNA molecule comprises a sequence selected from SEQ ID NOs: 25-29.

In some embodiments, the CRISPR nuclease has at least 100%, 99%, 98%, 97%, 96%, 95%, 94%, 93%, 92%, 91%, 90%, 85%, 80% identity to SEQ ID NO: 2, and the RNA molecule comprises a sequence selected from SEQ ID NOs: 30-39.

In some embodiments, the CRISPR nuclease has at least 100%, 99%, 98%, 97%, 96%, 95%, 94%, 93%, 92%, 91%, 90%, 85%, 80% identity to SEQ ID NO: 3, and the RNA molecule comprises a sequence selected from SEQ ID NOs: 40-52.

In some embodiments, the CRISPR nuclease has at least 100%, 99%, 98%, 97%, 96%, 95%, 94%, 93%, 92%, 91%, 90%, 85%, 80% identity to SEQ ID NO: 4, and the RNA molecule comprises a sequence selected from SEQ ID NOs: 53-62.

In some embodiments, the CRISPR nuclease has at least 100%, 99%, 98%, 97%, 96%, 95%, 94%, 93%, 92%, 91%, 90%, 85%, 80% identity to SEQ ID NO: 5, and the RNA molecule comprises a sequence selected from SEQ ID NOs: 63-90.

In some embodiments, the CRISPR nuclease has at least 100%, 99%, 98%, 97%, 96%, 95%, 94%, 93%, 92%, 91%, 90%, 85%, 80% identity to SEQ ID NO: 6, and the RNA molecule comprises a sequence selected from SEQ ID NOs: 91-98.

In some embodiments, the CRISPR nuclease has at least 100%, 99%, 98%, 97%, 96%, 95%, 94%, 93%, 92%, 91%, 90%, 85%, 80% identity to SEQ ID NO: 7, and the RNA molecule comprises a sequence selected from SEQ ID NOs: 99-108.

In some embodiments, the CRISPR nuclease has at least 100%, 99%, 98%, 97%, 96%, 95%, 94%, 93%, 92%, 91%, 90%, 85%, 80% identity to SEQ ID NO: 8, and the RNA molecule comprises a sequence selected from SEQ ID NOs: 109-120.

This invention also provides a non-naturally occurring composition comprising:
a) a CRISPR nuclease comprising a sequence having at least 95% identity to the amino acid sequence selected from the group consisting of SEQ ID NOs: 1-8 or a nucleic acid molecule comprising a sequence encoding the CRISPR nuclease; and
b) one or more RNA molecules, or one or more DNA polynucleotide encoding the one or more RNA molecules, comprising at least one of:
i) a nuclease-binding RNA nucleotide sequence capable of interacting with/binding to the CRISPR nuclease; and
ii) a DNA-targeting RNA nucleotide sequence comprising a sequence complementary to a sequence in a target DNA sequence,
wherein the CRISPR nuclease is capable of complexing with the one or more RNA molecules to form a complex capable of hybridizing with the target DNA sequence.

In an embodiment, the CRISPR nuclease and the one or more RNA molecules form a CRISPR complex that is capable of binding to the target DNA sequence to effect cleavage of the target DNA sequence.

In an embodiment, the CRISPR nuclease and at least one of the one or more RNA molecules do not naturally occur together.

In an embodiment:
a) the CRISPR nuclease comprises an RNA-binding portion and an activity portion that exhibits site-directed enzymatic activity;
b) the DNA-targeting RNA nucleotide sequence comprises a nucleotide sequence that is complementary to a sequence in a target DNA sequence; and
c) the nuclease-binding RNA nucleotide sequence comprises a sequence that interacts with the RNA-binding portion of the CRISPR nuclease.

In an embodiment, the nuclease-binding RNA nucleotide sequence and the DNA-targeting RNA nucleotide sequence are on a single guide RNA molecule (sgRNA), wherein the sgRNA molecule can form a complex with the CRISPR nuclease and serve as the DNA targeting module.

In an embodiment, the nuclease-binding RNA nucleotide sequence is on a first RNA molecule and the DNA-targeting RNA nucleotide sequence is on a single guide RNA molecule, and wherein the first and second RNA sequence interact by base-pairing or are fused together to form one or more RNA molecules or sgRNA that complex with the CRISPR nuclease and serve as the targeting module.

In an embodiment, the sgRNA has a length of up to 1000 bases, 900 bases, 800 bases, 700 bases, 600 bases, 500 bases, 400 bases, 300 bases, 200 bases, 100 bases, 50 bases.

In an embodiment, the composition further comprises a donor template for homology directed repair (HDR).

In some embodiments, (a) the CRISPR nuclease has at least 100%, 99%, 98%, 97%, 96%, 95%, 94%, 93%, 92%, 91%, 90%, 85%, 80% identity to SEQ ID NO: 1, or (b) the nucleic acid molecule comprising a sequence encoding the CRISPR nuclease comprises a sequence of at least a 95% sequence identity to the nucleic acid sequence as set forth in SEQ ID NO: 9 or 17 and the PAM is NGCNNT. In some embodiments, the DNA-targeting RNA molecule comprises a sequence selected from SEQ ID NOs: 25-29.

In some embodiments, (a) the CRISPR nuclease has at least 100%, 99%, 98%, 97%, 96%, 95%, 94%, 93%, 92%, 91%, 90%, 85%, 80% identity to SEQ ID NO: 2, or (b) the nucleic acid molecule comprising a sequence encoding the CRISPR nuclease comprises a sequence of at least a 95% sequence identity to the nucleic acid sequence as set forth in SEQ ID NO: 10 or 18 and the PAM is NSHNAC. In some embodiments, the DNA-targeting RNA molecule comprises a sequence selected from SEQ ID NOs: 30-39.

In some embodiments, (a) the CRISPR nuclease has at least 100%, 99%, 98%, 97%, 96%, 95%, 94%, 93%, 92%, 91%, 90%, 85%, 80% identity to SEQ ID NO: 3, or (b) the nucleic acid molecule comprising a sequence encoding the CRISPR nuclease comprises a sequence of at least a 95% sequence identity to the nucleic acid sequence as set forth in SEQ ID NO: 11 or 19 and the PAM is NRRCM. In some embodiments, the DNA-targeting RNA molecule comprises a sequence selected from SEQ ID NOs: 40-52.

In some embodiments, (a) the CRISPR nuclease has at least 100%, 99%, 98%, 97%, 96%, 95%, 94%, 93%, 92%, 91%, 90%, 85%, 80% identity to SEQ ID NO: 4, or (b) the nucleic acid molecule comprising a sequence encoding the CRISPR nuclease comprises a sequence of at least a 95% sequence identity to the nucleic acid sequence as set forth in SEQ ID NO: 12 or 20 and the PAM is NGSNNT. In some embodiments, the DNA-targeting RNA molecule comprises a sequence selected from SEQ ID NOs: 53-62.

In some embodiments, (a) the CRISPR nuclease has at least 100%, 99%, 98%, 97%, 96%, 95%, 94%, 93%, 92%, 91%, 90%, 85%, 80% identity to SEQ ID NO: 5, or (b) the nucleic acid molecule comprising a sequence encoding the CRISPR nuclease comprises a sequence of at least a 95% sequence identity to the nucleic acid sequence as set forth in SEQ ID NO: 13 or 21 and the PAM is NGR or NGG. In some embodiments, the DNA-targeting RNA molecule comprises a sequence selected from SEQ ID NOs: 63-90.

In some embodiments, (a) the CRISPR nuclease has at least 100%, 99%, 98%, 97%, 96%, 95%, 94%, 93%, 92%, 91%, 90%, 85%, 80% identity to SEQ ID NO: 6, or (b) the nucleic acid molecule comprising a sequence encoding the CRISPR nuclease comprises a sequence of at least a 95% sequence identity to the nucleic acid sequence as set forth in SEQ ID NO: 14 or 22 and the PAM is NNRGAY. In some embodiments, the DNA-targeting RNA molecule comprises a sequence selected from SEQ ID NOs: 91-98.

In some embodiments, (a) the CRISPR nuclease has at least 100%, 99%, 98%, 97%, 96%, 95%, 94%, 93%, 92%, 91%, 90%, 85%, 80% identity to SEQ ID NO: 7, or (b) the nucleic acid molecule comprising a sequence encoding the CRISPR nuclease comprises a sequence of at least a 95% sequence identity to the nucleic acid sequence as set forth in SEQ ID NO: 15 or 23 and the PAM is NRRAA. In some embodiments, the DNA-targeting RNA molecule comprises a sequence selected from SEQ ID NOs: 99-108.

In some embodiments, (a) the CRISPR nuclease has at least 100%, 99%, 98%, 97%, 96%, 95%, 94%, 93%, 92%, 91%, 90%, 85%, 80% identity to SEQ ID NO: 8, or (b) the nucleic acid molecule comprising a sequence encoding the CRISPR nuclease comprises a sequence of at least a 95% sequence identity to the nucleic acid sequence as set forth in SEQ ID NO: 16 or 24 and the PAM is NRRNTT. In some embodiments, the DNA-targeting RNA molecule comprises a sequence selected from SEQ ID NOs: 109-120.

In an embodiment, the CRISPR nuclease comprises 1-10, 10-20, 20-30, 30-40, 40-50, 50-60, 60-70, 70-80, 80-90, 90-100, 100-110, 110-120, 120-130, 130-140, or 140-150 amino acid substitutions, deletions, and/or insertions compared to the amino acid sequence of the wild-type of the CRISPR nuclease.

In an embodiment, the CRISPR nuclease exhibits at least 2%, 5%, 7% 10%, 15%, 20%, 25%, 30%, or 35% increased specificity compared the wild-type of the CRISPR nuclease.

In an embodiment, the CRISPR nuclease exhibits at least 2%, 5%, 7% 10%, 15%, 20%, 25%, 30%, or 35% increased activity compared the wild-type of the CRISPR nuclease.

In an embodiment, the CRISPR nuclease has altered PAM specificity compared to the wild-type of the CRISPR nuclease.

In an embodiment, the CRISPR nuclease is non-naturally occurring.

In an embodiment, the CRISPR nuclease is engineered and comprises unnatural or synthetic amino acids.

In an embodiment, the CRISPR nuclease is engineered and comprises one or more of a nuclear localization sequences (NLS), cell penetrating peptide sequences, and/or affinity tags.

In an embodiment, the CRISPR nuclease comprises one or more nuclear localization sequences of sufficient strength to drive accumulation of a CRISPR complex comprising the CRISPR nuclease in a detectable amount in the nucleus of a eukaryotic cell.

This invention also provides a method of modifying a nucleotide sequence at a target site in a cell-free system or the genome of a cell comprising introducing into the cell any of the compositions of the invention.

In an embodiment, the cell is a eukaryotic cell.

In another embodiment, the cell is a prokaryotic cell.

In some embodiments, the one or more RNA molecules further comprises an RNA sequence comprising a nucleotide molecule that can form a complex with the RNA nuclease (tracrRNA) or a DNA polynucleotide encoding an RNA molecule comprising a nucleotide sequence that can form a complex with the CRISPR nuclease.

In an embodiment, the CRISPR nuclease comprises 1, 2, 3, 4, 5, 6, 7, 8, 9, 10, or more NLSs at or near the amino-terminus, 1, 2, 3, 4, 5, 6, 7, 8, 9, 10, or more NLSs at or near carboxy-terminus, or a combination of 1, 2, 3, 4, 5, 6, 7, 8, 9, 10, or more NLSs at or near the amino-terminus and 1, 2, 3, 4, 5, 6, 7, 8, 9, 10, or more NLSs at or near carboxy-terminus. In an embodiment 1-4 NLSs are fused with the CRISPR nuclease. In an embodiment, an NLS is located within the open-reading frame (ORF) of the CRISPR nuclease.

Methods of fusing an NLS at or near the amino-terminus, at or near carboxy-terminus, or within the ORF of an expressed protein are well known in the art. As an example, to fuse an NLS to the amino-terminus of a CRISPR nuclease, the nucleic acid sequence of the NLS is placed immediately after the start codon of the CRISPR nuclease on the nucleic acid encoding the NLS-fused CRISPR nuclease. Conversely, to fuse an NLS to the carboxy-terminus of a CRISPR nuclease the nucleic acid sequence of the NLS is placed after the codon encoding the last amino acid of the CRISPR nuclease and before the stop codon.

Any combination of NLSs, cell penetrating peptide sequences, and/or affinity tags at any position along the ORF of the CRISPR nuclease is contemplated in this invention.

The amino acid sequences and nucleic acid sequences of the CRISPR nucleases provided herein may include NLS and/or TAGs inserted so as to interrupt the contiguous amino acid or nucleic acid sequences of the CRISPR nucleases.

In an embodiment, the one or more NLSs are in tandem repeats.

In an embodiment, the one or more NLSs are considered in proximity to the N- or C-terminus when the nearest amino acid of the NLS is within about 1, 2, 3, 4, 5, 10, 15, 20, 25, 30, 40, 50, or more amino acids along the polypeptide chain from the N- or C-terminus.

As discussed, the CRISPR nuclease may be engineered to comprise one or more of a nuclear localization sequences (NLS), cell penetrating peptide sequences, and/or affinity tags.

In an embodiment, the CRISPR nuclease exhibits increased specificity to a target site compared to the wild-type of the CRISPR nuclease when complexed with the one or more RNA molecules.

In an embodiment, the complex of the CRISPR nuclease and one or more RNA molecules exhibits at least maintained on-target editing activity of the target site and reduced off-target activity compared to the wild-type of the CRISPR nuclease.

In an embodiment, the composition further comprises a recombinant nucleic acid molecule comprising a heterologous promoter operably linked to the nucleotide acid molecule comprising the sequence encoding the CRISPR nuclease.

In an embodiment, the CRISPR nuclease or nucleic acid molecule comprising a sequence encoding the CRISPR nuclease is non-naturally occurring or engineered.

This invention also provides a non-naturally occurring or engineered composition comprising a vector system comprising the nucleic acid molecule comprising a sequence encoding any of the CRISPR nucleases of the invention.

This invention also provides use of any of the compositions of the invention for the treatment of a subject afflicted with a disease associated with a genomic mutation comprising modifying a nucleotide sequence at a target site in the genome of the subject.

This invention provides a method of modifying a nucleotide sequence at a target site in the genome of a mammalian cell comprising introducing into the cell (i) a composition comprising a CRISPR nuclease having at least 95% identity to an amino acid sequence selected from the group consisting of SEQ ID NOs: 1-8 or a nucleic acid molecule comprising a sequence encoding a CRISPR nuclease which sequence has at least 95% identity to a nucleic acid sequence selected from the group consisting of SEQ ID NOs: 9-24 and (ii) a DNA-targeting RNA molecule, or a DNA polynucleotide encoding a DNA-targeting RNA molecule, comprising a nucleotide sequence that is complementary to a sequence in the target DNA.

In some embodiments, the method is performed ex vivo. In some embodiments, the method is performed in vivo. In some embodiments, some steps of the method are performed ex vivo and some steps are performed in vivo. In some embodiments the mammalian cell is a human cell.

In an embodiment, the method further comprises introducing into the cell: (iii) an RNA molecule comprising a nuclease-binding RNA sequence or a DNA polynucleotide encoding an RNA molecule comprising a nuclease-binding RNA that interacts with the CRISPR nuclease.

In an embodiment, the DNA targeting RNA molecule is a crRNA molecule suitable to form an active complex with the CRISPR nuclease.

In an embodiment, the RNA molecule comprising a nuclease-binding RNA sequence is a tracrRNA molecule suitable to form an active complex with the CRISPR nuclease.

In an embodiment, the DNA-targeting RNA molecule and the RNA molecule comprising a nuclease-biding RNA sequence are fused in the form of a single guide RNA molecule.

In an embodiment, the method further comprises introducing into the cell: (iv) an RNA molecule comprising a sequence complementary to a protospacer sequence.

In an embodiment, the CRISPR nuclease forms a complex with the one or more RNA molecules and effects a double strand break in the 3' of a Protospacer Adjacent Motif (PAM).

In an embodiment, the CRISPR nuclease forms a complex with the one or more RNA molecules and effects a double strand break in the 5' of a Protospacer Adjacent Motif (PAM).

In some embodiments, (a) the CRISPR nuclease has at least 100%, 99%, 98%, 97%, 96%, 95%, 94%, 93%, 92%, 91%, 90%, 85%, 80% identity to SEQ ID NO: 1, or (b) the nucleic acid molecule comprising a sequence encoding the CRISPR nuclease comprises a sequence of at least a 95% sequence identity to the nucleic acid sequence as set forth in SEQ ID NO: 9 or 17 and the PAM is NGCNNT. In some embodiments, the DNA-targeting RNA molecule comprises a sequence selected from SEQ ID NOs: 25-29.

In some embodiments, (a) the CRISPR nuclease has at least 100%, 99%, 98%, 97%, 96%, 95%, 94%, 93%, 92%, 91%, 90%, 85%, 80% identity to SEQ ID NO: 2, or (b) the nucleic acid molecule comprising a sequence encoding the CRISPR nuclease comprises a sequence of at least a 95% sequence identity to the nucleic acid sequence as set forth in SEQ ID NO: 10 or 18 and the PAM is NSHNAC. In some embodiments, the DNA-targeting RNA molecule comprises a sequence selected from SEQ ID NOs: 30-39.

In some embodiments, (a) the CRISPR nuclease has at least 100%, 99%, 98%, 97%, 96%, 95%, 94%, 93%, 92%, 91%, 90%, 85%, 80% identity to SEQ ID NO: 3, or (b) the nucleic acid molecule comprising a sequence encoding the CRISPR nuclease comprises a sequence of at least a 95% sequence identity to the nucleic acid sequence as set forth in SEQ ID NO: 11 or 19 and the PAM is NRRCM. In some embodiments, the DNA-targeting RNA molecule comprises a sequence selected from SEQ ID NOs: 40-52.

In some embodiments, (a) the CRISPR nuclease has at least 100%, 99%, 98%, 97%, 96%, 95%, 94%, 93%, 92%, 91%, 90%, 85%, 80% identity to SEQ ID NO: 4, or (b) the nucleic acid molecule comprising a sequence encoding the CRISPR nuclease comprises a sequence of at least a 95% sequence identity to the nucleic acid sequence as set forth in SEQ ID NO: 12 or 20 and the PAM is NGSNNT. In some embodiments, the DNA-targeting RNA molecule comprises a sequence selected from SEQ ID NOs: 53-62.

In some embodiments, (a) the CRISPR nuclease has at least 100%, 99%, 98%, 97%, 96%, 95%, 94%, 93%, 92%, 91%, 90%, 85%, 80% identity to SEQ ID NO: 5, or (b) the nucleic acid molecule comprising a sequence encoding the CRISPR nuclease comprises a sequence of at least a 95% sequence identity to the nucleic acid sequence as set forth in SEQ ID NO: 13 or 21 and the PAM is NGR or NGG. In some embodiments, the DNA-targeting RNA molecule comprises a sequence selected from SEQ ID NOs: 63-90.

In some embodiments, (a) the CRISPR nuclease has at least 100%, 99%, 98%, 97%, 96%, 95%, 94%, 93%, 92%, 91%, 90%, 85%, 80% identity to SEQ ID NO: 6, or (b) the nucleic acid molecule comprising a sequence encoding the CRISPR nuclease comprises a sequence of at least a 95% sequence identity to the nucleic acid sequence as set forth in SEQ ID NO: 14 or 22 and the PAM is NNRGAY. In some embodiments, the DNA-targeting RNA molecule comprises a sequence selected from SEQ ID NOs: 91-98.

In some embodiments, (a) the CRISPR nuclease has at least 100%, 99%, 98%, 97%, 96%, 95%, 94%, 93%, 92%, 91%, 90%, 85%, 80% identity to SEQ ID NO: 7, or (b) the nucleic acid molecule comprising a sequence encoding the CRISPR nuclease comprises a sequence of at least a 95% sequence identity to the nucleic acid sequence as set forth in SEQ ID NO: 15 or 23 and the PAM is NRRAA. In this some embodiments, the DNA-targeting RNA molecule comprises a sequence selected from SEQ ID NOs: 99-108.

In some embodiments, (a) the CRISPR nuclease has at least 100%, 99%, 98%, 97%, 96%, 95%, 94%, 93%, 92%, 91%, 90%, 85%, 80% identity to SEQ ID NO: 8, or (b) the nucleic acid molecule comprising a sequence encoding the CRISPR nuclease comprises a sequence of at least a 95% sequence identity to the nucleic acid sequence as set forth in SEQ ID NO: 16 or 24 and the PAM is NRRNTT. In some embodiments, the DNA-targeting RNA molecule comprises a sequence selected from SEQ ID NOs: 109-120.

In an embodiment of any of the methods described herein, the method is for treating a subject afflicted with a disease associated with a genomic mutation comprising modifying a nucleotide sequence at a target site in the genome of the subject.

In an embodiment, the method comprises first selecting a subject afflicted with a disease associated with a genomic mutation and obtaining the cell from the subject.

This invention also provides a modified cell or cells obtained by any of the methods described herein. In an embodiment these modified cell or cells are capable of giving rise to progeny cells. In an embodiment these modified cell or cells are capable of giving rise to progeny cells after engraftment.

This invention also provides a composition comprising these modified cells and a pharmaceutically acceptable carrier. Also provided is an in vitro or ex vivo method of preparing this, comprising mixing the cells with the pharmaceutically acceptable carrier.

DNA-Targeting RNA Molecules

The "guide sequence portion" of an RNA molecule refers to a nucleotide sequence that is capable of hybridizing to a specific target DNA sequence, e.g., the guide sequence portion has a nucleotide sequence which is partially or fully complementary to the DNA sequence being targeted along the length of the guide sequence portion. In some embodiments, the guide sequence portion is 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length, or approximately 17-50, 17-49, 17-48, 17-47, 17-46, 17-45, 17-44, 17-43, 17-42, 17-41, 17-40, 17-39, 17-38, 17-37, 17-36, 17-35, 17-34, 17-33, 17-31, 17-30, 17-29, 17-28, 17-27, 17-26, 17-25, 17-24, 17-22, 17-21, 18-25, 18-24, 18-23, 18-22, 18-21, 19-25, 19-24, 19-23, 19-22, 19-21, 19-20, 20-22, 18-20, 20-21, 21-22, or 17-20 nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence. Accordingly, a molecule comprising a "guide sequence portion" is a type of targeting molecule. Throughout this application, the terms "guide molecule," "RNA guide molecule," "guide RNA molecule," and "gRNA molecule" are synonymous with a molecule comprising a guide sequence portion, and the term "spacer" is synonymous with a "guide sequence portion."

In embodiments of the present invention, the CRISPR nuclease has its greatest cleavage activity when used with an RNA molecule comprising a guide sequence portion having 20, 21, 22, 23, 24, 25, 26, 27, 28, 29, or 30 nucleotides.

In some embodiments, the OMNI-79 CRISPR nuclease has its greatest cleavage activity when used with an RNA molecule comprising a guide sequence portion having 25-26 nucleotides, compared to its cleavage activity when used with an RNA molecule comprising a guide sequence portion having 24 or fewer nucleotides, and/or 27 or more nucleotides.

According to some aspects of the invention, the disclosed methods comprise a method of modifying a nucleotide sequence at a target site in a cell-free system or the genome of a cell comprising introducing into the cell the composition of any one of the embodiments described herein.

In some embodiments, the cell is a eukaryotic cell, preferably a mammalian cell or a plant cell.

According to some aspects of the invention, the disclosed methods comprise a use of any one of the compositions described herein for the treatment of a subject afflicted with a disease associated with a genomic mutation comprising modifying a nucleotide sequence at a target site in the genome of the subject.

According to some aspects of the invention, the disclosed methods comprise a method of treating subject having a mutation disorder comprising targeting any one of the compositions described herein to an allele associated with the mutation disorder.

In some embodiments, the mutation disorder is related to a disease or disorder selected from any of a neoplasia, age-related macular degeneration, schizophrenia, neurological, neurodegenerative, or movement disorder, Fragile X Syndrome, secretase-related disorders, prion-related disorders, ALS, addiction, autism, Alzheimer's Disease, neutropenia, inflammation-related disorders, Parkinson's Disease, blood and coagulation diseases and disorders, cell dysregulation and oncology diseases and disorders, inflammation and immune-related diseases and disorders, metabolic, liver, kidney and protein diseases and disorders, muscular and skeletal diseases and disorders, dermatological diseases and disorders, neurological and neuronal diseases and disorders, and ocular diseases and disorders.

In some embodiments, the mutation disorder is beta thalassemia or sickle cell anemia.

In some embodiments, the allele associated with the disease is BCL11A.

OMNI-79 CRISPR Nuclease Domains

The characteristic targeted nuclease activity of a CRISPR nuclease is imparted by the various functions of its specific domains. In this application the OMNI-79 domains are defined as Domain A, Domain B, Domain C, Domain D, Domain E, Domain F, Domain G, Domain H, and Domain I.

As used herein, Domain A begins at an amino acid position within 1-10 and ends at an amino acid position within 35-45 of SEQ ID NO: 5. Based on a preferred analysis of a local alignment generated using the Smith-Waterman algorithm, in an embodiment Domain A has been identified as amino acids 1-40 of SEQ ID NO: 5

As used herein, Domain E begins at an amino acid position within 442-452 and ends at an amino acid position within 502-512 of SEQ ID NO: 5. Based on a preferred analysis of a local alignment generated using the Smith-Waterman algorithm, in an embodiment Domain E has been identified as amino acids 447-507 of SEQ ID NO: 5.

As used herein, Domain G begins at an amino acid position within 660-670 and ends at an amino acid position within 817-827 of SEQ ID NO: 5. Based on a preferred analysis of a local alignment generated using the Smith-Waterman algorithm, in an embodiment Domain G has been identified as amino acids 665-822 of SEQ ID NO: 5.

As used herein, Domain B begins at an amino acid position within 36-46 and ends at an amino acid position within 71-81 of SEQ ID NO: 5. Based on a preferred analysis of a local alignment generated using the Smith-Waterman algorithm, in an embodiment Domain B has been identified as amino acids 41-76 of SEQ ID NO: 5.

As used herein, Domain C begins at an amino acid position within 72-82 and ends at an amino acid position within 223-233 of SEQ ID NO: 5. Based on an analysis of a local alignment generated using the Smith-Waterman algorithm, in an embodiment Domain C has been identified as amino acids 77-228 of SEQ ID NO: 5

As used herein, Domain D begins at an amino acid position within 224-234 and ends at an amino acid position within 441-451 of SEQ ID NO: 5. Based on an analysis of a local alignment generated using the Smith-Waterman algorithm, in an embodiment Domain D has been identified as amino acids 229-446 of SEQ ID NO: 5.

As used herein, Domain F begins at an amino acid position within 534-544 and ends at an amino acid position within 643-653 of SEQ ID NO: 5. Based on a preferred analysis of a local alignment generated using the Smith-Waterman algorithm, in an embodiment Domain F has been identified as amino acids 539-648 of SEQ ID NO: 5.

As used herein, Domain H begins at an amino acid position within 818-828 and ends at an amino acid position within 916-926 of SEQ ID NO: 5. Based on a preferred analysis of a local alignment generated using the Smith-Waterman algorithm, in an embodiment Domain H has been identified as amino acids 823-921 of SEQ ID NO: 5.

As used herein, Domain I begins at an amino acid position within 917-927 and ends at an amino acid position within 1057-1067 of SEQ ID NO: 5. Based on a preferred analysis of a local alignment generated using the Smith-Waterman algorithm, in an embodiment Domain I has been identified as amino acids 922-1062 of SEQ ID NO: 5.

The activity of each OMNI-79 nuclease domain is described herein, with each domain activity providing aspects of the advantageous features of the nuclease.

Specifically, OMNI-79 Domain A, Domain E, and Domain G form a structural unit of the CRISPR OMNI-79 nuclease which contains a nuclease active site that participates in DNA strand cleavage. The structural unit formed by Domain A, Domain E, and Domain G cleaves a DNA strand which a guide RNA molecule binds at a DNA target site.

Domain B is involved in initiating DNA cleavage activity upon the binding of OMNI-79 CRISPR nuclease to a target a DNA site.

Domain C and Domain D bind a guide RNA molecule and participate in providing specificity for target site recognition. More specifically, Domain C and Domain D are involved in sensing a DNA target site, with Domain D involved in regulating the activation of a nuclease domain (e.g. Domain F), and Domain C involved in locking the nuclease domain at the target site. Accordingly, Domains C and Domain D participate in controlling cleavage of off-target sequences.

Domain F contains a nuclease active site that participates in DNA strand cleavage. Domain F cleaves a DNA strand that is displaced by a guide RNA molecule binding at a double-stranded DNA target site.

Domain H is also participates in the recognition of guide RNA molecules or complexes (e.g. binding regions in tracrRNA molecules, crRNA:tracrRNA complexes, or sgRNA scaffolds).

Domain I is involved in providing PAM site specificity to OMNI-79 nuclease, including aspects of PAM site interrogation and recognition. Domain I also performs topoisomerase activity.

Further description of other CRISPR nuclease domains and their general functions can be found in, inter alia, Mir et al., ACS Chem. Biol. (2019), Palermo et al., Quarterly Reviews of Biophysics (2018), Jiang and Doudna, Annual Review of Biophysics (2017), Nishimasu et al., Cell (2014) and Nishimasu et al., Cell (2015), incorporated herein by reference.

In one aspect of the invention, an amino acid sequence having similarity to an OMNI-79 domain may be utilized in the design and manufacture of a non-naturally occurring peptide, e.g. a CRISPR nuclease, such that the peptide displays the advantageous features of the OMNI-79 domain activity.

In an embodiment, such a peptide, e.g. a CRISPR nuclease, comprises an amino acid sequence that has at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequence of at least one of Domain A Domain B, Domain C, Domain D, Domain E, Domain F, Domain G, Domain H, or Domain I of the OMNI-79 nuclease. In some embodiments, the identity is to at least one, at least two, at least three, at least four, at least five, at least six, at least seven or at least eight amino acid sequences of Domain A, Domain B, Domain C, Domain D, Domain E, Domain F, Domain G, Domain H, or Domain I of the OMNI-79 nuclease. Each possibility represents a separate embodiment. In some embodiments the identity is to the amino acid sequence of at least one of Domain A, Domain B, Domain C, Domain D, Domain F, Domain G, Domain H, or Domain I of the OMNI-79 nuclease. In some embodiments the identity is to the amino acid sequence of at least one of Domain F and Domain G of the OMNI-79 nuclease. In some embodiments, the CRISPR nuclease comprises an amino acid sequence corresponding to amino acid sequences of Domain G and Domain F of the OMNI-79 nuclease. In some embodiments, the CRISPR nuclease comprises an amino acid sequence having at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to amino acid sequences of Domain G and Domain F of the OMNI-79 nuclease. In an embodiment, the peptide exhibits extensive amino acid variability relative to the full length OMNI-79 amino acid sequence (SEQ ID NO: 5) outside of the peptide amino acid sequence having at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequence of at least one of Domain A Domain B, Domain C, Domain D, Domain E, Domain F, Domain G, Domain H, or Domain I of the OMNI-79 nuclease. In an embodiment, the peptide comprises an intervening amino acid sequence between two domain sequences. In an embodiment, the intervening amino acid sequence is 1-10, 10-20, 20-40, 40-50 or up to 100 amino acids in length. In an embodiment, the intervening sequence is a linker sequence.

In one aspect of the invention, an amino acid sequence encoding any one of the domains of the OMNI-79 nuclease described herein in the peptide may comprise one or more amino acid substitutions relative to the original OMNI-79 domain sequence. The amino acid substitution may be a conservative substitution, i.e. substitution for an amino acid having similar chemical properties as the original amino acid. For example, a positively charged amino acid may be substituted for an alternate positively charged amino acid, e.g. an arginine residue may be substituted for a lysine residue, or a polar amino acid may be substituted for a different polar amino acid. Conservative substitutions are more tolerable, and the amino acid sequence encoding any one of the domains of the OMNI-79 nuclease may contain as many as 10% of such substitutions. The amino acid substitution may be a radical substitution, i.e. substitution for an amino acid having different chemical properties as the original amino acid. For example, a positively charged amino acid may be substituted for a negatively charged amino acid, e.g. an arginine residue may be substituted for a glutamic acid residue, or a polar amino acid may be substituted for a non-polar amino acid. The amino acid substitution may be a semi-conservative substitution, or the amino acid substitution may be to any other amino acid. The substitution may alter the activity relative to the original OMNI-79 domain function e.g. reduce catalytic nuclease activity.

According to some aspects of the invention, the disclosed compositions comprise a non-naturally occurring composition comprising a CRISPR nuclease, wherein the CRISPR nuclease comprises an amino acid sequence corresponding to the amino acid sequence of at least one of Domain A Domain B, Domain C, Domain D, Domain E, Domain F, Domain G, Domain H, or Domain I of the OMNI-79 nuclease. In some embodiments of the invention, the CRISPR nuclease comprises at least one, at least two, at least three, at least four, or at least five amino acid sequences, wherein each amino acid sequence corresponds to any one of the amino acid sequences Domain A Domain B, Domain C, Domain D, Domain E, Domain F, Domain G, Domain H, or Domain I of the OMNI-79 nuclease. Accordingly, the CRISPR nuclease may include any combination of amino acid sequences that corresponds to any of Domain A Domain B, Domain C, Domain D, Domain E, Domain F, Domain G, Domain H, or Domain I of the OMNI-79 nuclease. In some embodiments, the amino acid sequence is at least 100-250, 250-500, 500-1000, 1000-1500, 1000-1700, or 1000-2000 amino acids in length.

Diseases and Therapies

Certain embodiments of the invention target a nuclease to a specific genetic locus associated with a disease or disorder as a form of gene editing, method of treatment, or therapy. For example, to induce editing or knockout of a gene, a novel nucleases disclosed herein may be specifically targeted to a pathogenic mutant allele of the gene using a custom designed guide RNA molecule. The guide RNA molecule is preferably designed by first considering the PAM requirement of the nuclease, which as shown herein is also dependent on the system in which the gene editing is being performed. For example, a guide RNA molecule designed to target an OMNI-79 nuclease to a target site is designed to contain a spacer region complementary to a region neighboring a sequence complimentary to the OMNI-79 PAM sequence "NGG." The guide RNA molecule is further preferably designed to contain a spacer region (i.e. the region of the guide RNA molecule having complementarity to the target allele) of sufficient and preferably optimal length in order to increase specific activity of the nuclease and reduce off-target effects.

As a non-limiting example, the guide RNA molecule may be designed to target the nuclease to a specific region of a mutant allele, e.g. near the start codon, such that upon DNA damage caused by the nuclease a non-homologous end joining (NHEJ) pathway is induced and leads to silencing of the mutant allele by introduction of frameshift mutations. This approach to guide RNA molecule design is particularly useful for altering the effects of dominant negative mutations and thereby treating a subject. As a separate non-limiting example, the guide RNA molecule may be designed to target a specific pathogenic mutation of a mutated allele, such that upon DNA damage caused by the nuclease a homology directed repair (HDR) pathway is induced and leads to template mediated correction of the mutant allele. This approach to guide RNA molecule design is particularly useful for altering haploinsufficiency effects of a mutated allele and thereby treating a subject.

Non-limiting examples of specific genes which may be targeted for alteration to treat a disease or disorder are presented herein below. Specific disease-associated genes and mutations that induce a mutation disorder are described in the literature. Such mutations can be used to design a DNA-targeting RNA molecule to target a CRISPR composition to an allele of the disease associated gene, where the CRISPR composition causes DNA damage and induces a DNA repair pathway to alter the allele and thereby treat the mutation disorder.

Mutations in the ELANE gene are associated with neutropenia. Accordingly, without limitation, embodiments of the invention that target ELANE may be used in methods of treating subjects afflicted with neutropenia.

CXCR4 is a co-receptor for the human immunodeficiency virus type 1 (HIV-1) infection. Accordingly, without limitation, embodiments of the invention that target CXCR4 may be used in methods of treating subjects afflicted with HIV-1 or conferring resistance to HIV-1 infection in a subject.

Programmed cell death protein 1 (PD-1) disruption enhances CAR-T cell mediated killing of tumor cells and PD-1 may be a target in other cancer therapies. Accordingly, without limitation, embodiments of the invention that target PD-1 may be used in methods of treating subjects afflicted with cancer. In an embodiment, the treatment is CAR-T cell therapy with T cells that have been modified according to the invention to be PD-1 deficient.

In addition, BCL11A is a gene that plays a role in the suppression of hemoglobin production. Globin production may be increased to treat diseases such as thalassemia or sickle cell anemia by inhibiting BCL11A. See for example, PCT International Publication No. WO 2017/077394A2; U.S. Publication No. US2011/0182867A1; Humbert et al. Sci. Transl. Med. (2019); and Canver et al. Nature (2015). Accordingly, without limitation, embodiments of the invention that target an enhancer of BCL11A may be used in methods of treating subjects afflicted with beta thalassemia or sickle cell anemia.

Embodiments of the invention may also be used for targeting any disease-associated gene, for studying, altering, or treating any of the diseases or disorders listed in Table A or Table B below. Indeed, any disease-associated with a genetic locus may be studied, altered, or treated by using the nucleases disclosed herein to target the appropriate disease-associated gene, for example, those listed in U.S. Publication No. 2018/0282762A1 and European Patent No. EP3079726B1.

TABLE A

Diseases, Disorders and their associated genes

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); gf2 (3 variants); Igf 1 Receptor; Igf 2 Receptor; Bax; Bcl2; caspases family (9 members: 1, 2, 3, 4, 6, 7, 8, 9, 12); Kras; Ape |
| Age-related Macular Degeneration | Aber; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cp1x1); Tph1 Tryptophan hydroxylase; Tph2 Tryptophan hydroxylase 2; Neurexin 1; GSK3; GSK3a; GSK3b |

TABLE A-continued

Diseases, Disorders and their associated genes

| DISEASE/DISORDERS | GENE(S) |
|---|---|
| Neurological, Neuro degenerative, and Movement Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLADx); CBP (Creb-BP—global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion related disorders | Prp |
| ALS | SOD1; ALS2; STEX; FUS; TARDBP; VEGF (VEGF-a; VEGF-b; VEGF-c) |
| Addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1;Uchl3; APP |
| Inflammation | IL-10; IL-1 (IL-1a; IL-1b); IL-13; IL-17 (IL-17a (CTLA8); IL-17b; IL-17c; IL-17d; IL-17f); Il-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

Diseases, Disorders and their associated genes

| DISEASE CATEGORY | DISEASE AND ASSOCIATED GENES |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, AS AT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, |

TABLE B-continued

Diseases, Disorders and their associated genes

| DISEASE CATEGORY | DISEASE AND ASSOCIATED GENES |
|---|---|
| | LVWM, CACH, CLE, EIF2B4); Sickle cell anemia (HBB); Thalassemia (HBA2, HBB, HBD, LCRB, HBA1) |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTSI, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN) |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AUD, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), Il-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4) |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63) |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); |
| | Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1) |
| Dermatological diseases and disorders | Albinisim (TYR, OCA2, TYRP1, SLC45A2, LYST), Ectodermal dysplasias (EDAR, EDARADD, WNT10A), Ehlers-Danlos syndrome (COL5A1, COL5A2, COL1A1, COL1A2, COL3A1, TNXB, ADAMTS2, PLOD1, FKBP14), Ichthyosis-associated disorders (FLG, STS, TGM1, ALOXE3/ALOX12B, KRT1, KRT10, ABCA12, KRT2, GJB2, TGM1, ABCA12, CYP4F22, ALOXE3, CERS3, NSHDL, EBP, MBTPS2, GJB2, SPINK5, AGHD5, PHYH, PEX7, ALDH3A2, ERCC2, ERCC3, GFT2H5, GBA), Incontinentia pigmenti (IKBKG, NEMO), Tuberous sclerosis (TSC1, TSC2), Premature aging syndromes (POLR3A, PYCR1, LMNA, POLD1, WRN, DMPK) |
| Neurological and Neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN1, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 |

TABLE B-continued

Diseases, Disorders and their associated genes

| DISEASE CATEGORY | DISEASE AND ASSOCIATED GENES |
|---|---|
| | (Machado-Joseph's Dx), ATXN1 and ATXN2 (spinocerebellar ataxias), DMPK (myotonic dystrophy), Atrophin-1 and Atn1 (DRPLA Dx), CBP (Creb-BP—global instability), VLDLR (Alzheimer's), Atxn7, Atxn10) |
| Ocular diseases and disorders | Age-related macular degeneration (Aber, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49 ,CP47, CRYAA, CRYA1, PAX6, AN2, MGDA, CRYBA1, CRYB1, CRYGC, CRYG3, CCL, LIM2, MP 19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2) |

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of and any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

It is understood that where a numerical range is recited herein, the present invention contemplates each integer between, and including, the upper and lower limits, unless otherwise stated.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, in Irons, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers, A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "nucleotide analog" or "modified nucleotide" refers to a nucleotide that contains one or more chemical modifications (e.g., substitutions), in or on the nitrogenous base of the nucleoside (e.g., cytosine (C), thymine (T) or uracil (U), adenine (A) or guanine (G)), in or on the sugar moiety of the nucleoside (e.g., ribose, deoxyribose, modified ribose, modified deoxyribose, six-membered sugar analog, or open-chain sugar analog), or the phosphate. Each of the RNA sequences described herein may comprise one or more nucleotide analogs.

As used herein, the following nucleotide identifiers listed in Table C below are used to represent a referenced nucleotide base(s):

| Nucleotide reference | Base(s) represented | | | |
|---|---|---|---|---|
| A | A | | | |
| C | | C | | |
| G | | | G | |
| T | | | | T |

| Nucleotide reference | Base(s) represented | | | |
| --- | --- | --- | --- | --- |
| W | A | | | T |
| S | | C | G | |
| M | A | C | | |
| K | | | G | T |
| R | A | | G | |
| Y | | C | | T |
| B | | C | G | T |
| D | A | | G | T |
| H | A | C | | T |
| V | A | C | G | |
| N | A | C | G | T |

As used herein, the term "targeting sequence" or "targeting molecule" refers a nucleotide sequence or molecule comprising a nucleotide sequence that is capable of hybridizing to a specific target sequence, e.g., the targeting sequence has a nucleotide sequence which is at least partially complementary to the sequence being targeted along the length of the targeting sequence. The targeting sequence or targeting molecule may be part of a targeting RNA molecule that can form a complex with a CRISPR nuclease with the targeting sequence serving as the targeting portion of the CRISPR complex. When the molecule having the targeting sequence is present contemporaneously with the CRISPR molecule, the RNA molecule is capable of targeting the CRISPR nuclease to the specific target sequence. Each possibility represents a separate embodiment. A targeting RNA molecule can be custom designed to target any desired sequence.

The term "targets" as used herein, refers to preferential hybridization of a targeting sequence or a targeting molecule to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

In the context of targeting a DNA sequence that is present in a plurality of cells, it is understood that the targeting encompasses hybridization of the guide sequence portion of the RNA molecule with the sequence in one or more of the cells, and also encompasses hybridization of the RNA molecule with the target sequence in fewer than all of the cells in the plurality of cells. Accordingly, it is understood that where an RNA molecule targets a sequence in a plurality of cells, a complex of the RNA molecule and a CRISPR nuclease is understood to hybridize with the target sequence in one or more of the cells, and also may hybridize with the target sequence in fewer than all of the cells. Accordingly, it is understood that the complex of the RNA molecule and the CRISPR nuclease introduces a double strand break in relation to hybridization with the target sequence in one or more cells and may also introduce a double strand break in relation to hybridization with the target sequence in fewer than all of the cells. As used herein, the term "modified cells" refers to cells in which a double strand break is affected by a complex of an RNA molecule and the CRISPR nuclease as a result of hybridization with the target sequence, i.e. on-target hybridization.

As used herein the term "wild type" is a term of the art understood by skilled persons and means the typical form of an organism, strain, gene or characteristic as it occurs in nature as distinguished from mutant or variant forms. Accordingly, as used herein, where a sequence of amino acids or nucleotides refers to a wild type sequence, a variant refers to variant of that sequence, e.g., comprising substitutions, deletions, insertions. In embodiments of the present invention, an engineered CRISPR nuclease is a variant CRISPR nuclease comprising at least one amino acid modification (e.g., substitution, deletion, and/or insertion) compared to the CRISPR nuclease of any of the CRISPR nucleases indicated in Tables 1a-1b.

The terms "non-naturally occurring" or "engineered" are used interchangeably and indicate human manipulation. The terms, when referring to nucleic acid molecules or polypeptides may mean that the nucleic acid molecule or the polypeptide is at least substantially free from at least one other component with which they are naturally associated in nature and as found in nature.

As used herein the term "amino acid" includes natural and/or unnatural or synthetic amino acids, including glycine and both the D or l, optical isomers, and amino acid analogs and peptidomimetics.

As used herein, "genomic DNA" refers to linear and/or chromosomal DNA and/or to plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at pre-determined target sites in a genomic DNA sequence, resulting in mutation, insertion, and/or deletion of DNA sequences at the target site(s) in a genome.

"Eukaryotic" cells include, but are not limited to, fungal cells (such as yeast), plant cells, animal cells, mammalian cells and human cells.

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity.

The term "PAM" as used herein refers to a nucleotide sequence of a target DNA located in proximity to the targeted DNA sequence and recognized by the CRISPR nuclease. The PAM sequence may differ depending on the nuclease identity.

The term "mutation disorder" or "mutation disease" as used herein refers to any disorder or disease that is related to dysfunction of a gene caused by a mutation. A dysfunctional gene manifesting as a mutation disorder contains a mutation in at least one of its alleles and is referred to as a "disease-associated gene." The mutation may be in any portion of the disease-associated gene, for example, in a regulatory, coding, or non-coding portion. The mutation may be any class of mutation, such as a substitution, insertion, or deletion. The mutation of the disease-associated gene may manifest as a disorder or disease according to the mechanism of any type of mutation, such as a recessive, dominant negative, gain-of-function, loss-of-function, or a mutation leading to haploinsufficiency of a gene product.

A skilled artisan will appreciate that embodiments of the present invention disclose RNA molecules capable of complexing with a nuclease, e.g. a CRISPR nuclease, such as to associate with a target genomic DNA sequence of interest next to a protospacer adjacent motif (PAM). The nuclease then mediates cleavage of target DNA to create a double-stranded break within the protospacer.

In embodiments of the present invention, a CRISPR nuclease and a targeting molecule form a CRISPR complex that binds to a target DNA sequence to effect cleavage of the target DNA sequence. A CRISPR nuclease may form a CRISPR complex comprising the CRISPR nuclease and RNA molecule without a further, separate tracrRNA molecule. Alternatively, CRISPR nucleases may form a CRISPR complex between the CRISPR nuclease, an RNA molecule, and a tracrRNA molecule.

The term "protein binding sequence" or "nuclease binding sequence" refers to a sequence capable of binding with a CRISPR nuclease to form a CRISPR complex. A skilled artisan will understand that a tracrRNA capable of binding with a CRISPR nuclease to form a CRISPR complex comprises a protein or nuclease binding sequence.

An "RNA binding portion" of a CRISPR nuclease refers to a portion of the CRISPR nuclease which may bind to an RNA molecule to form a CRISPR complex, e.g. the nuclease binding sequence of a tracrRNA molecule. An "activity portion" or "active portion" of a CRISPR nuclease refers to a portion of the CRISPR nuclease which effects a double strand break in a DNA molecule, for example when in complex with a DNA-targeting RNA molecule.

An RNA molecule may comprise a sequence sufficiently complementary to a tracrRNA molecule so as to hybridize to the tracrRNA via basepairing and promote the formation of a CRISPR complex. (See U.S. Pat. No. 8,906,616). In embodiments of the present invention, the RNA molecule may further comprise a portion having a tracer mate sequence.

In embodiments of the present invention, the targeting molecule may further comprise the sequence of a tracrRNA molecule. Such embodiments may be designed as a synthetic fusion of the guide portion of the RNA molecule (gRNA or crRNA) and the trans-activating crRNA (tracrRNA), together forming a single guide RNA (sgRNA). (See Jinek et al., Science (2012)). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base pairing and may be advantageous in certain applications of the invention described herein.

In embodiments of the present invention an RNA molecule may comprise a "nexus" region and/or "hairpin" regions which may further define the structure of the RNA molecule. (See Briner et al., Molecular Cell (2014)).

As used herein, the term "direct repeat sequence" refers to two or more repeats of a specific amino acid sequence of nucleotide sequence.

As used herein, an RNA sequence or molecule capable of "interacting with" or "binding" with a CRISPR nuclease refers to the RNA sequence or molecules ability to form a CRISPR complex with the CRISPR nuclease.

As used herein, the term "operably linked" refers to a relationship (i.e. fusion, hybridization) between two sequences or molecules permitting them to function in their intended manner. In embodiments of the present invention, when an RNA molecule is operably linked to a promoter, both the RNA molecule and the promotor are permitted to function in their intended manner.

As used herein, the term "heterologous promoter" refers to a promoter that does not naturally occur together with the molecule or pathway being promoted.

As used herein, a sequence or molecule has an X % "sequence identity" to another sequence or molecule if X % of bases or amino acids between the sequences of molecules are the same and in the same relative position. For example, a first nucleotide sequence having at least a 95% sequence identity with a second nucleotide sequence will have at least 95% of bases, in the same relative position, identical with the other sequence.

Nuclear Localization Sequences

The terms "nuclear localization sequence" and "NLS" are used interchangeably to indicate an amino acid sequence/peptide that directs the transport of a protein with which it is associated from the cytoplasm of a cell across the nuclear envelope barrier. The term "NLS" is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C-termini of the polypeptide. In addition, a polypeptide having an NLS coupled by its N- or C-terminus to amino acid side chains located randomly along the amino acid sequence of the polypeptide will be translocated. Typically, an NLS consists of one or more short sequences of positively charged lysines or arginines exposed on the protein surface, but other types of NLS are known. Non-limiting examples of NLSs include an NLS sequence derived from: the SV40 virus large T-antigen, nucleoplasmin, c-myc, the hRNPA1 M9 NLS, the IBB domain from importin-alpha, myoma T protein, human p53, mouse c-abl IV, influenza vims NS1, Hepatitis virus delta antigen, mouse Mx1 protein, human poly(ADP-ribose) polymerase, and the steroid hormone receptors (human) glucocorticoid.

Delivery

The CRISPR nuclease or CRISPR compositions described herein may be delivered as a protein, DNA molecules, RNA molecules, Ribonucleoproteins (RNP), nucleic acid vectors, or any combination thereof. In some embodiments, the RNA molecule comprises a chemical modification. Non-limiting examples of suitable chemical modifications include 2'-0-methyl (M), 2'-0-methyl, 3'phosphorothioate (MS) or 2'-0-methyl, 3'thioPACE (MSP), pseudouridine, and 1-methyl pseudo-uridine. Each possibility represents a separate embodiment of the present invention.

The CRISPR nucleases and/or polynucleotides encoding same described herein, and optionally additional proteins (e.g., ZFPs, TALENs, transcription factors, restriction enzymes) and/or nucleotide molecules such as guide RNA may be delivered to a target cell by any suitable means. The target cell may be any type of cell e.g., eukaryotic or prokaryotic, in any environment e.g., isolated or not, maintained in culture, in vitro, ex vivo, in vivo or in planta.

In some embodiments, the composition to be delivered includes mRNA of the nuclease and RNA of the guide. In some embodiments, the composition to be delivered includes mRNA of the nuclease, RNA of the guide and a donor template. In some embodiments, the composition to be delivered includes the CRISPR nuclease and guide RNA. In some embodiments, the composition to be delivered includes the CRISPR nuclease, guide RNA and a donor template for gene editing via, for example, homology directed repair. In some embodiments, the composition to be delivered includes mRNA of the nuclease, DNA-targeting RNA and the tracrRNA. In some embodiments, the composition to be delivered includes mRNA of the nuclease, DNA-targeting RNA and the tracrRNA and a donor template. In some embodiments, the composition to be delivered includes the CRISPR nuclease DNA-targeting RNA and the tracrRNA. In some embodiments, the composition to be delivered includes the CRISPR nuclease, DNA-targeting RNA and the tracrRNA and a donor template for gene editing via, for example, homology directed repair.

Any suitable viral vector system may be used to deliver RNA compositions. Conventional viral and non-viral based gene transfer methods can be used to introduce nucleic acids and/or CRISPR nuclease in cells (e.g., mammalian cells, plant cells, etc.) and target tissues. Such methods can also be used to administer nucleic acids encoding and/or CRISPR nuclease protein to cells in vitro. In certain embodiments, nucleic acids and/or CRISPR nuclease are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson, Science (1992); Nabel and Felgner, TIBTECH (1993); Mitani and Caskey, TIBTECH (1993); Dillon, TIBTECH (1993); Miller, Nature (1992); Van Brunt, Biotechnology (1988); Vigne et al., Restorative Neurology and Neuroscience 8:35-36 (1995); Kremer and Perricaudet, British Medical Bulletin (1995); Haddada et al., Current Topics in Microbiology and Immunology (1995); and Yu et al., Gene Therapy 1:13-26 (1994).

Methods of non-viral delivery of nucleic acids and/or proteins include electroporation, lipofection, microinjection, biolistics, particle gun acceleration, virosomes, liposomes, immunoliposomes, polycation or lipid:nucleic acid conjugates, artificial virions, and agent-enhanced uptake of nucleic acids or can be delivered to plant cells by bacteria or viruses (e.g., Agrobacterium, Rhizobium sp. NGR234, Sinorhizoboiummeliloti, Mesorhizobium loti, tobacco mosaic virus, potato virus X, cauliflower mosaic virus and cassava vein mosaic virus. See, e.g., Chung et al. Trends Plant Sci. (2006). Sonoporation using, e.g., the Sonitron 2000 system (Rich-Mar) can also be used for delivery of nucleic acids. Cationic-lipid mediated delivery of proteins and/or nucleic acids is also contemplated as an in vivo or in vitro delivery method. See Zuris et al., Nat. Biotechnol. (2015), Coelho et al., N. Engl. J. Med. (2013); Judge et al., Mol. Ther. (2006); and Basha et al., Mol. Ther. (2011).

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those disclosed in PCT International Publication Nos. WO/1991/017424 and WO/1991/016024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science (1995); Blaese et al., Cancer Gene Ther. (1995); Behr et al., Bioconjugate Chem. (1994); Remy et al., Bioconjugate Chem. (1994); Gao and Huang, Gene Therapy (1995); Ahmad and Allen, Cancer Res., (1992); U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al., Nature Biotechnology (2009)).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, recombinant retroviral, lentivirus, adenoviral, adeno-associated, vaccinia and herpes simplex virus vectors for gene transfer. However, an RNA virus is preferred for delivery of the RNA compositions described herein. Additionally, high transduction efficiencies have been observed in many different cell types and target tissues. Nucleic acid of the invention may be delivered by non-integrating lentivirus. Optionally, RNA delivery with Lentivirus is utilized. Optionally the lentivirus includes mRNA of the nuclease, RNA of the guide. Optionally the lentivirus includes mRNA of the nuclease, RNA of the guide and a donor template. Optionally, the lentivirus includes the nuclease protein, guide RNA. Optionally, the lentivirus includes the nuclease protein, guide RNA and/or a donor template for gene editing via, for example, homology directed repair. Optionally the lentivirus includes mRNA of the nuclease, DNA-targeting RNA, and the tracrRNA. Optionally the lentivirus includes mRNA of the nuclease, DNA-targeting RNA, and the tracrRNA, and a donor template. Optionally, the lentivirus includes the nuclease protein, DNA-targeting RNA, and the tracrRNA. Optionally, the lentivirus includes the nuclease protein, DNA-targeting RNA, and the tracrRNA, and a donor template for gene editing via, for example, homology directed repair.

As mentioned above, the compositions described herein may be delivered to a target cell using a non-integrating lentiviral particle method, e.g. a LentiFlash® system. Such a method may be used to deliver mRNA or other types of RNAs into the target cell, such that delivery of the RNAs to the target cell results in assembly of the compositions described herein inside of the target cell. See also PCT International Publication Nos. WO2013/014537, WO2014/016690, WO2016185125, WO2017194902, and WO2017194903.

The tropism of a retrovirus can be altered by incorporating foreign envelope proteins, expanding the potential target population of target cells. Lentiviral vectors are retroviral vectors capable of transducing or infecting non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher Panganiban, J. Virol. (1992); Johann et al., J. Virol. (1992); Sommerfelt et al., Virol. (1990); Wilson et al., J. Virol. (1989); Miller et al., J. Virol. (1991); PCT International Publication No. WO/1994/026877A1).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood (1995); Kohn et al., Nat. Med. (1995); Malech et al., PNAS (1997)). PA317/pLASN was the first therapeutic vector used in a gene therapy trial. (Blaese et al., Science (1995)). Transduction efficiencies of 50% or greater have been observed for MFG-S packaged vectors. (Ellem et al., Immunol Immunother. (1997); Dranoff et al., Hum. Gene Ther. (1997).

Packaging cells are used to form virus particles that are capable of infecting a host cell. Such cells include 293 cells, which package adenovirus, AAV, and psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to non-viral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector. In some embodiments, delivery of mRNA in-vivo and ex-vivo, and RNPs delivery may be utilized.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an RNA composition, and re-infused back into the subject organism (e.g., patient). Various cell types suitable for ex vivo transfection are well known to those of skill in the art (see, e.g., Freshney, "Culture of Animal Cells, A Manual of Basic Technique and Specialized Applications (6th edition, 2010)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells, any plant cell (differentiated or undifferentiated) as well as insect cells such as Spodopterafugiperda (Sf), or fungal cells such as *Saccharomyces, Pichia* and *Schizosaccharomyces*. In certain embodiments, the cell line is a CHO-K 1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in-vitro or can be introduced into a mammal (such as the donor of the cells) where they will engraft in the bone marrow. Methods for differentiating CD34+ cells in vitro into clinically important immune cell types using cytokines such a GM-CSF, IFN-gamma. and TNF-alpha are known (as a non-limiting example see, Inaba et al., J. Exp. Med. (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+(panB cells), GR-1 (granulocytes), and Tad (differentiated antigen presenting cells) (as a non-limiting example see Inaba et al., J. Exp. Med. (1992)). Stem cells that have been modified may also be used in some embodiments.

Notably, any one of the CRISPR nucleases described herein may be suitable for genome editing in post-mitotic cells or any cell which is not actively dividing, e.g., arrested cells. Examples of post-mitotic cells which may be edited using a CRISPR nuclease of the present invention include, but are not limited to, myocyte, a cardiomyocyte, a hepatocyte, an osteocyte and a neuron.

Vectors (e.g., retroviruses, liposomes, etc.) containing therapeutic RNA compositions can also be administered directly to an organism for transduction of cells in vivo. Alternatively, naked RNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of transgenes into immune cells (e.g., T-cells) include non-integrating lentivirus vectors. See, for example, U.S. Patent Publication No. 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

DNA Repair by Homologous Recombination

The term "homology-directed repair" or "HDR" refers to a mechanism for repairing DNA damage in cells, for example, during repair of double-stranded and single-stranded breaks in DNA. HDR requires nucleotide sequence homology and uses a "nucleic acid template" (nucleic acid template or donor template used interchangeably herein) to repair the sequence where the double-stranded or single break occurred (e.g., DNA target sequence). This results in the transfer of genetic information from, for example, the nucleic acid template to the DNA target sequence. HDR may result in alteration of the DNA target sequence (e.g., insertion, deletion, mutation) if the nucleic acid template sequence differs from the DNA target sequence and part or all of the nucleic acid template polynucleotide or oligonucleotide is incorporated into the DNA target sequence. In some embodiments, an entire nucleic acid template polynucleotide, a portion of the nucleic acid template polynucleotide, or a copy of the nucleic acid template is integrated at the site of the DNA target sequence.

The terms "nucleic acid template" and "donor", refer to a nucleotide sequence that is inserted or copied into a genome. The nucleic acid template comprises a nucleotide sequence, e.g., of one or more nucleotides, that will be added to or will template a change in the target nucleic acid or may be used to modify the target sequence. A nucleic acid template sequence may be of any length, for example between 2 and 10,000 nucleotides in length (or any integer value there between or there above), preferably between about 100 and 1,000 nucleotides in length (or any integer there between), more preferably between about 200 and 500 nucleotides in length. A nucleic acid template may be a single stranded nucleic acid, a double stranded nucleic acid. In some embodiment, the nucleic acid template comprises a nucleotide sequence, e.g., of one or more nucleotides, that corresponds to wild type sequence of the target nucleic acid, e.g., of the target position. In some embodiment, the nucleic acid template comprises a ribonucleotide sequence, e.g., of one or more ribonucleotides, that corresponds to wild type sequence of the target nucleic acid, e.g., of the target position. In some embodiment, the nucleic acid template comprises modified ribonucleotides.

Insertion of an exogenous sequence (also called a "donor sequence," donor template" or "donor"), for example, for correction of a mutant gene or for increased expression of a wild-type gene can also be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See, e.g., U.S. Patent Publication Nos. 2010/0047805; 2011/0281361; 2011/0207221; and 2019/0330620. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang and Wilson, Proc. Natl. Acad. Sci. USA (1987); Nehls et al., Science (1996). Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

Accordingly, embodiments of the present invention using a donor template for repair may use a DNA or RNA, single-stranded and/or double-stranded donor template that can be introduced into a cell in linear or circular form. In embodiments of the present invention a gene-editing composition comprises: (1) an RNA molecule comprising a guide sequence to affect a double strand break in a gene prior to repair and (2) a donor RNA template for repair, the RNA molecule comprising the guide sequence is a first RNA molecule and the donor RNA template is a second RNA molecule. In some embodiments, the guide RNA molecule and template RNA molecule are connected as part of a single molecule.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to 'correct' a mutated sequence in an endogenous gene (e.g., the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by recombinant viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus, for example a CCR5 gene, a CXCR4 gene, a PPP1R12c (also known as AAVS1) gene, an albumin gene or a Rosa gene. See, e.g., U.S. Pat. Nos. 7,951,925 and 8,110,379; U.S. Publication Nos. 2008/0159996; 20100/0218264; 2010/0291048; 2012/0017290; 2011/0265198; 2013/0137104; 2013/0122591; 2013/0177983 and 2013/0177960 and U.S. Provisional Application No. 61/823,689).

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

For the foregoing embodiments, each embodiment disclosed herein is contemplated as being applicable to each of the other disclosed embodiment. For example, it is understood that any of the RNA molecules or compositions of the present invention may be utilized in any of the methods of the present invention.

As used herein, all headings are simply for organization and are not intended to limit the disclosure in any manner. The content of any individual section may be equally applicable to all sections.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Generally, the nomenclature used herein, and the laboratory procedures utilized in the present invention include molecular, biochemical, microbiological and recombinant DNA techniques. Such techniques are thoroughly explained in the literature. See, for example, Sambrook et al., "Molecular Cloning: A laboratory Manual" (1989); Ausubel, R. M. (Ed.), "Current Protocols in Molecular Biology" Volumes I-III (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (Eds.), "Genome Analysis: A Laboratory Manual Series", Vols. 1-4, Cold Spring Harbor Laboratory Press, New York (1998); Methodologies as set forth in U.S. Pat. Nos. 4,666,828; 4,683,202; 4,801,531; 5,192,659 and 5,272,057; Cellis, J. E. (Ed.), "Cell Biology: A Laboratory Handbook", Volumes I-III (1994); Freshney, "Culture of Animal Cells—A Manual of Basic Technique" Third Edition, Wiley-Liss, N. Y. (1994); Coligan J. E. (Ed.), "Current Protocols in Immunology" Volumes I-III (1994); Stites et al. (Eds.), "Basic and Clinical Immunology" (8th Edition), Appleton & Lange, Norwalk, C T (1994); Mishell and Shiigi (Eds.), "Strategies for Protein Purification and Characterization—A Laboratory Course Manual" CSHL Press (1996); Clokie and Kropinski (Eds.), "Bacteriophage Methods and Protocols", Volume 1: Isolation, Characterization, and Interactions (2009), all of which are incorporated by reference. Other general references are provided throughout this document.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Experimental Details

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

CRISPR repeat (crRNA), transactivating crRNA (tracrRNA), nuclease polypeptide, and PAM sequences were predicted from different metagenomic databases of sequences of environmental samples. The list of bacterial species/strains from which the CRISPR repeat, tracRNA sequence, and nucleases polypeptide sequence were predicted is provided in Tables 1a-1b.

Construction of OMNI Nuclease Polypeptides

For construction of OMNI nuclease polypeptides, the open reading frame of several identified OMNI nucleases (OMNIs) were codon optimized for human cell line expression. The ORF was cloned into the bacterial plasmid pb-NNC and into the mammalian plasmid pmOMNI (Table 4).

Prediction and Construction of sgRNA

For each OMNI the sgRNA was predicted by detection of the CRISPR repeat array sequence (crRNA) and a trans-activating crRNA (tracrRNA) in the respective bacterial genome. The native pre-mature crRNA and tracrRNA sequences were connected in-silico with tetra-loop 'gaaa' and the secondary structure elements of the duplex were predicted by using an RNA secondary structure prediction tool.

The predicted secondary structures of the full duplex RNA elements (crRNA-tracrRNA chimera) was used for identification of possible tracr sequences for the design of a sgRNA having various versions for each OMNI nuclease. By shortening the duplex at the upper stem at different locations, the crRNA and tracrRNA were connected with tetra-loop 'gaaa', thereby generating possible sgRNA scaffolds (sgRNA designs of all OMNIs are listed in Tables 2a-2d). At least two versions of possible designed scaffolds for each OMNI were synthesized and connected downstream to a 22 nt universal unique spacer sequence (T2, SEQ ID NO: 41) and cloned into a bacterial expressing plasmid under a constitutive promoter and into a mammalian expression plasmid under a U6 promoter (pbSGR2 and pmGuide, respectively, Table 4).

Figure 1C:
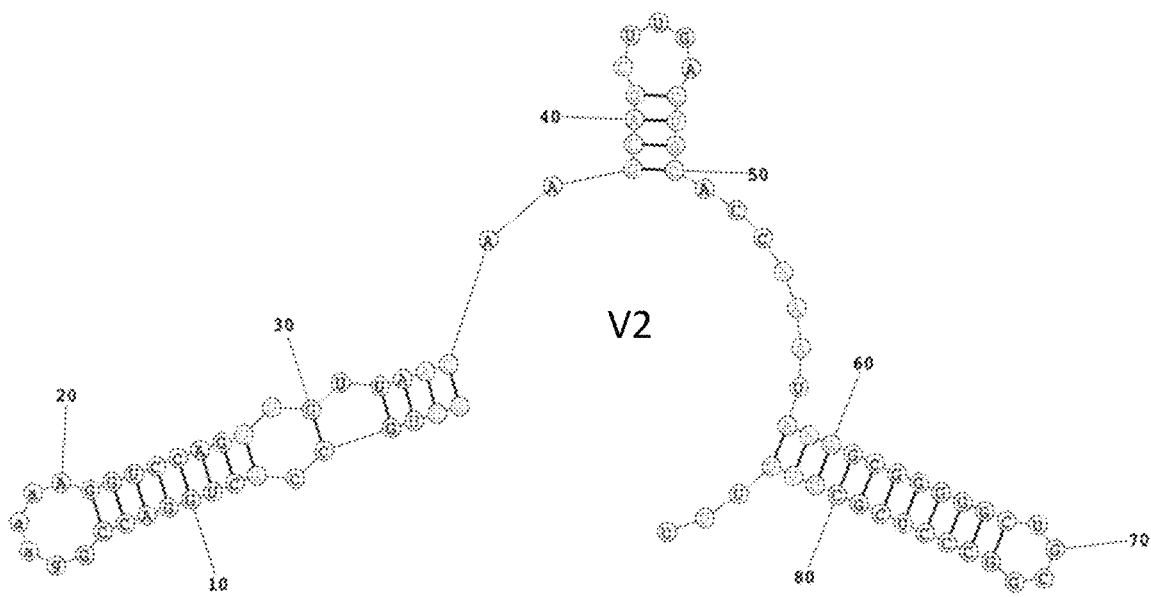
Figure 2A:
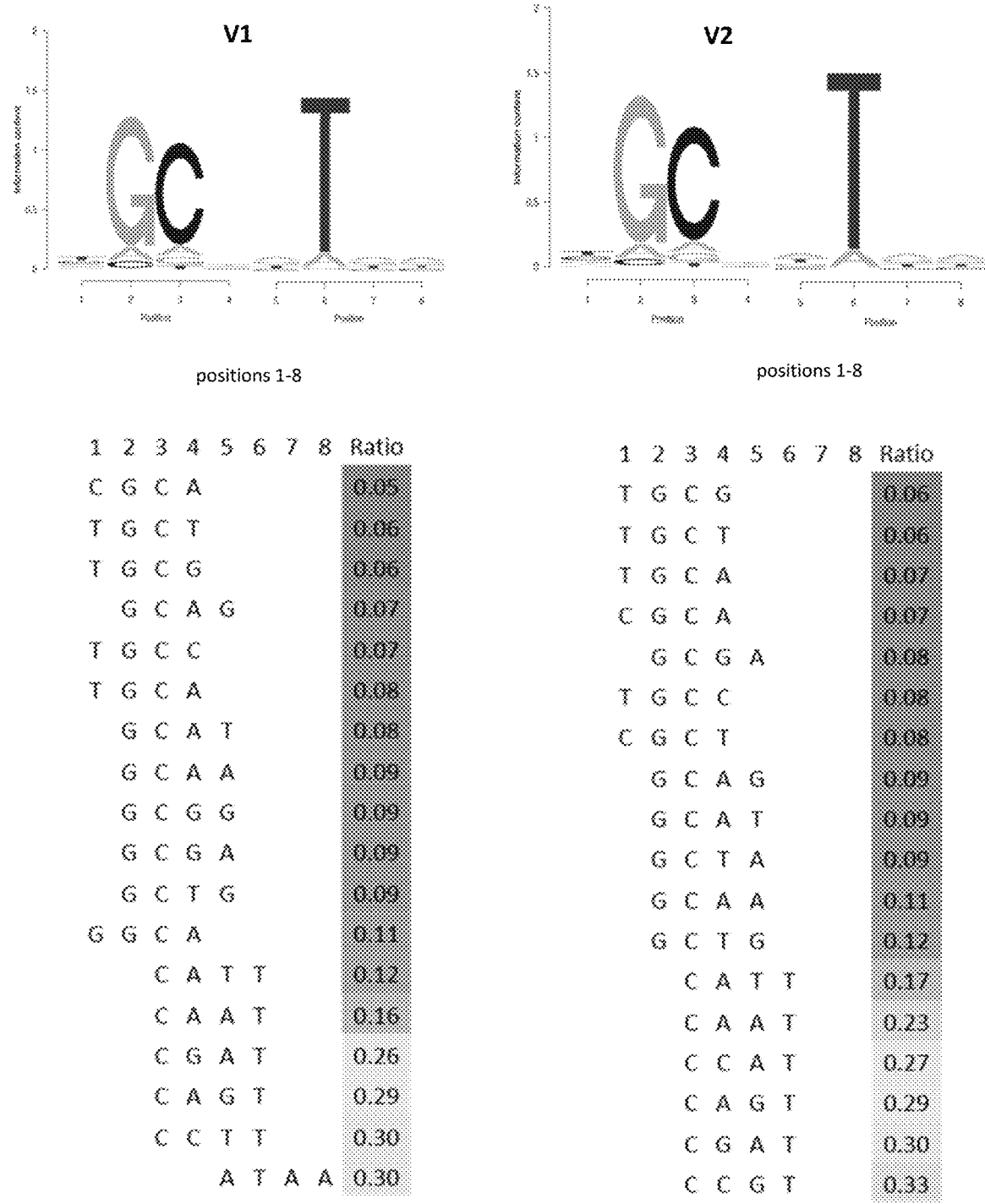
Figure 2C:
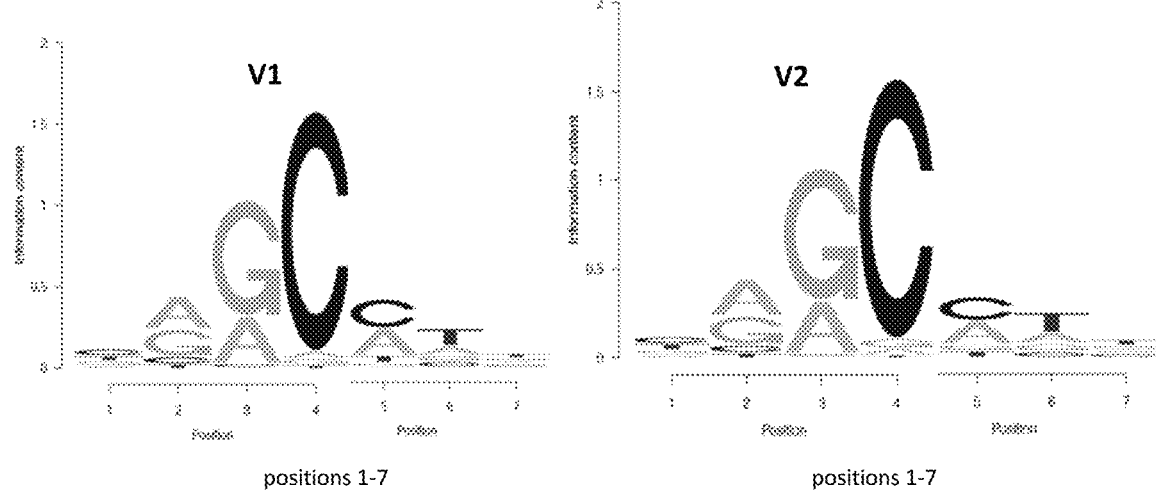
Figure 2D:
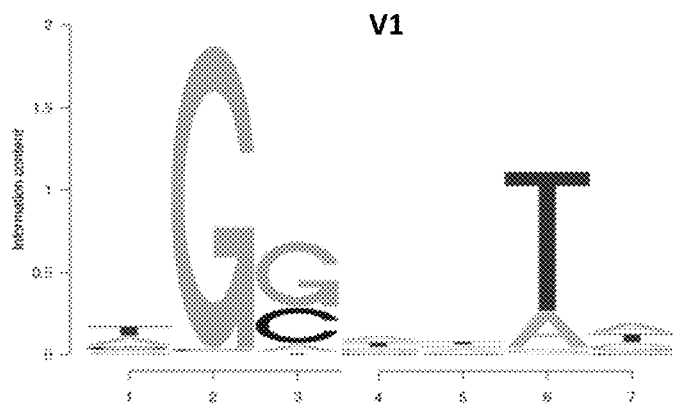
Figure 2E:
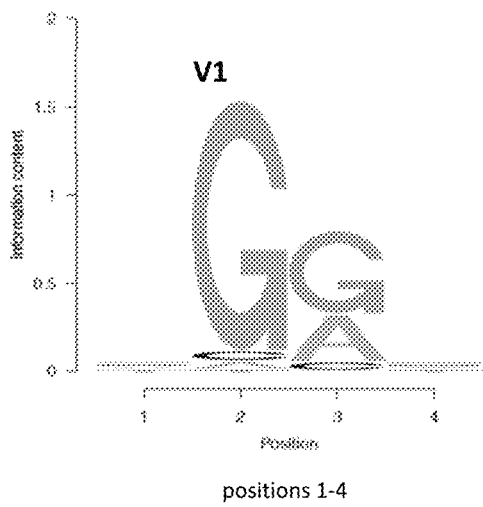
Figure 2E:
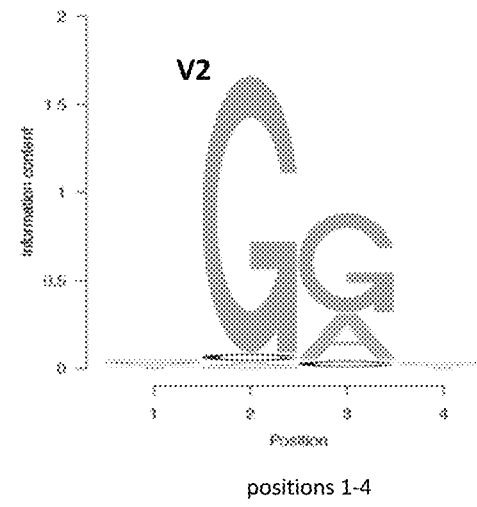
Figure 2G:
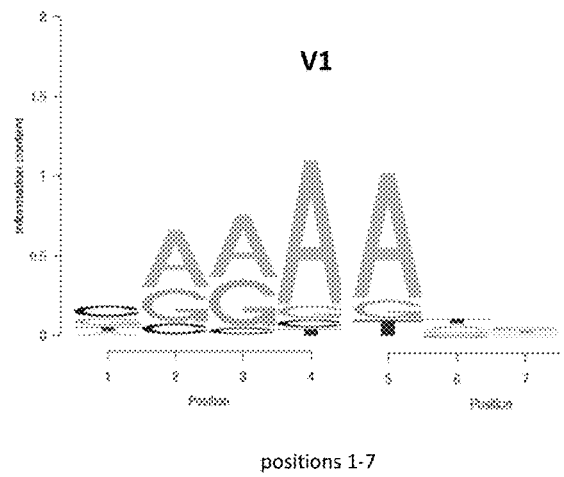
Figure 2G:
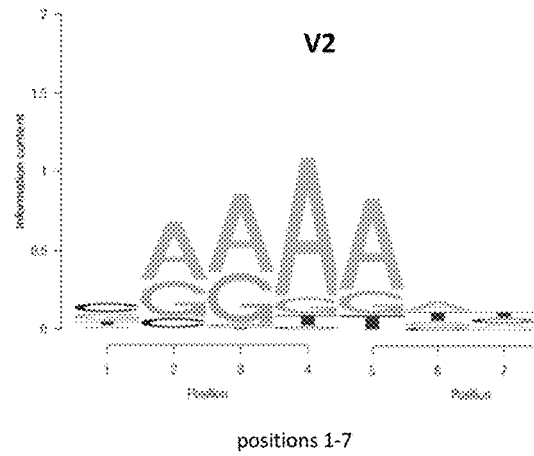
Figure 2H:
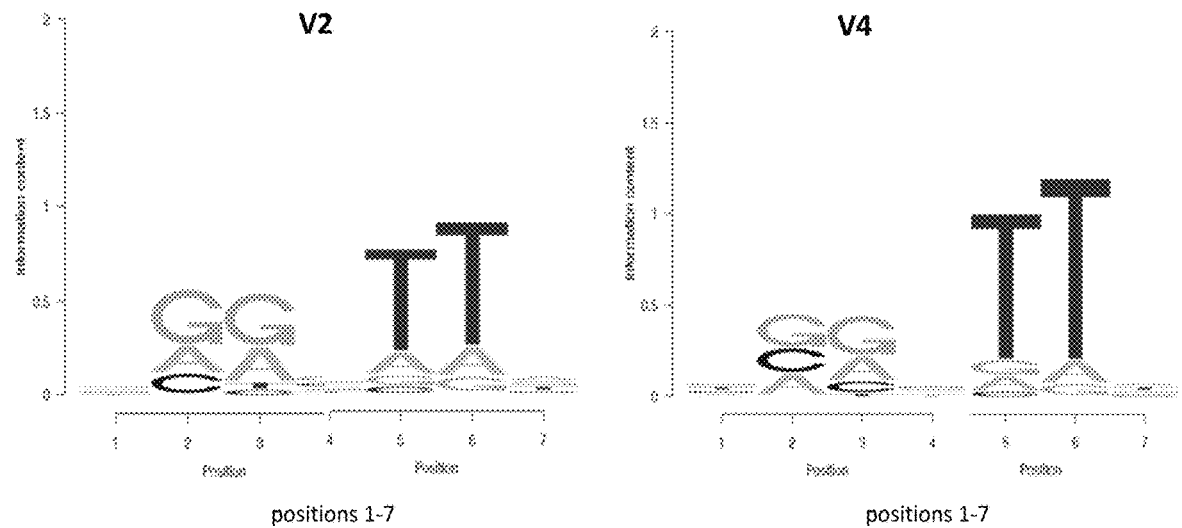

In order to overcome potential transcriptional and structural constraints and to assess the plasticity of the sgRNA scaffold in the human cellular environmental context, several versions of the sgRNA were tested. In each case the modifications represent small variations in the nucleotide sequence of the possible sgRNA (FIG. 1C, Tables 2a-2d).

```
T1-
                                          (SEQ ID NO: 241)
GGTGCGGTTCACCAGGGTGTCG

T2-
                                          (SEQ ID NO: 242)
GGAAGAGCAGAGCCTTGGTCTC
```

In-Vitro Depletion Assay by TXTL

Depletion of PAM sequences in-vitro was followed by Maxwell et al, Methods. 2018. Briefly, linear DNA expressing the OMNI nucleases and an sgRNA under T7 promoter were added to a TXTL mix (Arbor Bioscience) together with a linear construct expressing T7 polymerase. RNA expression and protein translation by the TXTL mix result in the formation of the RNP complex. Since linear DNA was used, Chili sequences, a RecBCD inhibitor, were added to protect the DNA from degradation. The sgRNA spacer is designed to target a library of plasmids containing the targeting protospacer (pbPOS T2 library, Table 4) flanked by an 8N randomized set of potential PAM sequences. Depletion of PAM sequences from the library was measured by high-throughput sequencing upon using PCR to add the necessary adapters and indices to both the cleaved library and to a control library expressing a non-targeting gRNA (T1). Following deep sequencing, the in-vitro activity was confirmed by the fraction of the depleted sequences having the same PAM sequence relative to their occurrence in the control by the OMNI nuclease indicating functional DNA cleavage by an in-vitro system (FIGS. 2A-2H, Tables 3a-3c).

Nuclease Expression in a Mammalian Cells

Figures 3A, 3B:
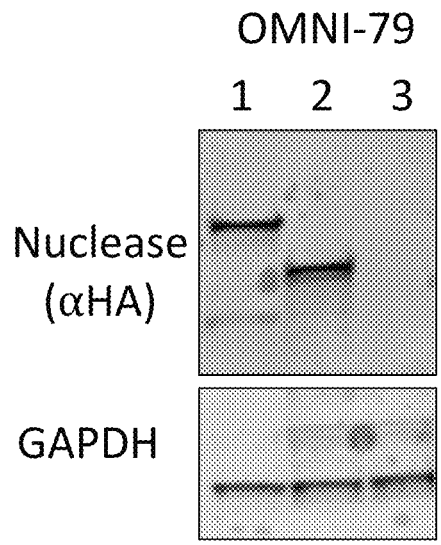
FIG. 3A: In-vivo PAM enrichment by DNA transfection results for OMNI nucleases. Hek293 cells with a PAM library of 6N after the T2 site were transfected with an OMNI-79 nuclease and a T2 sgRNA. Cells were harvested at Day 6 and probed on a western blot using an antibody against an HA-tag to confirm expression of the OMNI-79 nuclease in the mammalian system. Lane 1 is a lysate containing SpCas9-HA, Lane 2 is a lysate containing OMNI-79-HA, and Lane 3 is a non-transfected lysate.
FIG. 3B: NGS analysis: NGS analysis was used to select indel containing sequences. Nucleotide frequencies for every position of the PAM in the enriched population is described for both V1 and V2 versions of the sgRNA.

First, expression of each of the optimized DNA sequences coding for OMNI nucleases in mammalian cells was validated. To this end, an expression vector coding for an HA-tagged OMNI nuclease or *Streptococcus Pyogenes* Cas9 (SpCas9) linked to mCherry by a P2A peptide (pmOMNI, Table 4) was introduced into Hek293T cells using the Jet-Optimus™ transfection reagent (polyplus-transfection). The P2A peptide is a self-cleaving peptide which can induce the cleaving of the recombinant protein in a cell such that the OMNI nuclease and the mCherry are separated upon expression. The mCherry serves as indicator for transcription efficiency of the OMNI from expression vector. Expression of all OMNI proteins was confirmed by a western blot assay using anti-HA antibody (FIG. 3A).

PAM Identification and Activity in Mammalian Cells

While a PAM sequence preference is considered as an inherent property of the nuclease, it may be affected, to some extent, by the cellular environment, genomic composition and genome size. Since the human cellular environment is significantly different from the bacterial environment with respect to those properties, a "fine tuning" step has been introduced to address potential differences in PAM preferences in the human cellular context. To this end, a PAM library was constructed in a human cell line. The PAM library was introduced to the cells using a viral vector (see Table 4), as a constant target sequence followed by a stretch of 6N. Upon introduction of an OMNI and an sgRNA targeting the library constant target site, NGS analysis was used to identify the edited sequences and the PAM associated with them. The enriched edited sequences were then used to define the PAM consensus. This methodology was applied to determine the optimized PAM requirements of OMNI nuclease in mammalian cells (FIG. 3B, Tables 3a-3c "mammalian refinements"). The OMNI-79 PAM is an NGG motif that is similar to the NGR PAM identified by TXTL.

Activity in Human Cells on Endogenous Genomic Targets

OMNIs were also assayed for their ability to promote editing on specific genomic locations in human cells. To this end, for each OMNI a corresponding OMNI-P2A-mCherry expression vector (pmOMNI, Table 4) was transfected into HeLa cells together with an sgRNA designed to target a specific location in the human genome (pmGuide, Table 4). At 72h, cells were harvested. Half of the cells were used for quantification of transfection efficiency by FACS using mCherry fluorescence as a marker. The other half of the cells were lysed, and their genomic DNA content was used to PCR amplify the corresponding putative genomic targets. Amplicons were subjected to NGS and the resulting sequences were then used to calculate the percentage of editing events in each target site. Short Insertions or deletions (indels) around the cut site are the typical outcome of repair of DNA ends following nuclease-induced DNA cleavage. The calculation of percent editing was therefore deduced from the fraction of indel-containing sequences within each amplicon.

Genomic activity of each OMNI was assessed using a panel of a minimum of 6 and up to a maximum of 31 unique sgRNAs each designed to target a different genomic location. The results of these experiments are summarized in Table 5. As can be seen in the table (column 6, "% indels"), several OMNIs exhibit significant editing levels compared to the negative control (column 9, "% editing in neg control") in several target sites tested. OMNI-59 and OMNI-67 exhibited significant editing levels in 1/6 sites tested, OMNI-79 exhibited high and significant editing levels in 19/31 sites tested with editing activity >5%, and OMNI-81 exhibited high and significant editing levels in 6/10 sites tested.

OMNI-79 Activity with gRNA Variation

Figure 4A:
FIGS. 4A-4B: OMNI79 activity with gRNA variation.
Figure 4A:
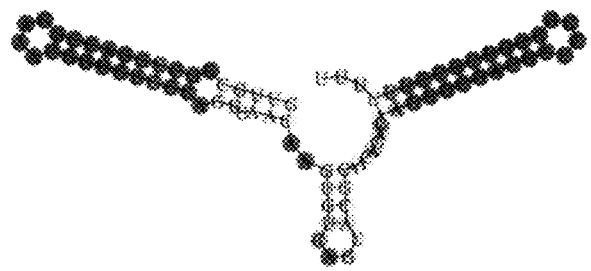
Figure 4A:

Other gRNA molecules sharing the same repeat sequence as an OMNI-79 gRNA molecule were also identified. Specifically, two gRNA molecules that share the repeat sequence and are predicted to form a similar structure were identified (FIG. 4A). We next tested the ability of OMNI-79 to function with these gRNA molecules by DNA-targeting such a complex to several genomic locations. OMNI-79 plasmid was transfected into HeLa cells together with a sgRNA molecule designed to target a specific location in the human genome (pmGuide, Table 4, spacer sequence, Table 5) designed with the native scaffold (*Novosphingobium* sp. SYSU G00007 "WT") or an alternative scaffold ("SpSaNXO2" or "SpSpCAP1"). At 72 hours cells were harvested and half of the cells were used for quantification of transfection efficiency by FACS, using mCherry fluorescence as marker. The rest of the cells were lysed, and their genomic DNA content was used in a PCR reaction which amplified the corresponding putative genomic targets. Amplicons were subjected to next-generation sequencing (NGS) and the resulting sequences were then used calculate the percentage of editing events in each target site. Short insertions or deletions (indels) around the cut site are the typical outcome of repair of DNA ends following nuclease induced DNA cleavage. The calculation of % editing was therefore deduced from the fraction of indels containing sequences within each amplicon.

Figure 4B:
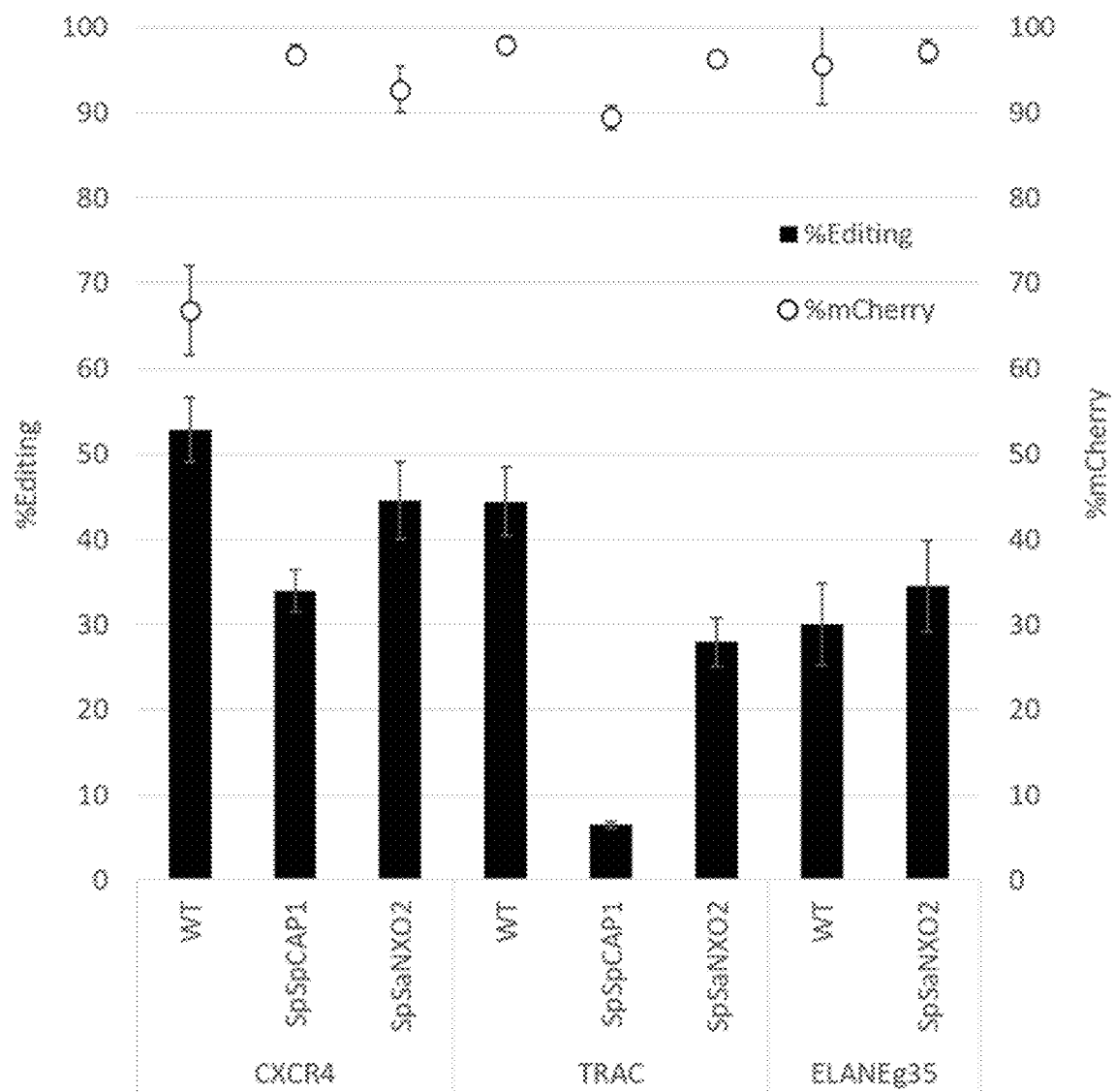

As can be seen in FIG. 4B, the editing level obtained by OMNI-79 using the SpSaNXO2 scaffold is comparable to the editing level obtained using the native gRNA molecule in all sites tested. The editing level obtained by OMNI-79 using the SpSpCAP1 gRNA molecule is reduced compared with the editing level obtained using the native gRNA molecule.

OMNI-79 Activity Via AAV Delivery

OMNI-79 was subcloned into an AAV packaging construct under a CMV promoter together with a gRNA molecule targeting ELANE g35, CXCR4 or serpinA s12 under U6 promoter regulation between the ITR components (Table 4). AAV particles were produced by co-transfection of all packaging component plasmids into HEK293 cells, and particles purification (VectorBuilder).

Figure 5A:
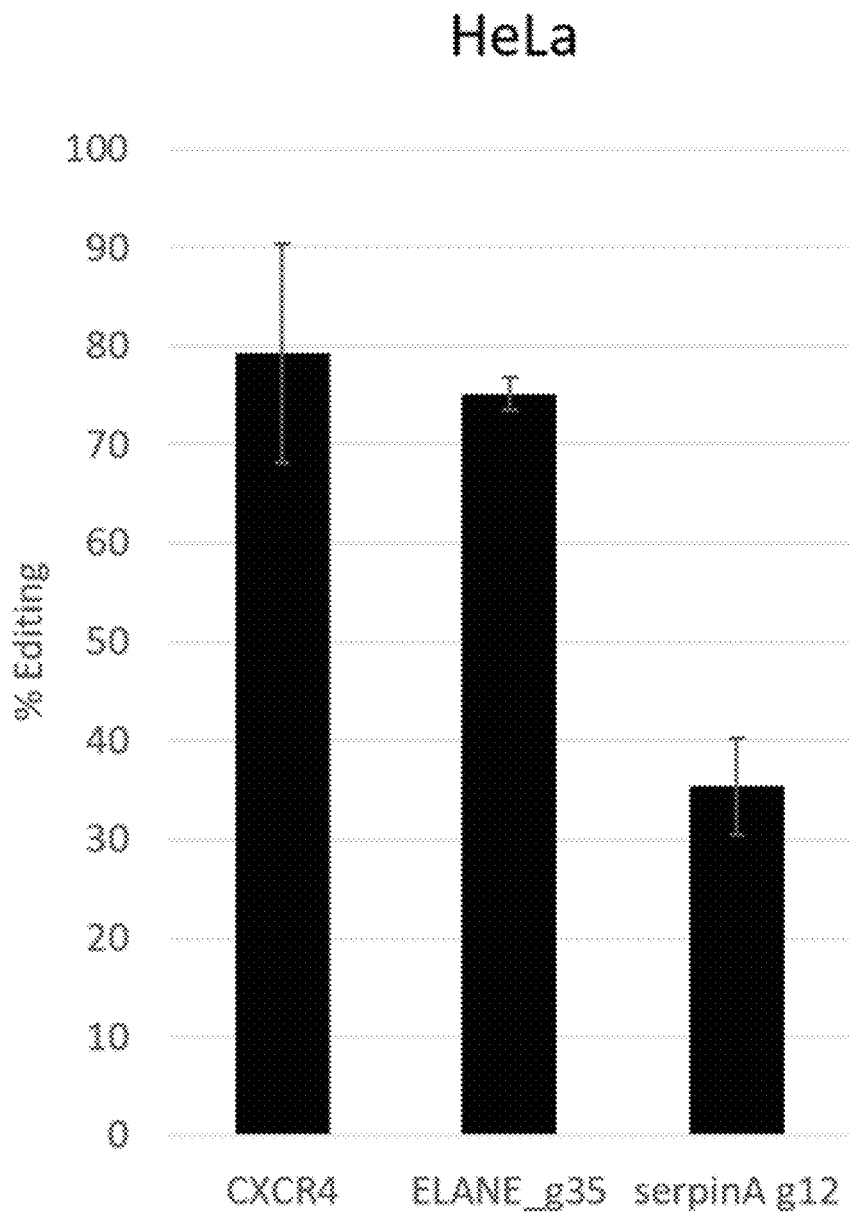
FIGS. 5A-5B: OMNI79 activity via AAV delivery.

AAV particles containing OMNI-79 and a gRNA molecule were used to infect HeLa cells at MOI of 100,000 particles/cell in a 48-well plate format. At 72 hours cells were lysed, and their genomic DNA content was used in a PCR reaction which amplified the corresponding putative genomic targets. Amplicons were subjected to NGS and the resulting sequences were then used calculate the percentage of editing events. As can be seen in FIG. 5A, editing was observed in all sites tested. Editing level using AAV delivery was higher in all three (3) sites, compared with DNA transfection (see table 5).

Figure 5B:
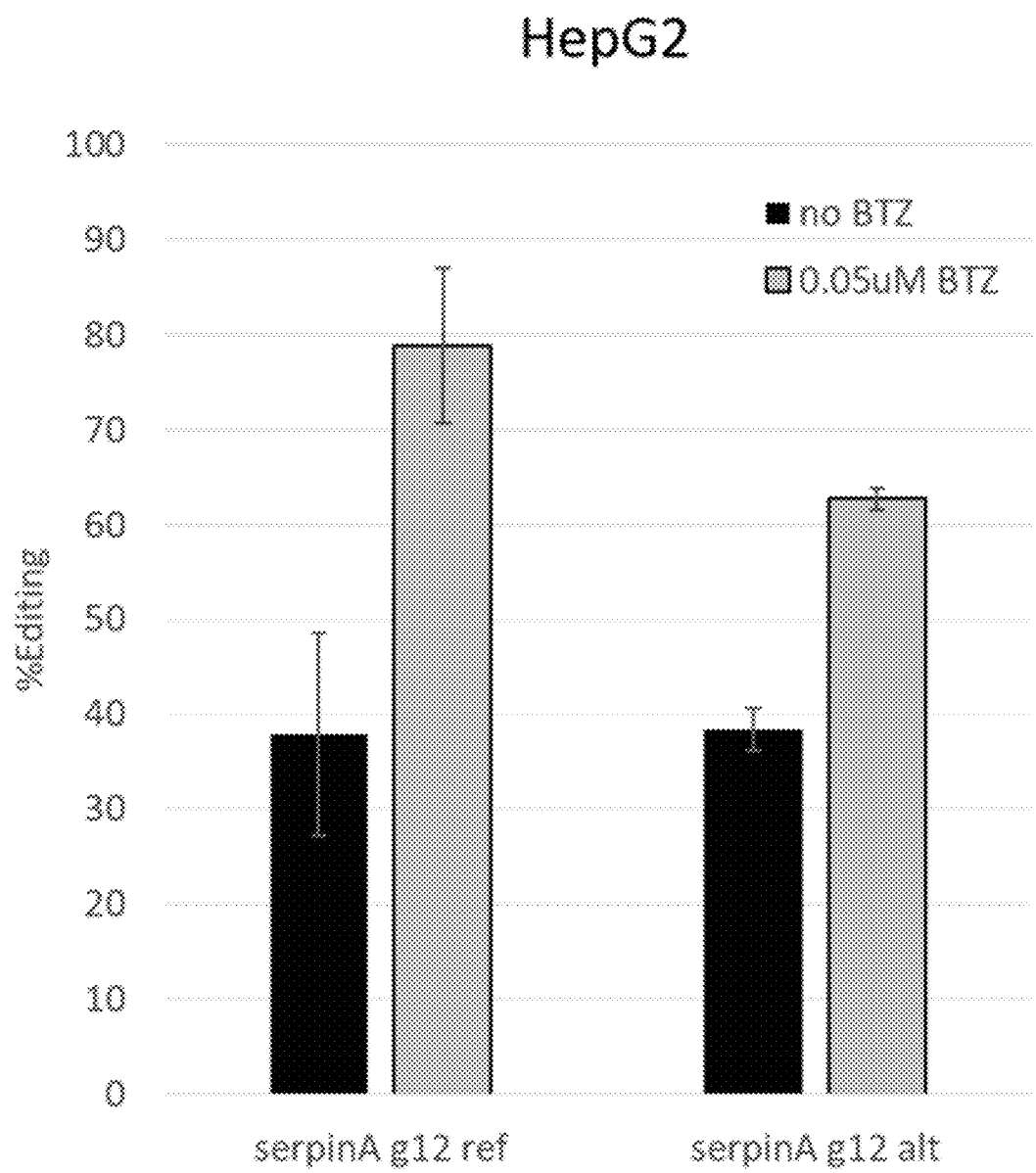

We next tested editing efficiency of OMNI-79 by AAV delivery in the difficult to transfect cell line HepG2. AAV particles were used to infect HepG2 cells at MOI of 100,000 particles/cell in a 48-well plate format with or without a reversible proteasome inhibitor Bortezomib (BTZ). Since serpinA s12 was designed to target a SNP site (rs6647) both gRNA molecules targeting the ref or SNP sequences were tested. As can be seen in FIG. 5B, editing of serpinA s12 site in HepG2 is comparable to the editing observed in HeLa cells. Adding BTZ resulted in increased editing by 1.5-2 fold.

Purifying OMNI-79 Protein

The OMNI-79 open-reading frame was cloned into bacterial expression plasmids (T7-NLS-OMNI-NLS-HA-Histag, pET9a, Table 4) and expressed in KRX cells (Promega). Cells were grown in the following growth media Terrific Broth+0.4% glycerol+0.1% rhamanose+0.05% glucose. Culturing was done for four (4) hours until a OD600 nm reading of 5-6 was attained and the temperature was lowered to 18° C. 16-20 hours before harvesting and freezing cells at −80° C. Cell paste was resuspended in lysis buffer (20 mM Hepes, 1000 mM NaCl, 50 mM imidazole pH7.5, 1 mM TCEP) supplemented with EDTA-free complete protease inhibitor cocktail set III (Calbiochem). Cells were lysed using MC Multi Shot (Constant Systems) French press. Cell disruption was measured by the drop of OD600 nm to less than 10% of starting the OD600 nm. Clarification of the lysate was done in LYNX6000 centrifuge (Thermo Scientific) at 45,000×g for 30 minutes at 4° C. The cleared lysate was incubated with Ni Sepharose 6 Fast Flow resin (Cytiva). The resin was loaded onto gravity column and washed with wash buffer (20 mM Hepes, 500 mM NaCl, 50 mM imidazole pH7.5, 1 mM TCEP) and OMNI protein was eluted with elution buffer (20 mM Hepes, 200 mM NaCl, 500 mM imidazole, 1 mM TCEP). The elution sample was loaded using AKTA Avant (Cytiva) on pre-equilibrated HiTrap SP 5 ml (Cytiva) (20 mM Hepes pH7.5, 200 mM NaCl) and eluted using a linear gradient of 20 column volumes 0 to 100% buffer B (20 mM Hepes, 1000 mM NaCl pH7.5). Fractions of the OMNI-79 nuclease were pooled and concentrated and loaded onto a centricone (Amicon Ultra ultra 15 50K, Merck). The concentrated OMNI-79 protein was further purified by SEC on HiLoad 16/600 Superdex 200 pg-SEC, AKTA Pure (Cytiva) with a 20 mM Hepes pH 7.5, 300 mM NaCl, 10% glycerol. Fractions containing OMNI-79 protein were pooled and concentrated and loaded onto a centricone (Amicon Ultra 15 50K, Merck) with a final storage buffer of 20 mM Hepes pH 7.5, 300 mM NaCl, 10% glycerol, 1 mM TCEP. Purified OMNI protein was concentrated to 10-20 mg/ml, filtered with SpinX® (Merck), aliquoted, flash-frozen in liquid nitrogen, and stored at −80° C.

OMNI-79 Spacer Optimization

Figure 6A:
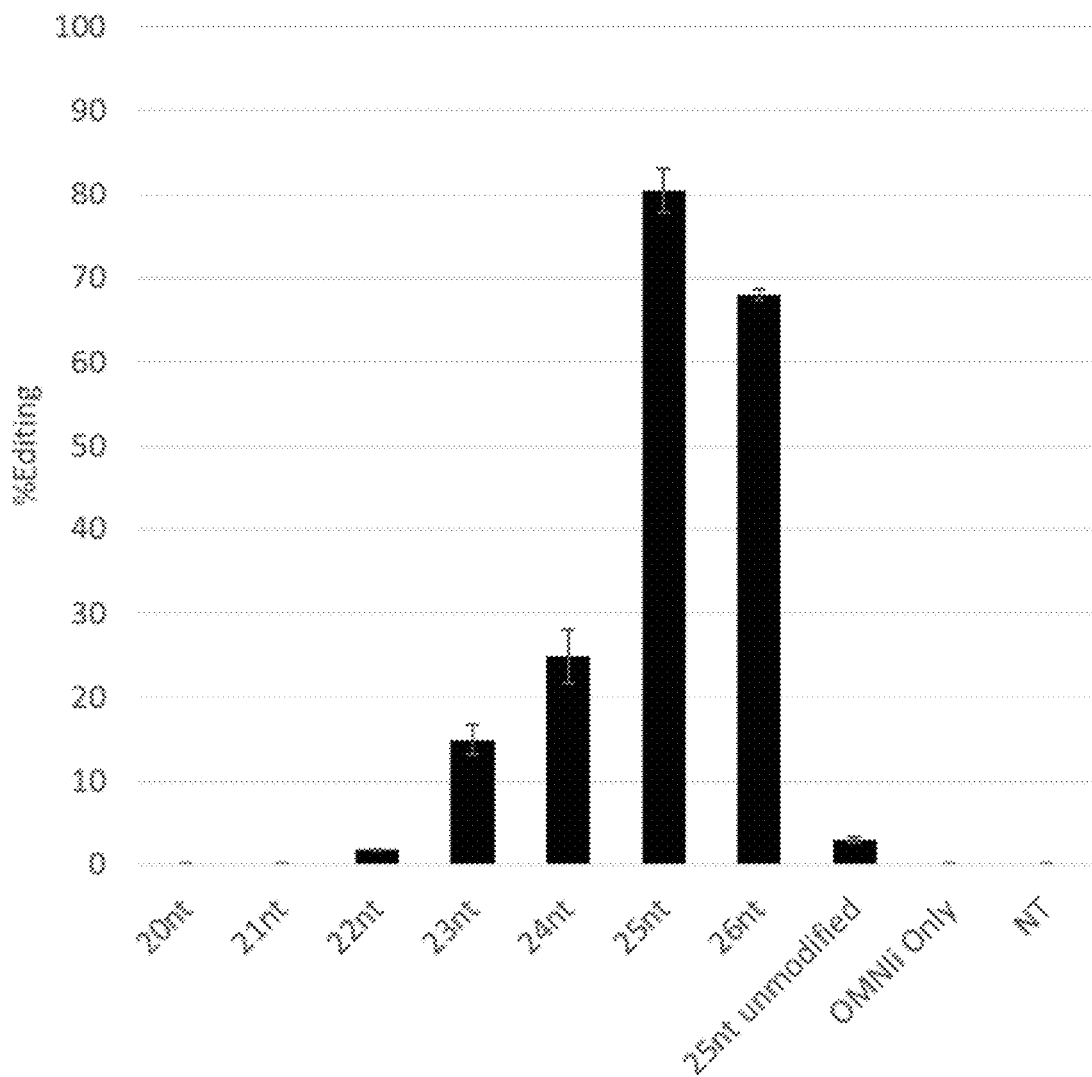
FIG. 6: OMNI-79 CRISPR nuclease spacer optimization. OMNI-79 protein was purified and a RNP complex was assembled using a gRNA molecule targeting ELANE g35 with a spacer length of 20 nt, 21 nt, 22 nt, 23 nt, 24 nt, 25 nt, or 26 nt. All gRNA molecules are synthetic with 2'-O-methyl 3'-phosphorothioate modifications of the first and last three (3) nucleotides. The gRNA molecule with 25-nucleotide long spacer was also synthesized as a version without modifications. Activity of OMNI-79 CRISPR nuclease using the different gRNA molecules was tested in U2OS cells (FIG. 6A) or in an in-vitro activity assay (FIG. 6B).
Figure 6B:
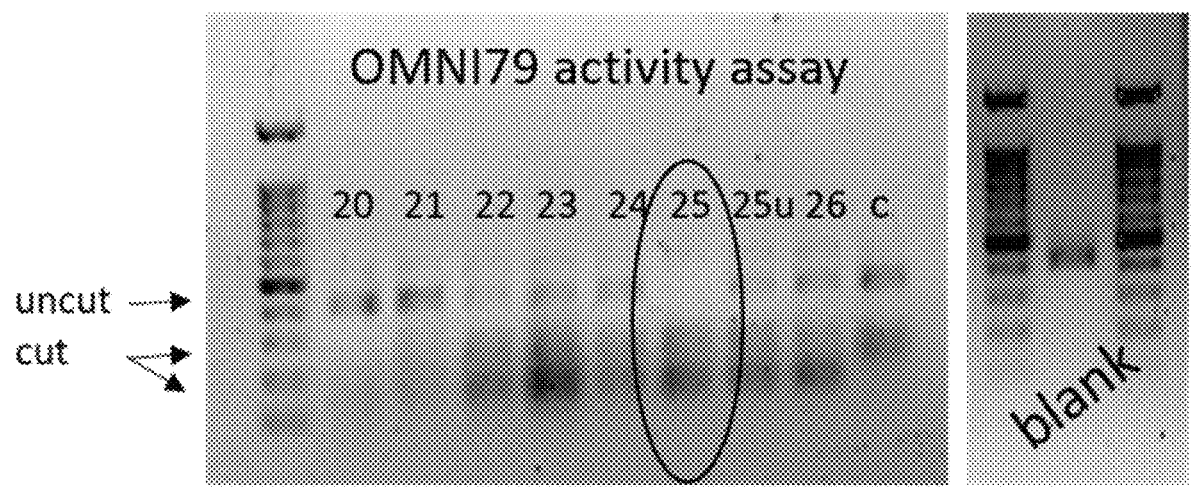

Synthetic sgRNA molecules of OMNI-79 were synthesized with three 2'-O-methyl 3'-phosphorothioate at the 3' and 5' ends (Agilent). An activity assay of OMNI-79 RNP with different spacer lengths (20-26 nucleotides) of guide 35 (FIG. 6B, Table 6). Briefly, 4 pmol of OMNI-79 nuclease were mixed with 6 pmol of synthetic guide. After 10 mins of incubation at room temperature, the RNP complexes were reacted with 100 ng of on-target template. Only spacers larger than 22 nucleotides show cleavage of the on-target template. Furthermore, full cleavage of the on-target template was observed with a 25-nucleotide spacer length only. Using a 25-nucleotide spacer, we compared gRNA molecules synthesized with or without the 2'-O-methyl 3'-phosphorothioate at the 3' and 5' ends, and found this modification to be important to achieve activity, likely due to RNA protection effects.

Spacer length optimization was also tested in a mammalian cell context. RNPs were assembled by mixing 100 uM nuclease with 120 uM of synthetic guide molecules having different spacer lengths (20-26 nucleotides, Table 6) and 100 uM Cas9 electroporation enhancer (IDT). After 10 mins of incubation at room temperature, the RNP complexes were mixed with 200,000 pre-washed U2OS cells and electroporated using Lonza SE Cell Line 4D-Nucleofector™ X Kit with DN100 or program, according to the manufacture's protocol. At 72 hours cells were lysed, and their genomic DNA content was used in PCR reaction which amplified the corresponding putative genomic targets. Amplicons were subjected to NGS and the resulting sequences were then used calculate the percentage of editing events. As can be seen in FIG. 6A and Table 6, spacers of 20-23 nucleotides show a low editing level, the 24-nucleotide spacer shows a medium editing level, and spacers of 25-26 nucleotides show the highest editing level. In this context as well, 2'-O-methyl 3'-phosphorothioate at the 3' and 5' ends were found to be important for activity, likely due to RNA protection.

TABLE 1

OMNI CRISPR nuclease sequences

| "OMNI" Name | SEQ ID NO of Amino Acid Sequence | Source Organism | SEQ ID NO of DNA sequence encoding OMNI | SEQ ID NO of DNA sequence codon optimized for encoding OMNI in human cells |
|---|---|---|---|---|
| OMNI-59 | 1 | Comamonadaceae bacterium NML00-0135 | 9 | 17 |
| OMNI-61 | 2 | Demequina sediminicola | 10 | 18 |
| OMNI-67 | 3 | Fuerstia marisgermanicae | 11 | 19 |
| OMNI-76 | 4 | Nitrosomonas sp. Nm33 | 12 | 20 |
| OMNI-79 | 5 | Novosphingobium sp. SYSU G00007 | 13 | 21 |
| OMNI-80 | 6 | Paracoccus bengalensis | 14 | 22 |
| OMNI-81 | 7 | Parvibium lacunae | 15 | 23 |
| OMNI-82 | 8 | Pelagicola sp. LXJ1103 | 16 | 24 |

TABLE 1-continued

OMNI CRISPR nuclease sequences

| "OMNI" Name | Nickase having inactivated RuvC domain | Nickase having inactivated HNH domain | Dead nuclease having inactivated RuvC and HNH domains |
|---|---|---|---|
| OMNI-59 | (D24 or E557 or H785 or D788) | (E644* or H645 or N668) | (D24 or E557 or H785 or D788) and (E644* or H645 or N668) |
| OMNI-61 | (D19 or E528 or H750 or D753) | (D609* or H610 or N633) | (D19 or E528 or H750 or D753) and (D609* or H610 or N633) |
| OMNI-67 | (D8 or E503 or H729 or D732) | (E584* or H585 or N607) | (D8 or E503 or H729 or D732) and (E584* or H585 or N607) |
| OMNI-76 | (D12 or E543 or H770 or D773) | (E630* or H631 or N654) | (D12 or E543 or H770 or D773) and (E630* or H631 or N654) |
| OMNI-79 | (D8 or E502 or H735 or D738) | (D586* or H587 or N610) | (D8 or E502 or H735 or D738) and (D586* or H587 or N610) |
| OMNI-80 | (D8 or E523 or H757 or D760) | (D607* or H608 or N631) | (D8 or E523 or H757 or D760) and (D607* or H608 or N631) |
| OMNI-81 | (D12 or E527 or H756 or D759) | (E615* or H616 or N639) | (D12 or E527 or H756 or D759) and (E615* or H616 or N639) |
| OMNI-82 | (D6 or E524 or H756 or D759) | (D608* or H609 or N632) | (D6 or E524 or H756 or D759) and (D608* or H609 or N632) |

Table 1. OMNI nuclease sequences: Table 1 lists the OMNI name, its corresponding nuclease protein sequence, its DNA sequence, its human optimized DNA sequence, alternative positions to be substituted to generate a nickase having an inactivated RuvC domain, alternative positions to be substituted to generate a nickase having an inactivated HNH domain, and alternative positions to be substituted to generate a catalytically dead nuclease having inactivated RUVC and HNH domains. Substitution to any other amino acid is permissible for each of the amino acid positions indicated in the columns listing nickase or dead nucleases, except if followed by an asterisk, which indicates that any substitution other than aspartic acid (D) to glutamic acid (E) or glutamic acid (E) to aspartic acid (D) results in inactivation.

TABLE 2

OMNI Guide Sequences

| | | OMNI-59 | OMNI-61 | OMNI-67 |
|---|---|---|---|---|
| crRNA:tracrRNA duplex VI | crRNA (Repeat) | GUUCCGGUCA (SEQ ID NO: 25) | GUUGCGGCCAG AGCU (SEQ ID NO: 30) | GCUGUGGUUC GUCGGG (SEQ ID NO: 40) |
| | Partial crRNA 1 | Not listed | Not listed | GCUGUGGUUC GUCGG (SEQ ID NO: 41) |
| | Partial crRNA 2 | Not listed | GUUGCGGCCAG A (SEQ ID NO: 31) | GCUGUGGUUC GU (SEQ ID NO: 42) |
| | Partial crRNA 3 | Not listed | GUUGCGGCCA (SEQ ID NO: 32) | GCUGUGGUUC (SEQ ID NO: 43) |
| | tracrRNA (Antirepeat) | UGGUCGCUAAC (SEQ ID NO: 26) | GGCUCUGCCGCU AAC (SEQ ID NO: 33) | CCUGACUUAUC ACAGU (SEQ ID NO: 44) |
| | Partial tracrRNA 1 | Not listed | Not listed | CUGACUUAUC ACAGU (SEQ ID NO: 45) |

TABLE 2-continued

OMNI Guide Sequences

| | | | | |
|---|---|---|---|---|
| | Partial tracrRNA 2 | Not listed | UCUGCCGCUAAC (SEQ ID NO: 34) | ACUUAUCACA GU (SEQ ID NO: 46) |
| | Partial tracrRNA 3 | Not listed | UGCCGCUAAC (SEQ ID NO: 35) | UUAUCACAGU (SEQ ID NO: 47) |
| TracrRNA sequences | TracrRNA Portion 1 | AAGCUGAUGCU UUUGUAGCUAG AUGCAAAAAAU G (SEQ ID NO: 27) | AAGGAGAAACU UGUUGGAUCAG GACUCCACAAGA U (SEQ ID NO: 36) | AAGGUUCUCU ACCGC (SEQ ID NO: 48) |
| | tracrRNA Portion 1-partial | Not listed | AAGGAGAAACU UGUU (SEQ ID NO: 37) | GGUUCUCUACC (SEQ ID NO: 49) |
| | TracrRNA Portion 2 | GAAAGCCGGGC AUGCCCGGCUUU CGGCUUUU (SEQ ID NO: 28) | GAGACGGCUCCC UCGUGGGGCCG UUUU (SEQ ID NO: 38) | ACGGCAAUGU GUUUACACAU CCGUU (SEQ ID NO: 50) |
| | TracrRNA Portion 3 | Not listed | Not listed | AAGGACGGUC CUGGACCGUCC UUUUUUU (SEQ ID NO: 51) |
| sgRNA Versions | sgRNA VI | GUUCCGGUCAgaa aUGGUCGCUAAC AAGCUGAUGCU UUUGUAGCUAG AUGCAAAAAAU GGAAAGCCGGG CAUGCCCGGCUU UCGGCUUUU (SEQ ID NO: 29) | GUUGCGGCCAG AGCUgaaaGGCUC UGCCGCUAACAA GGAGAAACUUG UUGGAUCAGGA CUCCACAAGAUG AGACGGCUCCCU CGUGGGGCCGU UUU (SEQ ID NO: 39) | GCUGUGGUUC GUCGGGgaaaCC UGACUUAUCA CAGUAAGGUU CUCUACCGCAC GGCAAUGUGU UUACACAUCCG UUAAGGACGG UCCUGGACCGU CCUUUUUUU (SEQ ID NO: 52) |

| | | OMNI-76 | OMNI-79 sgRNA 1 | OMNI-79 sgRNA 2 |
|---|---|---|---|---|
| crRNA:trac rRNA duplex VI | crRNA (Repeat) | GUUCCGGCUAG AG (SEQ ID NO: 53) | GUUGCCGCUGG A (SEQ ID NO: 63) | GUUGCCGCUG GACCG (SEQ ID NO: 71) |
| | Partial crRNA 2 | GUUCCGGCUAG A (SEQ ID NO: 54) | Not listed | GUUGCCGCUG GA (SEQ ID NO: 72) |
| | Partial crRNA 3 | GUUCCGGCUA (SEQ ID NO: 55) | GUUGCCGCUG (SEQ ID NO: 64) | GUUGCCGCUG (SEQ ID NO: 73) |
| | tracrRNA (Antirepeat) | CUCUGGACGCUA AC (SEQ ID NO: 56) | UCCAGUUGUUA AC (SEQ ID NO: 65) | CGGUCUGGCA GUUAAC (SEQ ID NO: 74) |
| | Partial tracrRNA 2 | UCUGGACGCUA AC (SEQ ID NO: 57) | Not listed | UCUGGCAGUU AAC (SEQ ID NO: 75) |
| | Partial tracrRNA 3 | UGGACGCUAAC (SEQ ID NO: 58) | CAGUUGUUAAC (SEQ ID NO: 66) | UGGCAGUUAA C (SEQ ID NO: 76) |
| TracrRNA sequences | TracrRNA Portion 1 | AAGCUGAAAGA UGCACCAAAUG AU (SEQ ID NO: 59) | AAGCAGCUUGA CUGCACCAAAU (SEQ ID NO: 67) | AAGUGUCAGU ACGCAACAGA U (SEQ ID NO: 77) |
| | tracrRNA Portion 1-partial | GCUGAAAGAUG C (SEQ ID NO: 60) | GCAGCUUGACU GC (SEQ ID NO: 68) | GUGUCAGUAC GC (SEQ ID NO: 78) |
| | TracrRNA Portion 2 | AGGGUCGCUAU AGGCGACCCUUU UU (SEQ ID NO: 61) | AAGGCGGGGC UGCGGCCCUCGC UUUUUU (SEQ ID NO: 69) | AAGGGCGACG CUCCGGCGUCG CCUUUUUU (SEQ ID NO: 79) |

TABLE 2-continued

OMNI Guide Sequences

| | | | | |
|---|---|---|---|---|
| sgRNA Versions | sgRNA VI | GUUCCGGCUAG AGgaaaCUCUGGA CGCUAACAAGCU GAAAGAUGCAC CAAAUGAUAGG GUCGCUAUAGG CGACCCUUUUU (SEQ ID NO: 62) | GUUGCCGCUGG AgaaaUCCAGUUG UUAACAAGCAG CUUGACUGCACC AAAUAAGGCGG GGGCUGCGGCCC UCGCUUUUUU (SEQ ID NO: 70) | GUUGCCGCUG GACCGgaaaCGG UCUGGCAGUU AACAAGUGUC AGUACGCAAC AGAUAAGGGC GACGCUCCGGC GUCGCCUUUU UU (SEQ ID NO: 80) |

| | | OMNI-79 sgRNA 3 | OMNI-80 |
|---|---|---|---|
| crRNA:trac rRNA duplex VI | crRNA (Repeat) | GUUGCCGCUGG AC (SEQ ID NO: 81) | GUUGCGGUUGG (SEQ ID NO: 91) |
| | Partial crRNA 2 | GUUGCCGCUGG A (SEQ ID NO: 82) | Not listed |
| | Partial crRNA 3 | GUUGCCGCUG (SEQ ID NO: 83) | GUUGCGGUUG (SEQ ID NO: 92) |
| | tracrRNA (Antirepeat) | GUCUGGCGGUU AAC (SEQ ID NO: 84) | CUGGCUGUUAA C (SEQ ID NO: 93) |
| | Partial tracrRNA 2 | UCUGGCGGUUA AC (SEQ ID NO: 85) | Not listed |
| | Partial tracrRNA 3 | UGGCGGUUAAC (SEQ ID NO: 86) | UGGCUGUUAAC (SEQ ID NO: 94) |
| TracrRNA sequences | TracrRNA Portion 1 | AAGCAGCCAGUC UGCACCAGAU (SEQ ID NO: 87) | AAGCAGCUUGA CUGCACCAAAU (SEQ ID NO: 95) |
| | tracrRNA Portion 1-partial | GCAGCCAGUCUG C (SEQ ID NO: 88) | GCAGCUUGACU GC (SEQ ID NO: 96) |
| | TracrRNA Portion 2 | AAGGGCGGCGC UCCGGCGCCGCC UUUUUU (SEQ ID NO: 89) | AAGGGCAGGGC UGCGGCCCUGCC UUUU (SEQ ID NO: 97) |
| sgRNA Versions | sgRNA VI | GUUGCCGCUGG ACgaaaGUCUGGC GGUUAACAAGC AGCCAGUCUGCA CCAGAUAAGGG CGGCGCUCCGGC GCCGCCUUUUUU (SEQ ID NO: 90) | GUUGCGGUUGGg aaaCUGGCUGUUA ACAAGCAGCUU GACUGCACCAAA UAAGGGCAGGG CUGCGGCCCUGC CUUUU (SEQ ID NO: 98) |

| | | OMNI-81 | OMNI-82 |
|---|---|---|---|
| crRNA:trac rRNA duplex VI | crRNA (Repeat) | GUUCCGGCUAG AG (SEQ ID NO: 99) | GUUGCGGCUGG ACCGC (SEQ ID NO: 109) |
| | Partial crRNA 1 | Not listed | GUUGCGGCUGG ACCG (SEQ ID NO: 110) |
| | Partial crRNA 2 | GUUCCGGCUAG A (SEQ ID NO: 100) | GUUGCGGCUGG A (SEQ ID NO: 111) |
| | Partial crRNA 3 | GUUCCGGCUA (SEQ ID NO: 101) | GUUGCGGCUG (SEQ ID NO: 112) |
| | tracrRNA (Antirepeat) | CUCUAGACGCUA AC (SEQ ID NO: 102) | GCGGUCGAGCU GUUAAC (SEQ ID NO: 113) |

TABLE 2-continued

| | | OMNI Guide Sequences | |
|---|---|---|---|
| | Partial tracrRNA 1 | Not listed | CGGUCGAGCUG UUAAC (SEQ ID NO: 114) |
| | Partial tracrRNA 2 | UCUAGACGCUA AC (SEQ ID NO: 103) | UCGAGCUGUUA AC (SEQ ID NO: 115) |
| | Partial tracrRNA 3 | UAGACGCUAAC (SEQ ID NO: 104) | GAGCUGUUAAC (SEQ ID NO: 116) |
| TracrRNA | TracrRNA Portion 1 | AAGCUGAAAGA UGCACCAAAUG (SEQ ID NO: 105) | AAGCAUUCGAU UGCACCACAUU (SEQ ID NO: 117) |
| sequences | tracrRNA Portion 1-partial | GCUGAAAGAUG C (SEQ ID NO: 106) | GCAUUCGAUUG C (SEQ ID NO: 118) |
| | TracrRNA Portion 2 | GAAAGCCGCUA UAUGCGGCUUU CGUCUUUU (SEQ ID NO: 107) | GAAGCGCAGGG CCACGGCCCUGC GUUUU (SEQ ID NO: 119) |
| sgRNA Versions | sgRNA VI | GUUCCGGCUAG AGgaaaCUCUAGA CGCUAACAAGCU GAAAGAUGCAC CAAAUGGAAAG CCGCUAUAUGCG GCUUUCGUCUU UU (SEQ ID NO: 108) | GUUGCGGCUGG ACCGCgaaaGCGG UCGAGCUGUUA ACAAGCAUUCG AUUGCACCACAU UGAAGCGCAGG GCCACGGCCCUG CGUUUU (SEQ ID NO: 120) |

TABLE 3

OMNI PAM Sequences

| | | OMNI-59 | OMNI-61 | OMNI-67 |
|---|---|---|---|---|
| TXTL Depletion | PAM General Activity (1-Depletion score)* | NGCNNT 0.95, 0.94 | NSHNAC 0.42, 0.54 | NRRCM 0.95, 0.95 |
| | sgRNA | V1, V2 | V1, V3 | V1, V2 |
| Mammalian refinements | PAM Mammlian | No data shown | No data shown | No data shown |

| | | OMNI-76 | OMNI-79 | OMNI-80 |
|---|---|---|---|---|
| TXTL Depletion | PAM General Activity (1-Depletion score)* | NGSNNT 0.2 | NGR 0.97, 0.95 | NNRGAY 0.57, 0.48 |
| | sgRNA | V1 | V1, V2 | V1, V2 |
| Mammalian refinements | PAM Mammlian | No data shown | NGG | No data shown |

| | | OMNI-81 | OMNI-82 |
|---|---|---|---|
| TXTL Depletion | PAM General Activity (1-Depletion score)* | NRRAA 0.92, 0.94 | NRRNTT 0.55, 0.58 |
| | sgRNA | V1, V2 | V2, V4 |
| Mammalian refinements | PAM Mammlian | No data shown | No data shown |

*Depletion score - Average of the ratios from two most depleted sites

TABLE 4

Plasmids and Constructs

| Plasmid/Viral Vector | Purpose | Elements | Example |
|---|---|---|---|
| pbNNC-3 | Expressing OMNI polypeptide in the bacterial system | T7 promoter HA Tag-Linker-OMNI ORF (Human optimized)-SV40 NLS-8XHisTag-T7 terminator | pbNNC3-OMNI-79 (SEQ ID NO: 121) |
| pbSGRT1/T2 | Expressing OMNI sgRNA in the bacterial system | T7promoter-T1/T2 spacer sgRNA scaffold-T7 terminator | pbSGR2-T2-OMNI-79 V1 (SEQ ID NO: 122) |
| pbPOS T2 library | Bacterial/TXTL depletion assay | T2 protospacer-8N PAM library-chloramphenicol acetyltransferase | pbPOS T2 library (SEQ ID NO: 123) |
| pET9a | Expression and purification of OMNI proteins | T7 promoter-SV40 NLS-OMNI ORF (human optimized)-HA-SV40 NLS-8 His-tag-T7 terminator | pET9a-OMNI-79 (SEQ ID NO: 124) |
| pmOMNI | Expressing OMNI polypeptide in the mammalian system | CMV promoter-Kozak-SV40 NLS-OMNI ORF (human optimized)-HA-SV40 NLS-P2A-mCherry-bGH poly(A) | pmOMNI-79 (SEQ ID NO: 125) |

TABLE 4-continued

Plasmids and Constructs

| Plasmid/Viral Vector | Purpose | Elements | Example |
|---|---|---|---|
| pmGuide T2/Endogenic site | Expressing OMNI sgRNA in the mammalian system | signal U6 promoter-Endogenic spacer sgRNA scaffold | pmGuide T2-OMNI-79 V1 (SEQ ID NO: 126) |
| pPMLl3.1 | Viral vector for PAM library in mammalian cells | LTR-HIV-1 Ψ-CMV promoter-T2-PAM library (6N)-GFP-SV40 promoter-blastocydin S deaminase-LTR | pPMLl3.1 (SEQ ID NO: 127) |
| AAV viral vector | AAV viral vector encoding OMNI nuclease and guide RNA molecule | AAV-U6 promoter-spacer sequence (e.g. serpina s12, SEQ ID NO: 194)-scaffold sequence (e.g. DNA-encoding sequence of SEQ ID NO: 241)-CMV promoter-OMNI CRISPR nuclease sequence (e.g. SEQ ID NO: 21)-BGH terminator | AAV-OMNI-79 (SEQ ID NO: 128) |

Appendix—Details of construct elements

| Element | Protein Sequence | DNA sequence |
|---|---|---|
| HA Tag | SEQ ID NO: 129 | SEQ ID NO: 133 |
| NLS | SEQ ID NO: 130 | SEQ ID NO: 134 |
| P2A | SEQ ID NO: 131 | SEQ ID NO: 135 |
| mCherry | SEQ ID NO: 132 | SEQ ID NO: 136 |

TABLE 5

Activity of OMNIs in human cells on endogenous genomic targets

| Nuclease | Genomic site | Corresponding Spacer name | Spacer sequence | 3' (PAM containing) genomic sequence | % indels | % transfection | % editing in neg control | % transfection in neg control |
|---|---|---|---|---|---|---|---|---|
| OMNI-59 | CXCR4 site 1 | OMNI59_CXCR4_S1 | SEQ ID NO: 137 | SEQ ID NO: 159 | 2.8 | 41.7 | 0.05 | 36 |
| | CXCR4 site 2 | OMNI59_CXCR4_S2 | SEQ ID NO: 138 | SEQ ID NO: 160 | 0 | 44.8 | 0.05 | 36 |
| | PDCD1 site 1 | OMNI59_PDCD1_S1 | SEQ ID NO: 139 | SEQ ID NO: 161 | 0 | 44.5 | 0.05 | 36 |
| | PDCD1 site 2 | OMNI59_PDCD1_S2 | SEQ ID NO: 140 | SEQ ID NO: 162 | 0 | 53 | 0.05 | 36 |
| | TRAC site 1 | OMNI59_TRAC_S1 | SEQ ID NO: 141 | SEQ ID NO: 163 | 0 | 44.5 | 0.05 | 36 |
| | TRAC site 2 | OMNI59_TRAC_S2 | SEQ ID NO: 142 | SEQ ID NO: 164 | 0.3 | 42 | 0.05 | 36 |
| OMNI-67 | CXCR4 site 1 | OMNI67_CXCR4_S3 | SEQ ID NO: 143 | SEQ ID NO: 165 | 0/0 | 87/69 | 0.00 | 86/61.5 |
| | CXCR4 site 2 | OMNI67_CXCR4_S4 | SEQ ID NO: 144 | SEQ ID NO: 166 | 0/0 | 94/80 | 0.00 | 86/61.5 |
| | PDCD1 site 1 | OMNI67_PDCD1_S3 | SEQ ID NO: 145 | SEQ ID NO: 167 | 0/0 | 94/81 | 0.00 | 86/61.5 |
| | PDCD1 site 2 | OMNI67_PDCD1_S4 | SEQ ID NO: 146 | SEQ ID NO: 168 | 0/0 | 92/82 | 0.00 | 86/61.5 |
| | TRAC site 1 | OMNI67_TRAC_S3 | SEQ ID NO: 147 | SEQ ID NO: 169 | 0/0 | 94/84 | 0.00 | 86/61.5 |
| | TRAC site 2 | OMNI67_TRAC_S4 | SEQ ID NO: 148 | SEQ ID NO: 170 | 3.3/2.5 | 94/85 | 0.00 | 86/61.5 |
| OMNI-79 | CXCR4 site 1 | OMNI79_CXCR4_S25 | SEQ ID NO: 149 | SEQ ID NO: 171 | 27/0.08 | 74/96 | 0/0 | 85/91.5 |
| | CXCR4 site 2 | OMNI79_CXCR4_S26 | SEQ ID NO: 150 | SEQ ID NO: 172 | 0.42/0.07 | 42/83 | 0/0 | 85/91.5 |
| | g58_Ref | OMNI79_g58_Ref | SEQ ID NO: 151 | SEQ ID NO: 173 | 0/0 | 58/89 | 0/0 | 85/91.5 |
| | g35 | OMNI-79_g35 | SEQ ID NO: 152 | SEQ ID NO: 174 | 39.3/44 | 85/82.5 | 0/0 | 85/91.5 |
| | PDCD1S24 | OMNI79_PDCD1_S24 | SEQ ID NO: 181 | TGGGCT | 6.702694334 | 92.80 | 0 | 91.3 |
| | PDCD1S25 | OMNI79_PDCD1_S25 | SEQ ID NO: 182 | AGGATG | 0 | 91.13 | 0 | 91.3 |
| | TRACS21 | OMNI79_TRAC_S21 | SEQ ID NO: 183 | TGGACT | 44.46183445 | 98.27 | 0 | 91.3 |
| | TRACS24 | OMNI79_TRAC_S24 | SEQ ID NO: 184 | CGGAAC | 2.806238147 | 88.87 | 0 | 91.3 |
| | EMXS2 | OMNI79_EMX_S2 | SEQ ID NO: 185 | GGGAGC | 44.95355661 | 82.47 | 0 | 91.3 |

TABLE 5-continued

Activity of OMNIs in human cells on endogenous genomic targets

| Nuclease | Genomic site | Corresponding Spacer name | Spacer sequence | 3' (PAM containing) genomic sequence | % indels | % transfection | % editing in neg control | % transfection in neg control |
|---|---|---|---|---|---|---|---|---|
| | EMXS3 | OMNI79_EMX_S3 | SEQ ID NO: 186 | AGGGGACC | 1.48249255 | 70.70 | 0 | 91.3 |
| | SAMD9 rs070_1 | OMNI79_SAMD9_rs070_1 | SEQ ID NO: 187 | SEQ ID NO: 212 | 0 | 51.8 | 0 | 41.97 |
| | SAMD9 rs070_2 | OMNI79_SAMD9_rs070_2 | SEQ ID NO: 188 | SEQ ID NO: 213 | 0 | 51.57 | 0 | 41.97 |
| | SAMD9 rs201 | OMNI79_SAMD9_rs201_alt | SEQ ID NO: 189 | SEQ ID NO: 214 | 1 | 56.43 | 0 | 41.97 |
| | SAMD9 rs499_1 | OMNI79_SAMD9_rs499_1 | SEQ ID NO: 190 | SEQ ID NO: 215 | 28 | 55.3 | 0 | 41.97 |
| | SAMD9 rs499_2 | OMNI79_SAMD9_rs499_2 | SEQ ID NO: 191 | SEQ ID NO: 216 | 0 | 48.67 | 0 | 41.97 |
| | SAMD9L rs532_1 | OMNI79_SAMD9L_rs532_1 | SEQ ID NO: 192 | SEQ ID NO: 217 | 0 | 63.37 | 0 | 44.13 |
| | SAMD9L rs532_2 | OMNI79_SAMD9L_rs532_2 | SEQ ID NO: 193 | SEQ ID NO: 218 | 29 | 65.17 | 0 | 44.13 |
| | Serpina_S12 | OMNI79_Serpina_S12 | SEQ ID NO: 194 | SEQ ID NO: 219 | 33.37 | 75.17 | N/A | 80.13 |
| | Serpina_S13 | OMNI-79_Serpina_S13 | SEQ ID NO: 195 | SEQ ID NO: 220 | 8.55 | 86.2 | N/A | 80.13 |
| | Serpina_S14 | OMNI79_Serpina_S14 | SEQ ID NO: 196 | SEQ ID NO: 221 | 7.86 | 84.37 | N/A | 80.13 |
| | Serpina_S22 | OMNI79_Serpina_S22 | SEQ ID NO: 197 | SEQ ID NO: 222 | 19.14 | 68.37 | N/A | 80.13 |
| | Serpina_S23 | OMNI79_Serpina_S23 | SEQ ID NO: 198 | SEQ ID NO: 223 | 55.57 | 87.6 | N/A | 80.13 |
| | Serpina_S32 | OMNI79_Serpina_S32 | SEQ ID NO: 199 | SEQ ID NO: 224 | 5.38 | 71.03 | N/A | 80.13 |
| | Serpina_S33 | OMNI79_Serpina_S33 | SEQ ID NO: 200 | SEQ ID NO: 225 | 2.49 | 76.77 | N/A | 80.13 |
| | Serpina_S34 | OMNI79_Serpina_S34 | SEQ ID NO: 201 | SEQ ID NO: 226 | 8.47 | 63.07 | N/A | 80.13 |
| | Serpina_S38 | OMNI79_Serpina_S38 | SEQ ID NO: 202 | SEQ ID NO: 227 | 5.89 | 26.23 | N/A | 80.13 |
| | Serpina_S39 | OMNI79_Serpina_S39 | SEQ ID NO: 203 | SEQ ID NO: 228 | 6.95 | 91.43 | N/A | 80.13 |
| | Serpina_S40 | OMNI79_Serpina_S40 | SEQ ID NO: 204 | SEQ ID NO: 229 | 6.63 | 91.27 | N/A | 80.13 |
| | Serpina_S49 | OMNI79_Serpina_S49 | SEQ ID NO: 205 | SEQ ID NO: 230 | 16.97 | 89.1 | N/A | 80.13 |
| | Serpina_S50 | OMNI79_Serpina_S50 | SEQ ID NO: 206 | SEQ ID NO: 231 | 13.15 | 64.5 | N/A | 80.13 |
| | Serpina_S51 | OMNI79_Serpina_S51 | SEQ ID NO: 207 | SEQ ID NO: 232 | 13.22 | 79 | N/A | 80.13 |
| OMNI-81 | CXCR4 site 1 | OMNI81_CXCR4_S6 | SEQ ID NO: 153 | SEQ ID NO: 175 | 30.21/13.2 | 92/72 | 0.04/0 | 94/70.7 |
| | CXCR4 site 2 | OMNI81_CXCR4_S7 | SEQ ID NO: 154 | SEQ ID NO: 176 | 5.25/1.44 | 94/68 | 0/0 | 94/70.7 |
| | PDCD1 site 1 | OMNI81_PDCD1_S7 | SEQ ID NO: 155 | SEQ ID NO: 177 | 47.84/7.94 | 95/41 | 0/0 | 94/70.7 |
| | PDCD1 site 2 | OMNI81_PDCD1_S8 | SEQ ID NO: 156 | SEQ ID NO: 178 | 11.5/5.91 | 97/83 | 0/0 | 94/70.7 |
| | TRAC site 1 | OMNI81_TRAC_S6 | SEQ ID NO: 157 | SEQ ID NO: 179 | 0/0 | 95/83 | 0.22/0.18 | 94/70.7 |
| | TRAC site 2 | OMNI81_TRAC_S7 | SEQ ID NO: 158 | SEQ ID NO: 180 | 0.69 | 71 | 0.00 | 70.70 |
| | EMXS11 | OMNI81_EMX_S11 | SEQ ID NO: 208 | CAGAA | 11.50 | 85.77 | 0 | 94.2 |
| | EMXS12 | OMNI81_EMX_S12 | SEQ ID NO: 209 | AGGAA | 0.00 | 76.37 | 0 | 94.2 |
| | B2MS8 | OMNI81_B2M_S8 | SEQ ID NO: 210 | AGGAA | 0.00 | 93.33 | 0 | 94.2 |
| | B2MS9 | OMNI81_B2M_S9 | SEQ ID NO: 211 | TGAAAAA | 3.43 | 83.87 | 0.087625783 | 94.2 |

Table 5. Nuclease activity in endogenous context in mammalian cells: OMNI nucleases were expressed in a mammalian cell system (HeLa) by DNA transfection together with an sgRNA expressing plasmid. Cell lysates were used for site specific genomic DNA amplification and NGS. The percentage of indels was measured and analyzed to determine the editing level. Each sgRNA is composed of the tracrRNA (see Table 2) and the spacer detailed here. The spacer 3' genomic sequence contains the expected PAM relevant for each OMNI nuclease. Transfection efficiency (% transfection) was measured by flow cytometry of the mCherry signal, as described above. All tests were performed in triplicates with two repeats. OMNI nuclease only (no guide) transfected cells served as a negative control. Results from repeat experiments are separated by a dash ("/") symbol.

TABLE 6

OMNI-79 spacer length optimization

| Spacer Name | Spacer sequence |
|---|---|
| ELANE 835 19nt | GUCCGGGCUGGGAGCGGGU (SEQ ID NO: 233) |
| ELANE 835 20nt | AGUCCGGGCUGGGAGCGGGU (SEQ ID NO: 234) |
| ELANE g35 21nt | CAGUCCGGGCUGGGAGCGGGU (SEQ ID NO: 235) |
| ELANE 835 22nt | GCAGUCCGGGCUGGGAGCGGGU (SEQ ID NO: 236) |
| ELANE 835 23nt | UGCAGUCCGGGCUGGGAGCGGGU (SEQ ID NO: 237) |
| ELANE g35 24nt | CUGCAGUCCGGGCUGGGAGCGGGU (SEQ ID NO: 238) |
| ELANE 835 25nt | GCUGCAGUCCGGGCUGGGAGCGGGU (SEQ ID NO: 239) |
| ELANE g35 26nt | UGCUGCAGUCCGGGCUGGGAGCGGGU (SEQ ID NO: 240) |

Table 6. OMNI-79 spacer length optimization: OMNI-79 spacer optimization was performed using an RNA guide molecule comprising a version of the ELANE g35 spacer having different lengths. The OMNI-79 scaffold sequence used with each spacer is SEQ ID NO: 241. Results are shown in FIGS. 6A-6B.

REFERENCES

1. Ahmad and Allen (1992) "Antibody-mediated Specific Binging and Cytotoxicity of Liposome-entrapped Doxorubicin to Lung Cancer Cells in Vitro", Cancer Research 52:4817-20.
2. Anderson (1992) "Human gene therapy", Science 256: 808-13.
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200.
4. Behr (1994) "Gene transfer with synthetic cationic amphiphiles: Prospects for gene therapy", Bioconjugate Chem 5:382-89.
5. Blaese et al. (1995) "Vectors in cancer therapy: how will they deliver", Cancer Gene Ther. 2:291-97.
6. Blaese et al. (1995) "T lymphocyte-directed gene therapy for ADA-SCID: initial trial results after 4 years", Science 270(5235):475-80.
7. Briner et al. (2014) "Guide RNA functional modules direct Cas9 activity and orthogonality", Molecular Cell 56:333-39.
8. Buchschacher and Panganiban (1992) "Human immunodeficiency virus vectors for inducible expression of foreign genes", J. Virol. 66:2731-39.
9. Burstein et al. (2017) "New CRISPR-Cas systems from uncultivated microbes", Nature 542:237-41.
10. Canver et al., (2015) "BCL11A enhancer dissection by Cas9-mediated in situ saturating mutagenesis", Nature Vol. 527, Pgs. 192-214.
11. Chang and Wilson (1987) "Modification of DNA ends can decrease end-joining relative to homologous recombination in mammalian cells", Proc. Natl. Acad. Sci. USA 84:4959-4963.
12. Charlesworth et al. (2019) "Identification of preexisting adaptive immunity to Cas9 proteins in humans", Nature Medicine, 25(2), 249.
13. Chung et al. (2006) "*Agrobacterium* is not alone: gene transfer to plants by viruses and other bacteria", Trends Plant Sci. 11(1):1-4.
14. Coelho et al. (2013) "Safety and efficacy of RNAi therapy for transthyretin amyloidosis" N. Engl. J. Med. 369, 819-829.
15. Crystal (1995) "Transfer of genes to humans: early lessons and obstacles to success", Science 270(5235): 404-10.
16. Dillon (1993) "Regulation gene expression in gene therapy" Trends in Biotechnology 11(5):167-173.
17. Dranoff et al. (1997) "A phase I study of vaccination with autologous, irradiated melanoma cells engineered to secrete human granulocyte macrophage colony stimulating factor", Hum. Gene Ther. 8(1):111-23.
18. Dunbar et al. (1995) "Retrovirally marked CD34-enriched peripheral blood and bone marrow cells contribute to long-term engraftment after autologous transplantation", Blood 85:3048-57.
19. Ellem et al. (1997) "A case report: immune responses and clinical course of the first human use of granulocyte/macrophage-colony-stimulating-factor-transduced autologous melanoma cells for immunotherapy", Cancer Immunol Immunother 44:10-20.
20. Gao and Huang (1995) "Cationic liposome-mediated gene transfer" Gene Ther. 2(10):710-22.
21. Haddada et al. (1995) "Gene Therapy Using Adenovirus Vectors", in: The Molecular Repertoire of Adenoviruses III: Biology and Pathogenesis, ed. Doerfler and Bohm, pp. 297-306.
22. Han et al. (1995) "Ligand-directed retro-viral targeting of human breast cancer cells", Proc. Natl. Acad. Sci. USA 92(21):9747-51.
23. Humbert et al., (2019) "Therapeutically relevant engraftment of a CRISPR-Cas9—edited HSC-enriched population with HbF reactivation in nonhuman primates", Sci. Trans. Med., Vol. 11, Pgs. 1-13.
24. Inaba et al. (1992) "Generation of large numbers of dendritic cells from mouse bone marrow cultures supplemented with granulocyte/macrophage colony-stimulating factor", J Exp Med. 176(6):1693-702.
25. Jiang and Doudna (2017) "CRISPR-Cas9 Structures and Mechanisms", Annual Review of Biophysics 46:505-29.
26. Jinek et al. (2012) "A programmable dual-RNA-guided DNA endonuclease in adaptive bacterial immunity", Science 337(6096):816-21.
27. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40.
28. Judge et al. (2006) "Design of noninflammatory synthetic siRNA mediating potent gene silencing in vivo", Mol Ther. 13(3):494-505.
29. Kohn et al. (1995) "Engraftment of gene-modified umbilical cord blood cells in neonates with adenosine deaminase deficiency", Nature Medicine 1:1017-23.
30. Kremer and Perricaudet (1995) "Adenovirus and adeno-associated virus mediated gene transfer", Br. Med. Bull. 51(1):31-44.
31. Macdiarmid et al. (2009) "Sequential treatment of drug-resistant tumors with targeted minicells containing siRNA or a cytotoxic drug", Nat Biotechnol. 27(7):643-51.
32. Malech et al. (1997) "Prolonged production of NADPH oxidase-corrected granulocytes after gene therapy of chronic granulomatous disease", PNAS 94(22):12133-38.

33. Maxwell et al. (2018) "A detailed cell-free transcription-translation-based assay to decipher CRISPR protospacer adjacent motifs", Methods 14348-57
34. Miller et al. (1991) "Construction and properties of retrovirus packaging cells based on gibbon ape leukemia virus", J Virol. 65(5):2220-24.
35. Miller (1992) "Human gene therapy comes of age", Nature 357:455-60.
36. Mir et al. (2019) "Type II-C CRISPR-Cas9 Biology, Mechanism and Application", ACS Chem. Biol. 13(2): 357-365.
37. Mitani and Caskey (1993) "Delivering therapeutic genes—matching approach and application", Trends in Biotechnology 11(5):162-66.
38. Nabel and Felgner (1993) "Direct gene transfer for immunotherapy and immunization", Trends in Biotechnology 11(5):211-15.
39. Nehls et al. (1996) "Two genetically separable steps in the differentiation of thymic epithelium" Science 272: 886-889.
40. Nishimasu et al. "Crystal structure of Cas9 in complex with guide RNA and target DNA" (2014) Cell 156(5): 935-49.
41. Nishimasu et al. (2015) "Crystal Structure of *Staphylococcus aureus* Cas9" Cell 162(5):1113-26.
42. Palermo et al. (2018) "Key role of the REC lobe during CRISPR-Cas9 activation by 'sensing', 'regulating', and 'locking' the catalytic HNH domain" Quarterly Reviews of Biophysics 51, e9, 1-11.
43. Remy et al. (1994) "Gene Transfer with a Series of Lipophilic DNA-Binding Molecules", Bioconjugate Chem. 5(6):647-54.
44. Sentmanat et al. (2018) "A Survey of Validation Strategies for CRISPR-Cas9 Editing", Scientific Reports 8:888, doi:10.1038/s41598-018-19441-8.
45. Sommerfelt et al. (1990) "Localization of the receptor gene for type D simian retroviruses on human chromosome 19", J. Virol. 64(12):6214-20.
46. Van Brunt (1988) "Molecular framing: transgenic animals as bioactors" Biotechnology 6:1149-54.
47. Vigne et al. (1995) "Third-generation adenovectors for gene therapy", Restorative Neurology and Neuroscience 8(1,2): 35-36.
48. Wagner et al. (2019) "High prevalence of *Streptococcus pyogenes* Cas9-reactive T cells within the adult human population" Nature Medicine, 25(2), 242
49. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78.
50. Yu et al. (1994) "Progress towards gene therapy for HIV infection", Gene Ther. 1(1):13-26.
51. Zetsche et al. (2015) "Cpf1 is a single RNA-guided endonuclease of a class 2 CRISPR-Cas system" Cell 163(3):759-71.
52. Zuris et al. (2015) "Cationic lipid-mediated delivery of proteins enables efficient protein based genome editing in vitro and in vivo" Nat Biotechnol. 33(1):73-80.

What is claimed is:

1. A non-naturally occurring composition comprising a CRISPR nuclease comprising a sequence having at least 90% identity to the amino acid sequence set forth in SEQ ID NO: 5, or a nucleic acid molecule comprising a sequence encoding the CRISPR nuclease; wherein the CRISPR nuclease further comprises one or more nuclear localization sequences (NLSs).

2. The composition of claim 1, further comprising one or more RNA molecules, or a DNA polynucleotide encoding any one of the one or more RNA molecules, wherein the one or more RNA molecules and the CRISPR nuclease do not naturally occur together and the one or more RNA molecules are capable of forming a complex with the CRISPR nuclease and/or target the complex to a target site, and wherein the one or more RNA molecules are
    a) a CRISPR RNA (crRNA) molecule and a transactivating CRISPR RNA (tracrRNA) molecule, or
    b) a single-guide RNA (sgRNA) molecule.

3. The composition of claim 2, wherein the CRISPR nuclease comprises a sequence having at least 90% identity to the amino acid sequence set forth in SEQ ID NO: 5, and at least one RNA molecule comprises a sequence selected from the group consisting of SEQ ID NOs: 63-90.

4. The composition of claim 3, wherein the CRISPR nuclease comprises a sequence having at least 90% identity to the amino acid sequence set forth in SEQ ID NO: 5 and
    i) at least one RNA molecule is a CRISPR RNA (crRNA) molecule comprising a guide sequence portion and a sequence selected from the group consisting of SEQ ID NOs: 63, 64, 71-73, and 81-83; and further comprising a transactivating CRISPR RNA (tracrRNA) molecule comprising a sequence set forth in the group consisting of SEQ ID NOs: 65-69, 74-79, and 84-89; or
    ii) at least one RNA molecule is a single-guide RNA (sgRNA) molecule comprising a guide sequence portion and a sequence selected from the group consisting of SEQ ID NOs: 63-90.

5. The composition of claim 2, wherein the crRNA molecule or sgRNA molecule comprises a guide sequence portion that is 25 or 26 nucleotides in length.

6. The composition of claim 2, wherein the composition is an engineered, non-naturally occurring composition comprising a CRISPR associated system comprising:
    one or more RNA molecules, or one or more nucleotide sequences encoding the one or more RNA molecules, wherein at least one of the one or more RNA molecules comprises a guide sequence portion linked to a direct repeat sequence, wherein the guide sequence portion is capable of hybridizing with a target sequence; and
    a CRISPR nuclease comprising an amino acid sequence having at least 90% identity to the amino acid sequence of SEQ ID NO: 5, or a nucleic acid molecule comprising a sequence encoding the CRISPR nuclease; and
wherein the one or more RNA molecules hybridize to the target sequence, wherein the target sequence is adjacent to the 3' end of a complimentary sequence of a NGR or NGG Protospacer Adjacent Motif (PAM), and the one or more RNA molecules form a complex with the CRISPR nuclease.

7. The composition of claim 2, wherein the crRNA molecule or sgRNA molecule comprises a guide sequence portion that is 17-30 nucleotides in length.

8. The composition of claim 2, further comprising a donor template molecule.

9. The composition of claim 8, wherein the donor template molecule is a DNA molecule.

10. The composition of claim 7, wherein the crRNA molecule or sgRNA molecule comprises a guide sequence portion that is 19-23 nucleotides in length.

11. The composition of claim 1, wherein the CRISPR nuclease comprises a sequence having at least 90% identity to the amino acid sequence of SEQ ID NO: 5, and wherein the CRISPR nuclease is a nickase formed by an amino acid substitution at D8, E502, H735 or D738 of SEQ ID NO: 5, or
   wherein the CRISPR nuclease comprises a sequence having at least 90% identity to the amino acid sequence of SEQ ID NO: 5, and wherein the CRISPR nuclease is a nickase formed by an amino acid substitution at D586, H587 or N610 of SEQ ID NO: 5, or
   wherein the CRISPR nuclease comprises a sequence having at least 90% identity to the amino acid sequence of SEQ ID NO: 5, and wherein the CRISPR nuclease is a catalytically inactive nuclease formed by an amino acid substitution at D8, E502, H735 or D738 of SEQ ID NO: 5, and an amino acid substitution at D586, H587 or N610 of SEQ ID NO: 5.

12. The composition of claim 1, wherein the CRISPR nuclease comprises a sequence having at least 95% identity to the amino acid sequence set forth in SEQ ID NO: 5.

13. The composition of claim 1, wherein the CRISPR nuclease is linked to a further protein.

14. The composition of claim 1, wherein the CRISPR nuclease is a nickase or a catalytically inactive nuclease.

15. A method of modifying a nucleotide sequence at a target site in a cell-free system or the genome of a cell comprising introducing into the cell-free system or the cell the composition of claim 2.

16. The method of claim 15, wherein the cell is a mammalian cell.

17. The method of claim 15, wherein the CRISPR nuclease forms a complex with the at least one RNA molecule or RNA molecules, and effects a DNA break in a DNA strand adjacent to a NGR or NGG protospacer adjacent motif (PAM) sequence, and/or effects a DNA break in a DNA strand adjacent to a sequence that is complementary to the PAM sequence.

18. The method of claim 15, wherein the CRISPR nuclease effects a DNA break in a DNA strand adjacent to a NGR or NGG PAM sequence and effects a DNA break in a DNA strand adjacent a sequence that is complementary to the PAM sequence, or
   wherein the CRISPR nuclease is a nickase formed by an amino acid substitution at D8, E502, H735 or D738 of SEQ ID NO: 5, and effects a DNA break in a DNA strand adjacent to the PAM sequence, or
   wherein the CRISPR nuclease is a nickase formed by an amino acid substitution at D586, H587 or N610 of SEQ ID NO: 5, and effects a DNA break in a DNA strand adjacent to a sequence that is complementary to the PAM sequence.

19. The method of claim 15, wherein the CRISPR nuclease and one or more RNA molecules are introduced to the cell as a ribonucleoprotein (RNP) complex.

20. The method of claim 15, wherein the nucleic acid molecule comprising a sequence encoding the CRISPR nuclease is an mRNA molecule.

21. The method of claim 15, wherein the nucleic acid molecule comprising a sequence encoding the CRISPR nuclease is a DNA molecule.

* * * * *